US012163150B2

(12) United States Patent
Tangy et al.

(10) Patent No.: US 12,163,150 B2
(45) **Date of Patent: *Dec. 10, 2024**

(54) RECOMBINANT MEASLES VIRUSES EXPRESSING EPITOPES OF ANTIGENS OF RNA VIRUSES—USE FOR THE PREPARATION OF VACCINE COMPOSITIONS

(71) Applicants: Frederic Tangy, Les Lilas (FR); Clarisse Lorin, Paris (FR); Lucile Mollet, Orleans (FR); Frederic Delebecque, Paris (FR)

(72) Inventors: Frederic Tangy, Les Lilas (FR); Clarisse Lorin, Paris (FR); Lucile Mollet, Orleans (FR); Frederic Delebecque, Paris (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 815 days.

This patent is subject to a terminal disclaimer.

(21) Appl. No.: 17/063,597

(22) Filed: Oct. 5, 2020

(65) Prior Publication Data

US 2021/0095315 A1 Apr. 1, 2021

Related U.S. Application Data

(60) Continuation of application No. 17/015,846, filed on Sep. 9, 2020, and a continuation of application No.
(Continued)

(30) Foreign Application Priority Data

Jun. 20, 2002 (FR) .................................. 02291550.8

(51) Int. Cl.
*C12N 15/86* (2006.01)
*A61K 39/00* (2006.01)
(Continued)

(52) U.S. Cl.
CPC .............. *C12N 15/86* (2013.01); *A61K 39/12* (2013.01); *A61K 39/165* (2013.01); *A61K 39/21* (2013.01);
(Continued)

(58) Field of Classification Search
None
See application file for complete search history.

(56) References Cited

U.S. PATENT DOCUMENTS 9,005,925 B2 * 4/2015 Tangy ...................... A61P 31/14
435/70.3
9,005,961 B2 * 4/2015 Tangy ...................... C12N 7/00
435/320.1
(Continued)

OTHER PUBLICATIONS

Wang Z, Hangartner L, Cornu TI, Martin LR, Zuniga A, Billeter MA, Naim HY. Recombinant measles viruses expressing heterologous antigens of mumps and simian immunodeficiency viruses. Vaccine. Mar. 21, 2001;19(17-19):2329-36. (Year: 2001).*

*Primary Examiner* — Michelle S Horning
(74) *Attorney, Agent, or Firm* — Arrigo, Lee, Guttman & Mouta-Bellum LLP

(57) ABSTRACT

The invention relates to a recombinant measles virus expressing a heterologous amino acid sequence derived from an antigen of a determined RNA virus, said recombinant measles virus being capable of eliciting a humoral and/or cellular immune response against measles virus or against said RNA virus or against both measles virus and
(Continued)

against said RNA virus. It also relates to the use of said recombinant measles virus for the preparation of immunogenic composition.

9 Claims, 61 Drawing Sheets

Specification includes a Sequence Listing.

Related U.S. Application Data

16/686,743, filed on Nov. 18, 2019, now Pat. No. 10,793,877, said application No. 17/015,846 is a continuation of application No. 16/686,743, filed on Nov. 18, 2019, now Pat. No. 10,793,877, which is a continuation of application No. 15/893,289, filed on Feb. 9, 2018, now Pat. No. 10,519,466, which is a division of application No. 14/667,326, filed on Mar. 24, 2015, now Pat. No. 9,914,937, which is a continuation of application No. 12/700,621, filed on Feb. 4, 2010, now Pat. No. 9,012,214, which is a continuation of application No. 11/014,842, filed on Dec. 20, 2004, now abandoned, which is a continuation of application No. PCT/EP03/07146, filed on Jun. 20, 2003.

(51) Int. Cl.

| | |
|---|---|
| ***A61K 39/12*** | (2006.01) |
| ***A61K 39/165*** | (2006.01) |
| ***A61K 39/21*** | (2006.01) |
| ***A61K 47/69*** | (2017.01) |
| ***C07K 14/005*** | (2006.01) |
| ***C12N 7/00*** | (2006.01) |

(52) U.S. Cl.

CPC ........ *A61K 47/6901* (2017.08); *C07K 14/005* (2013.01); *C12N 7/00* (2013.01); *A61K 2039/5256* (2013.01); *C12N 2740/16022* (2013.01); *C12N 2740/16122* (2013.01); *C12N 2760/18421* (2013.01); *C12N 2760/18422* (2013.01); *C12N 2760/18434* (2013.01); *C12N 2760/18443* (2013.01); *C12N 2760/18452* (2013.01); *C12N 2770/24122* (2013.01); *Y02A 50/30* (2018.01)

(56) References Cited

U.S. PATENT DOCUMENTS

| | | | | |
|---|---|---|---|---|
| 9,012,214 | B2 * | 4/2015 | Tangy | C12N 7/00 435/320.1 |
| 9,701,944 | B2 * | 7/2017 | Tangy | C07K 14/005 |
| 10,793,877 | B2 * | 10/2020 | Tangy | C12N 15/86 |
| 2021/0102220 | A1 * | 4/2021 | Tangy | A61K 39/12 |

* cited by examiner

```
              10         20         30         40         50
   1 GCGGCCGCTA ATACGACTCA CTATAGGGcc aactttgttt ggtctgatga
 101 AGGATAGTTC AATCAATGAT CATCTTCTAG TGCACTTAGG ATTCAAGATC
 201 TTTAAGGAGC TTAGCATTGT TCAAAAGAAA CAAGGACAAA CCACCCATTA
 301 CCAATCCCTG GAGATTCCTC AATTACCACT CGATCCAGAC TTCTGGACCG
 401 GGGCACTAAT AGGTATATTA TCCTTATTTG TGGAGTCTCC AGGTCAATTG
 501 TGTCCAGAGT GACCAGTCAC AATCTGGCCT TACCTTCGCA TCAAGAGGTA
 601 AGTAGTGATC AATCCAGGTT CGGATGGTTC GGGAACAAGG AAATCTCAGA
 701 TAGCCCAAAT TTGGGTCTTG CTCGCAAAGG CGGTTACGGC CCCAGACACG
 801 GGTAGTTGGT GAATTTAGAT TGGAGAGAAA ATGGTTGGAT GTGGTGAGGA
 901 CTGGATATCA AGAGAACACC CGGAAACAAA CCCAGGATTG CTGAAATGAT
1001 TGACTATTAA GTTTGGGATA GAAACTATGT ATCCTGCTCT TGGACTGCAT
1101 GCAAATGGGG GAAACTGCAC CCTACATGGT AATCCTGGAG AACTCAATTC
1201 GGAGTAGGAG TGGAACTTGA AAACTCCATG GGAGGTTTGA ACTTTGGCCG
1301 GGTCAGCTGG AAAGGTCAGT TCCACATTGG CATCTGAACT CGGTATCACT
1401 CAAGATCAGT AGAGCGGTTG GACCCAGACA AGCCCAAGTA TCATTTCTAC
1501 AGGAGGGTCA AACAGAGTCG AGGAGAAGCC AGGGAGAGCT ACAGAGAAAC
1601 CACCCCTAGA CATTGACACT GCAACGGAGT CCAGCCAAGA TCCGCAGGAC
1701 CTCGGAAGAA CAAGGCTCAG ACACGGACAC CCCTATAGTG TACAATGACA
1801 CTACCATCCA TCATTGTTAT AAAAAACTTA GGAACCAGGT CCACACAGCC
1901 CAGGCACGCC ATGTCAAAAA CGGACTGGAA TGCATCCGGG CTCTCAAGGC  ⟶ TO 11A CONT
2001 AAATATCAGA CAACCCAGGA CAGGAGCGAG CCACCTGCAG GGAAGAGAAG
2101 TGAAGGCGGT GCACCTCGCA TCCGCGGTCA GGGACCTGGA GAGAGCGATG
2201 ACTGGGTTAC AGTGTTATTA CGTTTATGAT CACAGCGGTG AAGCGGTTAA
2301 ATAGCACCCT CTCAGGAGGA GACAATGAAT CTGAAAACAG CGATGTGGAT
2401 TCCCATCTCT ATGGGGTTCA GGGCTTCTGA TGTTGAAACT GCAGAAGGAG
2501 AAGCTTGGGA AAACTCTCAA TGTTCCTCCG CCCCCGGACC CCGGTAGGGC
2601 CATTTGGAAC GGAGATCGCG TCTTTATTGA CAGGTGGTGC AACCCAATGT
2701 TGTCCCCGAG TGTGTGAGCA ATGCCGCACT GATACAGGAG TGGACACCCG
2801 GACTATTATG ATGATGAGCT GTTCTCTGAT GTCCAAGATA TTAAAACAGC
2901 CACTGCTGTT ATTGAAGGGA GAAGTTGAGT CAATTAAGAA GCAGATCAAC
3001 GATCGCCATT CCTGGACTTG GGAAGGATCC CAACGACCCC ACTGCAGATG
3101 GCACTGGCCG AAGTTCTCAA GAAACCCGTT GCCAGCCGAC AACTCCAAGG
3201 AGCTAAAGCC GATCGGGAAA AAGATGAGCT CAGCCGTCGG GTTTGTTCCT
3301 CCGGCTAGAG GAGGATCGGA AGCGTTACCT GATGACTCTC CTTGATGATA
3401 ATAATGAAGT AGCTACAGCT CAACTTACCT GCCAACCCCA TGCCAGTCGA
3501 TTGCCTCCCA AGGTCCACAA TGACAGAGAC CTACGACTTC GACAAGTCGG
3601 GATGGCAGGC TGGTGCCCCA GGTCAGAGTC ATAGATCCTG GTCTAGGCGA
3701 ACAGCGATTC CCTAGGGCCT CCAATCGGGC GAGCATTTGG GTTCCTGCCC
3801 CACTGAGCTT GACATAGTTG TTAGACGTAC AGCAGGGCTC AATGAAAAAC
3901 GTCCTAACAA CAGGGAGTGT CTTCAACGCA AACCAAGTGT GCAATGCGGT
```

FIG. 11A

```
    |    60    |    70    |    80    |    90    |   100
gtccgtgagg acgaaacccg gagtcccggg tcACCAAACA AAGTTGGGTA 100
CTATTATCAG GGACAAGAGC AGGATTAGGG ATATCCGAGA TGGCCACACT 200
CATCAGGATC CGGTGGAGCC ATCAGAGGAA TCAAACACAT TATTATAGTA 300
GTTGGTGAGG TTAATTGGAA ACCCGGATGT GAGCGGGCCC AAACTAACAG 400
ATTCAGAGGA TCACCGATGA CCCTGACGTT AGCATAAGGC TGTTAGAGGT 500
CCAACATGGA GGATGAGGCG GACCAATACT TTTCACATGA TGATCCAATT 600
TATTGAAGTG CAAGACCCTG AGGGATTCAA CATGATTCTG GGTACCATCC 700
GCAGCTGATT CGGAGCTAAG AAGGTGGATA AAGTACACCC AACAAAGAAG 800
ACAGGATTGC CGAGGACCTC TCCTTACGCC GATTCATGGT CGCTCTAATC 900
ATGTGACATT GATACATATA TCGTAGAGGC AGGATTAGCC AGTTTTATCC 1000
GAATTTGCTG GTGAGTTATC CACACTTGAG TCCTTGATGA ACCTTTACCA 1100
AGAACAAGTT CAGTGCAGGA TCATACCCTC TGCTCTGGAG CTATGCCATG 1200
ATCTTACTTT GATCCAGCAT ATTTTAGATT AGGGCAAGAG ATGGTAAGGA 1300
GCCGAGGATG CAAGGCTTGT TTCAGAGATT GCAATGCATA CTACTGAGGA 1400
ACGGTGATCA AAGTGAGAAT GAGCTACCGA GATTGGGGGG CAAGGAAGAT 1500
CGGGCCCAGC AGAGCAAGTG ATGCGAGAGC TGCCCATCTT CCAACCGGCA 1600
AGTCGAAGGT CAGCTGACGC CCTGCTTAGG CTGCAAGCCA TGGCAGGAAT 1700
GAAATCTTCT AGACTAGGTG CGAGAGGCCG AGGGCCAGAA CAACATCCGC 1800
GCCAGCCCAT CAACCATCCA CTCCCACGAT TGGAGCCAAT GGCAGAAGAG 1900
CGAGCCCATC GGCTCACTGG CCATCGAGGA AGCTATGGCA GCATGGTCAG 2000
GCAGGCAGTT CGGGTCTCAG CAAACCATGC CTCTCAGCAA TTGGATCAAC 2100
ACGACGCTGA AACTTTGGGA ATCCCCCCAA GAAATCTCCA GGCATCAAGC 2200
GGGAATCCAA GATGCTGACT CTATCATGGT TCAATCAGGC CTTGATGGTG 2300
ATTGGCGAAC CTGATACCGA GGGATATGCT ATCACTGACC GGGGATCTGC 2400
GGGAGATCCA CGAGCTCCTG AGACTCCAAT CCAGAGGCAA CAACTTTCCG 2500
CAGCACTTCC GGGACACCCA TTAAAAAGGG CACAGACGCG AGATTAGCCT 2600
GCTCGAAAGT CACCCTCGGA ACCATCAGGG CCAGGTGCAC CTGCGGGGAA 2700
AATCTGGTAC CACAATCTCC CCGAGATCCC AGAATAATGA AGAAGGGGGA 2800
CTTGGCCAAA ATACACGAGG ATAATCAGAA GATAATCTCC AAGCTAGAAT 2900
AGGCAAAATA TCAGCATATC CACCCTGGAA GGACACCTCT CAAGCATCAT 3000
TCGAAATCAA TCCCGACTTG AAACCCATCA TAGGCAGAGA TTCAGGCCGA 3100
AATGACAAAT GGACGGACCA GTTCCAGAGG ACAGCTGCTG AAGGAATTTC 3200
GACACCGGCC CTGCATCACG CAGTGTAATC CGCTCCATTA TAAAATCCAG 3300
TCAAAGGAGC CAATGATCTT GCCAAGTTCC ACCAGATGCT GATGAAGATA 3400
CCCAACTAGT ACAACCTAAA TCCATTATAA AAAACTTAGG AGCAAAGTGA 3500
CATGGGACAT CAAAGGGTCG ATCGCTCCGA TACAACCCAC CACCTACAGT 3600
CAGGAAGGAT GAATGCTTTA TGTACATGTT TCTGCTGGGG GTTGTTGAGG 3700
TTAGGTGTTG GCAGATCCAC AGCAAAGCCC GAAAAACTCC TCAAAGAGGC 3800
TGGTGTTCTA CAACAACACC CCACTAACTC TCCTCACACC TTGGAGAAAG 3900
TAATCTGATA CCGCTCGATA CCCCGCAGAG GTTCCGTGTT GTTTATATGA 4000
```

FROM 11A (arrow pointing to line 2000)

FIG. 11A CONT

4001 GCATCACCCG TCTTTCGGAT AACGGGTATT ACACCGTTCC TAGAAGAATG
4101 TAGGATTGAC AAGGCGATAG GCCCTGGGAA GATCATCGAC AATACAGAGC
4201 AAGAGTGAAG TCTACTCTGC CGATTATTGC AAAATGAAAA TCGAAAAGAT
4301 GAAGCACAGG CAAAATGAGC AAGACTCTCC ATGCACAACT CGGGTTCAAG
4401 ACTCTGGAGG AGCAGATGCA AGATAGTAAG AATCCAGGCA GTTTTGCAGC
4501 GACCAAGGAC TATTCAAAGT TCTGTAGACC GTAGTGCCCA GCAATGCCCG
4601 CCTCCGAAAG ACTCCACGGA CCAAGCGAGA GGCCAGCCAG CAGCCGACGG
4701 CACCACCAGC CACCCCAATC TGCATCCTCC TCGTGGGACC CCCGAGGACC
4801 CCCGGGAAAG AAACCCCCAG CAATTGGAAG GCCCCTCCCC CTCTTCCTCA
4901 GCAGGCATCC GACTCCCTAG ACAGATCCTC TCTCCCCGGC AAACTAAACA
5001 CACGGCGCCG CGCCCCCAAC CCCCGACAAC CAGAGGGAGC CCCCAACCAA
5101 GACCCAGCAC CCAACCATCG ACAATCCAAG ACGGGGGGGC CCCCCCAAAA
5201 CACACACGAC CACGGCAACC AAACCAGAAC CCAGACCACC CTGGGCCACC
5301 GCACCCCAGC CCCGATCCGG CGGGGAGCCA CCCAACCCGA ACCAGCACCC
5401 CAGCCTCTCC AAGTCCCCCG GTCTCCTCCT CTTCTCGAAG GGACCAAAAG
5501 ACCGGGAATC CCAGAATCAA GACTCATCCA ATGTCCATCA TGGGTCTCAA
5601 CCACCGGTCA AATCCATTGG GGCAATCTCT CTAAGATAGG GGTGGTAGGA
5701 AGTCATAAAA TTAATGCCCA ATATAACTCT CCTCAATAAC TGCACGAGGG
5801 AGAGATGCAC TTAATGCAAT GACCCAGAAT ATAAGACCGG TTCAGAGTGT
5901 CGGCCCTAGG CGTTGCCACA GCTGCTCAGA TAACAGCCGG CATTGCACTT
6001 GGAAACTACT AATCAGGCAA TTGAGACAAT CAGACAAGCA GGGCAGGAGA TO 11B CONT
6101 CCGTCTATGA ACCAACTATC TTGTGATTTA ATCGGCCAGA AGCTCGGGCT
6201 TACGGGACCC CATATCTGCG GAGATATCTA TCCAGGCTTT GAGCTATGCG
6301 TGATTTACTG GGCATCTTAG AGAGCGGAGG AATAAAGGCC CGGATAACTC
6401 CTGTCCGAGA TTAAGGGGGT GATTGTCCAC CGGCTAGAGG GGGTCTCGTA
6501 CCCAAGGGTA CCTTATCTCG AATTTTGATG AGTCATCGTG TACTTTCATG
6601 GCTCCAAGAA TGCCTCCGGG GGTACACCAA GTCCTGTGCT CGTACACTCG
6701 GCCAATTGTG CATCAATCCT TTGCAAGTGT TACACAACAG GAACGATCAT
6801 CGGTAGTCGA GGTGAACGGC GTGACCATCC AAGTCGGGAG CAGGAGGTAT
6901 GGAGAGGTTG GACGTAGGGA CAAATCTGGG GAATGCAATT GCTAAGTTGG
7001 AAAGGTTTAT CGAGCACTAG CATAGTCTAC ATCCTGATTG CAGTGTGTCT
7101 GTAACAAAAA GGGAGAACAA GTTGGTATGT CAAGACCAGG CCTAAAGCCT
7201 AACTCTTGAA ACACAAATGT CCCACAAGTC TCCTCTTCGT CATCAAGCAA
7301 GGCCGAACAA TATCGGTAGT TAATCAAAAC TTAGGGTGCA AGATCATCCA
7401 CATCCCAAGG GAAGTAGGAT AGTCATTAAC AGAGAACATC TTATGATTGA
7501 TCGGGTTGCT AGCCATTGCA GGCATTAGAC TTCATCGGGC AGCCATCTAC
7601 AATCGAGCAT CAGGTCAAGG ACGTGCTGAC ACCACTCTTC AAAATCATCG
7701 TTAATCTCTG ACAAGATTAA ATTCCTTAAT CCGGATAGGG AGTACGACTT
7801 ATGATCAATA CTGTGCAGAT GTGGCTGCTG AAGAGCTCAT GAATGCATTG
7901 CTCAAAGGGA AACTGCTCAG GGCCCACTAC AATCAGAGGT CAATTCTCAA
8001 TCATCTATAG TCACTATGAC ATCCCAGGGA ATGTATGGGG GAACTTACCT
8101 GCATGTACCG AGTGTTTGAA GTAGGTGTTA TCAGAAATCC GGGTTTGGGG

FIG. 11B

```
CTGGAATTCA GATCGGTCAA TGCAGTGGCC TTCAACCTGC TGGTGACCCT 4100
AACTTCCTGA GGCAACATTT ATGGTCCACA TCGGGAACTT CAGGAGAAAG 4200
GGGCCTGGTT TTTGCACTTG GTGGGATAGG GGGCACCAGT CTTCACATTA 4300
AAGACCTTAT GTTACCCGCT GATGGATATC AATGAAGACC TTAATCGATT 4400
CATCAGTTCC TCAAGAATTC CGCATTTACG ACGACGTGAT CATAAATGAT 4500
AAAACGACCC CCCTCACAAT GACAGCCAGA AGGCCCGGAC AAAAAAGCCC 4600
CAAGCGCGAA CACCAGGCGG CCCCAGCACA GAACAGCCCT GACACAAGGC 4700
AACCCCCAAG GCTGCCCCCG ATCCAAACCA CCAACCGCAT CCCCACCACC 4800
ACACAAGAAC TCCACAACCG AACCGCACAA GCGACCGAGG TGACCCAACC 4900
AAACTTAGGG CCAAGGAACA TACACACCCA ACAGAACCCA GACCCCGGCC 5000
TCCCGCCGGC TCCCCCGGTG CCCACAGGCA GGGACACCAA CCCCCGAACA 5100
AAAGGCCCCC AGGGGCCGAC AGCCAGCACC GCGAGGAAGC CCACCCACCC 5200
AGCTCCCAGA CTCGGCCATC ACCCCGCAGA AAGGAAAGGC CACAACCCGC 5300
AAGAGCGATC CCCGAAGGAC CCCCGAACCG CAAAGGACAT CAGTATCCCA 5400
ATCAATCCAC CACACCCGAC GACACTCAAC TCCCCACCCC TAAAGGAGAC 5500
GGTGAACGTC TCTGCCATAT TCATGGCAGT ACTGTTAACT CTCCAAACAC 5600
ATAGGAAGTG CAAGCTACAA AGTTATGACT CGTTCCAGCC ATCAATCATT 5700
TAGAGATTGC AGAATACAGG AGACTACTGA GAACAGTTTT GGAACCAATT 5800
AGCTTCAAGT AGGAGACACA AGAGATTTGC GGGAGTAGTC CTGGCAGGTG 5900
CACCAGTCCA TGCTGAACTC TCAAGCCATC GACAATCTGA GAGCGAGCCT 6000
```

FROM 11B

```
TGATATTGGC TGTTCAGGGT GTCCAAGACT ACATCAATAA TGAGCTGATA 6100
CAAATTGCTC AGATACTATA CAGAAATCCT GTCATTATTT GGCCCCAGTT 6200
CTTGGAGGAG ACATCAATAA GGTGTTAGAA AAGCTCGGAT ACAGTGGAGG 6300
ACGTCGACAC AGAGTCCTAC TTCATTGTCC TCAGTATAGC CTATCCGACG 6400
CAACATAGGC TCTCAAGAGT GGTATACCAC TGTGCCCAAG TATGTTGCAA 6500
CCAGAGGGGA CTGTGTGCAG CCAAAATGCC TTGTACCCGA TGAGTCCTCT 6600
TATCCGGGTC TTTTGGGAAC CGGTTCATTT TATCACAAGG GAACCTAATA 6700
TAATCAAGAC CCTGACAAGA TCCTAACATA CATTGCTGCC GATCACTGCC 6800
CCAGACGCTG TGTACTTGCA CAGAATTGAC CTCGGTCCTC CCATATCATT 6900
AGGATGCCAA GGAATTGTTG GAGTCATCGG ACCAGATATT GAGGAGTATG 7000
TGGAGGGTTG ATAGGGATCC CCGCTTTAAT ATGTTGCTGC AGGGGGCGTT 7100
GATCTTACGG GAACATCAAA ATCCTATGTA AGGTCGCTCT GATCCTCTAC 7200
CCACCGCACC CAGCATCAAG CCCACCTGAA ATTATCTCCG GCTTCCCTCT 7300
CAATGTCACC ACAACGAGAC CGGATAAATG CCTTCTACAA AGATAACCCC 7400
TAGACCTTAT GTTTTGCTGG CTGTTCTGTT TGTCATGTTT CTGAGCTTGA 7500
ACCGCAGAGA TCCATAAAAG CCTCAGCACC AATCTAGATG TAACTAACTC 7600
GTGATGAAGT GGGCCTGAGG ACACCTCAGA GATTCACTGA CCTAGTGAAA 7700
CAGAGATCTC ACTTGGTGTA TCAACCCGCC AGAGAGAATC AAATTGGATT 7800
GTGAACTCAA CTCTACTGGA GACCAGAACA ACCAATCAGT TCCTAGCTGT 7900
ACATGTCGCT GTCCCTGTTA GACTTGTATT TAGGTCGAGG TTACAATGTG 8000
AGTGGAAAAG CCTAATCTGA GCAGCAAAAG GTCAGAGTTG TCACAACTGA 8100
GCTCCGGTGT TCCATATGAC AAACTATCTT GAGCAACCAG TCAGTAATGA 8200
```

FIG. 11B
CONT

```
8201 TCTCAGCAAC TGTATGGTGG CTTTGGGGGA GCTCAAACTC GCAGCCCTTT
8301 GTCAGCTTCC AGCTCGTCAA GCTAGGTGTC TGGAAATCCC CAACCGACAT
8401 ACCTCTCATC TCACAGAGGT GTTATCGCTG ACAATCAAGC AAAATGGGCT
8501 ACAGGCGTGT AAGGGTAAAA TCCAAGCACT CTGCGAGAAT CCCGAGTGGG
8601 CTGAGTCTGA CAGTTGAGCT TAAAATCAAA ATTGCTTCGG GATTCGGGCC
8701 ATGTGTATTG GCTGACTATC CCGCCAATGA AGAACCTAGC CTTAGGTGTA
8801 CACTGTCCCA ATTAAGGAAG CAGGCGAAGA CTGCCATGCC CCAACATACC
8901 CTACCTGGTC AAGATCTCCA ATATGTTTTG GCAACCTACG ATACTTCCAG
9001 CTTACTTTTA TCCTTTTAGG TTGCCTATAA AGGGGGTCCC CATCGAATTA
9101 TGTGCTTGCG GACTCAGAAT CTGGTGGACA TATCACTCAC TCTGGGATGG
9201 AGATAGGGCT GCTAGTGAAC CAATCACATG ATGTCACCCA GACATCAGGC
9301 AAGTGGTTCC CCGTTATGGA CTCGCTATCT GTCAACCAGA TCTTATACCC
9401 TGGAGTATGC TCGAGTCCCT CACGCTTACA GCCTGGAGGA CCCTACACTG
9501 TATAAACAAT GTGGAAGTTG GGAATGTCAT CAAGTCCAAG CTTAGGAGTT
9601 AACATAGAAG ACAAAGAGTC AACGAGGAAG ATCCGTGAAC TCCTCAAAAA
9701 GGGACACTAA CTCACGGCTT GGCCTAGGCT CCGAATTGAG GGAGGACATC
9801 TGAGCCCTTT CTGTTTTGGT TTACAGTCAA GACTGAGATG AGGTCAGTGA
9901 TTCACTGGTA GTTCAGTTGA GTTGCTAATC TCTCGTGACC TTGTTGCTAT
10001 TGATGTATTG TGATGTCATA GAGGGGAGGT TAATGACAGA GACCGCTATG
10101 GAAACTGATA GATGGTTTCT TCCCTGCACT CGGGAATCCA ACTTATCAAA
10201 ATAACAGTAG AACTCAGAGG TGCTTTCCTT AACCACTGCT TTACTGAAAT
10301 AGTTAACTGA AGCTCTAGAT TACATTTTCA TAACTGATGA CATACATCTG
10401 AGCAGTAACG GCTGCTGAAA ATGTTAGGAA ATACATGAAT CAGCCTAAAG
10501 ATAATCAACG GCTATCGTGA CAGGCACGGA GGCAGTTGGC CACCGCTGAC
10601 AAGGGTTAAC ACATGAGCAG TGCGTTGATA ACTGGAAATC TTTTGCTGGA
10701 GTACCTAAAG GACAAGGCAC TTGCTGCTCT CCAAAGGGAA TGGGATTCAG
10801 CGGAGGCTTG TAGATGTTTT CCTTAATGAT TCGAGCTTTG ACCCATATGA
10901 ACCTGTCTTA CAGCCTGAAA GAAAAGGAGA TCAAGGAAAC AGGTAGACTT
11001 TCTAATCTCA AACGGGATTG GCAAATATTT TAAGGACAAT GGGATGGCCA
11101 GTCCCCAAAG ATCTCAAAGA AAGTCACAGG GGGGGGCCAG TCTTAAAAAC
11201 AAGGGTTTAT AGGGTTCCCT CAAGTAATTC GGCAGGACCA AGACACTGAT
11301 TGATCTCAAG AAGTACTGCC TTAATTGGAG ATATGAGACC ATCAGCTTGT
11401 CTGCATAAGA GGCTTGAGAC CTCTGTCCTG TATGTAAGTG ACCCTCATTG
11501 AAATCTTCAT TAAGTACCCT ATGGGAGGTA TAGAAGGGTA TTGTCAGAAG
11601 CGGAGTAAGG ATTGCTTCGT TAGTGCAAGG GGACAATCAG ACCATAGCCG
11701 GCTGCTAGAG TAACTAGAGA TTACTTTGTA ATTCTTAGGC AAAGGCTACA
11801 TTTTTGTCTA TTCAAAAGGA ATATATTATG ATGGGCTACT TGTGTCCCAA
11901 TGAAACAAGG GCAGCATGCA GTAATATTGC TACAACAATG GCTAAAAGCA
12001 GTGATACAGC AAATTCTGAT CTCTCTTGGC TTCACAATCA ATTCAACCAT
12101 GGATGGCACT GTTGCCCGCT CCTATTGGGG GGATGAATTA TCTGAATATG
12201 TGATCTCAAG AGAATGATTC TCGCCTCACT AATGCCTGAA GAGACCCTCC
12301 AGCGACCCTT ACTCAGCAAA TCTTGTATGT GTCCAGAGCA TCACTAGACT
```

```
GTCACGGGGA AGATTCTATC ACAATTCCCT ATCAGGGATC AGGGAAAGGT 8300
GCAATCCTGG GTCCCCTTAT CAACGGATGA TCCAGTGATA GACAGGCTTT 8400
GTCCCGACAA CACGAACAGA TGACAAGTTG CGAATGGAGA CATGCTTCCA 8500
CACCATTGAA GGATAACAGG ATTCCTTCAT ACGGGGTCTT GTCTGTTGAT 8600
ATTGATCACA CACGGTTCAG GGATGGACCT ATACAAATCC AACCACAACA 8700
ATCAACACAT TGGAGTGGAT ACCGAGATTC AAGGTTAGTC CCTACCTCTT 8800
TACCTGCGGA GGTGGATGGT GATGTCAAAC TCAGTTCCAA TCTGGTGATT 8900
GGTTGAACAT GCTGTGGTTT ATTACGTTTA CAGCCCAAGC CGCTCATTTT 9000
CAAGTGGAAT GCTTCACATG GGACCAAAAA CTCTGGTGCC GTCACTTCTG 9100
TGGGCATGGG AGTCAGCTGC ACAGTCACCC GGGAAGATGG AACCAATCGC 9200
ATACCCACTA GTGTGAAATA GACATCAGAA TTAAGAAAAA CGTAGGGTCC 9300
TGAAGTTCAC CTAGATAGCC CGATAGTTAC CAATAAGATA GTAGCCATCC 9400
TGTCAGAACA TCAAGCACCG CCTAAAAAAC GGATTTTCCA ACCAAATGAT 9500
ATCCGGCCCA CTCTCATATT CCATATCCAA ATTGTAATCA GGATTTATTT 9600
GGGGAATTCG CTGTACTCCA AAGTCAGTGA TAAGGTTTTC CAATGCTTAA 9700
AAGGAGAAAG TTATTAACTT GGGAGTTTAC ATGCACAGCT CCCAGTGGTT 9800
TTAAATCACA AACCCATACT TGCCATAGGA GGAGACACAC ACCTGTATTC 9900
AATCAGTAAA GAGTCTCAAC ATGTATATTA CCTGACATTT GAACTGGTTT 10000
ACTATTGATG CTAGGTATAC AGAGCTTCTA GGAAGAGTCA GATACATGTG 10100
TTGTAGCCAT GCTGGAGCCT CTTTCACTTG CTTACCTGCA GCTGAGGGAT 10200
ACATGATGTT CTTGACCAAA ACGGGTTTTC TGATGAAGGT ACTTATCATG 10300
ACAGGGGAGA TTTTCTCATT TTTCAGAAGT TTCGGCCACC CCAGACTTGA 10400
TCATTGTGTA TGAGACTCTG ATGAAAGGTC ATGCCATATT TTGTGGAATC 10500
CCTCCCCCTG CATGCTGCAG ACACAATCCG GAATGCTCAA GCTTCAGGTG 10600
GTGAAATTTG GCTGCTTTAT GCCTCTTAGC CTGGATAGTG ATCTGACAAT 10700
TTTACCCGAA AGAGTTCCTG CGTTACGACC CTCCCAAGGG AACCGGGTCA 10800
TGTGATAATG TATGTTGTAA GTGGAGCTTA CCTCCATGAC CCTGAGTTCA 10900
TTTGCTAAAA TGACTTACAA AATGAGGGCA TGCCAAGTGA TTGCTGAAAA 11000
AGGATGAGCA CGATTTGACT AAGGCACTCC ACACTCTAGC TGTCTCAGGA 11100
CTACTCCCGA AGCCCAGTCC ACACAAGTAC CAGGAACGTG AGAGCAGCAA 11200
CATCCGGAGA ATATGGAAGC TTACGAGACA GTCAGTGCAT TTATCACGAC 11300
TTGCACAGAG GCTAAATGAG ATTTACGGAT TGCCCTCATT TTTCCAGTGG 11400
CCCCCCCGAC CTTGACGCCC ATATCCCGTT ATATAAAGTC CCCAATGATC 11500
CTGTGGACCA TCAGCACCAT TCCCTATCTA TACCTGGCTG CTTATGAGAG 11600
TAACAAAAAG GGTACCCAGC ACATGGCCCT ACAACCTTAA GAAACGGGAA 11700
TGATATTGGC CATCACCTCA AGGCAAATGA GACAATTGTT TCATCACATT 11800
TCACTCAAGA GCATCGCAAG ATGTGTATTC TGGTCAGAGA CTATAGTTGA 11900
TCGAGAGAGG TTATGACCGT TACCTTGCAT ATTCCCTGAA CGTCCTAAAA 12000
GACCCGGGAT GTAGTCATAC CCCTCCTCAC AAACAACGAC CTCTTAATAA 12100
AGCAGGCTGT TTGTCAGAAA CATCGGTGAT CCAGTAACAT CATCAATTGC 12200
ATCAAGTAAT GACACAACAA CCGGGGGACT CTTCATTCCT AGACTGGGCT 12300
CCTCAAGAAC ATAACTGCAA GGTTTGTCCT GATCCATAGT CCAAACCCAA 12400
```

FROM 11C

FIG. 11C CONT

12401 TGTTAAAAGG ATTATTCCAT GATGACAGTA AAGAAGAGGA CGAGGGACTG
12501 AATCCTGGAT CATAGTGTCA CAGGGGCAAG AGAGTCTATT GCAGGCATGC
12601 ACCTCTCGAG TGATAACCAG ATTGTCCAAT TATGACTATG AACAATTCAG
12701 AAGAGTCATG TtCAGTGCAG CTGGCGAGAG CTCTAAGAAG CCATATGTGG
12801 ACTAGAATCT ATGCGAGGCC ACCTTATTCG GCGTCATGAG ACATGTGTCA
12901 TGCCAACTGG ATGATATTGA CAAGGAAACA TCATCCTTGA GAGTCCCATA
13001 GAGCCCCAAG TCGATCCTTG CGATCTGCTG TTAGAATAGC AACAGTGTAC
13101 GGCTAGGCAA AGGGCCAATG TGAGCCTGGA GGAGCTAAGG GTGATCACTC
13201 CAAGTGAAAT ACTCAGGTAC ATCCCTTGTC CGAGTGGCGA GGTATACCAC
13301 CTAACTTTAT ATACCAACAA GGAATGCTTC TAGGGTTGGG TGTTTTAGAA
13401 TCTTCACGTC GAAACAGATT GTTGCGTGAT CCCGATGATA GATCATCCCA
13501 CCATTGATAT ATGATAATGC ACCTTTAATT GACAGAGATG CAACAAGGCT
13601 CACCCCAACT ATATCACATT TTAGCTAAGT CCACAGCACT ATCTATGATT
13701 CATAGGGGAT GACGATATCA ATAGTTTCAT AACTGAGTTT CTGCTCATAG
13801 GCATTTGATG TACATTATCA TAGACCATCA GGGAAATATC AGATGGGTGA
13901 TTGTCAATGC TCTAAGCCAC CCAAAGATCT ACAAGAAATT CTGGCATTGT
14001 CACAACTGTG TGCAACATGG TTTACACATG CTATATGACC TACCTCGACC
14101 GACGAGGATG TAGTACCGGA CAGATTCGAC AACATCCAGG CAAAACACTT
14201 GAGGTCTAAG ACCGGTAGAG AAATGTGCAG TTCTAACCGA CCATATCAAG
14301 TATTGTAGAC CATTACTCAT GCTCTCTGAC TTATCTCCGG CGAGGATCGA
14401 GCTGAGGTAA ATGTCAGTCA GCCAAAGATC GGCAGCAACA ACATCTCAAA — TO 11D CONT
14501 TCAAAGATAT CAACACAAGC AAGCACAATC TTCCCATTTC AGGGGGCAAT
14601 TGCTTGCTAC AAAGCTGTTG AGATATCAAC ATTAATTAGG AGATGCCTTG
14701 ATCACTTATA AAGAGATACT TAAACTAAAC AAGTGCTTCT ATAATAGTGG
14801 CCGAAGTTGG CCTTGTCGAA CACAGAATGG GAGTAGGTAA TATTGTCAAA
14901 CTTCAATTTC ATAGTTAGTA ATATCCCTAC CTCTAGTGTG GGGTTTATCC
15001 GAATTGGCAG CCATCTTATC GATGGCTCTG CTCCTGGGCA AAATAGGATC
15101 TTATAAGTTA TGTAGGGTCT CATTATAGAG AAGTGAACCT TGTATACCCT
15201 CAAGGCTAAC CGGCTAATGA ATCCTGAAAA GATTAAGCAG CAGATAATTG
15301 AAGCAACTAA GCTGCATACA AGCAATTGTG GGAGACGCAG TTAGTAGAGG
15401 TCAATTGCGG GTTGGCAATT AACGGACCTA AGCTGTGCAA AGAATTGATC
15501 CCTCTACAGG GAGTTGGCAA GATTCAAAGA CAACCAAAGA AGTCAACAAG
15601 ATATCTAGGA TCACCCGCAA ATTCTGGGGG CACATTCTTC TTTACTCCGG
15701 TGATACTAGA CTTACACCAG AATATCTTCG TTAAGAATCT ATCCAAGTCA
15801 GGTAACAGTC AAGGAGACCA AAGAATGGTA TAAGTTAGTC GGATACAGTG
15901 GGTGGTTAGG CATTATTTGC AATATATTAA AGAAAACTTT GAAAATACGA
16001 gctggcgccg gctgggcaac attccgaggg gaccgtcccc tcggtaatgg
16101 agttggctgc tgccaccgct gagcaataac tagcataacc ccttggggcc
16201 atGCGGCCGC GGGCCCtatG GTACCCAGCT TTTGTTccct ttagtgaggg
16301 TTGTTATCCG CTCACAATTC CACACAACAT AGGAGCCGGA AGCATAAAGT
16401 CGCTCACTGC CCGCTTTCCA GTCGGGAAAC CTGTCGTGCC AGCTGCATTA
16501 CCGCTTCCTC GCTCACTGAC TCGCTGCGCT CGGTCGTTCG GCTGCGGCGA

FIG. 11D

```
     GCGGCATTCC TCATGGACAG GCATATTATA GTACCTAGGG CAGCTCATGA 12500
     TGGATACCAC AAAAGGCTTG ATTCGAGCCA GCATGAGGAA GGGGGGGTTA 12600
     AGCAGGGATG GTGCTATTGA CAGGAAGAAA GAGAAATGTC CTCATTGACA 12700
     GCGAGGCTAG CTCGAGGACG GCCTATTTAC GGCCTTGAGG TCCCTGATGT 12800
     TCTGCGAGTG TGGATCAGTC AACTACGGAT GGTTTTTTGT CCCCTCGGGT 12900
     TATTGGTTCT ACCACTGATG AGAGAACAGA CATGAAGCTT GCCTTCGTAA 13000
     TCATGGGCTT ACGGTGATGA TGATAGCTCT TGGAACGAAG CCTGGTTGTT 13100
     CCATCTCAAC TTCGACTAAT TTAGCGCATA GGTTGAGGGA TCGTAGCACT 13200
     AATCTCCAAC GACAATCTCT CATTTGTCAT ATCAGATAAG AAGGTTGATA 13300
     ACATTGTTTC GACTCGAGAA AGATACCGGA TCATCTAACA CGGTATTACA 13400
     GGATACCCAG CTCCCGCAAG CTAGAGCTGA GGGCAGAGCT ATGTACCAAC 13500
     ATACACCCAG AGCCATAGGA GGCACCTTGT GGAATTTGTT ACATGGTCCA 13600
     GACCTGGTAA CAAAATTTGA GAAGGACCAT ATGAATGAAA TTTCAGCTCT 13700
     AGCCAAGATT ATTCACTATC TACTTGGGCC AGTGTGCGGC CATCAATTGG 13800
     GCTGTTGTCA TCGTTCCTTT CTAGAATGAG CAAAGGAGTG TTTAAGGTGC 13900
     GGTATTATAG AGCCTATCCA TGGTCCTTCA CTTGATGCTC AAAACTTGCA 14000
     TGTTGTTGAA TGAAGAGTTA GAAGAGTTCA CATTTCTCTT GTGTGAAAGC 14100
     ATGTGTTCTG GCAGATTTGT ACTGTCAACC AGGGACCTGC CCACCAATTC 14200
     GCAGAGGCTA TGTTATCTCC AGCAGGATCT TCGTGGAACA TAAATCCAAT 14300
     TCAAACAGAT AAGATTGAGA GTTGATCCAG GATTCATTTT CGACGCCCTC 14400
FROM TATGAGCATC AAGGCTTTCA GACCCCCACA CGATGATGTT GCAAAATTGC 14500
11D  CTCGCCAATT ATGAAATCCA TGCTTTCCGC AGAATCGGGT TGAACTCATC 14600
     AGCCAGGGGA GGACGGCTTG TTCTTGGGTG AGGGATCGGG TTCTATGTTG 14700
     GGTTTCCGCC AATTCTAGAT CTGGTCAAAG GGAATTAGCA CCCTATCCCT 14800
     GTGCTCTTTA ACGGGAGGCC CGAAGTCACG TGGGTAGGCA GTGTAGATTG 14900
     ATTCAGATAT AGAGACCTTG CCTGACAAAG ATACTATAGA GAAGCTAGAG 15000
     AATACTGGTG ATTAAGCTTA TGCCTTTCAG CGGGGATTTT GTTCAGGGAT 15100
     AGATACAGCA ACTTCATCTC TACTGAATCT TATTTGGTTA TGACAGATCT 15200
     AATCATCTGT GAGGACTTCA CCTGGACTTA TAGGTCACAT CCTATCCATT 15300
     TGATATCAAT CCTACTCTGA AAAAACTTAC ACCTATAGAG CAGGTGCTGA 15400
     CACCATGATG TTGCCTCAGG GCAAGATGGA TTGCTTAATT CTATACTCAT 15500
     GGATGTTCCA CGCTTACCCC GTATTGGTAA GTAGCAGGCA ACGAGAACTT 15600
     GAACAAAAAG TTGATAAATA AGTTTATCCA GAATCTCAAG TCCGGCTATC 15700
     GAGAAACAGA TTATTATGAC GGGGGGTTTG AAACGTGAGT GGGTTTTTAA 15800
     CCCTGATTAA GGACTAATTG GTTGAACTCC GGAACCCTAA TCCTGCCCTA 15900
     AGTTTCTATT CCCAGCTTTG TCTGGTggcc ggcatggtcc cagcctcctc 16000
     cgaatgggac GCGGCCgatc cggctgctaa caaagcccga aaggaagctg 16100
     tctaaacggg tcttgagggg tttttgctg aaaggaggaa ctatatccgg 16200
     ttaattCCGA GCTTGGCGTA ATCATGGTCA TAGCTGTTTC CTGTGTGAAA 16300
     GTAAAGCCTG GGGTGCCTAA TGAGTGAGGT AACTCACATT AATTGCGTTG 16400
     ATGAATCGGC CAACGCGCGG GGAGAGGCGG TTTGCGTATT GGGCGCTCTT 16500
     GCGGTATCAG CTCACTCAAA GGCGGTAATA CGGTTATCCA CAGAATCAGG 16600
```

*FIG. 11D*
*CONT*

```
12401 TGTTAAAAGG ATTATTCCAT GATGACAGTA AAGAAGAGGA CGAGGGACTG
12501 AATCCTGGAT CATAGTGTCA CAGGGGCAAG AGAGTCTATT GCAGGCATGC
12601 ACCTCTCGAG TGATAACCAG ATTGTCCAAT TATGACTATG AACAATTCAG
12701 AAGAGTCATG TtCAGTGCAG CTGGCGAGAG CTCTAAGAAG CCATATGTGG
12801 ACTAGAATCT ATGCGAGGCC ACCTTATTCG GCGTCATGAG ACATGTGTCA
12901 TGCCAACTGG ATGATATTGA CAAGGAAACA TCATCCTTGA GAGTCCCATA
13001 GAGCCCCAAG TCGATCCTTG CGATCTGCTG TTAGAATAGC AACAGTGTAC
13101 GGCTAGGCAA AGGGCCAATG TGAGCCTGGA GGAGCTAAGG GTGATCACTC
13201 CAAGTGAAAT ACTCAGGTAC ATCCCTTGTC CGAGTGGCGA GGTATACCAC
13301 CTAACTTTAT ATACCAACAA GGAATGCTTC TAGGGTTGGG TGTTTTAGAA
13401 TCTTCACGTC GAAACAGATT GTTGCGTGAT CCCGATGATA GATCATCCCA
13501 CCATTGATAT ATGATAATGC ACCTTTAATT GACAGAGATG CAACAAGGCT
13601 CACCCCAACT ATATCACATT TTAGCTAAGT CCACAGCACT ATCTATGATT
13701 CATAGGGGAT GACGATATCA ATAGTTTCAT AACTGAGTTT CTGCTCATAG
13801 GCATTTGATG TACATTATCA TAGACCATCA GGGAAATATC AGATGGGTGA
13901 TTGTCAATGC TCTAAGCCAC CCAAAGATCT ACAAGAAATT CTGGCATTGT
14001 CACAACTGTG TGCAACATGG TTTACACATG CTATATGACC TACCTCGACC
14101 GACGAGGATG TAGTACCGGA CAGATTCGAC AACATCCAGG CAAAACACTT
14201 GAGGTCTAAG ACCGGTAGAG AAATGTGCAG TTCTAACCGA CCATATCAAG
14301 TATTGTAGAC CATTACTCAT GCTCTCTGAC TTATCTCCGG CGAGGATCGA
14401 GCTGAGGTAA ATGTCAGTCA GCCAAAGATC GGCAGCAACA ACATCTCAAA — TO 11D CONT
14501 TCAAAGATAT CAACACAAGC AAGCACAATC TTCCCATTTC AGGGGGCAAT
14601 TGCTTGCTAC AAAGCTGTTG AGATATCAAC ATTAATTAGG AGATGCCTTG
14701 ATCACTTATA AAGAGATACT TAAACTAAAC AAGTGCTTCT ATAATAGTGG
14801 CCGAAGTTGG CCTTGTCGAA CACAGAATGG GAGTAGGTAA TATTGTCAAA
14901 CTTCAATTTC ATAGTTAGTA ATATCCCTAC CTCTAGTGTG GGGTTTATCC
15001 GAATTGGCAG CCATCTTATC GATGGCTCTG CTCCTGGGCA AAATAGGATC
15101 TTATAAGTTA TGTAGGGTCT CATTATAGAG AAGTGAACCT TGTATACCCT
15201 CAAGGCTAAC CGGCTAATGA ATCCTGAAAA GATTAAGCAG CAGATAATTG
15301 AAGCAACTAA GCTGCATACA AGCAATTGTG GGAGACGCAG TTAGTAGAGG
15401 TCAATTGCGG GTTGGCAATT AACGGACCTA AGCTGTGCAA AGAATTGATC
15501 CCTCTACAGG GAGTTGGCAA GATTCAAAGA CAACCAAAGA AGTCAACAAG
15601 ATATCTAGGA TCACCCGCAA ATTCTGGGGG CACATTCTTC TTTACTCCGG
15701 TGATACTAGA CTTACACCAG AATATCTTCG TTAAGAATCT ATCCAAGTCA
15801 GGTAACAGTC AAGGAGACCA AAGAATGGTA TAAGTTAGTC GGATACAGTG
15901 GGTGGTTAGG CATTATTTGC AATATATTAA AGAAAACTTT GAAAATACGA
16001 gctggcgccg gctgggcaac attccgaggg gaccgtcccc tcggtaatgg
16101 agttggctgc tgccaccgct gagcaataac tagcataacc ccttggggcc
16201 atGCGGCCGC GGGCCCtatG GTACCCAGCT TTTGTTccct ttagtgaggg
16301 TTGTTATCCG CTCACAATTC CACACAACAT AGGAGCCGGA AGCATAAAGT
16401 CGCTCACTGC CCGCTTTCCA GTCGGGAAAC CTGTCGTGCC AGCTGCATTA
16501 CCGCTTCCTC GCTCACTGAC TCGCTGCGCT CGGTCGTTCG GCTGCGGCGA
```

FIG. 11D
CONT

```
          GCGGCATTCC TCATGGACAG GCATATTATA GTACCTAGGG CAGCTCATGA 12500
          TGGATACCAC AAAAGGCTTG ATTCGAGCCA GCATGAGGAA GGGGGGGTTA 12600
          AGCAGGGATG GTGCTATTGA CAGGAAGAAA GAGAAATGTC CTCATTGACA 12700
          GCGAGGCTAG CTCGAGGACG GCCTATTTAC GGCCTTGAGG TCCCTGATGT 12800
          TCTGCGAGTG TGGATCAGTC AACTACGGAT GGTTTTTTGT CCCCTCGGGT 12900
          TATTGGTTCT ACCACTGATG AGAGAACAGA CATGAAGCTT GCCTTCGTAA 13000
          TCATGGGCTT ACGGTGATGA TGATAGCTCT TGGAACGAAG CCTGGTTGTT 13100
          CCATCTCAAC TTCGACTAAT TTAGCGCATA GGTTGAGGGA TCGTAGCACT 13200
          AATCTCCAAC GACAATCTCT CATTTGTCAT ATCAGATAAG AAGGTTGATA 13300
          ACATTGTTTC GACTCGAGAA AGATACCGGA TCATCTAACA CGGTATTACA 13400
          GGATACCCAG CTCCCGCAAG CTAGAGCTGA GGGCAGAGCT ATGTACCAAC 13500
          ATACACCCAG AGCCATAGGA GGCACCTTGT GGAATTTGTT ACATGGTCCA 13600
          GACCTGGTAA CAAAATTTGA GAAGGACCAT ATGAATGAAA TTTCAGCTCT 13700
          AGCCAAGATT ATTCACTATC TACTTGGGCC AGTGTGCGGC CATCAATTGG 13800
          GCTGTTGTCA TCGTTCCTTT CTAGAATGAG CAAAGGAGTG TTTAAGGTGC 13900
          GGTATTATAG AGCCTATCCA TGGTCCTTCA CTTGATGCTC AAAACTTGCA 14000
          TGTTGTTGAA TGAAGAGTTA GAAGAGTTCA CATTTCTCTT GTGTGAAAGC 14100
          ATGTGTTCTG GCAGATTTGT ACTGTCAACC AGGGACCTGC CCACCAATTC 14200
          GCAGAGGCTA TGTTATCTCC AGCAGGATCT TCGTGGAACA TAAATCCAAT 14300
          TCAAACAGAT AAGATTGAGA GTTGATCCAG GATTCATTTT CGACGCCCTC 14400
FROM 11D  TATGAGCATC AAGGCTTTCA GACCCCCACA CGATGATGTT GCAAAATTGC 14500
          CTCGCCAATT ATGAAATCCA TGCTTTCCGC AGAATCGGGT TGAACTCATC 14600
          AGCCAGGGGA GGACGGCTTG TTCTTGGGTG AGGGATCGGG TTCTATGTTG 14700
          GGTTTCCGCC AATTCTAGAT CTGGTCAAAG GGAATTAGCA CCCTATCCCT 14800
          GTGCTCTTTA ACGGGAGGCC CGAAGTCACG TGGGTAGGCA GTGTAGATTG 14900
          ATTCAGATAT AGAGACCTTG CCTGACAAAG ATACTATAGA GAAGCTAGAG 15000
          AATACTGGTG ATTAAGCTTA TGCCTTTCAG CGGGGATTTT GTTCAGGGAT 15100
          AGATACAGCA ACTTCATCTC TACTGAATCT TATTTGGTTA TGACAGATCT 15200
          AATCATCTGT GAGGACTTCA CCTGGACTTA TAGGTCACAT CCTATCCATT 15300
          TGATATCAAT CCTACTCTGA AAAAACTTAC ACCTATAGAG CAGGTGCTGA 15400
          CACCATGATG TTGCCTCAGG GCAAGATGGA TTGCTTAATT CTATACTCAT 15500
          GGATGTTCCA CGCTTACCCC GTATTGGTAA GTAGCAGGCA ACGAGAACTT 15600
          GAACAAAAAG TTGATAAATA AGTTTATCCA GAATCTCAAG TCCGGCTATC 15700
          GAGAAACAGA TTATTATGAC GGGGGGTTTG AAACGTGAGT GGGTTTTTAA 15800
          CCCTGATTAA GGACTAATTG GTTGAACTCC GGAACCCTAA TCCTGCCCTA 15900
          AGTTTCTATT CCCAGCTTTG TCTGGTggcc ggcatggtcc cagcctcctc 16000
          cgaatgggac GCGGCCgatc cggctgctaa caaagcccga aaggaagctg 16100
          tctaaacggg tcttgagggg tttttgctg aaaggaggaa ctatatccgg 16200
          ttaattCCGA GCTTGGCGTA ATCATGGTCA TAGCTGTTTC CTGTGTGAAA 16300
          GTAAAGCCTG GGGTGCCTAA TGAGTGAGGT AACTCACATT AATTGCGTTG 16400
          ATGAATCGGC CAACGCGCGG GGAGAGGCGG TTTGCGTATT GGGCGCTCTT 16500
          GCGGTATCAG CTCACTCAAA GGCGGTAATA CGGTTATCCA CAGAATCAGG 16600
```

FIG. 11D CONT

```
16601 GGATAACGCA GGAAAGAACA TGTGAGCAAA AGGCCAGCAA AAGGCCAGGA
16701 GACGAGCATC ACAAAAATCG ACGCTCAAGT CAGAGGTGGC GAAACCCGAC
16801 CTCCTGTTCC GACCCTGCCG CTTACCGGAT ACCTGTCCGC CTTTCTCCCT
19001 GGTGTAGGTC GTTCGCTCCA AGCTGGGCTG TGTGCACGAA CCCCCCGTTC
17001 GTAAGACACG ACTTATCGCC ACTGGCAGCA GCCACTGGTA ACAGGATTAG
17201 ACTACGGCTA CACTAGAAGG ACAGTATTTG GTATCTGCGC TCTGCTGAAG
17301 CACCGCTGGT AGCGGTGGTT TTTTTGTTTG CAAGCAGCAG ATTACGCGCA
17401 GCTCAGTGGA ACGAAAACTC ACGTTAAGGG ATTTTGGTCA TGAGATTATC
17501 CAATCTAAAG TATATATGAG TAAACTTGGT CTGACAGTTA CCAATGCTTA
17601 TGCCTGACTG CCCGTCGTGT AGATAACTAC GATACGGGAG GGCTTACCAT
17701 GATTTATCAG CAATAAACCA GCCAGCCGGA AGGGCCGAGC GCAGAAGTGG
17801 CTAGAGTAAG TAGTTCGCCA GTTAATAGTT TGCGCAACGT TGTTGCCATT
17901 CTCCGGTTCC CAACGATCAA GGCGAGTTAC ATGATCCCCC ATGTTGTGAA
18001 GCCGCAGTGT TATCACTCAT GCTTATGGCA GCACTGCATA ATTCTCTTAC
18101 AGTCATTCTG AGAATAGTGT ATGCGGCGAC CGAGTTGCTC TTGCCCGGCG
18201 CATTGGAAAA CGTTCTTCGG GGCGAAAACT CTCAAGGATC TTACCGCTGT
18301 TCTTTTACTT TCACCAGCGT TTCTGGGTGA GCAAAAACAG GAAGGCAAAA
18401 TCTTCCTTTT TCAATATTAT TGAAGCATTT ATCAGGGTTA TTGTCTCATG
18501 GCGCACATTT CCCCGAAAAG TGCCACCTGA AATTGTAAAC GTTAATATTT
18601 TAGGCCGAAA TCGGCAAAAT CCCTTATAAA TCAAAAGAAT AGACCGAGAT
18701 TGGACTCCAA CGTCAAAGGG CGAAAAACCG TCTATCAGGG CGATGGCCCA
18801 AGCACTAAAT CGGAACCCTA AAGGGAGCCC CCGATTTAGA GCTTGACGGG
18901 GGCGCTAGGG CGCTGGCAAG TGTAGCGGTC ACGCTGCGCG TAACCACCAC
      GGCTgCGCAA CTGTTGGGAA GGGCGATCGG TGCGGGCCTC TTCGCTATTA
               | 10       | 20       | 30       | 40       | 50
```

FROM 11E

```
ACCGTAAAAA GGCCGCGTTG CTGGCGTTTT TCCATAGGCT CGGCCCCCCT 16700
AGGACTATAA AGATACCAGG CGTTCCCCCC TGGAAGCTCC CTCGTGCGCT 16800
TCGGGAAGCG TGGCGCTTTC TCAATGCTCA CGCTGTAGGT ATCTCAGTTC 16900
AGCCCGACCG CTGCGCCTTA TCCGGTAACT ATCGTCTTGA GTCCAACCCG 17000
CAGAGCGAGG TATGTAGGCG GTGCTACAGA GTTCTTGAAG TGGTGGCCTA 17100
CCAGTTACCT TCGGAAAAAG AGTTGGTAGC TCTTGATCCG GCAAACAAAC 17200
GAAAAAAAGG ATCTCAAGAA GATCCTTTGA TCTTTTCTAC GGGGTCTGAC 17300
AAAAAGGATC TTCACCTAGA TCCTTTTAAA TTAAAAATGA AGTTTTAAAT 17400
ATCAGTGAGG CACCTATCTC AGCGATCTGT CTATTTCGTT CATCCATAGT 17500
CTGGCCCCAG TGCTGCAATG ATACCGCGAG ACCCACGCTC ACCGGCTCCA 17600
TCCTGCAACT TTATCCGCCT CCATCCAGTC TATTAATTGT TGCCGGGAAG 17700
GCTACAGGCA TCGTGGTGTC ACGCTCGTCG TTTGGTATGG CTTCATTCAG 17800
AAAAAGCGGT TAGCTCCTTC GGTCCTCCGA TCGTTGTCAG AAGTAAGTTG 17900
TGTCATGCCA TCCGTAAGAT GCTTTTCTGT GACTGGTGAG TACTCAACCA 18000
TCAATACGGG ATAATACCGC GCCACATAGC AGAACTTTAA AAGTGCTCAT 18100
TGAGATCCAG TTCGATGTAA CCCACTCGTG CACCCAACTG ATCTTCAGCA 18200
TGCCGCAAAA AAGGGAATAA GGGCGACACG GAAATGTTGA ATACTCATAC 18300
AGCGGATACA TATTTGAATG TATTTAGAAA AATAAACAAA TAGGGGTTCC 18400
TGTTAAAATT CGCGTTAAAT TTTTGTTAAA TCAGCTCATT TTTTAACCAA 18500
AGGGTTGAGT GTTGTTCCAG TTTGGAACAA GAGTCCACTA TTAAAGAACG 18600
CTACGTGAAC CATCACCCTA ATCAAGTTTT TTGGGGTCGA GGTGCCGTAA 18700
GAAAGCCGGC GAACGTGGCG AGAAAGGAAG GGAAGAAAGC GAAAGGAGCG 18800
ACCCGCCGCG CTTAATGCGC CGCTACAGGG CGCGTCCCAT TCGCCATTCA 18900
CGCCAGCCAC CGCGGTG                                     18967
    |   60     |   70     |   80     |   90     |  100
```

FIG. 11E CONT

```
           |    10    |    20    |    30    |    40    |    50
   1  ATGcgagtcg tgattgccct actggtcttg gctgttggtc cggcctactc
 101  gaggaacttg ggtttcagct accctggagc aagacaagtg tgtcactgtt
 201  tgatagacct gctgaggtga ggaaagtgtg ttacaatgca gttctcactc
 301  gaagagaacg aaggggacaa tgcgtgcaag cgcacttatt ctgatagagg
 401  ccaaattcac ttgtgccaaa tccatgagtt tgtttgaggt tgatcagacc
 501  aaattggact accgacatta agactctcaa gtttgatgcc ctgtcaggct
 601  gtgcaaactg cggtggactt tggtaacagt tacatcgctg agatggaaac
 701  ggcagagtgg aagtggcggg gtgtggagag agatgcatca tcttgtcgaa
 801  ggaaggctcc ttgaaaacag ctcttactgg cgcaatgagg gttacaaagg
 901  agagtgaaat tgtcagcttt gacactcaag ggacatcct acaaaatatg
1001  ctgttgtgat gcaggtgaaa gtgtcaaaag gagcccctg caggattcca
1101  tacagttaac cccatcgcct caaccaatga tgatgaagtg ctgattgagg
1201  cgtctcactt accagtggca caaagaggga agctcaatag gaaagttgtt
1301  cctgggattt cagctccgct ggagggttct tcacttcggt tgggaaagga
1401  ctggataaca aaggtcatca tgggggcggt acttatatgg gttggcatca
           |    10    |    20    |    30    |    40    |    50
```

SEQUENCE OF YFV 17D204 Env GENE EXPRESSED IN MV

FIG. 12A

```
    |    60     |    70     |    80     |    90     |   100
agctcactgc attggaatta ctgacaggga tttcattgag ggggtgcatg  100
atggcccctg acaagccttc attggacatc tcactagaga cagtagccat  200
atgtgaagat taatgacaag tgccccagca ctggagaggc ccacctagct  300
ctggggcaat ggctgtggcc tatttgggaa agggagcatt gtggcatgcg  400
aaaattcagt atgtcatcag agcacaattg catgtagggg ccaagcagga  500
cccaggaagt cgagttcatt gggtatggaa aagctacact ggaatgccag  600
agagagctgg atagtggaca gacagtgggc ccaggacttg accctgccat  700
tttgaacctc cgcatgccgc cactatcaga gtactggccc tgggaaacca  800
acacaaatga caacaacctt tacaaactac atggtggaca tgtttcttgc  900
cactgacaaa atgttttttg tcaagaaccc aactgacact ggccatggca  1000
gtgatagtag ctgatgatct tacagcggca atcaataaag gcattttggt  1100
tgaacccacc ttttggagac agctacatta tcgttgggag aggagattca  1200
cactcagacc atgaaaggcg tggaacgcct ggccgtcatg ggagacaccg  1300
attcatacgg tgtttggctc tgcctttcag gggctatttg gcggcttgaa  1400
acacaTAA                                                1458
    |    60     |    70     |    80     |    90     |   100
```

SEQUENCE OF YFV 17D204 Env GENE EXPRESSED IN MV

*FIG. 12B*

```
        |    10     |    20     |    30     |    40     |    50
   1  ATGagagttg tgtttgtcgt gctattgctt ttggtggccc cagcttacag
 101  gagcaacatg ggtggatttg gttctcgaag gcgacagctg cgtgactatc
 201  ggtcaacctg gcagaggtcc gcagttattg ctatttggct accgtcagcg
 301  aaacgtgctg acccagcttt tgtgtgcaga caaggagtgg tggacagggg
 401  ccaaatttgc ctgctctacc aaggcaatag gaagaaccat cttgaaagag
 501  gtcgcacgga aactactcca cacaggttgg agccactcag gcagggagat
 601  ggagaggtga cagtggactg tgaaccacgg tcagggattg acaccaatgc
 701  ggttcatgga cctcaacctc ccttggagca gtgctggaag tactgtgtgg  --> TO 12C CONT
 801  gtctgtgata gcattgggct cacaagaggg agctctgcat caagctttgg
 901  ggtcatttga agtgtagagt gaagatggaa aaattgcagt tgaagggaac
1001  acacaggtca cggcactgtg gtgttggaat tgcagtacac tggcacggat
1101  gccagtgggc agattggtca ctgtcaaccc ttttgtttca gtggccacgg
1201  atagtggtgg gcagaggaga acaacagatc aatcaccatt ggcacaagtc
1301  gactagccgc tctaggagac acagcttggg actttggatc agttggaggg
1401  ccgctcactg ttcggaggca tgtcctggat aacgcaagga ttgctggggg
        |    10     |    20     |    30     |    40     |    50
```

WNV ENV GENE EXPRESSED IN MV

FIG. 12C

FROM 12C

```
      |    60       |    70       |    80       |    90       |   100
cttcaactgc cttggaatga gcaacagaga cttcttggaa ggagtgtctg  100
atgtctaagg acaagcctac catcgatgtg aagatgatga atatggaggc  200
atctctccac caaagctgcg tgcccgacca tgggagaagc tcacaatgac  300
ctggggcaac ggctgcggat tatttggcaa aggaagcatt gacacatgcg  400
aatatcaagt acgaagtggc cattttgtc catggaccaa ctactgtgga  500
tcagcatcac tcctgcggcg ccttcataca cactaaagct tggagaatat  600
atactacgtg atgactgttg gaacaaagac gttcttggtc catcgtgagt  700
aggaacagag agacgttaat ggagtttgag gaaccacacg ccacgaagca  800
ctggagccat tcctgtggaa ttttcaagca acactgtcaa gttgacgtcg  900
aacctatggc gtctgttcaa aggctttcaa gtttcttggg actcccgcag  1000
ggaccttgca aagttcctat ctcgtcagtg gcttcattga acgacctaac  1100
ccaacgctaa ggtcctgatt gaattggaac caccctttgg agactcatac  1200
tggaagcagc attggcaaag cctttacaac caccctcaaa ggagcgcaga  1300
gtgttcacct cagttgggaa ggctgtccat caagtgttcg gaggagcatt  1400
ctctcctgtt gtggatgggc atcaatgctc gtgatTAA               1488
      |    60       |    70       |    80       |    90       |   100
```

FIG. 12C
CONT

```
         |    10         |    20         |    30         |    40         |    50
   1  ATGaggtcca tagctctcac gtttctcgca gttggaggag ttctgctctt
 101  ggcaagagct gagatgtgga agtggagtgt tcatacacaa tgatgtggag
 201  caagatcatt cagaaagctc ataaggaagg agtgtgcggt ctacgatcag
 301  caagatcatt cagaaagctc ataaggaagg agtgtgcggt ctacgatcag
 401  aattggaaat tggctggaag gcctggggaa agagtatttt atttgcacca
 501  tccgactcag aatcgcgctt ggaatagctt agaagtggag gattttggat   ⟶ TO 12D CONT
 601  actgaatgtg actcgaagat cattggaacg gctgtcaaga acaacttggc
 701  ggaagcttga aagggcagtt ctgggtgaag tcaaatcatg tacgtggcct
 801  accagtcaca ctggcgggac cacgaagcaa tcacaatcgg agacctgggt
 901  ttcgattact gcccaggaac tacggtcacc ctgagtgaga gctgcggaca
1001  attggtgctg caggagctgc accttaccac cactgcgcta ccaaactgac
1101  gaccTAATGA
         |    10         |    20         |    30         |    40         |    50
```

WNV NS1 GENE EXPRESSED IN MV

*FIG. 12D*

FROM 12D

```
        |    60        |    70        |    80        |    90        |   100
cctctccgtg aacgtgcacg ctgacactgg gtgtgccata gacatcagcc  100
gcttggatgg accggtacaa gtattaccct gaaacgccac aaggcctagc  200
tttccagact ggagcatcaa atgtgggaag cagtgaagga cgagctgaac  300
ggagggaatg tacaagtcag cacctaaacg cctcaccgcc accacggaaa  400
gaactcgcca acaacacctt tgtggttgat ggtccggaga ccaaggaatg  500
ttggtctcac cagcactcgg atgttcctga aggtcagaga gagcaacaca  600
gatccacagt gacctgtcct attggattga aagcaggctc aatgatacgt  700
gagacgcata ccttgtgggg cgatggaatc cttgagagtg acttgataat  800
acaagacaca aaaccagggc ccatgggacg aaggccgggt agagattgac  900
ccgtggacct gccactcgca ccaccacaga gagcggaaag ttgataacag  1000
agcggctgtt ggtatggtat ggagatcaga ccacagagac atgatgaaaa  1100
                                                        1110
        |    60        |    70        |    80        |    90        |   100
```

FIG. 12D CONT

EXPRESSION OF sE PROTEIN FROM WNV IN MV INDUCED SYNCYTIA gp140HIV 89.6p atgagagtgaaggagaaatatcagcacttgtggagatgggggtggagatggggcaccatgctccttgggatgttgatgatctgtagtgc
tacagaaaaattgtgggtcacagtctattatggggtacctgtgtggagagaagcaaccaccactctattttgtgcatcagatgctaaagcc
tatgatacagaggtacataatgtttgggccacacatgcctgtgtacccacagaccccaacccacaagaagtagtattgggaaatgtgac
agaaaattttaacatgtggaaaaataacatggtagatcagatgcatgaggatataatcagtttatgggatgaaagcctaaagccatgtgta
aaattaaccccactctgtgttactttaaattgcactaatttgaatatcactaagaatactactaatctcactagtagcagctggggaatgatgg
aggaaggagaaataaaaaattgctctttctatatcaccacaagcataagaaataaggtaaagaaagaatatgcactttttaatagacttgat
gtagtaccagtaaaaaatactagtaatactaagtataggttaataagttgtaacacctcagtcattacacaggcctgtccaaaggtatccttt
cagccaattcccatacattattgtgtcccggctgggtttgcgatactaaagtgtaacaataagacattcaatggatcaggaccatgcacaa
atgtcagcacagtacaatgtacacatggaattaggccagtggtgtcaactcaactgctgttaaatggcagtctagcagaagaagacata
gtaattagatctgaagatttcacagacaatgttaaaaccataatagtacagctaaatgaatctgtagtaattaattgtacaagacccaacaa
caatacaagagaaaggttatctataggaccagggagagcattttatgcaagaagaaacataataggagatataagacaagcacattgta
acattagtagagcaaaatggaataacactttacaacagatagttataaaattaagagaaaaatttaggaataaaacaatagcctttaatcaa
tcctcaggaggggacccagaaattgtaatgcacagttttaattgtggaggggaatttttctactgtaatacagcacaactgtttaatagtact
tggaatgttgctggagggacaaatggcactgaaggaaatgacataatcacactccaatgcagaataaaacaaattataaatatgtggca
gaaagtaggaaaagcaatgtatgcccctcccatcacaggacaaattagatgttcatcaaatattacagggctgctactaacaagagatg
gaggtaatagtactgagactgagactgagatcttcagacctggaggaggagatatgagggacaattggagaagtgaattatataaatat
aaagtagtaagaattgaaccaataggagtagcacccaccagggcaaagagaagaacagtgcaaagagaaaaaagagcagtgggaa
taggagctgtgttccttgggttcttgggagcagcaggaagcactatgggcgcagcgtcagtgacgctgacggtacaggccaggctatt
attgtctggtatagtgcagcagcagaacaatctgctgagggctattgaggcgcaacagaatatgttgcgactcacagtctggggcatca
agcagctccaggcaagagtcctggctctggaaagatacctaagggatcaacagctcatgggaatttggggttgctctggaaaactcatt
tgcaccacttctgtgccttggaatgttagttggagtaataaatctgtggatgatatttggaataacatgacctggatggagtgggaaagag
aaattgacaattacacagactatatatatgacttacttgaaaaatcgcaaacccaacaagaaaagaatgaaaaagaattattggaattgga
taaatgggcaagtttgtggaattggtttgacataacaaactggctgtggtatataagataa

FIG. 16A

MRVKEKYQHLWRWGWRWGTMLLGMLMICSATEKLWVTVYYGVPVWREATTTLF
CASDAKAYDTEVHNVWATHACVPTDPNPQEVVLGNVTENFNMWKNNMVDQMHE
DIISLWDESLKPCVKLTPLCVTLNCTNLNITKNTTNLTSSSWGMMEEGEIKNCSFYITT
SIRNKVKKEYALFNRLDVVPVKNTSNTKYRLISCNTSVITQACPKVSFQPIPIHYCVPA
GFAILKCNNKTFNGSGPCTNVSTVQCTHGIRPVVSTQLLLNGSLAEEDIVIRSEDFTDN
VKTIIVQLNESVVINCTRPNNNTRERLSIGPGRAFYARRNIIGDIRQAHCNISRAKWNN
TLQQIVIKLREKFRNKTIAFNQSSGGDPEIVMHSFNCGGEFFYCNTAQLFNSTWNVAG
GTNGTEGNDIITLQCRIKQIINMWQKVGKAMYAPPITGQIRCSSNITGLLLTRDGGNST
ETETEIFRPGGGDMRDNWRSELYKYKVVRIEPIGVAPTRAKRRTVQREKRAVGIGAV
FLGFLGAAGSTMGAASVTLTVQARLLLSGIVQQQNNLLRAIEAQQNMLRLTVWGIK
QLQARVLALERYLRDQQLMGIWGCSGKLICTTSVPWNVSWSNKSVDDIWNNMTWM
EWEREIDNYTDYIYDLLEKSQTQQEKNEKELLELDKWASLWNWFDITNWLWYIR

FIG. 16B gp160HIV 89.6p atgagagtgaaggagaaatatcagcacttgtggagatgggggtggagatggggcaccatgctccttgggatgttgatgatctgtagtgc
tacagaaaaattgtgggtcacagtctattatggggtacctgtgtggagagaagcaaccaccactctattttgtgcatcagatgctaaagcc
tatgatacagaggtacataatgtttgggccacacatgcctgtgtacccacagaccccaacccacaagaagtagtattgggaaatgtgac
agaaaattttaacatgtggaaaaataacatggtagatcagatgcatgaggatataatcagtttatgggatgaaagcctaaagccatgtgta
aaattaaccccactctgtgttactttaaattgcactaatttgaatatcactaagaatactactaatctcactagtagcagctggggaatgatgg
aggaaggagaaataaaaaattgctctttctatatcaccacaagcataagaaataaggtaaagaaagaatatgcacttttttaatagacttgat
gtagtaccagtaaaaaatactagtaatactaagtataggttaataagttgtaacacctcagtcattacacaggcctgtccaaaggtatccttt
cagccaattcccatacattattgtgtcccggctgggtttgcgatactaaagtgtaacaataagacattcaatggatcaggaccatgcacaa
atgtcagcacagtacaatgtacacatggaattaggccagtggtgtcaactcaactgctgttaaatggcagtctagcagaagaagacata
gtaattagatctgaagatttcacagacaatgttaaaaccataatagtacagctaaatgaatctgtagtaattaattgtacaagacccaacaa
caatacaagagaaaggttatctataggaccagggagagcattttatgcaagaagaaacataataggagatataagacaagcacattgta
acattagtagagcaaaatggaataacactttacaacagatagttataaaattaagagaaaaatttaggaataaaacaatagcctttaatcaa
tcctcaggaggggacccagaaattgtaatgcacagttttaattgtggaggggaatttttctactgtaatacagcacaactgtttaatagtact
tggaatgttgctggagggacaaatggcactgaaggaaatgacataatcacactccaatgcagaataaaacaaattataaatatgtggca
gaaagtaggaaaagcaatgtatgcccctcccatcacaggacaaattagatgttcatcaaatattacagggctgctactaacaagagatg
gaggtaatagtactgagactgagactgagatcttcagacctggaggaggagatatgagggacaattggagaagtgaattatataaatat

FROM 16C aaagtagtaagaattgaaccaataggagtagcacccaccagggcaaagagaagaacagtgcaaagagaaaaaagagcagtgggaa
taggagctgtgttccttgggttcttgggagcagcaggaagcactatgggcgcagcgtcagtgacgctgacggtacaggccaggctatt
attgtctggtatagtgcagcagcagaacaatctgctgagggctattgaggcgcaacagaatatgttgcgactcacagtctggggcatca
agcagctccaggcaagagtcctggctctggaaagatacctaagggatcaacagctcatgggaatttggggttgctctggaaaactcatt
tgcaccacttctgtgccttggaatgttagttggagtaataaatctgtggatgatatttggaataacatgacctggatggagtgggaaagag
aaattgacaattacacagactatatatatgacttacttgaaaaatcgcaaacccaacaagaaaagaatgaaaaagaattattggaattgga
taaatgggcaagtttgtggaattggtttgacataacaaactggctgtggtatataagattattcataatgatagtaggaggcttgataggttt
aagaatagtttttgctgtactttctatagtaaatagagttaggcagggatattcaccattatcgtttcagaccctcctcccagcctcgagggg
acccgacaggcccgaaggaacagaagaagaaggtggagagagagacagagacagatccggtccatcagtgaacggatccttggc
acttatctgggacgatctgcggagcctgtgcctcttcagctaccaccgcttgagagacttactcttgattgtaacgaggattgtggaacttc
tgggacgcagggggtgggaagccctcaaatattggtggaatctcctacagtattggagtcaggaactaaagaatagtgctgttagcttg
ctacaatatgggtggagctatttccatgaggcggtccaggccgtctggagatctgcgacagagactcttgcgggcgcgtggggagact
tatgggagactcttaggagaggtggaagatggatactcgcaatccccaggaggattagacaagggcttgagctcactctcttgtga

FIG. 16C CONT

MRVKEKYQHLWRWGWRWGTMLLGMLMICSATEKLWVTVYYGVPVWREATTTLF
CASDAKAYDTEVHNVWATHACVPTDPNPQEVVLGNVTENFNMWKNNMVDQMHE
DIISLWDESLKPCVKLTPLCVTLNCTNLNITKNTTNLTSSSWGMMEEGEIKNCSFYITT
SIRNKVKKEYALFNRLDVVPVKNTSNTKYRLISCNTSVITQACPKVSFQPIPIHYCVPA
GFAILKCNNKTFNGSGPCTNVSTVQCTHGIRPVVSTQLLLNGSLAEEDNIRSEDFTDN
VKTIIVQLNESVVINCTRPNNNTRERLSIGPGRAFYARRNIIGDIRQAHCNISRAKWNN
TLQQNIKLREKFRNKTIAFNQSSGGDPEIVMHSFNCGGEFFYCNTAQLFNSTWNVAG
GTNGTEGNDIITLQCRIKQIINMWQKVGKAMYAPPITGQIRCSSNITGLLLTRDGGNST
ETETEIFRPGGGDMRDNWRSELYKYKVVRIEPIGVAPTRAKRRTVQREKRAVGIGAV
FLGFLGAAGSTMGAASVTLTVQARLLLSGNQQQNNLLRAIEAQQNMLRLTVWGIK
QLQARVLALERYLRDQQLMGIWGCSGKLICTTSVPWNVSWSNKSVDDIWNNMTWM
EWEREIDNYTDYIYDLLEKSQTQQEKNEKELLELDKWASLWNWFDITNWLWYIRLFI
MNGGLIGLRNFAVLSNNRVRQGYSPLSFQTLLPASRGPDRPEGTEEEGGERDRDRS
GPSVNGSLALIWDDLRSLCLFSYHRLRDLLLNTRIVELLGRRGWEALKYWWNLLQY
WSQELKNSAVSLLQYGWSYFHEAVQAVWRSATETLAGAWGDLWETLRRGGRWIL
AIPRRIRQGLELTLL

FIG. 16D gp140V3HIV atgagagtgaaggagaaatatcagcacttgtggagatgggggtggagatggggcaccatgctccttgggatgttgatgatctgtagtgc
tacagaaaaattgtgggtcacagtctattatggggtacctgtgtggagagaagcaaccaccactctatttgtgcatcagatgctaaagcc
tatgatacagaggtacataatgtttgggccacacatgcctgtgtacccacagaccccaacccacaagaagtagtattgggaaatgtgac
agaaaattttaacatgtggaaaaataacatggtagatcagatgcatgaggatataatcagtttatgggatgaaagcctaaagccatgtgta
aaattaaccccactctgtgttactttaaattgcactaatttgaatatcactaagaatactactaatctcactagtagcagctggggaatgatgg
aggaaggagaaataaaaaattgctctttctatatcaccacaagcataagaaataaggtaaagaaagaatatgcacttttttaatagacttgat
gtagtaccagtaaaaaatactagtaatactaagtataggttaataagttgtaacacctcagtcattacacaggcctgtccaaaggtatccttt
cagccaattcccatacattattgtgtcccggctgggtttgcgatactaaagtgtaacaataagacattcaatggatcaggaccatgcacaa
atgtcagcacagtacaatgtacacatggaattaggccagtggtgtcaactcaactgctgttaaatggcagtctagcagaagaagacata
gtaattagatctgaagatttcacagacaatgttaaaaccataatagtacagctaaatgaatctgtagtaattaattgtacaagacccaacaa
caatgctgcagaattggataaatgggcaagtgctgcaagacaagcacattgtaacattagtagagcaaaatggaataacactttacaac
agatagttataaaattaagagaaaaatttaggaataaaacaatagcctttaatcaatcctcaggaggggacccagaaattgtaatgcaca
gttttaattgtggaggggaatttttctactgtaatacagcacaactgtttaatagtacttggaatgttgctggagggacaaatggcactgaag
gaaatgacataatcacactccaatgcagaataaaacaaattataaatatgtggcagaaagtaggaaaagcaatgtatgcccctcccatca
caggacaaattagatgttcatcaaatattacagggctgctactaacaagagatggaggtaatagtactgagactgagactgagatcttca
gacctggaggaggagatatgagggacaattggagaagtgaattatataaatataaagtagtaagaattgaaccaataggagtagcacc
caccagggcaaagagaagaacagtgcaaagagaaaaaagagcagtgggaataggagctgtgttccttgggttcttgggagcagcag
gaagcactatgggcgcagcgtcagtgacgctgacggtacaggccaggctattattgtctggtatagtgcagcagcagaacaatctgct
gagggctattgaggcgcaacagaatatgttgcgactcacagtctggggcatcaagcagctccaggcaagagtcctggctctggaaag
atacctaagggatcaacagctcatgggaatttggggttgctctggaaaactcatttgcaccacttctgtgccttggaatgttagttggagta
ataaatctgtggatgatatttggaataacatgacctggatggagtgggaaagagaaattgacaattacacagactatatatatgacttactt
gaaaaatcgcaaacccaacaagaaaagaatgaaaaagaattattggaattggataaatgggcaagtttgtggaattggtttgacataaca
aactggctgtggtatataagataa

FIG. 16E

MRVKEKYQHLWRWGWRWGTMLLGMLMICSATEKLWVTVYYGVPVWREATTTLF
CASDAKAYDTEVHNVWATHACVPTDPNPQEVVLGNVTENFNMWKNNMVDQMHE
DIISLWDESLKPCVKLTPLCVTLNCTNLNITKNTTNLTSSSWGMMEEGEIKNCSFYITT
SIRNKVKKEYALFNRLDVVPVKNTSNTKYRLISCNTSVITQACPKVSFQPIPIHYCVPA
GFAILKCNNKTFNGSGPCTNVSTVQCTHGIRPVVSTQLLLNGSLAEEDIVIRSEDFTDN
VKTIIVQLNESVVINCTRPNNNAAELDKWASAARQAHCNISRAKWNNTLQQIVIKLR
EKFRNKTIAFNQSSGGDPEIVMHSFNCGGEFFYCNTAQLFNSTWNVAGGTNGTEGND
IITLQCRIKQIINMWQKVGKAMYAPPITGQIRCSSNITGLLLTRDGGNSTETETEIFRPG
GGDMRDNWRSELYKYKVVRIEPIGVAPTRAKRRTVQREKRAVGIGAVFLGFLGAAG
STMGAASVTLTVQARLLLSGIVQQQNNLLRAIEAQQNMLRLTVWGIKQLQARVLAL
ERYLRDQQLMGIWGCSGKLICTTSVPWNVSWSNKSVDDIWNNMTWMEWEREIDNY
TDYIYDLLEKSQTQQEKNEKELLELDKWASLWNWFDITNWLWYIR

FIG. 16F gp160ΔV3$_{HIV}$ atgagagtgaaggagaaatatcagcacttgtggagatgggggtggagatggggcaccatgctccttgggatgttgatgatctgtagtgc
tacagaaaaattgtgggtcacagtctattatggggtacctgtgtggagagaagcaaccaccactctattttgtgcatcagatgctaaagcc
tatgatacagaggtacataatgtttgggccacacatgcctgtgtacccacagaccccaacccacaagaagtagtattgggaaatgtgac
agaaaattttaacatgtggaaaaataacatggtagatcagatgcatgaggatataatcagtttatgggatgaaagcctaaagccatgtgta
aaattaaccccactctgtgttactttaaattgcactaatttgaatatcactaagaatactactaatctcactagtagcagctggggaatgatgg
aggaaggagaaataaaaaattgctctttctatatcaccacaagcataagaaataaggtaaagaaagaatatgcactttttaatagacttgat
gtagtaccagtaaaaaatactagtaatactaagtataggttaataagttgtaacacctcagtcattacacaggcctgtccaaaggtatccttt
cagccaattcccatacattattgtgtcccggctgggtttgcgatactaaagtgtaacaataagacattcaatggatcaggaccatgcacaa
atgtcagcacagtacaatgtacacatggaattaggccagtggtgtcaactcaactgctgttaaatggcagtctagcagaagaagacata
gtaattagatctgaagatttcacagacaatgttaaaaccataatagtacagctaaatgaatctgtagtaattaattgtacaagacccaacaa
caatgctgcagaattggataaatgggcaagtgctgcaagacaagcacattgtaacattagtagagcaaaatggaataacactttacaac
agatagttataaaattaagagaaaaatttaggaataaaacaatagcctttaatcaatcctcaggaggggacccagaaattgtaatgcaca
gttttaattgtggaggggaatttttctactgtaatacagcacaactgtttaatagtacttggaatgttgctggagggacaaatggcactgaag
gaaatgacataatcacactccaatgcagaataaaacaaattataaatatgtggcagaaagtaggaaaagcaatgtatgcccctcccatca
caggacaaattagatgttcatcaaatattacagggctgctactaacaagagatggaggtaatagtactgagactgagactgagatcttca
gacctggaggaggagatatgagggacaattggagaagtgaattatataaatataaagtagtaagaattgaaccaataggagtagcacc
caccagggcaaagagaagaacagtgcaaagagaaaaaagagcagtgggaataggagctgtgttccttgggttcttgggagcagcag

FROM
16G gaagcactatgggcgcagcgtcagtgacgctgacggtacaggccaggctattattgtctggtatagtgcagcagcagaacaatctgct
gagggctattgaggcgcaacagaatatgttgcgactcacagtctggggcatcaagcagctccaggcaagagtcctggctctggaaag
atacctaagggatcaacagctcatgggaatttggggttgctctggaaaactcatttgcaccacttctgtgccttggaatgttagttggagta
ataaatctgtggatgatatttggaataacatgacctggatggagtgggaaagagaaattgacaattacacagactatatatatgacttactt
gaaaaatcgcaaacccaacaagaaaagaatgaaaaagaattattggaattggataaatgggcaagtttgtggaattggtttgacataaca
aactggctgtggtatataagattattcataatgatagtaggaggcttgataggtttaagaatagtttttgctgtactttctatagtaaatagagtt
aggcagggatattcaccattatcgtttcagaccctcctcccagcctcgaggggacccgacaggcccgaaggaacagaagaagaagg
tggagagagagacagagacagatccggtccatcagtgaacggatccttggcacttatctgggacgatctgcggagcctgtgcctcttc
agctaccaccgcttgagagacttactcttgattgtaacgaggattgtggaacttctgggacgcagggggtgggaagccctcaaatattg
gtggaatctcctacagtattggagtcaggaactaaagaatagtgctgttagcttgctacaatatgggtggagctatttccatgaggcggtc
caggccgtctggagatctgcgacagagactcttgcgggcgcgtggggagacttatgggagactcttaggagaggtggaagatggata
ctcgcaatccccaggaggattagacaagggcttgagctcactctcttgtga

FIG. 16G
CONT

MRVKEKYQHLWRWGWRWGTMLLGMLMICSATEKLWVTVYYGVPVWREATTTLF
CASDAKAYDTEVHNVWATHACVPTDPNPQEVVLGNVTENFNMWKNNMVDQMHE
DIISLWDESLKPCVKLTPLCVTLNCTNLNITKNTTNLTSSSWGMMEEGEIKNCSFYITT
SIRNKVKKEYALFNRLDVVPVKNTSNTKYRLISCNTSVITQACPKVSFQPIPIHYCVPA
GFAILKCNNKTFNGSGPCTNVSTVQCTHGIRPVVSTQLLLNGSLAEEDNIRSEDFTDN
VKTIIVQLNESVVINCTRPNNNAAELDKWASAARQAHCNISRAKWNNTLQQIVIKLR
EKFRNKTIAFNQSSGGDPEIVMHSFNCGGEFFYCNTAQLFNSTWNVAGGTNGTEGND
IITLQCRIKQIINMWQKVGKAMYAPPITGQIRCSSNITGLLLTRDGGNSTETETEIFRPG
GGDMRDNWRSELYKYKVVRIEPIGVAPTRAKRRTVQREKRAVGIGAVFLGFLGAAG
STMGAASVTLTVQARLLLSGIVQQQNNLLRAIEAQQNMLRLTVWGIKQLQARVLAL
ERYLRDQQLMGIWGCSGKLICTTSVPWNVSWSNKSVDDIWNNMTWMEWEREIDNY
TDYIYDLLEKSQTQQEKNEKELLELDKWASLWNWFDITNWLWYIRLFIMIVGGLIGL
RIVFAVLSIVNRVRQGYSPLSFQTLLPASRGPDRPEGTEEEGGERDRDRSGPSVNGSLA
LIWDDLRSLCLFSYHRLRDLLLIVTRNELLGRRGWEALKYWWNLLQYWSQELKNS
AVSLLQYGWSYFHEAVQAVWRSATETLAGAWGDLWETLRRGGRWILAIPRRIRQGL
ELTLL

FIG. 16H gp140$_{HIV}$ ΔV1V2 atgagagtgaaggagaaatatcagcacttgtggagatgggggtggagatggggcaccatgctccttgggatgttgatgatctgtagtgc
tacagaaaaattgtgggtcacagtctattatggggtacctgtgtggagagaagcaaccaccactctattttgtgcatcagatgctaaagcc
tatgatacagaggtacataatgtttgggccacacatgcctgtgtacccacagaccccaacccacaagaagtagtattgggaaatgtgac
agaaaattttaacatgtggaaaaataacatggtagatcagatgcatgaggatataatcagtttatgggatgaaagcctaaagccatgtgta
aaattaaccccactctgtgttactttaaattgtaacacctcagtcattacacaggcctgtccaaaggtatcctttcagccaattcccatacatt
attgtgtcccggctgggtttgcgatactaaagtgtaacaataagacattcaatggatcaggaccatgcacaaatgtcagcacagtacaat
gtacacatggaattaggccagtggtgtcaactcaactgctgttaaatggcagtctagcagaagaagacatagtaattagatctgaagattt
cacagacaatgttaaaaccataatagtacagctaaatgaatctgtagtaattaattgtacaagacccaacaacaatacaagagaaaggtta
tctataggaccagggagagcattttatgcaagaagaaacataataggagatataagacaagcacattgtaacattagtagagcaaaatg
gaataacactttacaacagatagttataaaattaagagaaaaatttaggaataaaacaatagcctttaatcaatcctcaggaggggaccca
gaaattgtaatgcacagttttaattgtggaggggaatttttctactgtaatacagcacaactgtttaatagtacttggaatgttgctggaggga
caaatggcactgaaggaaatgacataatcacactccaatgcagaataaaacaaattataaatatgtggcagaaagtaggaaaagcaat
gtatgcccctcccatcacaggacaaattagatgttcatcaaatattacagggctgctactaacaagagatggaggtaatagtactgagac
tgagactgagatcttcagacctggaggaggagatatgagggacaattggagaagtgaattatataaatataaagtagtaagaattgaac
caataggagtagcacccaccagggcaaagagaagaacagtgcaaagagaaaaaagagcagtgggaataggagctgtgttccttgg
gttcttgggagcagcaggaagcactatgggcgcagcgtcagtgacgctgacggtacaggccaggctattattgtctggtatagtgcag
cagcagaacaatctgctgagggctattgaggcgcaacagaatatgttgcgactcacagtctggggcatcaagcagctccaggcaaga
gtcctggctctggaaagatacctaagggatcaacagctcatgggaatttggggttgctctggaaaactcatttgcaccacttctgtgcctt
ggaatgttagttggagtaataaatctgtggatgatatttggaataacatgacctggatggagtgggaaagagaaattgacaattacacag
actatatatatgacttacttgaaaaatcgcaaacccaacaagaaaagaatgaaaaagaattattggaattggataaatgggcaagtttgtg
gaattggtttgacataacaaactggctgtggtatataagatga

*FIG. 16I*

MRVKEKYQHLWRWGWRWGTMLLGMLMICSATEKLWVTVYYGVPVWREATTTLF
CASDAKAYDTEVHNVWATHACVPTDPNPQEVVLGNVTENFNMWKNNMVDQMHE
DIISLWDESLKPCVKLTPLCVTLNCNTSVITQACPKVSFQPIPIHYCVPAGFAILKCNNK
TFNGSGPCTNVSTVQCTHGIRPVVSTQLLLNGSLAEEDIVIRSEDFTDNVKTIIVQLNES
VVINCTRPNNNTRERLSIGPGRAFYARRNIIGDIRQAHCNISRAKWNNTLQQIVIKLRE
KFRNKTIAFNQSSGGDPEIVMHSFNCGGEFFYCNTAQLFNSTWNVAGGTNGTEGNDII
TLQCRIKQIINMWQKVGKAMYAPPITGQIRCSSNITGLLLTRDGGNSTETETEIFRPGG
GDMRDNWRSELYKYKVVRIEPIGVAPTRAKRRTVQREKRAVGIGAVFLGFLGAAGS
TMGAASVTLTVQARLLLSGIVQQQNNLLRAIEAQQNMLRLTVWGIKQLQARVLALE
RYLRDQQLMGIWGCSGKLICTTSVPWNVSWSNKSVDDIWNNMTWMEWEREIDNYT
DYIYDLLEKSQTQQEKNEKELLELDKWASLWNWFDITNWLWYIR

FIG. 16J gp160$_{HIV}$ ΔV1V2 atgagagtgaaggagaaatatcagcacttgtggagatggggtggagatggggcaccatgctccttgggatgttgatgatctgtagtgc
tacagaaaaattgtgggtcacagtctattatggggtacctgtgtggagagaagcaaccaccactctattttgtgcatcagatgctaaagcc
tatgatacagaggtacataatgtttgggccacacatgcctgtgtacccacagaccccaacccacaagaagtagtattggaaatgtgac
agaaaattttaacatgtggaaaaataacatggtagatcagatgcatgaggatataatcagtttatgggatgaaagcctaaagccatgtgta
aaattaaccccactctgtgttactttaaattgtaacacctcagtcattacacaggcctgtccaaaggtatcctttcagccaattcccatacatt
attgtgtcccggctgggtttgcgatactaaagtgtaacaataagacattcaatggatcaggaccatgcacaaatgtcagcacagtacaat
gtacacatggaattaggccagtggtgtcaactcaactgctgttaaatggcagtctagcagaagaagacatagtaattagatctgaagattt
cacagacaatgttaaaaccataatagtacagctaaatgaatctgtagtaattaattgtacaagacccaacaacaatacaagagaaaggtta
tctataggaccagggagagcattttatgcaagaagaaacataataggagatataagacaagcacattgtaacattagtagagcaaaatg
gaataacactttacaacagatagttataaaattaagagaaaaatttaggaataaaacaatagcctttaatcaatcctcaggaggggaccca
gaaattgtaatgcacagttttaattgtggaggggaatttttctactgtaatacagcacaactgtttaatagtacttggaatgttgctggaggga
caaatggcactgaaggaaatgacataatcacactccaatgcagaataaaacaaattataaatatgtggcagaaagtaggaaaagcaat
gtatgcccctcccatcacaggacaaattagatgttcatcaaatattacagggctgctactaacaagagatggaggtaatagtactgagac
tgagactgagatcttcagacctggaggaggagatatgagggacaattggagaagtgaattatataaatataaagtagtaagaattgaac
caataggagtagcacccaccagggcaaagagaagaacagtgcaaagagaaaaaagagcagtgggaataggagctgtgttccttgg

FROM 16K gttcttgggagcagcaggaagcactatgggcgcagcgtcagtgacgctgacggtacaggccaggctattattgtctggtatagtgcag
cagcagaacaatctgctgagggctattgaggcgcaacagaatatgttgcgactcacagtctggggcatcaagcagctccaggcaaga
gtcctggctctggaaagatacctaagggatcaacagctcatgggaatttggggttgctctggaaaactcatttgcaccacttctgtgcctt
ggaatgttagttggagtaataaatctgtggatgatatttggaataacatgacctggatggagtgggaaagagaaattgacaattacacag
actatatatatgacttacttgaaaaatcgcaaacccaacaagaaaagaatgaaaaagaattattggaattggataaatgggcaagtttgtg
gaattggtttgacataacaaactggctgtggtatataagattattcataatgatagtaggaggcttgataggtttaagaatagtttttgctgta
ctttctatagtaaatagagttaggcagggatattcaccattatcgtttcagaccctcctcccagcctcgaggggacccgacaggcccgaa
ggaacagaagaagaaggtggagagagagacagagacagatccggtccatcagtgaacggatccttggcacttatctgggacgatct
gcggagcctgtgcctcttcagctaccaccgcttgagagacttactcttgattgtaacgaggattgtggaacttctgggacgcagggggtg
ggaagccctcaaatattggtggaatctcctacagtattggagtcaggaactaaagaatagtgctgttagcttgctacaatatgggtggag
ctatttccatgaggcggtccaggccgtctggagatctgcgacagagactcttgcgggcgcgtggggagacttatgggagactcttagg
agaggtggaagatggatactcgcaatccccaggaggattagacaagggcttgagctcactctcttgtga

FIG. 16K CONT

MRVKEKYQHLWRWGWRWGTMLLGMLMICSATEKLWVTVYYGVPVWREATTTLF
CASDAKAYDTEVHNVWATHACVPTDPNPQEVVLGNVTENFNMWKNNMVDQMHE
DIISLWDESLKPCVKLTPLCVTLNCNTSVITQACPKVSFQPIPIHYCVPAGFAILKCNNK
TFNGSGPCTNVSTVQCTHGIRPVVSTQLLLNGSLAEEDIVIRSEDFTDNVKTIIVQLNES
VVINCTRPNNNTRERLSIGPGRAFYARRNIIGDIRQAHCNISRAKWNNTLQQIVIKLRE
KFRNKTIAFNQSSGGDPEIVMHSFNCGGEFFYCNTAQLFNSTWNVAGGTNGTEGNDII
TLQCRIKQIINMWQKVGKAMYAPPITGQIRCSSNITGLLLTRDGGNSTETETEIFRPGG
GDMRDNWRSELYKYKVVRIEPIGVAPTRAKRRTVQREKRAVGIGAVFLGFLGAAGS
TMGAASVTLTVQARLLLSGIVQQQNNLLRAIEAQQNMLRLTVWGIKQLQARVLALE
RYLRDQQLMGIWGCSGKLICTTSVPWNVSWSNKSVDDIWNNMTWMEWEREIDNYT
DYIYDLLEKSQTQQEKNEKELLELDKWASLWNWFDITNWLWYIRLFIMIVGGLIGLRI
VFAVLSIVNRVRQGYSPLSFQTLLPASRGPDRPEGTEEEGGERDRDRSGPSVNGSLALI
WDDLRSLCLFSYHRLRDLLLIVTRIVELLGRRGWEALKYWWNLLQYWSQELKNSAV
SLLQYGWSYFHEAVQAVWRSATETLAGAWGDLWETLRRGGRWILAIPRRIRQGLEL
TLL

FIG. 16L gp140$_{HIV}$ ΔV1V2V3 atgagagtgaaggagaaatatcagcacttgtggagatgggggtggagatggggcaccatgctccttgggatgttgatgatctgtagtgc
tacagaaaaattgtgggtcacagtctattatggggtacctgtgtggagagaagcaaccaccactctatttgtgcatcagatgctaaagcc
tatgatacagaggtacataatgtttgggccacacatgcctgtgtacccacagaccccaacccacaagaagtagtattgggaaatgtgac
agaaaattttaacatgtggaaaaataacatggtagatcagatgcatgaggatataatcagtttatgggatgaaagcctaaagccatgtgta
aaattaaccccactctgtgttactttaaattgtaacacctcagtcattacacaggcctgtccaaaggtatcctttcagccaattcccatacatt
attgtgtcccggctgggtttgcgatactaaagtgtaacaataagacattcaatggatcaggaccatgcacaaatgtcagcacagtacaat
gtacacatggaattaggccagtggtgtcaactcaactgctgttaaatggcagtctagcagaagaagacatagtaattagatctgaagattt
cacagacaatgttaaaaccataatagtacagctaaatgaatctgtagtaattaattgtacaagacccaacaacaatgctgcagaattggat
aaatgggcaagtgctgcaagacaagcacattgtaacattagtagagcaaaatggaataacactttacaacagatagttataaaattaaga
gaaaaatttaggaataaaacaatagcctttaatcaatcctcaggaggggacccagaaattgtaatgcacagttttaattgtggaggggaat
ttttctactgtaatacagcacaactgtttaatagtacttggaatgttgctggagggacaaatggcactgaaggaaatgacataatcacactc
caatgcagaataaaacaaattataaatatgtggcagaaagtaggaaaagcaatgtatgcccctcccatcacaggacaaattagatgttca
tcaaatattacagggctgctactaacaagagatggaggtaatagtactgagactgagactgagatcttcagacctggaggaggagatat
gagggacaattggagaagtgaattatataaatataaagtagtaagaattgaaccaataggagtagcacccaccagggcaaagagaag
aacagtgcaaagagaaaaaagagcagtgggaataggagctgtgttccttgggttcttgggagcagcaggaagcactatgggcgcag
cgtcagtgacgctgacggtacaggccaggctattattgtctggtatagtgcagcagcagaacaatctgctgagggctattgaggcgcaa
cagaatatgttgcgactcacagtctggggcatcaagcagctccaggcaagagtcctggctctggaaagatacctaagggatcaacagc
tcatgggaatttggggttgctctggaaaactcatttgcaccacttctgtgccttggaatgttagttggagtaataaatctgtggatgatatttg
gaataacatgacctggatggagtgggaaagagaaattgacaattacacagactatatatatgacttacttgaaaaatcgcaaacccaaca
agaaaagaatgaaaaagaattattggaattggataaatgggcaagtttgtggaattggtttgacataacaaactggctgtggtatataaga
taat

FIG. 16M

MRVKEKYQHLWRWGWRWGTMLLGMLMICSATEKLWVTVYYGVPVWREATTTLF
CASDAKAYDTEVHNVWATHACVPTDPNPQEVVLGNVTENFNMWKNNMVDQMHE
DIISLWDESLKPCVKLTPLCVTLNCNTSVITQACPKVSFQPIPIHYCVPAGFAILKCNNK
TFNGSGPCTNVSTVQCTHGIRPVVSTQLLLNGSLAEEDIVIRSEDFTDNVKTIIVQLNES
VVINCTRPNNNAAELDKWASAARQAHCNISRAKWNNTLQQIVIKLREKFRNKTIAFN
QSSGGDPEIVMHSFNCGGEFFYCNTAQLFNSTWNVAGGTNGTEGNDIITLQCRIKQII
NMWQKVGKAMYAPPITGQIRCSSNITGLLLTRDGGNSTETETEIFRPGGGDMRDNWR
SELYKYKVVRIEPIGVAPTRAKRRTVQREKRAVGIGAVFLGFLGAAGSTMGAASVTL
TVQARLLLSGIVQQQNNLLRAIEAQQNMLRLTVWGIKQLQARVLALERYLRDQQLM
GIWGCSGKLICTTSVPWNVSWSNKSVDDIWNNMTWMEWEREIDNYTDYIYDLLEKS
QTQQEKNEKELLELDKWASLWNWFDITNWLWYIR

FIG. 16N gp160$_{HIV}$ΔV1V2V3 atgagagtgaaggagaaatatcagcacttgtggagatggggtggagatggggcaccatgctccttgggatgttgatgatctgtagtgc
tacagaaaaattgtgggtcacagtctattatggggtacctgtgtggagagaagcaaccaccactctattttgtgcatcagatgctaaagcc
tatgatacagaggtacataatgtttgggccacacatgcctgtgtacccacagaccccaacccacaagaagtagtattgggaaatgtgac
agaaaattttaacatgtggaaaaataacatggtagatcagatgcatgaggatataatcagtttatgggatgaaagcctaaagccatgtgta
aaattaaccccactctgtgttactttaaattgtaacacctcagtcattacacaggcctgtccaaaggtatcctttcagccaattcccatacatt
attgtgtcccggctgggtttgcgatactaaagtgtaacaataagacattcaatggatcaggaccatgcacaaatgtcagcacagtacaat
gtacacatggaattaggccagtggtgtcaactcaactgctgttaaatggcagtctagcagaagaagacatagtaattagatctgaagattt
cacagacaatgttaaaaccataatagtacagctaaatgaatctgtagtaattaattgtacaagacccaacaacaatgctgcagaattggat
aaatgggcaagtgctgcaagacaagcacattgtaacattagtagagcaaaatggaataacactttacaacagatagttataaaattaaga
gaaaaatttaggaataaaacaatagcctttaatcaatcctcaggaggggacccagaaattgtaatgcacagttttaattgtggaggggaat
ttttctactgtaatacagcacaactgtttaatagtacttggaatgttgctggagggacaaatggcactgaaggaaatgacataatcacactc
caatgcagaataaaacaaattataaatatgtggcagaaagtaggaaaagcaatgtatgcccctcccatcacaggacaaattagatgttca
tcaaatattacagggctgctactaacaagagatggaggtaatagtactgagactgagactgagatcttcagacctggaggaggagatat
gagggacaattggagaagtgaattatataaatataaagtagtaagaattgaaccaataggagtagcacccaccagggcaaagagaag
aacagtgcaaagagaaaaaagagcagtgggaataggagctgtgttccttgggttcttgggagcagcaggaagcactatgggcgcag

FROM 16O cgtcagtgacgctgacggtacaggccaggctattattgtctggtatagtgcagcagcagaacaatctgctgagggctattgaggcgcaa
cagaatatgttgcgactcacagtctggggcatcaagcagctccaggcaagagtcctggctctggaaagatacctaagggatcaacagc
tcatgggaatttggggttgctctggaaaactcatttgcaccacttctgtgccttggaatgttagttggagtaataaatctgtggatgatatttg
gaataacatgacctggatggagtgggaaagagaaattgacaattacacagactatatatatgacttacttgaaaaatcgcaaacccaaca
agaaaagaatgaaaaagaattattggaattggataaatgggcaagtttgtggaattggtttgacataacaaactggctgtggtatataaga
ttattcataatgatagtaggaggcttgataggtttaagaatagtttttgctgtactttctatagtaaatagagttaggcagggatattcaccatt
atcgtttcagaccctcctcccagcctcgaggggacccgacaggcccgaaggaacagaagaagaaggtggagagagagacagaga
cagatccggtccatcagtgaacggatccttggcacttatctgggacgatctgcggagcctgtgcctcttcagctaccaccgcttgagag
acttactcttgattgtaacgaggattgtggaacttctgggacgcagggggtgggaagccctcaaatattggtggaatctcctacagtattg
gagtcaggaactaaagaatagtgctgttagcttgctacaatatgggtggagctatttccatgaggcggtccaggccgtctggagatctgc
gacagagactcttgcgggcgcgtggggagacttatgggagactcttaggagaggtggaagatggatactcgcaatccccaggagga
ttagacaagggcttgagctcactctcttgtga

*FIG. 16O CONT*

MRVKEKYQHLWRWGWRWGTMLLGMLMICSATEKLWVTVYYGVPVWREATTTLF
CASDAKAYDTEVHNVWATHACVPTDPNPQEVVLGNVTENFNMWKNNMVDQMHE
DIISLWDESLKPCVKLTPLCVTLNCNTSVITQACPKVSFQPIPIHYCVPAGFAILKCNNK
TFNGSGPCTNVSTVQCTHGIRPVVSTQLLLNGSLAEEDIVIRSEDFTDNVKTIIVQLNES
VVINCTRPNNNAAELDKWASAARQAHCNISRAKWNNTLQQIVIKLREKFRNKTIAFN
QSSGGDPEIVMHSFNCGGEFFYCNTAQLFNSTWNVAGGTNGTEGNDIITLQCRIKQII
NMWQKVGKAMYAPPITGQIRCSSNITGLLLTRDGGNSTETETEIFRPGGGDMRDNWR
SELYKYKVVRIEPIGVAPTRAKRRTVQREKRAVGIGAVFLGFLGAAGSTMGAASVTL
TVQARLLLSGIVQQQNNLLRAIEAQQNMLRLTVWGIKQLQARVLALERYLRDQQLM
GIWGCSGKLICTTSVPWNVSWSNKSVDDIWNNMTWMEWEREIDNYTDYIYDLLEKS
QTQQEKNEKELLELDKWASLWNWFDITNWLWYIRLFIMIVGGLIGLRIVFAVLSIVNR
VRQGYSPLSFQTLLPASRGPDRPEGTEEEGGERDRDRSGPSVNGSLALIWDDLRSLCL
FSYHRLRDLLLIVTRIVELLGRRGWEALKYWWNLLQYWSQELKNSAVSLLQYGWSY
FHEAVQAVWRSATETLAGAWGDLWETLRRGGRWILAIPRRIRQGLELTLL

FIG. 16P

$Gag_{HIV}$ (p17-p24Δmyr)

Atgggcgcccgcgccagcgtgctgagcggcggcgagctggaccgctgggagaagatccgcctgcgccccggcggcaagaaga
agtacaagctgaagcacatcgtgtgggccagccgcgagctggagcgcttcgccgtgaaccccggcctgctggagaccagcgaggg
ctgccgccagatcctgggccagctgcagcccagcctgcagaccggcagcgaggagctgcgcagcctgtacaacaccgtggccacc
ctgtactgcgtgcaccagcgcatcgaggtgaaggacaccaaggaggccctggagaagatcgaggaggagcagaacaagagcaag
aagaaggcccagcaggccgccgccgacaccggcaacagcagccaagtgagccagaactaccccatcgtgcagaacctgcaggg
ccagatggtgcaccaggccatcagcccccgcaccctgaacgcctgggtgaaggtggtggaggagaaggccttcagccccgaggtg
atccccatgttcagcgccctgagcgagggcgccacccccaggacctgaacaccatgctgaacaccgtgggcggccaccaggccg
ccatgcagatgctgaaggagaccatcaacgaggaggccgccgagtgggaccgcctgcaccccgtgcacgccggccccatcgccc
ccggccagatgcgcgagccccgcggcagcgacatcgccggcaccacgagcaccctgcaggagcagatcggctggatgaccaac
aacccccctatccccgtgggcgagatctacaagcgctggatcatcctgggcctgaacaagatcgtgcgcatgtacagccccacgagc
atcctggacatccgccagggccccaaggagcccttccgcgactacgtggaccgcttctacaagaccctgcgggccgagcaggccag
ccaggaggtgaagaactggatgaccgagaccctgctggtgcagaacgccaaccccgactgcaagaccatcctgaaggccctgggc
cccgccgccaccctggaggagatgatgaccgcctgccagggcgtgggcggccccggccacaaggcccgcgtgctgtaa

FIG. 16Q

MGARASVLSGGELDRWEKIRLRPGGKKKYKLKHIVWASRELERFAVNPGLLETSEG
CRQILGQLQPSLQTGSEELRSLYNTVATLYCVHQRIEVKDTKEALEKIEEEQNKSKKK
AQQAAADTGNSSQVSQNYPIVQNLQGQMVHQAISPRTLNAWVKVVEEKAFSPEVIP
MFSALSEGATPQDLNTMLNTVGGHQAAMQMLKETINEEAAEWDRLHPVHAGPIAPG
QMREPRGSDIAGTTSTLQEQIGWMTNNPPIPVGEIYKRWIILGLNKIVRMYSPTSILDIR
QGPKEPFRDYVDRFYKTLRAEQASQEVKNWMTETLLVQNANPDCKTILKALGPAAT
LEEMMTACQGVGGPGHKARVL

FIG. 16R

$Tat_{HIV}$

Atggagccagtagatcctagactagagccctggaagcatccagggagtaagcctaaaactgcttgtaccaattgctattgtaaaaagtg
ttgctttcattgccaagtttgtttcacaacaaaagccttaggcatctcctatggcaggaagaagcggagacagcgacgaagagctcatca
gaacagtcagactcatcaagcttctctatcaaagcagccctcctcccagcctcgaggggacccgacaggcccgaaggaacagaaga
agaaggtggagagagagacagagacagatccggtccatcagtga

FIG. 16S

MEPVDPRLEPWKHPGSKPKTACTNCYCKKCCFHCQVCFTTKALGISYGRKKRRQRR
RAHQNSQTHQASLSKQPSSQPRGDPTGPKEQKKKVERETETDPVHQ

FIG. 16T

SEQUENCE LISTING

```
<160> NUMBER OF SEQ ID NOS: 43

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

tatcgtacga tgagagtgaa ggagaaatat                                    30


<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

atagcgcgca tcacaagaga gtgagctcaa                                    30


<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

tatgcgcgct tatcttatat accacagcca gt                                 32
```

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 4
ataagacatt caatggatca ggac 24

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5
tgcccattta tccaattctg cagcattgtt gttgggtctt gtacaatt 48

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
gataaatggg caagtgctgc aagacaagca cattgtaaca ttgt 44

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
ctactcctat tggttcaatt ctta 24

<210> SEQ ID NO 8
<211> LENGTH: 11
<212> TYPE: PRT
<213> ORGANISM: Human immunodeficiency virus type 1

<400> SEQUENCE: 8

Ala Ala Glu Leu Asp Lys Trp Ala Ser Ala Ala
1 5 10

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
atttaaagta acacagagtg gggttaattt 30

<210> SEQ ID NO 10
<211> LENGTH: 42
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 10
gttactttaa attgtaacac ctcagtcatt acacaggcct gt 42

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttgcataaaa tgctctccct ggtcctatag 30

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tatcgtacga tgcgagtcgt gattgcccta ctg 33

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atagcgcgct tatgtgttga tgccaaccca 30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tatcgtacga tgagaaacat gacaatgtcc 30

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atagcgcgct taatggcttt catgcgtttt cc 32

<210> SEQ ID NO 16
<211> LENGTH: 18967
<212> TYPE: DNA
<213> ORGANISM: Artificial Sequence -continued
<220> FEATURE:
<223> OTHER INFORMATION: Description of Artificial Sequence: Synthetic
complete polynucleotide sequence of the pTM-MVSChw
plasmid (CNCM I-2889)

<400> SEQUENCE: 16

```
gcggccgcta atacgactca ctatagggcc aactttgttt ggtctgatga gtccgtgagg     60

acgaaacccg gagtcccggg tcaccaaaca aagttgggta aggatagttc aatcaatgat    120

catcttctag tgcacttagg attcaagatc ctattatcag ggacaagagc aggattaggg    180

atatccgaga tggccacact tttaaggagc ttagcattgt tcaaaagaaa caaggacaaa    240

ccacccatta catcaggatc cggtggagcc atcagaggaa tcaaacacat tattatagta    300

ccaatccctg gagattcctc aattaccact cgatccagac ttctggaccg gttggtgagg    360

ttaattggaa acccggatgt gagcgggccc aaactaacag gggcactaat aggtatatta    420

tccttatttg tggagtctcc aggtcaattg attcagagga tcaccgatga ccctgacgtt    480

agcataaggc tgttagaggt tgtccagagt gaccagtcac aatctggcct taccttcgca    540

tcaagaggta ccaacatgga ggatgaggcg gaccaatact tttcacatga tgatccaatt    600

agtagtgatc aatccaggtt cggatggttc gggaacaagg aaatctcaga tattgaagtg    660

caagaccctg agggattcaa catgattctg ggtaccatcc tagcccaaat ttgggtcttg    720

ctcgcaaagg cggttacggc cccagacacg gcagctgatt cggagctaag aaggtggata    780

aagtacaccc aacaaagaag ggtagttggt gaatttagat tggagagaaa atggttggat    840

gtggtgagga acaggattgc cgaggacctc tccttacgcc gattcatggt cgctctaatc    900

ctggatatca agagaacacc cggaaacaaa cccaggattg ctgaaatgat atgtgacatt    960

gatacatata tcgtagaggc aggattagcc agttttatcc tgactattaa gtttgggata   1020

gaaactatgt atcctgctct tggactgcat gaatttgctg gtgagttatc cacacttgag   1080

tccttgatga acctttacca gcaaatgggg gaaactgcac cctacatggt aatcctggag   1140

aactcaattc agaacaagtt cagtgcagga tcataccctc tgctctggag ctatgccatg   1200

ggagtaggag tggaacttga aaactccatg ggaggtttga actttggccg atcttacttt   1260

gatccagcat attttagatt agggcaagag atggtaagga ggtcagctgg aaaggtcagt   1320

tccacattgg catctgaact cggtatcact gccgaggatg caaggcttgt ttcagagatt   1380

gcaatgcata ctactgagga caagatcagt agagcggttg gacccagaca agcccaagta   1440

tcatttctac acggtgatca aagtgagaat gagctaccga gattgggggg caaggaagat   1500

aggagggtca aacagagtcg aggagaagcc agggagagct acagagaaac cgggcccagc   1560

agagcaagtg atgcgagagc tgcccatctt ccaaccggca caccccctaga cattgacact   1620

gcaacggagt ccagccaaga tccgcaggac agtcgaaggt cagctgacgc cctgcttagg   1680

ctgcaagcca tggcaggaat ctcggaagaa caaggctcag acacggacac ccctatagtg   1740

tacaatgaca gaaatcttct agactaggtg cgagaggccg agggccagaa caacatccgc   1800

ctaccatcca tcattgttat aaaaaactta ggaaccaggt ccacacagcc gccagcccat   1860

caaccatcca ctcccacgat tggagccaat ggcagaagag caggcacgcc atgtcaaaaa   1920

cggactggaa tgcatccggg ctctcaaggc cgagcccatc ggctcactgg ccatcgagga   1980

agctatggca gcatggtcag aaatatcaga caacccagga caggagcgag ccacctgcag   2040

ggaagagaag gcaggcagtt cgggtctcag caaaccatgc ctctcagcaa ttggatcaac   2100

tgaaggcggt gcacctcgca tccgcggtca gggacctgga gagagcgatg acgacgctga   2160
```

-continued

```
aactttggga atccccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata ataatgaagt agctacagct   3420
caacttacct gccaacccca tgccagtcga cccaactagt acaacctaaa tccattataa   3480
aaaacttagg agcaaagtga ttgcctccca aggtccacaa tgacagagac ctacgacttc   3540
gacaagtcgg catgggacat caaagggtcg atcgctccga tacaacccac cacctacagt   3600
gatggcaggc tggtgcccca ggtcagagtc atagatcctg gtctaggcga caggaaggat   3660
gaatgcttta tgtacatgtt tctgctgggg gttgttgagg acagcgattc cctagggcct   3720
ccaatcgggc gagcatttgg gttcctgccc ttaggtgttg gcagatccac agcaaagccc   3780
gaaaaactcc tcaaagaggc cactgagctt gacatagttg ttagacgtac agcagggctc   3840
aatgaaaaac tggtgttcta caacaacacc ccactaactc tcctcacacc ttggagaaag   3900
gtcctaacaa cagggagtgt cttcaacgca aaccaagtgt gcaatgcggt taatctgata   3960
ccgctcgata ccccgcagag gttccgtgtt gtttatatga gcatcacccg tctttcggat   4020
aacgggtatt acaccgttcc tagaagaatg ctggaattca gatcggtcaa tgcagtggcc   4080
ttcaacctgc tggtgaccct taggattgac aaggcgatag gccctgggaa gatcatcgac   4140
aatacagagc aacttcctga ggcaacattt atggtccaca tcgggaactt caggagaaag   4200
aagagtgaag tctactctgc cgattattgc aaaatgaaaa tcgaaaagat gggcctggtt   4260
tttgcacttg gtgggatagg gggcaccagt cttcacatta gaagcacagg caaaatgagc   4320
aagactctcc atgcacaact cgggttcaag aagaccttat gttacccgct gatggatatc   4380
aatgaagacc ttaatcgatt actctggagg agcagatgca agatagtaag aatccaggca   4440
gttttgcagc catcagttcc tcaagaattc cgcatttacg acgacgtgat cataaatgat   4500
gaccaaggac tattcaaagt tctgtagacc gtagtgccca gcaatgcccg aaaacgaccc   4560
```

-continued

```
ccctcacaat gacagccaga aggcccggac aaaaaagccc cctccgaaag actccacgga   4620
ccaagcgaga ggccagccag cagccgacgg caagcgcgaa caccaggcgg ccccagcaca   4680
gaacagccct gacacaaggc caccaccagc caccccaatc tgcatcctcc tcgtgggacc   4740
cccgaggacc aacccccaag gctgcccccg atccaaacca ccaaccgcat ccccaccacc   4800
cccgggaaag aaacccccag caattggaag gcccctcccc ctcttcctca acacaagaac   4860
tccacaaccg aaccgcacaa gcgaccgagg tgacccaacc gcaggcatcc gactccctag   4920
acagatcctc tctccccggc aaactaaaca aaacttaggg ccaaggaaca tacacaccca   4980
acagaaccca gaccccggcc cacggcgccg cgcccccaac ccccgacaac cagagggagc   5040
ccccaaccaa tcccgccggc tcccccggtg cccacaggca gggacaccaa cccccgaaca   5100
gacccagcac ccaaccatcg acaatccaag acggggggc cccccaaaa aaaggccccc   5160
aggggccgac agccagcacc gcgaggaagc ccacccaccc cacacacgac cacggcaacc   5220
aaaccagaac ccagaccacc ctgggccacc agctcccaga ctcggccatc accccgcaga   5280
aaggaaaggc cacaacccgc gcaccccagc cccgatccgg cggggagcca cccaacccga   5340
accagcaccc aagagcgatc cccgaaggac ccccgaaccg caaaggacat cagtatccca   5400
cagcctctcc aagtccccg gtctcctcct cttctcgaag ggaccaaaag atcaatccac   5460
cacacccgac gacactcaac tccccacccc taaaggagac accgggaatc ccagaatcaa   5520
gactcatcca atgtccatca tgggtctcaa ggtgaacgtc tctgccatat tcatggcagt   5580
actgttaact ctccaaacac ccaccggtca aatccattgg ggcaatctct ctaagatagg   5640
ggtggtagga ataggaagtg caagctacaa agttatgact cgttccagcc atcaatcatt   5700
agtcataaaa ttaatgccca atataactct cctcaataac tgcacgaggg tagagattgc   5760
agaatacagg agactactga gaacagtttt ggaaccaatt agagatgcac ttaatgcaat   5820
gacccagaat ataagaccgg ttcagagtgt agcttcaagt aggagacaca agagatttgc   5880
gggagtagtc ctggcaggtg cggccctagg cgttgccaca gctgctcaga taacagccgg   5940
cattgcactt caccagtcca tgctgaactc tcaagccatc gacaatctga gagcgagcct   6000
ggaaactact aatcaggcaa ttgagacaat cagacaagca gggcaggaga tgatattggc   6060
tgttcagggt gtccaagact acatcaataa tgagctgata ccgtctatga accaactatc   6120
ttgtgattta atcggccaga agctcgggct caaattgctc agatactata cagaaatcct   6180
gtcattattt ggccccagtt tacgggaccc catatctgcg gagatatcta tccaggcttt   6240
gagctatgcg cttggaggag acatcaataa ggtgttagaa aagctcggat acagtggagg   6300
tgatttactg ggcatcttag agagcggagg aataaaggcc cggataactc acgtcgacac   6360
agagtcctac ttcattgtcc tcagtatagc ctatccgacg ctgtccgaga ttaagggggt   6420
gattgtccac cggctagagg gggtctcgta caacataggc tctcaagagt ggtataccac   6480
tgtgcccaag tatgttgcaa cccaagggta ccttatctcg aattttgatg agtcatcgtg   6540
tactttcatg ccagagggga ctgtgtgcag ccaaaatgcc ttgtacccga tgagtcctct   6600
gctccaagaa tgcctccggg ggtacaccaa gtcctgtgct cgtacactcg tatccgggtc   6660
ttttgggaac cggttcattt tatcacaagg gaacctaata gccaattgtg catcaatcct   6720
ttgcaagtgt tacacaacag gaacgatcat taatcaagac cctgacaaga tcctaacata   6780
cattgctgcc gatcactgcc cggtagtcga ggtgaacggc gtgaccatcc aagtcgggag   6840
caggaggtat ccagacgctg tgtacttgca cagaattgac ctcggtcctc ccatatcatt   6900
```

-continued

```
ggagaggttg gacgtaggga caaatctggg gaatgcaatt gctaagttgg aggatgccaa   6960
ggaattgttg gagtcatcgg accagatatt gaggagtatg aaaggtttat cgagcactag   7020
catagtctac atcctgattg cagtgtgtct tggagggttg atagggatcc ccgctttaat   7080
atgttgctgc agggggcgtt gtaacaaaaa gggagaacaa gttggtatgt caagaccagg   7140
cctaaagcct gatcttacgg gaacatcaaa atcctatgta aggtcgctct gatcctctac   7200
aactcttgaa acacaaatgt cccacaagtc tcctcttcgt catcaagcaa ccaccgcacc   7260
cagcatcaag cccacctgaa attatctccg gcttccctct ggccgaacaa tatcggtagt   7320
taatcaaaac ttagggtgca agatcatcca caatgtcacc acaacgagac cggataaatg   7380
ccttctacaa agataacccc catcccaagg gaagtaggat agtcattaac agagaacatc   7440
ttatgattga tagaccttat gttttgctgg ctgttctgtt tgtcatgttt ctgagcttga   7500
tcgggttgct agccattgca ggcattagac ttcatcgggc agccatctac accgcagaga   7560
tccataaaag cctcagcacc aatctagatg taactaactc aatcgagcat caggtcaagg   7620
acgtgctgac accactcttc aaaatcatcg gtgatgaagt gggcctgagg acacctcaga   7680
gattcactga cctagtgaaa ttaatctctg acaagattaa attccttaat ccggataggg   7740
agtacgactt cagagatctc acttggtgta tcaacccgcc agagagaatc aaattggatt   7800
atgatcaata ctgtgcagat gtggctgctg aagagctcat gaatgcattg gtgaactcaa   7860
ctctactgga gaccagaaca accaatcagt tcctagctgt ctcaaaggga aactgctcag   7920
ggcccactac aatcagaggt caattctcaa acatgtcgct gtccctgtta gacttgtatt   7980
taggtcgagg ttacaatgtg tcatctatag tcactatgac atcccaggga atgtatgggg   8040
gaacttacct agtggaaaag cctaatctga gcagcaaaag gtcagagttg tcacaactga   8100
gcatgtaccg agtgtttgaa gtaggtgtta tcagaaatcc gggtttgggg gctccggtgt   8160
tccatatgac aaactatctt gagcaaccag tcagtaatga tctcagcaac tgtatggtgg   8220
ctttggggga gctcaaactc gcagcccttt gtcacgggga agattctatc acaattccct   8280
atcagggatc agggaaaggt gtcagcttcc agctcgtcaa gctaggtgtc tggaaatccc   8340
caaccgacat gcaatcctgg gtccccttat caacggatga tccagtgata gacaggcttt   8400
acctctcatc tcacagaggt gttatcgctg acaatcaagc aaaatgggct gtcccgacaa   8460
cacgaacaga tgacaagttg cgaatggaga catgcttcca acaggcgtgt aagggtaaaa   8520
tccaagcact ctgcgagaat cccgagtggg caccattgaa ggataacagg attccttcat   8580
acggggtctt gtctgttgat ctgagtctga cagttgagct taaaatcaaa attgcttcgg   8640
gattcgggcc attgatcaca cacggttcag ggatggacct atacaaatcc aaccacaaca   8700
atgtgtattg gctgactatc ccgccaatga agaacctagc cttaggtgta atcaacacat   8760
tggagtggat accgagattc aaggttagtc cctacctctt cactgtccca attaaggaag   8820
caggcgaaga ctgccatgcc ccaacatacc tacctgcgga ggtggatggt gatgtcaaac   8880
tcagttccaa tctggtgatt ctacctggtc aagatctcca atatgttttg gcaacctacg   8940
atacttccag ggttgaacat gctgtggttt attacgttta cagcccaagc cgctcatttt   9000
cttactttta tccttttagg ttgcctataa agggggtccc catcgaatta caagtggaat   9060
gcttcacatg ggaccaaaaa ctctggtgcc gtcacttctg tgtgcttgcg gactcagaat   9120
ctggtggaca tatcactcac tctgggatgg tgggcatggg agtcagctgc acagtcaccc   9180
gggaagatgg aaccaatcgc agatagggct gctagtgaac caatcacatg atgtcaccca   9240
gacatcaggc atacccacta gtgtgaaata gacatcagaa ttaagaaaaa cgtagggtcc   9300
```

-continued

```
aagtggttcc ccgttatgga ctcgctatct gtcaaccaga tcttataccc tgaagttcac   9360
ctagatagcc cgatagttac caataagata gtagccatcc tggagtatgc tcgagtccct   9420
cacgcttaca gcctggagga ccctacactg tgtcagaaca tcaagcaccg cctaaaaaac   9480
ggattttcca accaaatgat tataaacaat gtggaagttg ggaatgtcat caagtccaag   9540
cttaggagtt atccggccca ctctcatatt ccatatccaa attgtaatca ggatttattt   9600
aacatagaag acaaagagtc aacgaggaag atccgtgaac tcctcaaaaa ggggaattcg   9660
ctgtactcca aagtcagtga taaggttttc caatgcttaa gggacactaa ctcacggctt   9720
ggcctaggct ccgaattgag ggaggacatc aaggagaaag ttattaactt gggagtttac   9780
atgcacagct cccagtggtt tgagcccttt ctgttttggt ttacagtcaa gactgagatg   9840
aggtcagtga ttaaatcaca aacccatact tgccatagga ggagacacac acctgtattc   9900
ttcactggta gttcagttga gttgctaatc tctcgtgacc ttgttgctat aatcagtaaa   9960
gagtctcaac atgtatatta cctgacattt gaactggttt tgatgtattg tgatgtcata  10020
gaggggaggt taatgacaga gaccgctatg actattgatg ctaggtatac agagcttcta  10080
ggaagagtca gatacatgtg gaaactgata gatggtttct tccctgcact cgggaatcca  10140
acttatcaaa ttgtagccat gctggagcct ctttcacttg cttacctgca gctgagggat  10200
ataacagtag aactcagagg tgctttcctt aaccactgct ttactgaaat acatgatgtt  10260
cttgaccaaa acgggttttc tgatgaaggt acttatcatg agttaactga agctctagat  10320
tacattttca taactgatga catacatctg acaggggaga ttttctcatt tttcagaagt  10380
ttcggccacc ccagacttga agcagtaacg gctgctgaaa atgttaggaa atacatgaat  10440
cagcctaaag tcattgtgta tgagactctg atgaaaggtc atgccatatt ttgtggaatc  10500
ataatcaacg gctatcgtga caggcacgga ggcagttggc caccgctgac cctcccccctg  10560
catgctgcag acacaatccg gaatgctcaa gcttcaggtg aagggttaac acatgagcag  10620
tgcgttgata actggaaatc ttttgctgga gtgaaatttg gctgctttat gcctcttagc  10680
ctggatagtg atctgacaat gtacctaaag gacaaggcac ttgctgctct ccaaagggaa  10740
tgggattcag tttacccgaa agagttcctg cgttacgacc ctcccaaggg aaccgggtca  10800
cggaggcttg tagatgtttt ccttaatgat tcgagctttg acccatatga tgtgataatg  10860
tatgttgtaa gtggagctta cctccatgac cctgagttca acctgtctta cagcctgaaa  10920
gaaaaggaga tcaaggaaac aggtagactt tttgctaaaa tgacttacaa aatgagggca  10980
tgccaagtga ttgctgaaaa tctaatctca aacgggattg gcaaatattt taaggacaat  11040
gggatggcca aggatgagca cgatttgact aaggcactcc acactctagc tgtctcagga  11100
gtccccaaag atctcaaaga aagtcacagg ggggggccag tcttaaaaac ctactcccga  11160
agcccagtcc acacaagtac caggaacgtg agagcagcaa aagggtttat agggttccct  11220
caagtaattc ggcaggacca agacactgat catccggaga atatggaagc ttacgagaca  11280
gtcagtgcat ttatcacgac tgatctcaag aagtactgcc ttaattggag atatgagacc  11340
atcagcttgt ttgcacagag gctaaatgag atttacggat tgccctcatt tttccagtgg  11400
ctgcataaga ggcttgagac ctctgtcctg tatgtaagtg accctcattg cccccccgac  11460
cttgacgccc atatcccgtt atataaagtc cccaatgatc aaatcttcat taagtaccct  11520
atgggaggta tagaagggta ttgtcagaag ctgtggacca tcagcaccat tccctatcta  11580
tacctggctg cttatgagag cggagtaagg attgcttcgt tagtgcaagg ggacaatcag  11640
```

-continued

```
accatagccg taacaaaaag ggtacccagc acatggccct acaaccttaa gaaacgggaa  11700
gctgctagag taactagaga ttactttgta attcttaggc aaaggctaca tgatattggc  11760
catcacctca aggcaaatga gacaattgtt tcatcacatt tttttgtcta ttcaaaagga  11820
atatattatg atgggctact tgtgtcccaa tcactcaaga gcatcgcaag atgtgtattc  11880
tggtcagaga ctatagttga tgaaacaagg gcagcatgca gtaatattgc tacaacaatg  11940
gctaaaagca tcgagagagg ttatgaccgt taccttgcat attccctgaa cgtcctaaaa  12000
gtgatacagc aaattctgat ctctcttggc ttcacaatca attcaaccat gacccgggat  12060
gtagtcatac ccctcctcac aaacaacgac ctcttaataa ggatggcact gttgcccgct  12120
cctattgggg ggatgaatta tctgaatatg agcaggctgt ttgtcagaaa catcggtgat  12180
ccagtaacat catcaattgc tgatctcaag agaatgattc tcgcctcact aatgcctgaa  12240
gagaccctcc atcaagtaat gacacaacaa ccgggggact cttcattcct agactgggct  12300
agcgaccctt actcagcaaa tcttgtatgt gtccagagca tcactagact cctcaagaac  12360
ataactgcaa ggtttgtcct gatccatagt ccaaacccaa tgttaaaagg attattccat  12420
gatgacagta aagaagagga cgagggactg gcggcattcc tcatggacag gcatattata  12480
gtacctaggg cagctcatga aatcctggat catagtgtca caggggcaag agagtctatt  12540
gcaggcatgc tggataccac aaaaggcttg attcgagcca gcatgaggaa ggggggggtta  12600
acctctcgag tgataaccag attgtccaat tatgactatg aacaattcag agcagggatg  12660
gtgctattga caggaagaaa gagaaatgtc ctcattgaca aagagtcatg ttcagtgcag  12720
ctggcgagag ctctaagaag ccatatgtgg gcgaggctag ctcgaggacg gcctatttac  12780
ggccttgagg tccctgatgt actagaatct atgcgaggcc accttattcg gcgtcatgag  12840
acatgtgtca tctgcgagtg tggatcagtc aactacggat ggtttttttgt cccctcgggt  12900
tgccaactgg atgatattga caaggaaaca tcatccttga gagtcccata tattggttct  12960
accactgatg agagaacaga catgaagctt gccttcgtaa gagccccaag tcgatccttg  13020
cgatctgctg ttagaatagc aacagtgtac tcatgggctt acggtgatga tgatagctct  13080
tggaacgaag cctggttgtt ggctaggcaa agggccaatg tgagcctgga ggagctaagg  13140
gtgatcactc ccatctcaac ttcgactaat ttagcgcata ggttgaggga tcgtagcact  13200
caagtgaaat actcaggtac atcccttgtc cgagtggcga ggtataccac aatctccaac  13260
gacaatctct catttgtcat atcagataag aaggttgata ctaactttat ataccaacaa  13320
ggaatgcttc tagggttggg tgttttagaa acattgtttc gactcgagaa agataccgga  13380
tcatctaaca cggtattaca tcttcacgtc gaaacagatt gttgcgtgat cccgatgata  13440
gatcatccca ggatacccag ctcccgcaag ctagagctga gggcagagct atgtaccaac  13500
ccattgatat atgataatgc acctttaatt gacagagatg caacaaggct atacacccag  13560
agccatagga ggcaccttgt ggaatttgtt acatggtcca caccccaact atatcacatt  13620
ttagctaagt ccacagcact atctatgatt gacctggtaa caaaatttga gaaggaccat  13680
atgaatgaaa tttcagctct catagggggat gacgatatca atagtttcat aactgagttt  13740
ctgctcatag agccaagatt attcactatc tacttgggcc agtgtgcggc catcaattgg  13800
gcatttgatg tacattatca tagaccatca gggaaatatc agatgggtga gctgttgtca  13860
tcgttccttt ctagaatgag caaaggagtg tttaaggtgc ttgtcaatgc tctaagccac  13920
ccaaagatct acaagaaatt ctggcattgt ggtattatag agcctatcca tggtccttca  13980
cttgatgctc aaaacttgca cacaactgtg tgcaacatgg tttacacatg ctatatgacc  14040
```

-continued

```
tacctcgacc tgttgttgaa tgaagagtta gaagagttca catttctctt gtgtgaaagc  14100
gacgaggatg tagtaccgga cagattcgac aacatccagg caaaacactt atgtgttctg  14160
gcagatttgt actgtcaacc agggacctgc ccaccaattc gaggtctaag accggtagag  14220
aaatgtgcag ttctaaccga ccatatcaag gcagaggcta tgttatctcc agcaggatct  14280
tcgtggaaca taaatccaat tattgtagac cattactcat gctctctgac ttatctccgg  14340
cgaggatcga tcaaacagat aagattgaga gttgatccag gattcatttt cgacgccctc  14400
gctgaggtaa atgtcagtca gccaaagatc ggcagcaaca acatctcaaa tatgagcatc  14460
aaggctttca gacccccaca cgatgatgtt gcaaaattgc tcaaagatat caacacaagc  14520
aagcacaatc ttcccatttc agggggcaat ctcgccaatt atgaaatcca tgctttccgc  14580
agaatcgggt tgaactcatc tgcttgctac aaagctgttg agatatcaac attaattagg  14640
agatgccttg agccagggga ggacggcttg ttcttgggtg agggatcggg ttctatgttg  14700
atcacttata aagagatact taaactaaac aagtgcttct ataatagtgg ggtttccgcc  14760
aattctagat ctggtcaaag ggaattagca ccctatccct ccgaagttgg ccttgtcgaa  14820
cacagaatgg gagtaggtaa tattgtcaaa gtgctcttta acgggaggcc cgaagtcacg  14880
tgggtaggca gtgtagattg cttcaatttc atagttagta atatccctac ctctagtgtg  14940
gggtttatcc attcagatat agagaccttg cctgacaaag atactataga gaagctagag  15000
gaattggcag ccatcttatc gatggctctg ctcctgggca aaataggatc aatactggtg  15060
attaagctta tgcctttcag cggggatttt gttcagggat ttataagtta tgtagggtct  15120
cattatagag aagtgaacct tgtataccct agatacagca acttcatctc tactgaatct  15180
tatttggtta tgacagatct caaggctaac cggctaatga atcctgaaaa gattaagcag  15240
cagataattg aatcatctgt gaggacttca cctggactta taggtcacat cctatccatt  15300
aagcaactaa gctgcataca agcaattgtg ggagacgcag ttagtagagg tgatatcaat  15360
cctactctga aaaaacttac acctatagag caggtgctga tcaattgcgg gttggcaatt  15420
aacggaccta agctgtgcaa agaattgatc caccatgatg ttgcctcagg gcaagatgga  15480
ttgcttaatt ctatactcat cctctacagg gagttggcaa gattcaaaga caaccaaaga  15540
agtcaacaag ggatgttcca cgcttacccc gtattggtaa gtagcaggca acgagaactt  15600
atatctagga tcacccgcaa attctggggg cacattcttc tttactccgg gaacaaaaag  15660
ttgataaata agtttatcca gaatctcaag tccggctatc tgatactaga cttacaccag  15720
aatatcttcg ttaagaatct atccaagtca gagaaacaga ttattatgac gggggggtttg  15780
aaacgtgagt gggtttttaa ggtaacagtc aaggagacca aagaatggta taagttagtc  15840
ggatacagtg ccctgattaa ggactaattg gttgaactcc ggaaccctaa tcctgcccta  15900
ggtggttagg cattatttgc aatatattaa agaaaacttt gaaaatacga agtttctatt  15960
cccagctttg tctggtggcc ggcatggtcc cagcctcctc gctggcgccg gctgggcaac  16020
attccgaggg gaccgtcccc tcggtaatgg cgaatgggac gcggccgatc cggctgctaa  16080
caaagcccga aaggaagctg agttggctgc tgccaccgct gagcaataac tagcataacc  16140
ccttggggcc tctaaacggg tcttgagggg ttttttgctg aaaggaggaa ctatatccgg  16200
atgcggccgc gggccctatg gtacccagct tttgttccct ttagtgaggg ttaattccga  16260
gcttggcgta atcatggtca tagctgtttc ctgtgtgaaa ttgttatccg ctcacaattc  16320
cacacaacat aggagccgga agcataaagt gtaaagcctg ggtgcctaa tgagtgaggt  16380
```

-continued

```
aactcacatt aattgcgttg cgctcactgc ccgctttcca gtcgggaaac ctgtcgtgcc  16440
agctgcatta atgaatcggc caacgcgcgg ggagaggcgg tttgcgtatt gggcgctctt  16500
ccgcttcctc gctcactgac tcgctgcgct cggtcgttcg gctgcggcga gcggtatcag  16560
ctcactcaaa ggcggtaata cggttatcca cagaatcagg ggataacgca ggaaagaaca  16620
tgtgagcaaa aggccagcaa aaggccagga accgtaaaaa ggccgcgttg ctggcgtttt  16680
tccataggct ccgcccccct gacgagcatc acaaaaatcg acgctcaagt cagaggtggc  16740
gaaacccgac aggactataa agataccagg cgtttccccc tggaagctcc ctcgtgcgct  16800
ctcctgttcc gaccctgccg cttaccggat acctgtccgc ctttctccct tcgggaagcg  16860
tggcgctttc tcaatgctca cgctgtaggt atctcagttc ggtgtaggtc gttcgctcca  16920
agctgggctg tgtgcacgaa ccccccgttc agcccgaccg ctgcgcctta tccggtaact  16980
atcgtcttga gtccaacccg gtaagacacg acttatcgcc actggcagca gccactggta  17040
acaggattag cagagcgagg tatgtaggcg gtgctacaga gttcttgaag tggtggccta  17100
actacggcta cactagaagg acagtatttg gtatctgcgc tctgctgaag ccagttacct  17160
tcggaaaaag agttggtagc tcttgatccg gcaaacaaac caccgctggt agcggtggtt  17220
tttttgtttg caagcagcag attacgcgca gaaaaaaagg atctcaagaa gatcctttga  17280
tcttttctac ggggtctgac gctcagtgga acgaaaactc acgttaaggg attttggtca  17340
tgagattatc aaaaaggatc ttcacctaga tccttttaaa ttaaaaatga agttttaaat  17400
caatctaaag tatatatgag taaacttggt ctgacagtta ccaatgctta atcagtgagg  17460
cacctatctc agcgatctgt ctatttcgtt catccatagt tgcctgactg cccgtcgtgt  17520
agataactac gatacgggag ggcttaccat ctggccccag tgctgcaatg ataccgcgag  17580
acccacgctc accggctcca gatttatcag caataaacca gccagccgga agggccgagc  17640
gcagaagtgg tcctgcaact ttatccgcct ccatccagtc tattaattgt tgccgggaag  17700
ctagagtaag tagttcgcca gttaatagtt tgcgcaacgt tgttgccatt gctacaggca  17760
tcgtggtgtc acgctcgtcg tttggtatgg cttcattcag ctccggttcc caacgatcaa  17820
ggcgagttac atgatccccc atgttgtgaa aaaaagcggt tagctccttc ggtcctccga  17880
tcgttgtcag aagtaagttg gccgcagtgt tatcactcat gcttatggca gcactgcata  17940
attctcttac tgtcatgcca tccgtaagat gcttttctgt gactggtgag tactcaacca  18000
agtcattctg agaatagtgt atgcggcgac cgagttgctc ttgcccggcg tcaatacggg  18060
ataataccgc gccacatagc agaactttaa aagtgctcat cattggaaaa cgttcttcgg  18120
ggcgaaaact ctcaaggatc ttaccgctgt tgagatccag ttcgatgtaa cccactcgtg  18180
cacccaactg atcttcagca tcttttactt tcaccagcgt ttctgggtga gcaaaaacag  18240
gaaggcaaaa tgccgcaaaa aagggaataa gggcgacacg gaaatgttga atactcatac  18300
tcttcctttt tcaatattat tgaagcattt atcagggtta ttgtctcatg agcggataca  18360
tatttgaatg tatttagaaa aataaacaaa taggggttcc gcgcacattt ccccgaaaag  18420
tgccacctga aattgtaaac gttaatattt tgttaaaatt cgcgttaaat ttttgttaaa  18480
tcagctcatt ttttaaccaa taggccgaaa tcggcaaaat cccttataaa tcaaaagaat  18540
agaccgagat agggttgagt gttgttccag tttggaacaa gagtccacta ttaaagaacg  18600
tggactccaa cgtcaaaggg cgaaaaaccg tctatcaggg cgatggccca ctacgtgaac  18660
catcacccta atcaagtttt ttggggtcga ggtgccgtaa agcactaaat cggaacccta  18720
aagggagccc ccgatttaga gcttgacggg gaaagccggc gaacgtggcg agaaaggaag  18780
```

-continued

```
ggaagaaagc gaaaggagcg ggcgctaggg cgctggcaag tgtagcggtc acgctgcgcg  18840

taaccaccac acccgccgcg cttaatgcgc cgctacaggg cgcgtcccat tcgccattca  18900

ggctgcgcaa ctgttgggaa gggcgatcgg tgcgggcctc ttcgctatta cgccagccac  18960

cgcggtg                                                            18967
```

<210> SEQ ID NO 17
<211> LENGTH: 1458
<212> TYPE: DNA
<213> ORGANISM: Yellow fever virus

<400> SEQUENCE: 17

```
atgcgagtcg tgattgccct actggtcttg gctgttggtc cggcctactc agctcactgc     60

attggaatta ctgacaggga tttcattgag ggggtgcatg gaggaacttg ggtttcagct    120

accctggagc aagacaagtg tgtcactgtt atggcccctg acaagccttc attggacatc    180

tcactagaga cagtagccat tgatagacct gctgaggtga ggaaagtgtg ttacaatgca    240

gttctcactc atgtgaagat taatgacaag tgccccagca ctggagaggc ccacctagct    300

gaagagaacg aaggggacaa tgcgtgcaag cgcacttatt ctgatagagg ctggggcaat    360

ggctgtggcc tatttgggaa agggagcatt gtggcatgcg ccaaattcac ttgtgccaaa    420

tccatgagtt tgtttgaggt tgatcagacc aaaattcagt atgtcatcag agcacaattg    480

catgtagggg ccaagcagga aaattggact accgacatta agactctcaa gtttgatgcc    540

ctgtcaggct cccaggaagt cgagttcatt gggtatggaa aagctacact ggaatgccag    600

gtgcaaactg cggtggactt tggtaacagt tacatcgctg agatggaaac agagagctgg    660

atagtggaca gacagtgggc ccaggacttg accctgccat ggcagagtgg aagtggcggg    720

gtgtggagag agatgcatca tcttgtcgaa tttgaacctc cgcatgccgc cactatcaga    780

gtactggccc tgggaaacca ggaaggctcc ttgaaaacag ctcttactgg cgcaatgagg    840

gttacaaagg acacaaatga caacaacctt tacaaactac atggtggaca tgtttcttgc    900

agagtgaaat tgtcagcttt gacactcaag ggacatcct acaaaaatatg cactgacaaa    960

atgtttttg tcaagaaccc aactgacact ggccatggca ctgttgtgat gcaggtgaaa   1020

gtgtcaaaag gagccccctg caggattcca gtgatagtag ctgatgatct tacagcggca   1080

atcaataaag gcattttggt tacagttaac cccatcgcct caaccaatga tgatgaagtg   1140

ctgattgagg tgaacccacc ttttggagac agctacatta tcgttgggag aggagattca   1200

cgtctcactt accagtggca caaagaggga agctcaatag gaaagttgtt cactcagacc   1260

atgaaaggcg tggaacgcct ggccgtcatg ggagacaccg cctgggattt cagctccgct   1320

ggagggttct tcacttcggt tgggaaagga attcatacgg tgtttggctc tgcctttcag   1380

gggctatttg gcggcttgaa ctggataaca aaggtcatca tgggggcggt acttatatgg   1440

gttggcatca acacataa                                                 1458
```

<210> SEQ ID NO 18
<211> LENGTH: 1488
<212> TYPE: DNA
<213> ORGANISM: West Nile virus

<400> SEQUENCE: 18

```
atgagagttg tgtttgtcgt gctattgctt ttggtggccc cagcttacag cttcaactgc     60

cttggaatga gcaacagaga cttcttggaa ggagtgtctg gagcaacatg ggtggatttg    120
```

-continued

```
gttctcgaag gcgacagctg cgtgactatc atgtctaagg acaagcctac catcgatgtg    180
aagatgatga atatggaggc ggtcaacctg gcagaggtcc gcagttattg ctatttggct    240
accgtcagcg atctctccac caaagctgcg tgcccgacca tgggagaagc tcacaatgac    300
aaacgtgctg acccagcttt tgtgtgcaga caaggagtgg tggacagggg ctggggcaac    360
ggctgcggat tatttggcaa aggaagcatt gacacatgcg ccaaatttgc ctgctctacc    420
aaggcaatag gaagaaccat cttgaaagag aatatcaagt acgaagtggc catttttgtc    480
catggaccaa ctactgtgga gtcgcacgga aactactcca cacaggttgg agccactcag    540
gcagggagat tcagcatcac tcctgcggcg ccttcataca cactaaagct tggagaatat    600
ggagaggtga cagtggactg tgaaccacgg tcagggattg acaccaatgc atactacgtg    660
atgactgttg gaacaaagac gttcttggtc catcgtgagt ggttcatgga cctcaacctc    720
ccttggagca gtgctggaag tactgtgtgg aggaacagag agacgttaat ggagtttgag    780
gaaccacacg ccacgaagca gtctgtgata gcattgggct cacaagaggg agctctgcat    840
caagctttgg ctggagccat tcctgtggaa ttttcaagca acactgtcaa gttgacgtcg    900
ggtcatttga agtgtagagt gaagatggaa aaattgcagt tgaagggaac aacctatggc    960
gtctgttcaa aggctttcaa gtttcttggg actcccgcag acacaggtca cggcactgtg   1020
gtgttggaat tgcagtacac tggcacggat ggaccttgca aagttcctat ctcgtcagtg   1080
gcttcattga acgacctaac gccagtgggc agattggtca ctgtcaaccc ttttgtttca   1140
gtggccacgg ccaacgctaa ggtcctgatt gaattggaac cacccctttgg agactcatac   1200
atagtggtgg gcagaggaga acaacagatc aatcaccatt ggcacaagtc tggaagcagc   1260
attggcaaag cctttacaac caccctcaaa ggagcgcaga gactagccgc tctaggagac   1320
acagcttggg actttggatc agttggaggg gtgttcacct cagttgggaa ggctgtccat   1380
caagtgttcg gaggagcatt ccgctcactg ttcggaggca tgtcctggat aacgcaagga   1440
ttgctggggg ctctcctgtt gtggatgggc atcaatgctc gtgattaa                1488
```

<210> SEQ ID NO 19
<211> LENGTH: 1110
<212> TYPE: DNA
<213> ORGANISM: West Nile virus

<400> SEQUENCE: 19

```
atgaggtcca tagctctcac gtttctcgca gttggaggag ttctgctctt cctctccgtg     60
aacgtgcacg ctgacactgg gtgtgccata gacatcagcc ggcaagagct gagatgtgga    120
agtggagtgt tcatacacaa tgatgtggag gcttggatgg accggtacaa gtattaccct    180
gaaacgccac aaggcctagc caagatcatt cagaaagctc ataaggaagg agtgtgcggt    240
ctacgatcag tttccagact ggagcatcaa atgtgggaag cagtgaagga cgagctgaac    300
actcttttga aggagaatgg tgtggacctt agtgtcgtgg ttgagaaaca ggagggaatg    360
tacaagtcag cacctaaacg cctcaccgcc accacggaaa aattggaaat tggctggaag    420
gcctggggaa agagtatttt atttgcacca gaactcgcca acaacacctt tgtggttgat    480
ggtccggaga ccaaggaatg tccgactcag aatcgcgctt ggaatagctt agaagtggag    540
gattttggat ttggtctcac cagcactcgg atgttcctga aggtcagaga gagcaacaca    600
actgaatgtg actcgaagat cattggaacg gctgtcaaga acaacttggc gatccacagt    660
gacctgtcct attggattga aagcaggctc aatgatacgt ggaagcttga aagggcagtt    720
ctgggtgaag tcaaatcatg tacgtggcct gagacgcata ccttgtgggg cgatggaatc    780
```

-continued cttgagagtg acttgataat accagtcaca ctggcgggac cacgaagcaa tcacaatcgg 840
agacctgggt acaagacaca aaaccagggc ccatgggacg aaggccgggt agagattgac 900
ttcgattact gcccaggaac tacggtcacc ctgagtgaga gctgcggaca ccgtggacct 960
gccactcgca ccaccacaga gagcggaaag ttgataacag attggtgctg caggagctgc 1020
accttaccac cactgcgcta ccaaactgac agcggctgtt ggtatggtat ggagatcaga 1080
ccacagagac atgatgaaaa gacctaatga 1110

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
tatcgtacga tgagagttgt gtttgtcgtg cta 33

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
atagcgcgct tagacagcct tcccaactga 30

<210> SEQ ID NO 22
<211> LENGTH: 1380
<212> TYPE: DNA
<213> ORGANISM: Artificial Sequence
<220> FEATURE:
<223> OTHER INFORMATION: Description of Artificial Sequence: Synthetic
polynucleotide sequence of the WNV env gene

<400> SEQUENCE: 22
atgagagttg tgtttgtcgt gctattgctt ttggtggccc cagcttacag cttcaactgc 60
cttggaatga gcaacagaga cttcttggaa ggagtgtctg gagcaacatg ggtggatttg 120
gttctcgaag gcgacagctg cgtgactatc atgtctaagg acaagcctac catcgatgtg 180
aagatgatga atatggaggc ggtcaacctg gcagaggtcc gcagttattg ctatttggct 240
accgtcagcg atctctccac caaagctgcg tgcccgacca tgggagaagc tcacaatgac 300
aaacgtgctg acccagcttt tgtgtgcaga caaggagtgg tggacagggg ctggggcaac 360
ggctgcggat tatttggcaa aggaagcatt gacacatgcg ccaaatttgc ctgctctacc 420
aaggcaatag gaagaaccat cttgaaagag aatatcaagt acgaagtggc catttttgtc 480
catggaccaa ctactgtgga gtcgcacgga aactactcca cacaggttgg agccactcag 540
gcagggagat tcagcatcac tcctgcggcg ccttcataca cactaaagct tggagaatat 600
ggagaggtga cagtggactg tgaaccacgg tcagggattg acaccaatgc atactacgtg 660
atgactgttg gaacaaagac gttcttggtc catcgtgagt ggttcatgga cctcaacctc 720
ccttggagca gtgctggaag tactgtgtgg aggaacagag agacgttaat ggagtttgag 780
gaaccacacg ccacgaagca gtctgtgata gcattgggct cacaagaggg agctctgcat 840
caagctttgg ctggagccat tcctgtggaa ttttcaagca acactgtcaa gttgacgtcg 900
ggtcatttga agtgtagagt gaagatggaa aaattgcagt tgaagggaac aacctatggc 960
gtctgttcaa aggctttcaa gtttcttggg actcccgcag acacaggtca cggcactgtg 1020
gtgttggaat tgcagtacac tggcacggat ggaccttgca aagttcctat ctcgtcagtg 1080
gcttcattga acgacctaac gccagtgggc agattggtca ctgtcaaccc ttttgtttca 1140
gtggccacgg ccaacgctaa ggtcctgatt gaattggaac caccctttgg agactcatac 1200
atagtggtgg gcagaggaga acaacagatc aatcaccatt ggcacaagtc tggaagcagc 1260
attggcaaag cctttacaac caccctcaaa ggagcgcaga gactagccgc tctaggagac 1320
acagcttggg actttggatc agttggaggg gtgttcacct cagttgggaa ggctgtctaa 1380

<210> SEQ ID NO 23
<211> LENGTH: 459
<212> TYPE: PRT
<213> ORGANISM: Artificial Sequence
<220> FEATURE:
<223> OTHER INFORMATION: Description of Artificial Sequence: Synthetic
WNV polypeptide sequence

<400> SEQUENCE: 23

Met Arg Val Val Phe Val Val Leu Leu Leu Leu Val Ala Pro Ala Tyr
1 5 10 15

Ser Phe Asn Cys Leu Gly Met Ser Asn Arg Asp Phe Leu Glu Gly Val
20 25 30

Ser Gly Ala Thr Trp Val Asp Leu Val Leu Glu Gly Asp Ser Cys Val
35 40 45

Thr Ile Met Ser Lys Asp Lys Pro Thr Ile Asp Val Lys Met Met Asn
50 55 60

Met Glu Ala Val Asn Leu Ala Glu Val Arg Ser Tyr Cys Tyr Leu Ala
65 70 75 80

Thr Val Ser Asp Leu Ser Thr Lys Ala Ala Cys Pro Thr Met Gly Glu
85 90 95

Ala His Asn Asp Lys Arg Ala Asp Pro Ala Phe Val Cys Arg Gln Gly
100 105 110

Val Val Asp Arg Gly Trp Gly Asn Gly Cys Gly Leu Phe Gly Lys Gly
115 120 125

Ser Ile Asp Thr Cys Ala Lys Phe Ala Cys Ser Thr Lys Ala Ile Gly
130 135 140

Arg Thr Ile Leu Lys Glu Asn Ile Lys Tyr Glu Val Ala Ile Phe Val
145 150 155 160

His Gly Pro Thr Thr Val Glu Ser His Gly Asn Tyr Ser Thr Gln Val
165 170 175

Gly Ala Thr Gln Ala Gly Arg Phe Ser Ile Thr Pro Ala Ala Pro Ser
180 185 190

Tyr Thr Leu Lys Leu Gly Glu Tyr Gly Glu Val Thr Val Asp Cys Glu
195 200 205

Pro Arg Ser Gly Ile Asp Thr Asn Ala Tyr Tyr Val Met Thr Val Gly
210 215 220

Thr Lys Thr Phe Leu Val His Arg Glu Trp Phe Met Asp Leu Asn Leu
225 230 235 240

Pro Trp Ser Ser Ala Gly Ser Thr Val Trp Arg Asn Arg Glu Thr Leu
245 250 255

Met Glu Phe Glu Glu Pro His Ala Thr Lys Gln Ser Val Ile Ala Leu
260 265 270

-continued

```
Gly Ser Gln Glu Gly Ala Leu His Gln Ala Leu Ala Gly Ala Ile Pro
        275                 280                 285

Val Glu Phe Ser Ser Asn Thr Val Lys Leu Thr Ser Gly His Leu Lys
    290                 295                 300

Cys Arg Val Lys Met Glu Lys Leu Gln Leu Lys Gly Thr Thr Tyr Gly
305                 310                 315                 320

Val Cys Ser Lys Ala Phe Lys Phe Leu Gly Thr Pro Ala Asp Thr Gly
                325                 330                 335

His Gly Thr Val Val Leu Glu Leu Gln Tyr Thr Gly Thr Asp Gly Pro
            340                 345                 350

Cys Lys Val Pro Ile Ser Ser Val Ala Ser Leu Asn Asp Leu Thr Pro
        355                 360                 365

Val Gly Arg Leu Val Thr Val Asn Pro Phe Val Ser Val Ala Thr Ala
    370                 375                 380

Asn Ala Lys Val Leu Ile Glu Leu Glu Pro Pro Phe Gly Asp Ser Tyr
385                 390                 395                 400

Ile Val Val Gly Arg Gly Glu Gln Gln Ile Asn His His Trp His Lys
                405                 410                 415

Ser Gly Ser Ser Ile Gly Lys Ala Phe Thr Thr Thr Leu Lys Gly Ala
            420                 425                 430

Gln Arg Leu Ala Ala Leu Gly Asp Thr Ala Trp Asp Phe Gly Ser Val
        435                 440                 445

Gly Gly Val Phe Thr Ser Val Gly Lys Ala Val
    450                 455
```

<210> SEQ ID NO 24
<211> LENGTH: 2046
<212> TYPE: DNA
<213> ORGANISM: Human immunodeficiency virus type 1

<400> SEQUENCE: 24

```
atgagagtga aggagaaata tcagcacttg tggagatggg ggtggagatg gggcaccatg     60

ctccttggga tgttgatgat ctgtagtgct acagaaaaat tgtgggtcac agtctattat    120

ggggtacctg tgtggagaga agcaaccacc actctatttt gtgcatcaga tgctaaagcc    180

tatgatacag aggtacataa tgtttgggcc acacatgcct gtgtacccac agaccccaac    240

ccacaagaag tagtattggg aaatgtgaca gaaaatttta acatgtggaa aaataacatg    300

gtagatcaga tgcatgagga tataatcagt ttatgggatg aaagcctaaa gccatgtgta    360

aaattaaccc cactctgtgt tactttaaat tgcactaatt tgaatatcac taagaatact    420

actaatctca ctagtagcag ctggggaatg atggaggaag gagaaataaa aaattgctct    480

ttctatatca ccacaagcat aagaaataag gtaaagaaag aatatgcact ttttaataga    540

cttgatgtag taccagtaaa aaatactagt aatactaagt ataggttaat aagttgtaac    600

acctcagtca ttacacaggc ctgtccaaag gtatcctttc agccaattcc catacattat    660

tgtgtcccgg ctgggtttgc gatactaaag tgtaacaata agacattcaa tggatcagga    720

ccatgcacaa atgtcagcac agtacaatgt acacatggaa ttaggccagt ggtgtcaact    780

caactgctgt taaatggcag tctagcagaa gaagacatag taattagatc tgaagatttc    840

acagacaatg ttaaaaccat aatagtacag ctaaatgaat ctgtagtaat taattgtaca    900

agacccaaca acaatacaag agaaaggtta tctataggac cagggagagc attttatgca    960

agaagaaaca taataggaga tataagacaa gcacattgta acattagtag agcaaaatgg   1020

aataacactt tacaacagat agttataaaa ttaagagaaa aatttaggaa taaaacaata   1080
```

```
gcctttaatc aatcctcagg aggggaccca gaaattgtaa tgcacagttt taattgtgga   1140

ggggaatttt tctactgtaa tacagcacaa ctgtttaata gtacttggaa tgttgctgga   1200

gggacaaatg gcactgaagg aaatgacata atcacactcc aatgcagaat aaaacaaatt   1260

ataaatatgt ggcagaaagt aggaaaagca atgtatgccc ctcccatcac aggacaaatt   1320

agatgttcat caaatattac agggctgcta ctaacaagag atggaggtaa tagtactgag   1380

actgagactg agatcttcag acctggagga ggagatatga gggacaattg gagaagtgaa   1440

ttatataaat ataaagtagt aagaattgaa ccaataggag tagcacccac cagggcaaag   1500

agaagaacag tgcaaagaga aaaaagagca gtgggaatag gagctgtgtt ccttgggttc   1560

ttgggagcag caggaagcac tatgggcgca gcgtcagtga cgctgacggt acaggccagg   1620

ctattattgt ctggtatagt gcagcagcag aacaatctgc tgagggctat tgaggcgcaa   1680

cagaatatgt tgcgactcac agtctggggc atcaagcagc tccaggcaag agtcctggct   1740

ctggaaagat acctaaggga tcaacagctc atgggaattt ggggttgctc tggaaaactc   1800

atttgcacca cttctgtgcc ttggaatgtt agttggagta ataaatctgt ggatgatatt   1860

tggaataaca tgacctggat ggagtgggaa agagaaattg acaattacac agactatata   1920

tatgacttac ttgaaaaatc gcaaacccaa caagaaaaga atgaaaaaga attattggaa   1980

ttggataaat gggcaagttt gtggaattgg tttgacataa caaactggct gtggtatata   2040

agataa                                                              2046
```

<210> SEQ ID NO 25
<211> LENGTH: 681
<212> TYPE: PRT
<213> ORGANISM: Human immunodeficiency virus type 1

<400> SEQUENCE: 25

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Arg Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Gly Asn Val Thr Glu Asn Phe Asn Met Trp
                85                  90                  95

Lys Asn Asn Met Val Asp Gln Met His Glu Asp Ile Ile Ser Leu Trp
            100                 105                 110

Asp Glu Ser Leu Lys Pro Cys Val Lys Leu Thr Pro Leu Cys Val Thr
        115                 120                 125

Leu Asn Cys Thr Asn Leu Asn Ile Thr Lys Asn Thr Thr Asn Leu Thr
    130                 135                 140

Ser Ser Ser Trp Gly Met Met Glu Glu Gly Glu Ile Lys Asn Cys Ser
145                 150                 155                 160

Phe Tyr Ile Thr Thr Ser Ile Arg Asn Lys Val Lys Lys Glu Tyr Ala
                165                 170                 175

Leu Phe Asn Arg Leu Asp Val Val Pro Val Lys Asn Thr Ser Asn Thr
            180                 185                 190
```

-continued

```
Lys Tyr Arg Leu Ile Ser Cys Asn Thr Ser Val Ile Thr Gln Ala Cys
        195                 200                 205

Pro Lys Val Ser Phe Gln Pro Ile Pro Ile His Tyr Cys Val Pro Ala
    210                 215                 220

Gly Phe Ala Ile Leu Lys Cys Asn Asn Lys Thr Phe Asn Gly Ser Gly
225                 230                 235                 240

Pro Cys Thr Asn Val Ser Thr Val Gln Cys Thr His Gly Ile Arg Pro
                245                 250                 255

Val Val Ser Thr Gln Leu Leu Leu Asn Gly Ser Leu Ala Glu Glu Asp
            260                 265                 270

Ile Val Ile Arg Ser Glu Asp Phe Thr Asp Asn Val Lys Thr Ile Ile
        275                 280                 285

Val Gln Leu Asn Glu Ser Val Val Ile Asn Cys Thr Arg Pro Asn Asn
    290                 295                 300

Asn Thr Arg Glu Arg Leu Ser Ile Gly Pro Gly Arg Ala Phe Tyr Ala
305                 310                 315                 320

Arg Arg Asn Ile Ile Gly Asp Ile Arg Gln Ala His Cys Asn Ile Ser
                325                 330                 335

Arg Ala Lys Trp Asn Asn Thr Leu Gln Gln Ile Val Ile Lys Leu Arg
            340                 345                 350

Glu Lys Phe Arg Asn Lys Thr Ile Ala Phe Asn Gln Ser Ser Gly Gly
        355                 360                 365

Asp Pro Glu Ile Val Met His Ser Phe Asn Cys Gly Gly Glu Phe Phe
    370                 375                 380

Tyr Cys Asn Thr Ala Gln Leu Phe Asn Ser Thr Trp Asn Val Ala Gly
385                 390                 395                 400

Gly Thr Asn Gly Thr Glu Gly Asn Asp Ile Ile Thr Leu Gln Cys Arg
                405                 410                 415

Ile Lys Gln Ile Ile Asn Met Trp Gln Lys Val Gly Lys Ala Met Tyr
            420                 425                 430

Ala Pro Pro Ile Thr Gly Gln Ile Arg Cys Ser Ser Asn Ile Thr Gly
        435                 440                 445

Leu Leu Leu Thr Arg Asp Gly Gly Asn Ser Thr Glu Thr Glu Thr Glu
    450                 455                 460

Ile Phe Arg Pro Gly Gly Gly Asp Met Arg Asp Asn Trp Arg Ser Glu
465                 470                 475                 480

Leu Tyr Lys Tyr Lys Val Val Arg Ile Glu Pro Ile Gly Val Ala Pro
                485                 490                 495

Thr Arg Ala Lys Arg Arg Thr Val Gln Arg Glu Lys Arg Ala Val Gly
            500                 505                 510

Ile Gly Ala Val Phe Leu Gly Phe Leu Gly Ala Ala Gly Ser Thr Met
        515                 520                 525

Gly Ala Ala Ser Val Thr Leu Thr Val Gln Ala Arg Leu Leu Leu Ser
    530                 535                 540

Gly Ile Val Gln Gln Gln Asn Asn Leu Leu Arg Ala Ile Glu Ala Gln
545                 550                 555                 560

Gln Asn Met Leu Arg Leu Thr Val Trp Gly Ile Lys Gln Leu Gln Ala
                565                 570                 575

Arg Val Leu Ala Leu Glu Arg Tyr Leu Arg Asp Gln Gln Leu Met Gly
            580                 585                 590

Ile Trp Gly Cys Ser Gly Lys Leu Ile Cys Thr Thr Ser Val Pro Trp
        595                 600                 605

Asn Val Ser Trp Ser Asn Lys Ser Val Asp Asp Ile Trp Asn Asn Met
```

-continued

```
    610                 615                 620

Thr Trp Met Glu Trp Glu Arg Glu Ile Asp Asn Tyr Thr Asp Tyr Ile
625                 630                 635                 640

Tyr Asp Leu Leu Glu Lys Ser Gln Thr Gln Gln Glu Lys Asn Glu Lys
                645                 650                 655

Glu Leu Leu Glu Leu Asp Lys Trp Ala Ser Leu Trp Asn Trp Phe Asp
            660                 665                 670

Ile Thr Asn Trp Leu Trp Tyr Ile Arg
        675                 680


<210> SEQ ID NO 26
<211> LENGTH: 2610
<212> TYPE: DNA
<213> ORGANISM: Human immunodeficiency virus type 1

<400> SEQUENCE: 26

atgagagtga aggagaaata tcagcacttg tggagatggg ggtggagatg gggcaccatg     60
ctccttggga tgttgatgat ctgtagtgct acagaaaaat tgtgggtcac agtctattat    120
ggggtacctg tgtggagaga agcaaccacc actctatttt gtgcatcaga tgctaaagcc    180
tatgatacag aggtacataa tgtttgggcc acacatgcct gtgtacccac agaccccaac    240
ccacaagaag tagtattggg aaatgtgaca gaaaatttta acatgtggaa aaataacatg    300
gtagatcaga tgcatgagga tataatcagt ttatgggatg aaagcctaaa gccatgtgta    360
aaattaaccc cactctgtgt tactttaaat tgcactaatt tgaatatcac taagaatact    420
actaatctca ctagtagcag ctggggaatg atggaggaag gagaaataaa aaattgctct    480
ttctatatca ccacaagcat aagaaataag gtaaagaaag aatatgcact tttaataga    540
cttgatgtag taccagtaaa aaatactagt aatactaagt ataggttaat aagttgtaac    600
acctcagtca ttacacaggc ctgtccaaag gtatcctttc agccaattcc catacattat    660
tgtgtcccgg ctgggtttgc gatactaaag tgtaacaata agacattcaa tggatcagga    720
ccatgcacaa atgtcagcac agtacaatgt acacatggaa ttaggccagt ggtgtcaact    780
caactgctgt taaatggcag tctagcagaa gaagacatag taattagatc tgaagatttc    840
acagacaatg ttaaaaccat aatagtacag ctaaatgaat ctgtagtaat taattgtaca    900
agacccaaca acaatacaag agaaaggtta tctataggac cagggagagc attttatgca    960
agaagaaaca taataggaga tataagacaa gcacattgta acattagtag agcaaaatgg   1020
aataacactt tacaacagat agttataaaa ttaagagaaa aatttaggaa taaaacaata   1080
gcctttaatc aatcctcagg aggggaccca gaaattgtaa tgcacagttt taattgtgga   1140
ggggaatttt tctactgtaa tacagcacaa ctgtttaata gtacttggaa tgttgctgga   1200
gggacaaatg gcactgaagg aaatgacata atcacactcc aatgcagaat aaaacaaatt   1260
ataaatatgt ggcagaaagt aggaaaagca atgtatgccc ctcccatcac aggacaaatt   1320
agatgttcat caaatattac agggctgcta ctaacaagag atggaggtaa tagtactgag   1380
actgagactg agatcttcag acctggagga ggagatatga gggacaattg gagaagtgaa   1440
ttatataaat ataaagtagt aagaattgaa ccaataggag tagcacccac cagggcaaag   1500
agaagaacag tgcaaagaga aaaaagagca gtgggaatag gagctgtgtt ccttgggttc   1560
ttgggagcag caggaagcac tatgggcgca gcgtcagtga cgctgacggt acaggccagg   1620
ctattattgt ctggtatagt gcagcagcag aacaatctgc tgagggctat tgaggcgcaa   1680
cagaatatgt tgcgactcac agtctggggc atcaagcagc tccaggcaag agtcctggct   1740
```

```
ctggaaagat acctaaggga tcaacagctc atgggaattt ggggttgctc tggaaaactc   1800

atttgcacca cttctgtgcc ttggaatgtt agttggagta ataaatctgt ggatgatatt   1860

tggaataaca tgacctggat ggagtgggaa agagaaattg acaattacac agactatata   1920

tatgacttac ttgaaaaatc gcaaacccaa caagaaaaga atgaaaaaga attattggaa   1980

ttggataaat gggcaagttt gtggaattgg tttgacataa caaactggct gtggtatata   2040

agattattca taatgatagt aggaggcttg ataggtttaa gaatagtttt tgctgtactt   2100

tctatagtaa atagagttag gcagggatat tcaccattat cgtttcagac cctcctccca   2160

gcctcgaggg gacccgacag gcccgaagga acagaagaag aaggtggaga gagagacaga   2220

gacagatccg gtccatcagt gaacggatcc ttggcactta tctgggacga tctgcggagc   2280

ctgtgcctct tcagctacca ccgcttgaga gacttactct tgattgtaac gaggattgtg   2340

gaacttctgg gacgcagggg gtgggaagcc ctcaaatatt ggtggaatct cctacagtat   2400

tggagtcagg aactaaagaa tagtgctgtt agcttgctac aatatgggtg gagctatttc   2460

catgaggcgg tccaggccgt ctggagatct gcgacagaga ctcttgcggg cgcgtgggga   2520

gacttatggg agactcttag gagaggtgga agatggatac tcgcaatccc caggaggatt   2580

agacaagggc ttgagctcac tctcttgtga                                    2610
```

<210> SEQ ID NO 27
<211> LENGTH: 869
<212> TYPE: PRT
<213> ORGANISM: Human immunodeficiency virus type 1

<400> SEQUENCE: 27

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Arg Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Gly Asn Val Thr Glu Asn Phe Asn Met Trp
                85                  90                  95

Lys Asn Asn Met Val Asp Gln Met His Glu Asp Ile Ile Ser Leu Trp
            100                 105                 110

Asp Glu Ser Leu Lys Pro Cys Val Lys Leu Thr Pro Leu Cys Val Thr
        115                 120                 125

Leu Asn Cys Thr Asn Leu Asn Ile Thr Lys Asn Thr Thr Asn Leu Thr
    130                 135                 140

Ser Ser Ser Trp Gly Met Met Glu Glu Gly Glu Ile Lys Asn Cys Ser
145                 150                 155                 160

Phe Tyr Ile Thr Thr Ser Ile Arg Asn Lys Val Lys Lys Glu Tyr Ala
                165                 170                 175

Leu Phe Asn Arg Leu Asp Val Val Pro Val Lys Asn Thr Ser Asn Thr
            180                 185                 190

Lys Tyr Arg Leu Ile Ser Cys Asn Thr Ser Val Ile Thr Gln Ala Cys
        195                 200                 205

Pro Lys Val Ser Phe Gln Pro Ile Pro Ile His Tyr Cys Val Pro Ala
```

-continued

```
    210                 215                 220

Gly Phe Ala Ile Leu Lys Cys Asn Asn Lys Thr Phe Asn Gly Ser Gly
225                 230                 235                 240

Pro Cys Thr Asn Val Ser Thr Val Gln Cys Thr His Gly Ile Arg Pro
                245                 250                 255

Val Val Ser Thr Gln Leu Leu Leu Asn Gly Ser Leu Ala Glu Glu Asp
            260                 265                 270

Ile Val Ile Arg Ser Glu Asp Phe Thr Asp Asn Val Lys Thr Ile Ile
        275                 280                 285

Val Gln Leu Asn Glu Ser Val Val Ile Asn Cys Thr Arg Pro Asn Asn
    290                 295                 300

Asn Thr Arg Glu Arg Leu Ser Ile Gly Pro Gly Arg Ala Phe Tyr Ala
305                 310                 315                 320

Arg Arg Asn Ile Ile Gly Asp Ile Arg Gln Ala His Cys Asn Ile Ser
                325                 330                 335

Arg Ala Lys Trp Asn Asn Thr Leu Gln Gln Ile Val Ile Lys Leu Arg
            340                 345                 350

Glu Lys Phe Arg Asn Lys Thr Ile Ala Phe Asn Gln Ser Ser Gly Gly
        355                 360                 365

Asp Pro Glu Ile Val Met His Ser Phe Asn Cys Gly Gly Glu Phe Phe
    370                 375                 380

Tyr Cys Asn Thr Ala Gln Leu Phe Asn Ser Thr Trp Asn Val Ala Gly
385                 390                 395                 400

Gly Thr Asn Gly Thr Glu Gly Asn Asp Ile Ile Thr Leu Gln Cys Arg
                405                 410                 415

Ile Lys Gln Ile Ile Asn Met Trp Gln Lys Val Gly Lys Ala Met Tyr
            420                 425                 430

Ala Pro Pro Ile Thr Gly Gln Ile Arg Cys Ser Ser Asn Ile Thr Gly
        435                 440                 445

Leu Leu Leu Thr Arg Asp Gly Gly Asn Ser Thr Glu Thr Glu Thr Glu
    450                 455                 460

Ile Phe Arg Pro Gly Gly Gly Asp Met Arg Asp Asn Trp Arg Ser Glu
465                 470                 475                 480

Leu Tyr Lys Tyr Lys Val Val Arg Ile Glu Pro Ile Gly Val Ala Pro
                485                 490                 495

Thr Arg Ala Lys Arg Arg Thr Val Gln Arg Glu Lys Arg Ala Val Gly
            500                 505                 510

Ile Gly Ala Val Phe Leu Gly Phe Leu Gly Ala Ala Gly Ser Thr Met
        515                 520                 525

Gly Ala Ala Ser Val Thr Leu Thr Val Gln Ala Arg Leu Leu Leu Ser
    530                 535                 540

Gly Ile Val Gln Gln Gln Asn Asn Leu Leu Arg Ala Ile Glu Ala Gln
545                 550                 555                 560

Gln Asn Met Leu Arg Leu Thr Val Trp Gly Ile Lys Gln Leu Gln Ala
                565                 570                 575

Arg Val Leu Ala Leu Glu Arg Tyr Leu Arg Asp Gln Gln Leu Met Gly
            580                 585                 590

Ile Trp Gly Cys Ser Gly Lys Leu Ile Cys Thr Thr Ser Val Pro Trp
        595                 600                 605

Asn Val Ser Trp Ser Asn Lys Ser Val Asp Asp Ile Trp Asn Asn Met
    610                 615                 620

Thr Trp Met Glu Trp Glu Arg Glu Ile Asp Asn Tyr Thr Asp Tyr Ile
625                 630                 635                 640
```

```
Tyr Asp Leu Leu Glu Lys Ser Gln Thr Gln Gln Glu Lys Asn Glu Lys
                645                 650                 655

Glu Leu Leu Glu Leu Asp Lys Trp Ala Ser Leu Trp Asn Trp Phe Asp
            660                 665                 670

Ile Thr Asn Trp Leu Trp Tyr Ile Arg Leu Phe Ile Met Ile Val Gly
        675                 680                 685

Gly Leu Ile Gly Leu Arg Ile Val Phe Ala Val Leu Ser Ile Val Asn
    690                 695                 700

Arg Val Arg Gln Gly Tyr Ser Pro Leu Ser Phe Gln Thr Leu Leu Pro
705                 710                 715                 720

Ala Ser Arg Gly Pro Asp Arg Pro Glu Gly Thr Glu Glu Glu Gly Gly
                725                 730                 735

Glu Arg Asp Arg Asp Arg Ser Gly Pro Ser Val Asn Gly Ser Leu Ala
            740                 745                 750

Leu Ile Trp Asp Asp Leu Arg Ser Leu Cys Leu Phe Ser Tyr His Arg
        755                 760                 765

Leu Arg Asp Leu Leu Leu Ile Val Thr Arg Ile Val Glu Leu Leu Gly
    770                 775                 780

Arg Arg Gly Trp Glu Ala Leu Lys Tyr Trp Trp Asn Leu Leu Gln Tyr
785                 790                 795                 800

Trp Ser Gln Glu Leu Lys Asn Ser Ala Val Ser Leu Leu Gln Tyr Gly
                805                 810                 815

Trp Ser Tyr Phe His Glu Ala Val Gln Ala Val Trp Arg Ser Ala Thr
            820                 825                 830

Glu Thr Leu Ala Gly Ala Trp Gly Asp Leu Trp Glu Thr Leu Arg Arg
        835                 840                 845

Gly Gly Arg Trp Ile Leu Ala Ile Pro Arg Arg Ile Arg Gln Gly Leu
    850                 855                 860

Glu Leu Thr Leu Leu
865
```

<210> SEQ ID NO 28
<211> LENGTH: 2010
<212> TYPE: DNA
<213> ORGANISM: Human immunodeficiency virus type 1

<400> SEQUENCE: 28

```
atgagagtga aggagaaata tcagcacttg tggagatggg ggtggagatg gggcaccatg     60

ctccttggga tgttgatgat ctgtagtgct acagaaaaat tgtgggtcac agtctattat    120

ggggtacctg tgtggagaga agcaaccacc actctatttt gtgcatcaga tgctaaagcc    180

tatgatacag aggtacataa tgtttgggcc acacatgcct gtgtacccac agaccccaac    240

ccacaagaag tagtattggg aaatgtgaca gaaaatttta acatgtggaa aaataacatg    300

gtagatcaga tgcatgagga tataatcagt ttatgggatg aaagcctaaa gccatgtgta    360

aaattaaccc cactctgtgt tactttaaat tgcactaatt tgaatatcac taagaatact    420

actaatctca ctagtagcag ctggggaatg atggaggaag gagaaataaa aaattgctct    480

ttctatatca ccacaagcat aagaaataag gtaaagaaag aatatgcact ttttaataga    540

cttgatgtag taccagtaaa aaatactagt aatactaagt ataggttaat aagttgtaac    600

acctcagtca ttacacaggc ctgtccaaag gtatcctttc agccaattcc catacattat    660

tgtgtcccgg ctgggtttgc gatactaaag tgtaacaata agacattcaa tggatcagga    720

ccatgcacaa atgtcagcac agtacaatgt acacatggaa ttaggccagt ggtgtcaact    780
```

```
caactgctgt taaatggcag tctagcagaa gaagacatag taattagatc tgaagatttc    840

acagacaatg ttaaaaccat aatagtacag ctaaatgaat ctgtagtaat taattgtaca    900

agacccaaca acaatgctgc agaattggat aaatgggcaa gtgctgcaag acaagcacat    960

tgtaacatta gtagagcaaa atggaataac actttacaac agatagttat aaaattaaga   1020

gaaaaattta ggaataaaac aatagccttt aatcaatcct caggaggggga cccagaaatt   1080

gtaatgcaca gttttaattg tggaggggaa tttttctact gtaatacagc acaactgttt   1140

aatagtactt ggaatgttgc tggagggaca aatggcactg aaggaaatga cataatcaca   1200

ctccaatgca gaataaaaca aattataaat atgtggcaga aagtaggaaa agcaatgtat   1260

gcccctccca tcacaggaca aattagatgt tcatcaaata ttacagggct gctactaaca   1320

agagatggag gtaatagtac tgagactgag actgagatct tcagacctgg aggaggagat   1380

atgagggaca attggagaag tgaattatat aaatataaag tagtaagaat tgaaccaata   1440

ggagtagcac ccaccagggc aaagagaaga acagtgcaaa gagaaaaaag agcagtggga   1500

ataggagctg tgttccttgg gttcttggga gcagcaggaa gcactatggg cgcagcgtca   1560

gtgacgctga cggtacaggc caggctatta ttgtctggta tagtgcagca gcagaacaat   1620

ctgctgaggg ctattgaggc gcaacagaat atgttgcgac tcacagtctg gggcatcaag   1680

cagctccagg caagagtcct ggctctggaa agatacctaa gggatcaaca gctcatggga   1740

atttggggtt gctctggaaa actcatttgc accacttctg tgccttggaa tgttagttgg   1800

agtaataaat ctgtggatga tatttggaat aacatgacct ggatggagtg ggaaagagaa   1860

attgacaatt acacagacta tatatatgac ttacttgaaa aatcgcaaac ccaacaagaa   1920

aagaatgaaa aagaattatt ggaattggat aaatgggcaa gtttgtggaa ttggtttgac   1980

ataacaaact ggctgtggta tataagataa                                    2010
```

```
<210> SEQ ID NO 29
<211> LENGTH: 669
<212> TYPE: PRT
<213> ORGANISM: Human immunodeficiency virus type 1

<400> SEQUENCE: 29

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Arg Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Gly Asn Val Thr Glu Asn Phe Asn Met Trp
                85                  90                  95

Lys Asn Asn Met Val Asp Gln Met His Glu Asp Ile Ile Ser Leu Trp
            100                 105                 110

Asp Glu Ser Leu Lys Pro Cys Val Lys Leu Thr Pro Leu Cys Val Thr
        115                 120                 125

Leu Asn Cys Thr Asn Leu Asn Ile Thr Lys Asn Thr Thr Asn Leu Thr
    130                 135                 140

Ser Ser Ser Trp Gly Met Met Glu Glu Gly Glu Ile Lys Asn Cys Ser
```

-continued

```
145                 150                 155                 160

Phe Tyr Ile Thr Thr Ser Ile Arg Asn Lys Val Lys Lys Glu Tyr Ala
                165                 170                 175

Leu Phe Asn Arg Leu Asp Val Val Pro Val Lys Asn Thr Ser Asn Thr
            180                 185                 190

Lys Tyr Arg Leu Ile Ser Cys Asn Thr Ser Val Ile Thr Gln Ala Cys
        195                 200                 205

Pro Lys Val Ser Phe Gln Pro Ile Pro Ile His Tyr Cys Val Pro Ala
    210                 215                 220

Gly Phe Ala Ile Leu Lys Cys Asn Asn Lys Thr Phe Asn Gly Ser Gly
225                 230                 235                 240

Pro Cys Thr Asn Val Ser Thr Val Gln Cys Thr His Gly Ile Arg Pro
                245                 250                 255

Val Val Ser Thr Gln Leu Leu Leu Asn Gly Ser Leu Ala Glu Glu Asp
            260                 265                 270

Ile Val Ile Arg Ser Glu Asp Phe Thr Asp Asn Val Lys Thr Ile Ile
        275                 280                 285

Val Gln Leu Asn Glu Ser Val Val Ile Asn Cys Thr Arg Pro Asn Asn
    290                 295                 300

Asn Ala Ala Glu Leu Asp Lys Trp Ala Ser Ala Ala Arg Gln Ala His
305                 310                 315                 320

Cys Asn Ile Ser Arg Ala Lys Trp Asn Asn Thr Leu Gln Gln Ile Val
                325                 330                 335

Ile Lys Leu Arg Glu Lys Phe Arg Asn Lys Thr Ile Ala Phe Asn Gln
            340                 345                 350

Ser Ser Gly Gly Asp Pro Glu Ile Val Met His Ser Phe Asn Cys Gly
        355                 360                 365

Gly Glu Phe Phe Tyr Cys Asn Thr Ala Gln Leu Phe Asn Ser Thr Trp
    370                 375                 380

Asn Val Ala Gly Gly Thr Asn Gly Thr Glu Gly Asn Asp Ile Ile Thr
385                 390                 395                 400

Leu Gln Cys Arg Ile Lys Gln Ile Ile Asn Met Trp Gln Lys Val Gly
                405                 410                 415

Lys Ala Met Tyr Ala Pro Pro Ile Thr Gly Gln Ile Arg Cys Ser Ser
            420                 425                 430

Asn Ile Thr Gly Leu Leu Leu Thr Arg Asp Gly Gly Asn Ser Thr Glu
        435                 440                 445

Thr Glu Thr Glu Ile Phe Arg Pro Gly Gly Gly Asp Met Arg Asp Asn
    450                 455                 460

Trp Arg Ser Glu Leu Tyr Lys Tyr Lys Val Val Arg Ile Glu Pro Ile
465                 470                 475                 480

Gly Val Ala Pro Thr Arg Ala Lys Arg Arg Thr Val Gln Arg Glu Lys
                485                 490                 495

Arg Ala Val Gly Ile Gly Ala Val Phe Leu Gly Phe Leu Gly Ala Ala
            500                 505                 510

Gly Ser Thr Met Gly Ala Ala Ser Val Thr Leu Thr Val Gln Ala Arg
        515                 520                 525

Leu Leu Leu Ser Gly Ile Val Gln Gln Gln Asn Asn Leu Leu Arg Ala
    530                 535                 540

Ile Glu Ala Gln Gln Asn Met Leu Arg Leu Thr Val Trp Gly Ile Lys
545                 550                 555                 560

Gln Leu Gln Ala Arg Val Leu Ala Leu Glu Arg Tyr Leu Arg Asp Gln
                565                 570                 575
```

```
Gln Leu Met Gly Ile Trp Gly Cys Ser Gly Lys Leu Ile Cys Thr Thr
            580                 585                 590

Ser Val Pro Trp Asn Val Ser Trp Ser Asn Lys Ser Val Asp Asp Ile
        595                 600                 605

Trp Asn Asn Met Thr Trp Met Glu Trp Glu Arg Glu Ile Asp Asn Tyr
    610                 615                 620

Thr Asp Tyr Ile Tyr Asp Leu Leu Glu Lys Ser Gln Thr Gln Gln Glu
625                 630                 635                 640

Lys Asn Glu Lys Glu Leu Leu Glu Leu Asp Lys Trp Ala Ser Leu Trp
                645                 650                 655

Asn Trp Phe Asp Ile Thr Asn Trp Leu Trp Tyr Ile Arg
            660                 665
```

<210> SEQ ID NO 30
<211> LENGTH: 2574
<212> TYPE: DNA
<213> ORGANISM: Human immunodeficiency virus type 1

<400> SEQUENCE: 30

```
atgagagtga aggagaaata tcagcacttg tggagatggg ggtggagatg gggcaccatg     60

ctccttggga tgttgatgat ctgtagtgct acagaaaaat tgtgggtcac agtctattat    120

ggggtacctg tgtggagaga agcaaccacc actctatttt gtgcatcaga tgctaaagcc    180

tatgatacag aggtacataa tgtttgggcc acacatgcct gtgtacccac agaccccaac    240

ccacaagaag tagtattggg aaatgtgaca gaaaatttta acatgtggaa aaataacatg    300

gtagatcaga tgcatgagga tataatcagt ttatgggatg aaagcctaaa gccatgtgta    360

aaattaaccc cactctgtgt tactttaaat tgcactaatt tgaatatcac taagaatact    420

actaatctca ctagtagcag ctggggaatg atggaggaag gagaaataaa aaattgctct    480

ttctatatca ccacaagcat aagaaataag gtaaagaaag aatatgcact tttaatagaa    540

cttgatgtag taccagtaaa aaatactagt aatactaagt ataggttaat aagttgtaac    600

acctcagtca ttacacaggc ctgtccaaag gtatcctttc agccaattcc catacattat    660

tgtgtcccgg ctgggtttgc gatactaaag tgtaacaata agacattcaa tggatcagga    720

ccatgcacaa atgtcagcac agtacaatgt acacatggaa ttaggccagt ggtgtcaact    780

caactgctgt taaatggcag tctagcagaa gaagacatag taattagatc tgaagatttc    840

acagacaatg ttaaaaccat aatagtacag ctaaatgaat ctgtagtaat taattgtaca    900

agacccaaca acaatgctgc agaattggat aaatgggcaa gtgctgcaag acaagcacat    960

tgtaacatta gtagagcaaa atggaataac actttacaac agatagttat aaaattaaga   1020

gaaaaattta ggaataaaac aatagccttt aatcaatcct caggagggga cccagaaatt   1080

gtaatgcaca gttttaattg tggaggggaa tttttctact gtaatacagc acaactgttt   1140

aatagtactt ggaatgttgc tggagggaca aatggcactg aaggaaatga cataatcaca   1200

ctccaatgca gaataaaaca aattataaat atgtggcaga aagtaggaaa agcaatgtat   1260

gcccctccca tcacaggaca aattagatgt tcatcaaata ttacagggct gctactaaca   1320

agagatggag gtaatagtac tgagactgag actgagatct tcagacctgg aggaggagat   1380

atgagggaca attggagaag tgaattatat aaatataaag tagtaagaat tgaaccaata   1440

ggagtagcac ccaccagggc aaagagaaga acagtgcaaa gagaaaaaag agcagtggga   1500

ataggagctg tgttccttgg gttcttggga gcagcaggaa gcactatggg cgcagcgtca   1560
```

-continued

```
gtgacgctga cggtacaggc caggctatta ttgtctggta tagtgcagca gcagaacaat   1620

ctgctgaggg ctattgaggc gcaacagaat atgttgcgac tcacagtctg gggcatcaag   1680

cagctccagg caagagtcct ggctctggaa agatacctaa gggatcaaca gctcatggga   1740

atttggggtt gctctggaaa actcatttgc accacttctg tgccttggaa tgttagttgg   1800

agtaataaat ctgtggatga tatttggaat aacatgacct ggatggagtg ggaaagagaa   1860

attgacaatt acacagacta tatatatgac ttacttgaaa aatcgcaaac ccaacaagaa   1920

aagaatgaaa aagaattatt ggaattggat aaatgggcaa gtttgtggaa ttggtttgac   1980

ataacaaact ggctgtggta tataagatta ttcataatga tagtaggagg cttgataggt   2040

ttaagaatag tttttgctgt actttctata gtaaatagag ttaggcaggg atattcacca   2100

ttatcgtttc agaccctcct cccagcctcg aggggacccg acaggcccga aggaacagaa   2160

gaagaaggtg gagagagaga cagagacaga tccggtccat cagtgaacgg atccttggca   2220

cttatctggg acgatctgcg gagcctgtgc ctcttcagct accaccgctt gagagactta   2280

ctcttgattg taacgaggat tgtggaactt ctgggacgca gggggtggga agccctcaaa   2340

tattggtgga atctcctaca gtattggagt caggaactaa agaatagtgc tgttagcttg   2400

ctacaatatg ggtggagcta tttccatgag gcggtccagg ccgtctggag atctgcgaca   2460

gagactcttg cgggcgcgtg gggagactta tgggagactc ttaggagagg tggaagatgg   2520

atactcgcaa tccccaggag gattagacaa gggcttgagc tcactctctt gtga         2574
```

<210> SEQ ID NO 31
<211> LENGTH: 857
<212> TYPE: PRT
<213> ORGANISM: Human immunodeficiency virus type 1

<400> SEQUENCE: 31

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Arg Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Gly Asn Val Thr Glu Asn Phe Asn Met Trp
                85                  90                  95

Lys Asn Asn Met Val Asp Gln Met His Glu Asp Ile Ile Ser Leu Trp
            100                 105                 110

Asp Glu Ser Leu Lys Pro Cys Val Lys Leu Thr Pro Leu Cys Val Thr
        115                 120                 125

Leu Asn Cys Thr Asn Leu Asn Ile Thr Lys Asn Thr Thr Asn Leu Thr
    130                 135                 140

Ser Ser Ser Trp Gly Met Met Glu Glu Gly Glu Ile Lys Asn Cys Ser
145                 150                 155                 160

Phe Tyr Ile Thr Thr Ser Ile Arg Asn Lys Val Lys Lys Glu Tyr Ala
                165                 170                 175

Leu Phe Asn Arg Leu Asp Val Val Pro Val Lys Asn Thr Ser Asn Thr
            180                 185                 190

Lys Tyr Arg Leu Ile Ser Cys Asn Thr Ser Val Ile Thr Gln Ala Cys
```

-continued

```
        195                 200                 205

Pro Lys Val Ser Phe Gln Pro Ile Pro Ile His Tyr Cys Val Pro Ala
    210                 215                 220

Gly Phe Ala Ile Leu Lys Cys Asn Asn Lys Thr Phe Asn Gly Ser Gly
225                 230                 235                 240

Pro Cys Thr Asn Val Ser Thr Val Gln Cys Thr His Gly Ile Arg Pro
                245                 250                 255

Val Val Ser Thr Gln Leu Leu Leu Asn Gly Ser Leu Ala Glu Glu Asp
            260                 265                 270

Ile Val Ile Arg Ser Glu Asp Phe Thr Asp Asn Val Lys Thr Ile Ile
        275                 280                 285

Val Gln Leu Asn Glu Ser Val Val Ile Asn Cys Thr Arg Pro Asn Asn
    290                 295                 300

Asn Ala Ala Glu Leu Asp Lys Trp Ala Ser Ala Ala Arg Gln Ala His
305                 310                 315                 320

Cys Asn Ile Ser Arg Ala Lys Trp Asn Asn Thr Leu Gln Gln Ile Val
                325                 330                 335

Ile Lys Leu Arg Glu Lys Phe Arg Asn Lys Thr Ile Ala Phe Asn Gln
            340                 345                 350

Ser Ser Gly Gly Asp Pro Glu Ile Val Met His Ser Phe Asn Cys Gly
        355                 360                 365

Gly Glu Phe Phe Tyr Cys Asn Thr Ala Gln Leu Phe Asn Ser Thr Trp
    370                 375                 380

Asn Val Ala Gly Gly Thr Asn Gly Thr Glu Gly Asn Asp Ile Ile Thr
385                 390                 395                 400

Leu Gln Cys Arg Ile Lys Gln Ile Ile Asn Met Trp Gln Lys Val Gly
                405                 410                 415

Lys Ala Met Tyr Ala Pro Pro Ile Thr Gly Gln Ile Arg Cys Ser Ser
            420                 425                 430

Asn Ile Thr Gly Leu Leu Leu Thr Arg Asp Gly Gly Asn Ser Thr Glu
        435                 440                 445

Thr Glu Thr Glu Ile Phe Arg Pro Gly Gly Gly Asp Met Arg Asp Asn
    450                 455                 460

Trp Arg Ser Glu Leu Tyr Lys Tyr Lys Val Val Arg Ile Glu Pro Ile
465                 470                 475                 480

Gly Val Ala Pro Thr Arg Ala Lys Arg Arg Thr Val Gln Arg Glu Lys
                485                 490                 495

Arg Ala Val Gly Ile Gly Ala Val Phe Leu Gly Phe Leu Gly Ala Ala
            500                 505                 510

Gly Ser Thr Met Gly Ala Ala Ser Val Thr Leu Thr Val Gln Ala Arg
        515                 520                 525

Leu Leu Leu Ser Gly Ile Val Gln Gln Gln Asn Asn Leu Leu Arg Ala
    530                 535                 540

Ile Glu Ala Gln Gln Asn Met Leu Arg Leu Thr Val Trp Gly Ile Lys
545                 550                 555                 560

Gln Leu Gln Ala Arg Val Leu Ala Leu Glu Arg Tyr Leu Arg Asp Gln
                565                 570                 575

Gln Leu Met Gly Ile Trp Gly Cys Ser Gly Lys Leu Ile Cys Thr Thr
            580                 585                 590

Ser Val Pro Trp Asn Val Ser Trp Ser Asn Lys Ser Val Asp Asp Ile
        595                 600                 605

Trp Asn Asn Met Thr Trp Met Glu Trp Glu Arg Glu Ile Asp Asn Tyr
    610                 615                 620
```

```
Thr Asp Tyr Ile Tyr Asp Leu Leu Glu Lys Ser Gln Thr Gln Gln Glu
625                 630                 635                 640

Lys Asn Glu Lys Glu Leu Leu Glu Leu Asp Lys Trp Ala Ser Leu Trp
                645                 650                 655

Asn Trp Phe Asp Ile Thr Asn Trp Leu Trp Tyr Ile Arg Leu Phe Ile
            660                 665                 670

Met Ile Val Gly Gly Leu Ile Gly Leu Arg Ile Val Phe Ala Val Leu
        675                 680                 685

Ser Ile Val Asn Arg Val Arg Gln Gly Tyr Ser Pro Leu Ser Phe Gln
    690                 695                 700

Thr Leu Leu Pro Ala Ser Arg Gly Pro Asp Arg Pro Glu Gly Thr Glu
705                 710                 715                 720

Glu Glu Gly Gly Glu Arg Asp Arg Asp Arg Ser Gly Pro Ser Val Asn
                725                 730                 735

Gly Ser Leu Ala Leu Ile Trp Asp Asp Leu Arg Ser Leu Cys Leu Phe
            740                 745                 750

Ser Tyr His Arg Leu Arg Asp Leu Leu Leu Ile Val Thr Arg Ile Val
        755                 760                 765

Glu Leu Leu Gly Arg Arg Gly Trp Glu Ala Leu Lys Tyr Trp Trp Asn
    770                 775                 780

Leu Leu Gln Tyr Trp Ser Gln Glu Leu Lys Asn Ser Ala Val Ser Leu
785                 790                 795                 800

Leu Gln Tyr Gly Trp Ser Tyr Phe His Glu Ala Val Gln Ala Val Trp
                805                 810                 815

Arg Ser Ala Thr Glu Thr Leu Ala Gly Ala Trp Gly Asp Leu Trp Glu
            820                 825                 830

Thr Leu Arg Arg Gly Gly Arg Trp Ile Leu Ala Ile Pro Arg Arg Ile
        835                 840                 845

Arg Gln Gly Leu Glu Leu Thr Leu Leu
    850                 855
```

<210> SEQ ID NO 32
<211> LENGTH: 1842
<212> TYPE: DNA
<213> ORGANISM: Human immunodeficiency virus type 1

<400> SEQUENCE: 32

```
atgagagtga aggagaaata tcagcacttg tggagatggg ggtggagatg gggcaccatg     60

ctccttggga tgttgatgat ctgtagtgct acagaaaaat tgtgggtcac agtctattat    120

ggggtacctg tgtggagaga agcaaccacc actctatttt gtgcatcaga tgctaaagcc    180

tatgatacag aggtacataa tgtttgggcc acacatgcct gtgtacccac agaccccaac    240

ccacaagaag tagtattggg aaatgtgaca gaaaatttta acatgtggaa aaataacatg    300

gtagatcaga tgcatgagga tataatcagt ttatgggatg aaagcctaaa gccatgtgta    360

aaattaaccc cactctgtgt tactttaaat tgtaacacct cagtcattac acaggcctgt    420

ccaaaggtat cctttcagcc aattcccata cattattgtg tcccggctgg gtttgcgata    480

ctaaagtgta acaataagac attcaatgga tcaggaccat gcacaaatgt cagcacagta    540

caatgtacac atggaattag gccagtggtg tcaactcaac tgctgttaaa tggcagtcta    600

gcagaagaag acatagtaat tagatctgaa gatttcacag acaatgttaa aaccataata    660

gtacagctaa atgaatctgt agtaattaat tgtacaagac ccaacaacaa tacaagagaa    720

aggttatcta taggaccagg gagagcattt tatgcaagaa gaaacataat aggagatata    780
```

agacaagcac attgtaacat tagtagagca aaatggaata acactttaca acagatagtt 840
ataaaattaa gagaaaaatt taggaataaa acaatagcct ttaatcaatc ctcaggaggg 900
gacccagaaa ttgtaatgca cagttttaat tgtggagggg aatttttcta ctgtaataca 960
gcacaactgt ttaatagtac ttggaatgtt gctggaggga caaatggcac tgaaggaaat 1020
gacataatca cactccaatg cagaataaaa caaattataa atatgtggca gaaagtagga 1080
aaagcaatgt atgcccctcc catcacagga caaattagat gttcatcaaa tattacaggg 1140
ctgctactaa caagagatgg aggtaatagt actgagactg agactgagat cttcagacct 1200
ggaggaggag atatgaggga caattggaga agtgaattat ataaatataa agtagtaaga 1260
attgaaccaa taggagtagc acccaccagg gcaaagagaa gaacagtgca aagagaaaaa 1320
agagcagtgg gaataggagc tgtgttcctt gggttcttgg gagcagcagg aagcactatg 1380
ggcgcagcgt cagtgacgct gacggtacag gccaggctat tattgtctgg tatagtgcag 1440
cagcagaaca atctgctgag ggctattgag gcgcaacaga atatgttgcg actcacagtc 1500
tggggcatca agcagctcca ggcaagagtc ctggctctgg aaagatacct aagggatcaa 1560
cagctcatgg gaatttgggg ttgctctgga aaactcattt gcaccacttc tgtgccttgg 1620
aatgttagtt ggagtaataa atctgtggat gatatttgga ataacatgac ctggatggag 1680
tgggaaagag aaattgacaa ttacacagac tatatatatg acttacttga aaaatcgcaa 1740
acccaacaag aaaagaatga aaaagaatta ttggaattgg ataaatgggc aagtttgtgg 1800
aattggtttg acataacaaa ctggctgtgg tatataagat ga 1842

<210> SEQ ID NO 33
<211> LENGTH: 613
<212> TYPE: PRT
<213> ORGANISM: Human immunodeficiency virus type 1

<400> SEQUENCE: 33

Met Arg Val Lys Glu Lys Tyr Gln His Leu Trp Arg Trp Gly Trp Arg
1 5 10 15

Trp Gly Thr Met Leu Leu Gly Met Leu Met Ile Cys Ser Ala Thr Glu
20 25 30

Lys Leu Trp Val Thr Val Tyr Tyr Gly Val Pro Val Trp Arg Glu Ala
35 40 45

Thr Thr Thr Leu Phe Cys Ala Ser Asp Ala Lys Ala Tyr Asp Thr Glu
50 55 60

Val His Asn Val Trp Ala Thr His Ala Cys Val Pro Thr Asp Pro Asn
65 70 75 80

Pro Gln Glu Val Val Leu Gly Asn Val Thr Glu Asn Phe Asn Met Trp
85 90 95

Lys Asn Asn Met Val Asp Gln Met His Glu Asp Ile Ile Ser Leu Trp
100 105 110

Asp Glu Ser Leu Lys Pro Cys Val Lys Leu Thr Pro Leu Cys Val Thr
115 120 125

Leu Asn Cys Asn Thr Ser Val Ile Thr Gln Ala Cys Pro Lys Val Ser
130 135 140

Phe Gln Pro Ile Pro Ile His Tyr Cys Val Pro Ala Gly Phe Ala Ile
145 150 155 160

Leu Lys Cys Asn Asn Lys Thr Phe Asn Gly Ser Gly Pro Cys Thr Asn
165 170 175

Val Ser Thr Val Gln Cys Thr His Gly Ile Arg Pro Val Val Ser Thr

```
            180                 185                 190

Gln Leu Leu Leu Asn Gly Ser Leu Ala Glu Glu Asp Ile Val Ile Arg
        195                 200                 205

Ser Glu Asp Phe Thr Asp Asn Val Lys Thr Ile Ile Val Gln Leu Asn
    210                 215                 220

Glu Ser Val Val Ile Asn Cys Thr Arg Pro Asn Asn Asn Thr Arg Glu
225                 230                 235                 240

Arg Leu Ser Ile Gly Pro Gly Arg Ala Phe Tyr Ala Arg Arg Asn Ile
                245                 250                 255

Ile Gly Asp Ile Arg Gln Ala His Cys Asn Ile Ser Arg Ala Lys Trp
            260                 265                 270

Asn Asn Thr Leu Gln Gln Ile Val Ile Lys Leu Arg Glu Lys Phe Arg
        275                 280                 285

Asn Lys Thr Ile Ala Phe Asn Gln Ser Ser Gly Gly Asp Pro Glu Ile
    290                 295                 300

Val Met His Ser Phe Asn Cys Gly Gly Glu Phe Phe Tyr Cys Asn Thr
305                 310                 315                 320

Ala Gln Leu Phe Asn Ser Thr Trp Asn Val Ala Gly Gly Thr Asn Gly
                325                 330                 335

Thr Glu Gly Asn Asp Ile Ile Thr Leu Gln Cys Arg Ile Lys Gln Ile
            340                 345                 350

Ile Asn Met Trp Gln Lys Val Gly Lys Ala Met Tyr Ala Pro Pro Ile
        355                 360                 365

Thr Gly Gln Ile Arg Cys Ser Ser Asn Ile Thr Gly Leu Leu Leu Thr
    370                 375                 380

Arg Asp Gly Gly Asn Ser Thr Glu Thr Glu Thr Glu Ile Phe Arg Pro
385                 390                 395                 400

Gly Gly Gly Asp Met Arg Asp Asn Trp Arg Ser Glu Leu Tyr Lys Tyr
                405                 410                 415

Lys Val Val Arg Ile Glu Pro Ile Gly Val Ala Pro Thr Arg Ala Lys
            420                 425                 430

Arg Arg Thr Val Gln Arg Glu Lys Arg Ala Val Gly Ile Gly Ala Val
        435                 440                 445

Phe Leu Gly Phe Leu Gly Ala Ala Gly Ser Thr Met Gly Ala Ala Ser
    450                 455                 460

Val Thr Leu Thr Val Gln Ala Arg Leu Leu Leu Ser Gly Ile Val Gln
465                 470                 475                 480

Gln Gln Asn Asn Leu Leu Arg Ala Ile Glu Ala Gln Gln Asn Met Leu
                485                 490                 495

Arg Leu Thr Val Trp Gly Ile Lys Gln Leu Gln Ala Arg Val Leu Ala
            500                 505                 510

Leu Glu Arg Tyr Leu Arg Asp Gln Gln Leu Met Gly Ile Trp Gly Cys
        515                 520                 525

Ser Gly Lys Leu Ile Cys Thr Thr Ser Val Pro Trp Asn Val Ser Trp
    530                 535                 540

Ser Asn Lys Ser Val Asp Asp Ile Trp Asn Asn Met Thr Trp Met Glu
545                 550                 555                 560

Trp Glu Arg Glu Ile Asp Asn Tyr Thr Asp Tyr Ile Tyr Asp Leu Leu
                565                 570                 575

Glu Lys Ser Gln Thr Gln Gln Glu Lys Asn Glu Lys Glu Leu Leu Glu
            580                 585                 590

Leu Asp Lys Trp Ala Ser Leu Trp Asn Trp Phe Asp Ile Thr Asn Trp
        595                 600                 605
```

-continued

Leu Trp Tyr Ile Arg
610

<210> SEQ ID NO 34
<211> LENGTH: 2406
<212> TYPE: DNA
<213> ORGANISM: Human immunodeficiency virus type 1

<400> SEQUENCE: 34
atgagagtga aggagaaata tcagcacttg tggagatggg ggtggagatg gggcaccatg 60
ctccttggga tgttgatgat ctgtagtgct acagaaaaat tgtgggtcac agtctattat 120
ggggtacctg tgtggagaga agcaaccacc actctatttt gtgcatcaga tgctaaagcc 180
tatgatacag aggtacataa tgtttgggcc acacatgcct gtgtacccac agaccccaac 240
ccacaagaag tagtattggg aaatgtgaca gaaaatttta acatgtggaa aaataacatg 300
gtagatcaga tgcatgagga tataatcagt ttatgggatg aaagcctaaa gccatgtgta 360
aaattaaccc cactctgtgt tactttaaat tgtaacacct cagtcattac acaggcctgt 420
ccaaaggtat cctttcagcc aattcccata cattattgtg tcccggctgg gtttgcgata 480
ctaaagtgta acaataagac attcaatgga tcaggaccat gcacaaatgt cagcacagta 540
caatgtacac atggaattag gccagtggtg tcaactcaac tgctgttaaa tggcagtcta 600
gcagaagaag acatagtaat tagatctgaa gatttcacag acaatgttaa aaccataata 660
gtacagctaa atgaatctgt agtaattaat tgtacaagac ccaacaacaa tacaagagaa 720
aggttatcta taggaccagg gagagcattt tatgcaagaa gaaacataat aggagatata 780
agacaagcac attgtaacat tagtagagca aaatggaata acactttaca acagatagtt 840
ataaaattaa gagaaaaatt taggaataaa acaatagcct ttaatcaatc ctcaggaggg 900
gacccagaaa ttgtaatgca cagttttaat tgtggagggg aatttttcta ctgtaataca 960
gcacaactgt ttaatagtac ttggaatgtt gctggaggga caaatggcac tgaaggaaat 1020
gacataatca cactccaatg cagaataaaa caaattataa atatgtggca gaaagtagga 1080
aaagcaatgt atgcccctcc catcacagga caaattagat gttcatcaaa tattacaggg 1140
ctgctactaa caagagatgg aggtaatagt actgagactg agactgagat cttcagacct 1200
ggaggaggag atatgaggga caattggaga agtgaattat ataaatataa agtagtaaga 1260
attgaaccaa taggagtagc acccaccagg gcaaagagaa gaacagtgca aagagaaaaa 1320
agagcagtgg gaataggagc tgtgttcctt gggttcttgg gagcagcagg aagcactatg 1380
ggcgcagcgt cagtgacgct gacggtacag gccaggctat tattgtctgg tatagtgcag 1440
cagcagaaca atctgctgag ggctattgag gcgcaacaga atatgttgcg actcacagtc 1500
tggggcatca agcagctcca ggcaagagtc ctggctctgg aaagatacct aagggatcaa 1560
cagctcatgg gaatttgggg ttgctctgga aaactcattt gcaccacttc tgtgccttgg 1620
aatgttagtt ggagtaataa atctgtggat gatatttgga ataacatgac ctggatggag 1680
tgggaaagag aaattgacaa ttacacagac tatatatatg acttacttga aaaatcgcaa 1740
acccaacaag aaaagaatga aaaagaatta ttggaattgg ataaatgggc aagtttgtgg 1800
aattggtttg acataacaaa ctggctgtgg tatataagat tattcataat gatagtagga 1860
ggcttgatag gtttaagaat agtttttgct gtactttcta tagtaaatag agttaggcag 1920
ggatattcac cattatcgtt tcagaccctc ctcccagcct cgaggggacc cgacaggccc 1980
gaaggaacag aagaagaagg tggagagaga gacagagaca gatccggtcc atcagtgaac 2040

-continued

```
ggatccttgg cacttatctg ggacgatctg cggagcctgt gcctcttcag ctaccaccgc   2100

ttgagagact tactcttgat tgtaacgagg attgtggaac ttctgggacg cagggggtgg   2160

gaagccctca aatattggtg gaatctccta cagtattgga gtcaggaact aaagaatagt   2220

gctgttagct tgctacaata tgggtggagc tatttccatg aggcggtcca ggccgtctgg   2280

agatctgcga cagagactct tgcgggcgcg tggggagact tatgggagac tcttaggaga   2340

ggtggaagat ggatactcgc aatccccagg aggattagac aagggcttga gctcactctc   2400

ttgtga                                                              2406
```

```
<210> SEQ ID NO 35
<211> LENGTH: 801
<212> TYPE: PRT
<213> ORGANISM: Human immunodeficiency virus type 1

<400> SEQUENCE: 35

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Arg Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Gly Asn Val Thr Glu Asn Phe Asn Met Trp
                85                  90                  95

Lys Asn Asn Met Val Asp Gln Met His Glu Asp Ile Ile Ser Leu Trp
            100                 105                 110

Asp Glu Ser Leu Lys Pro Cys Val Lys Leu Thr Pro Leu Cys Val Thr
        115                 120                 125

Leu Asn Cys Asn Thr Ser Val Ile Thr Gln Ala Cys Pro Lys Val Ser
    130                 135                 140

Phe Gln Pro Ile Pro Ile His Tyr Cys Val Pro Ala Gly Phe Ala Ile
145                 150                 155                 160

Leu Lys Cys Asn Asn Lys Thr Phe Asn Gly Ser Gly Pro Cys Thr Asn
                165                 170                 175

Val Ser Thr Val Gln Cys Thr His Gly Ile Arg Pro Val Val Ser Thr
            180                 185                 190

Gln Leu Leu Leu Asn Gly Ser Leu Ala Glu Glu Asp Ile Val Ile Arg
        195                 200                 205

Ser Glu Asp Phe Thr Asp Asn Val Lys Thr Ile Ile Val Gln Leu Asn
    210                 215                 220

Glu Ser Val Val Ile Asn Cys Thr Arg Pro Asn Asn Asn Thr Arg Glu
225                 230                 235                 240

Arg Leu Ser Ile Gly Pro Gly Arg Ala Phe Tyr Ala Arg Arg Asn Ile
                245                 250                 255

Ile Gly Asp Ile Arg Gln Ala His Cys Asn Ile Ser Arg Ala Lys Trp
            260                 265                 270

Asn Asn Thr Leu Gln Gln Ile Val Ile Lys Leu Arg Glu Lys Phe Arg
        275                 280                 285

Asn Lys Thr Ile Ala Phe Asn Gln Ser Ser Gly Gly Asp Pro Glu Ile
    290                 295                 300
```

-continued

```
Val Met His Ser Phe Asn Cys Gly Gly Glu Phe Phe Tyr Cys Asn Thr
305                 310                 315                 320

Ala Gln Leu Phe Asn Ser Thr Trp Asn Val Ala Gly Gly Thr Asn Gly
                325                 330                 335

Thr Glu Gly Asn Asp Ile Ile Thr Leu Gln Cys Arg Ile Lys Gln Ile
            340                 345                 350

Ile Asn Met Trp Gln Lys Val Gly Lys Ala Met Tyr Ala Pro Pro Ile
        355                 360                 365

Thr Gly Gln Ile Arg Cys Ser Ser Asn Ile Thr Gly Leu Leu Leu Thr
    370                 375                 380

Arg Asp Gly Gly Asn Ser Thr Glu Thr Glu Thr Glu Ile Phe Arg Pro
385                 390                 395                 400

Gly Gly Gly Asp Met Arg Asp Asn Trp Arg Ser Glu Leu Tyr Lys Tyr
                405                 410                 415

Lys Val Val Arg Ile Glu Pro Ile Gly Val Ala Pro Thr Arg Ala Lys
            420                 425                 430

Arg Arg Thr Val Gln Arg Glu Lys Arg Ala Val Gly Ile Gly Ala Val
        435                 440                 445

Phe Leu Gly Phe Leu Gly Ala Ala Gly Ser Thr Met Gly Ala Ala Ser
    450                 455                 460

Val Thr Leu Thr Val Gln Ala Arg Leu Leu Leu Ser Gly Ile Val Gln
465                 470                 475                 480

Gln Gln Asn Asn Leu Leu Arg Ala Ile Glu Ala Gln Gln Asn Met Leu
                485                 490                 495

Arg Leu Thr Val Trp Gly Ile Lys Gln Leu Gln Ala Arg Val Leu Ala
            500                 505                 510

Leu Glu Arg Tyr Leu Arg Asp Gln Gln Leu Met Gly Ile Trp Gly Cys
        515                 520                 525

Ser Gly Lys Leu Ile Cys Thr Thr Ser Val Pro Trp Asn Val Ser Trp
    530                 535                 540

Ser Asn Lys Ser Val Asp Asp Ile Trp Asn Asn Met Thr Trp Met Glu
545                 550                 555                 560

Trp Glu Arg Glu Ile Asp Asn Tyr Thr Asp Tyr Ile Tyr Asp Leu Leu
                565                 570                 575

Glu Lys Ser Gln Thr Gln Gln Glu Lys Asn Glu Lys Glu Leu Leu Glu
            580                 585                 590

Leu Asp Lys Trp Ala Ser Leu Trp Asn Trp Phe Asp Ile Thr Asn Trp
        595                 600                 605

Leu Trp Tyr Ile Arg Leu Phe Ile Met Ile Val Gly Gly Leu Ile Gly
    610                 615                 620

Leu Arg Ile Val Phe Ala Val Leu Ser Ile Val Asn Arg Val Arg Gln
625                 630                 635                 640

Gly Tyr Ser Pro Leu Ser Phe Gln Thr Leu Leu Pro Ala Ser Arg Gly
                645                 650                 655

Pro Asp Arg Pro Glu Gly Thr Glu Glu Glu Gly Gly Glu Arg Asp Arg
            660                 665                 670

Asp Arg Ser Gly Pro Ser Val Asn Gly Ser Leu Ala Leu Ile Trp Asp
        675                 680                 685

Asp Leu Arg Ser Leu Cys Leu Phe Ser Tyr His Arg Leu Arg Asp Leu
    690                 695                 700

Leu Leu Ile Val Thr Arg Ile Val Glu Leu Leu Gly Arg Arg Gly Trp
705                 710                 715                 720
```

-continued

```
Glu Ala Leu Lys Tyr Trp Trp Asn Leu Leu Gln Tyr Trp Ser Gln Glu
                725                 730                 735

Leu Lys Asn Ser Ala Val Ser Leu Leu Gln Tyr Gly Trp Ser Tyr Phe
            740                 745                 750

His Glu Ala Val Gln Ala Val Trp Arg Ser Ala Thr Glu Thr Leu Ala
        755                 760                 765

Gly Ala Trp Gly Asp Leu Trp Glu Thr Leu Arg Arg Gly Gly Arg Trp
    770                 775                 780

Ile Leu Ala Ile Pro Arg Arg Ile Arg Gln Gly Leu Glu Leu Thr Leu
785                 790                 795                 800

Leu


<210> SEQ ID NO 36
<211> LENGTH: 1807
<212> TYPE: DNA
<213> ORGANISM: Human immunodeficiency virus type 1

<400> SEQUENCE: 36

atgagagtga aggagaaata tcagcacttg tggagatggg ggtggagatg ggcaccatg      60

ctccttggga tgttgatgat ctgtagtgct acagaaaaat tgtgggtcac agtctattat    120

ggggtacctg tgtggagaga agcaaccacc actctatttt gtgcatcaga tgctaaagcc    180

tatgatacag aggtacataa tgtttgggcc acacatgcct gtgtacccac agaccccaac    240

ccacaagaag tagtattggg aaatgtgaca gaaaatttta acatgtggaa aaataacatg    300

gtagatcaga tgcatgagga tataatcagt ttatgggatg aaagcctaaa gccatgtgta    360

aaattaaccc cactctgtgt tactttaaat tgtaacacct cagtcattac acaggcctgt    420

ccaaaggtat cctttcagcc aattcccata cattattgtg tcccggctgg gtttgcgata    480

ctaaagtgta acaataagac attcaatgga tcaggaccat gcacaaatgt cagcacagta    540

caatgtacac atggaattag gccagtggtg tcaactcaac tgctgttaaa tggcagtcta    600

gcagaagaag acatagtaat tagatctgaa gatttcacag acaatgttaa aaccataata    660

gtacagctaa atgaatctgt agtaattaat tgtacaagac ccaacaacaa tgctgcagaa    720

ttggataaat gggcaagtgc tgcaagacaa gcacattgta acattagtag agcaaaatgg    780

aataacactt tacaacagat agttataaaa ttaagagaaa aatttaggaa taaaacaata    840

gcctttaatc aatcctcagg aggggaccca gaaattgtaa tgcacagttt taattgtgga    900

ggggaatttt tctactgtaa tacagcacaa ctgtttaata gtacttggaa tgttgctgga    960

gggacaaatg gcactgaagg aaatgacata atcacactcc aatgcagaat aaaacaaatt   1020

ataaatatgt ggcagaaagt aggaaaagca atgtatgccc ctcccatcac aggacaaatt   1080

agatgttcat caaatattac agggctgcta ctaacaagag atggaggtaa tagtactgag   1140

actgagactg agatcttcag acctggagga ggagatatga gggacaattg gagaagtgaa   1200

ttatataaat ataaagtagt aagaattgaa ccaataggag tagcacccac cagggcaaag   1260

agaagaacag tgcaaagaga aaaaagagca gtgggaatag gagctgtgtt ccttgggttc   1320

ttgggagcag caggaagcac tatgggcgca gcgtcagtga cgctgacggt acaggccagg   1380

ctattattgt ctggtatagt gcagcagcag aacaatctgc tgagggctat tgaggcgcaa   1440

cagaatatgt tgcgactcac agtctggggc atcaagcagc tccaggcaag agtcctggct   1500

ctggaaagat acctaaggga tcaacagctc atgggaattt ggggttgctc tggaaaactc   1560

atttgcacca cttctgtgcc ttggaatgtt agttggagta ataaatctgt ggatgatatt   1620
```

-continued tggaataaca tgacctggat ggagtgggaa agagaaattg acaattacac agactatata 1680
tatgacttac ttgaaaaatc gcaaacccaa caagaaaaga atgaaaaaga attattggaa 1740
ttggataaat gggcaagttt gtggaattgg tttgacataa caaactggct gtggtatata 1800
agataat 1807

<210> SEQ ID NO 37
<211> LENGTH: 601
<212> TYPE: PRT
<213> ORGANISM: Human immunodeficiency virus type 1

<400> SEQUENCE: 37

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Arg Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Gly Asn Val Thr Glu Asn Phe Asn Met Trp
                85                  90                  95

Lys Asn Asn Met Val Asp Gln Met His Glu Asp Ile Ile Ser Leu Trp
            100                 105                 110

Asp Glu Ser Leu Lys Pro Cys Val Lys Leu Thr Pro Leu Cys Val Thr
        115                 120                 125

Leu Asn Cys Asn Thr Ser Val Ile Thr Gln Ala Cys Pro Lys Val Ser
    130                 135                 140

Phe Gln Pro Ile Pro Ile His Tyr Cys Val Pro Ala Gly Phe Ala Ile
145                 150                 155                 160

Leu Lys Cys Asn Asn Lys Thr Phe Asn Gly Ser Gly Pro Cys Thr Asn
                165                 170                 175

Val Ser Thr Val Gln Cys Thr His Gly Ile Arg Pro Val Val Ser Thr
            180                 185                 190

Gln Leu Leu Leu Asn Gly Ser Leu Ala Glu Glu Asp Ile Val Ile Arg
        195                 200                 205

Ser Glu Asp Phe Thr Asp Asn Val Lys Thr Ile Ile Val Gln Leu Asn
    210                 215                 220

Glu Ser Val Val Ile Asn Cys Thr Arg Pro Asn Asn Asn Ala Ala Glu
225                 230                 235                 240

Leu Asp Lys Trp Ala Ser Ala Ala Arg Gln Ala His Cys Asn Ile Ser
                245                 250                 255

Arg Ala Lys Trp Asn Asn Thr Leu Gln Gln Ile Val Ile Lys Leu Arg
            260                 265                 270

Glu Lys Phe Arg Asn Lys Thr Ile Ala Phe Asn Gln Ser Ser Gly Gly
        275                 280                 285

Asp Pro Glu Ile Val Met His Ser Phe Asn Cys Gly Gly Glu Phe Phe
    290                 295                 300

Tyr Cys Asn Thr Ala Gln Leu Phe Asn Ser Thr Trp Asn Val Ala Gly
305                 310                 315                 320

Gly Thr Asn Gly Thr Glu Gly Asn Asp Ile Ile Thr Leu Gln Cys Arg
                325                 330                 335

-continued

```
Ile Lys Gln Ile Ile Asn Met Trp Gln Lys Val Gly Lys Ala Met Tyr
            340                 345                 350

Ala Pro Pro Ile Thr Gly Gln Ile Arg Cys Ser Ser Asn Ile Thr Gly
        355                 360                 365

Leu Leu Leu Thr Arg Asp Gly Gly Asn Ser Thr Glu Thr Glu Thr Glu
    370                 375                 380

Ile Phe Arg Pro Gly Gly Gly Asp Met Arg Asp Asn Trp Arg Ser Glu
385                 390                 395                 400

Leu Tyr Lys Tyr Lys Val Val Arg Ile Glu Pro Ile Gly Val Ala Pro
                405                 410                 415

Thr Arg Ala Lys Arg Arg Thr Val Gln Arg Glu Lys Arg Ala Val Gly
            420                 425                 430

Ile Gly Ala Val Phe Leu Gly Phe Leu Gly Ala Ala Gly Ser Thr Met
        435                 440                 445

Gly Ala Ala Ser Val Thr Leu Thr Val Gln Ala Arg Leu Leu Leu Ser
    450                 455                 460

Gly Ile Val Gln Gln Gln Asn Asn Leu Leu Arg Ala Ile Glu Ala Gln
465                 470                 475                 480

Gln Asn Met Leu Arg Leu Thr Val Trp Gly Ile Lys Gln Leu Gln Ala
                485                 490                 495

Arg Val Leu Ala Leu Glu Arg Tyr Leu Arg Asp Gln Gln Leu Met Gly
            500                 505                 510

Ile Trp Gly Cys Ser Gly Lys Leu Ile Cys Thr Thr Ser Val Pro Trp
        515                 520                 525

Asn Val Ser Trp Ser Asn Lys Ser Val Asp Asp Ile Trp Asn Asn Met
    530                 535                 540

Thr Trp Met Glu Trp Glu Arg Glu Ile Asp Asn Tyr Thr Asp Tyr Ile
545                 550                 555                 560

Tyr Asp Leu Leu Glu Lys Ser Gln Thr Gln Gln Glu Lys Asn Glu Lys
                565                 570                 575

Glu Leu Leu Glu Leu Asp Lys Trp Ala Ser Leu Trp Asn Trp Phe Asp
            580                 585                 590

Ile Thr Asn Trp Leu Trp Tyr Ile Arg
        595                 600
```

<210> SEQ ID NO 38
<211> LENGTH: 2370
<212> TYPE: DNA
<213> ORGANISM: Human immunodeficiency virus type 1

<400> SEQUENCE: 38

```
atgagagtga aggagaaata tcagcacttg tggagatggg ggtggagatg gggcaccatg      60

ctccttggga tgttgatgat ctgtagtgct acagaaaaat tgtgggtcac agtctattat     120

ggggtacctg tgtggagaga agcaaccacc actctatttt gtgcatcaga tgctaaagcc     180

tatgatacag aggtacataa tgtttgggcc acacatgcct gtgtacccac agaccccaac     240

ccacaagaag tagtattggg aaatgtgaca gaaaatttta acatgtggaa aaataacatg     300

gtagatcaga tgcatgagga tataatcagt ttatgggatg aaagcctaaa gccatgtgta     360

aaattaaccc cactctgtgt tactttaaat tgtaacacct cagtcattac acaggcctgt     420

ccaaaggtat cctttcagcc aattcccata cattattgtg tcccggctgg gtttgcgata     480

ctaaagtgta acaataagac attcaatgga tcaggaccat gcacaaatgt cagcacagta     540

caatgtacac atggaattag gccagtggtg tcaactcaac tgctgttaaa tggcagtcta     600
```

-continued

```
gcagaagaag acatagtaat tagatctgaa gatttcacag acaatgttaa aaccataata    660

gtacagctaa atgaatctgt agtaattaat tgtacaagac ccaacaacaa tgctgcagaa    720

ttggataaat gggcaagtgc tgcaagacaa gcacattgta acattagtag agcaaaatgg    780

aataacactt tacaacagat agttataaaa ttaagagaaa aatttaggaa taaaacaata    840

gcctttaatc aatcctcagg aggggaccca gaaattgtaa tgcacagttt taattgtgga    900

ggggaatttt tctactgtaa tacagcacaa ctgtttaata gtacttggaa tgttgctgga    960

gggacaaatg gcactgaagg aaatgacata atcacactcc aatgcagaat aaaacaaatt   1020

ataaatatgt ggcagaaagt aggaaaagca atgtatgccc ctcccatcac aggacaaatt   1080

agatgttcat caaatattac agggctgcta ctaacaagag atggaggtaa tagtactgag   1140

actgagactg agatcttcag acctggagga ggagatatga gggacaattg gagaagtgaa   1200

ttatataaat ataaagtagt aagaattgaa ccaataggag tagcacccac cagggcaaag   1260

agaagaacag tgcaaagaga aaaaagagca gtgggaatag gagctgtgtt ccttgggttc   1320

ttgggagcag caggaagcac tatgggcgca gcgtcagtga cgctgacggt acaggccagg   1380

ctattattgt ctggtatagt gcagcagcag aacaatctgc tgagggctat tgaggcgcaa   1440

cagaatatgt tgcgactcac agtctggggc atcaagcagc tccaggcaag agtcctggct   1500

ctggaaagat acctaaggga tcaacagctc atgggaattt ggggttgctc tggaaaactc   1560

atttgcacca cttctgtgcc ttggaatgtt agttggagta ataaatctgt ggatgatatt   1620

tggaataaca tgacctggat ggagtgggaa agagaaattg acaattacac agactatata   1680

tatgacttac ttgaaaaatc gcaaacccaa caagaaaaga atgaaaaaga attattggaa   1740

ttggataaat gggcaagttt gtggaattgg tttgacataa caaactggct gtggtatata   1800

agattattca taatgatagt aggaggcttg ataggtttaa gaatagtttt tgctgtactt   1860

tctatagtaa atagagttag gcagggatat tcaccattat cgtttcagac cctcctccca   1920

gcctcgaggg gacccgacag gcccgaagga acagaagaag aaggtggaga gagagacaga   1980

gacagatccg gtccatcagt gaacggatcc ttggcactta tctgggacga tctgcggagc   2040

ctgtgcctct tcagctacca ccgcttgaga gacttactct tgattgtaac gaggattgtg   2100

gaacttctgg gacgcagggg gtgggaagcc ctcaaatatt ggtggaatct cctacagtat   2160

tggagtcagg aactaaagaa tagtgctgtt agcttgctac aatatgggtg gagctatttc   2220

catgaggcgg tccaggccgt ctggagatct gcgacagaga ctcttgcggg cgcgtgggga   2280

gacttatggg agactcttag gagaggtgga agatggatac tcgcaatccc caggaggatt   2340

agacaagggc ttgagctcac tctcttgtga                                    2370


<210> SEQ ID NO 39
<211> LENGTH: 789
<212> TYPE: PRT
<213> ORGANISM: Human immunodeficiency virus type 1

<400> SEQUENCE: 39

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Arg Glu Ala
        35                  40                  45

Thr Thr Thr Leu Phe Cys Ala Ser Asp Ala Lys Ala Tyr Asp Thr Glu
    50                  55                  60
```

-continued

```
Val His Asn Val Trp Ala Thr His Ala Cys Val Pro Thr Asp Pro Asn
65                  70                  75                  80

Pro Gln Glu Val Val Leu Gly Asn Val Thr Glu Asn Phe Asn Met Trp
                85                  90                  95

Lys Asn Asn Met Val Asp Gln Met His Glu Asp Ile Ile Ser Leu Trp
            100                 105                 110

Asp Glu Ser Leu Lys Pro Cys Val Lys Leu Thr Pro Leu Cys Val Thr
        115                 120                 125

Leu Asn Cys Asn Thr Ser Val Ile Thr Gln Ala Cys Pro Lys Val Ser
    130                 135                 140

Phe Gln Pro Ile Pro Ile His Tyr Cys Val Pro Ala Gly Phe Ala Ile
145                 150                 155                 160

Leu Lys Cys Asn Asn Lys Thr Phe Asn Gly Ser Gly Pro Cys Thr Asn
                165                 170                 175

Val Ser Thr Val Gln Cys Thr His Gly Ile Arg Pro Val Val Ser Thr
            180                 185                 190

Gln Leu Leu Leu Asn Gly Ser Leu Ala Glu Glu Asp Ile Val Ile Arg
        195                 200                 205

Ser Glu Asp Phe Thr Asp Asn Val Lys Thr Ile Ile Val Gln Leu Asn
    210                 215                 220

Glu Ser Val Val Ile Asn Cys Thr Arg Pro Asn Asn Asn Ala Ala Glu
225                 230                 235                 240

Leu Asp Lys Trp Ala Ser Ala Ala Arg Gln Ala His Cys Asn Ile Ser
                245                 250                 255

Arg Ala Lys Trp Asn Asn Thr Leu Gln Gln Ile Val Ile Lys Leu Arg
            260                 265                 270

Glu Lys Phe Arg Asn Lys Thr Ile Ala Phe Asn Gln Ser Ser Gly Gly
        275                 280                 285

Asp Pro Glu Ile Val Met His Ser Phe Asn Cys Gly Gly Glu Phe Phe
    290                 295                 300

Tyr Cys Asn Thr Ala Gln Leu Phe Asn Ser Thr Trp Asn Val Ala Gly
305                 310                 315                 320

Gly Thr Asn Gly Thr Glu Gly Asn Asp Ile Ile Thr Leu Gln Cys Arg
                325                 330                 335

Ile Lys Gln Ile Ile Asn Met Trp Gln Lys Val Gly Lys Ala Met Tyr
            340                 345                 350

Ala Pro Pro Ile Thr Gly Gln Ile Arg Cys Ser Ser Asn Ile Thr Gly
        355                 360                 365

Leu Leu Leu Thr Arg Asp Gly Gly Asn Ser Thr Glu Thr Glu Thr Glu
    370                 375                 380

Ile Phe Arg Pro Gly Gly Gly Asp Met Arg Asp Asn Trp Arg Ser Glu
385                 390                 395                 400

Leu Tyr Lys Tyr Lys Val Val Arg Ile Glu Pro Ile Gly Val Ala Pro
                405                 410                 415

Thr Arg Ala Lys Arg Arg Thr Val Gln Arg Glu Lys Arg Ala Val Gly
            420                 425                 430

Ile Gly Ala Val Phe Leu Gly Phe Leu Gly Ala Ala Gly Ser Thr Met
        435                 440                 445

Gly Ala Ala Ser Val Thr Leu Thr Val Gln Ala Arg Leu Leu Leu Ser
    450                 455                 460

Gly Ile Val Gln Gln Gln Asn Asn Leu Leu Arg Ala Ile Glu Ala Gln
465                 470                 475                 480
```

-continued

```
Gln Asn Met Leu Arg Leu Thr Val Trp Gly Ile Lys Gln Leu Gln Ala
                485                 490                 495

Arg Val Leu Ala Leu Glu Arg Tyr Leu Arg Asp Gln Gln Leu Met Gly
            500                 505                 510

Ile Trp Gly Cys Ser Gly Lys Leu Ile Cys Thr Thr Ser Val Pro Trp
        515                 520                 525

Asn Val Ser Trp Ser Asn Lys Ser Val Asp Asp Ile Trp Asn Asn Met
    530                 535                 540

Thr Trp Met Glu Trp Glu Arg Glu Ile Asp Asn Tyr Thr Asp Tyr Ile
545                 550                 555                 560

Tyr Asp Leu Leu Glu Lys Ser Gln Thr Gln Gln Glu Lys Asn Glu Lys
                565                 570                 575

Glu Leu Leu Glu Leu Asp Lys Trp Ala Ser Leu Trp Asn Trp Phe Asp
            580                 585                 590

Ile Thr Asn Trp Leu Trp Tyr Ile Arg Leu Phe Ile Met Ile Val Gly
        595                 600                 605

Gly Leu Ile Gly Leu Arg Ile Val Phe Ala Val Leu Ser Ile Val Asn
    610                 615                 620

Arg Val Arg Gln Gly Tyr Ser Pro Leu Ser Phe Gln Thr Leu Leu Pro
625                 630                 635                 640

Ala Ser Arg Gly Pro Asp Arg Pro Glu Gly Thr Glu Glu Glu Gly Gly
                645                 650                 655

Glu Arg Asp Arg Asp Arg Ser Gly Pro Ser Val Asn Gly Ser Leu Ala
            660                 665                 670

Leu Ile Trp Asp Asp Leu Arg Ser Leu Cys Leu Phe Ser Tyr His Arg
        675                 680                 685

Leu Arg Asp Leu Leu Leu Ile Val Thr Arg Ile Val Glu Leu Leu Gly
    690                 695                 700

Arg Arg Gly Trp Glu Ala Leu Lys Tyr Trp Trp Asn Leu Leu Gln Tyr
705                 710                 715                 720

Trp Ser Gln Glu Leu Lys Asn Ser Ala Val Ser Leu Leu Gln Tyr Gly
                725                 730                 735

Trp Ser Tyr Phe His Glu Ala Val Gln Ala Val Trp Arg Ser Ala Thr
            740                 745                 750

Glu Thr Leu Ala Gly Ala Trp Gly Asp Leu Trp Glu Thr Leu Arg Arg
        755                 760                 765

Gly Gly Arg Trp Ile Leu Ala Ile Pro Arg Arg Ile Arg Gln Gly Leu
    770                 775                 780

Glu Leu Thr Leu Leu
785
```

```
<210> SEQ ID NO 40
<211> LENGTH: 1092
<212> TYPE: DNA
<213> ORGANISM: Human immunodeficiency virus type 1

<400> SEQUENCE: 40

atgggcgccc gcgccagcgt gctgagcggc ggcgagctgg accgctggga gaagatccgc      60

ctgcgccccg gcggcaagaa gaagtacaag ctgaagcaca tcgtgtgggc cagccgcgag     120

ctggagcgct tcgccgtgaa ccccggcctg ctggagacca gcgagggctg ccgccagatc     180

ctgggccagc tgcagcccag cctgcagacc ggcagcgagg agctgcgcag cctgtacaac     240

accgtggcca ccctgtactg cgtgcaccag cgcatcgagg tgaaggacac caaggaggcc     300

ctggagaaga tcgaggagga gcagaacaag agcaagaaga aggcccagca ggccgccgcc     360
```

-continued

```
gacaccggca acagcagcca agtgagccag aactacccca tcgtgcagaa cctgcagggc    420

cagatggtgc accaggccat cagcccccgc accctgaacg cctgggtgaa ggtggtggag    480

gagaaggcct tcagccccga ggtgatcccc atgttcagcg ccctgagcga gggcgccacc    540

ccccaggacc tgaacaccat gctgaacacc gtgggcggcc accaggccgc catgcagatg    600

ctgaaggaga ccatcaacga ggaggccgcc gagtgggacc gcctgcaccc cgtgcacgcc    660

ggccccatcg cccccggcca gatgcgcgag ccccgcggca gcgacatcgc cggcaccacg    720

agcaccctgc aggagcagat cggctggatg accaacaacc cccctatccc cgtgggcgag    780

atctacaagc gctggatcat cctgggcctg aacaagatcg tgcgcatgta cagccccacg    840

agcatcctgg acatccgcca gggccccaag gagcccttcc gcgactacgt ggaccgcttc    900

tacaagaccc tgcgggccga gcaggccagc caggaggtga agaactggat gaccgagacc    960

ctgctggtgc agaacgccaa ccccgactgc aagaccatcc tgaaggccct gggccccgcc   1020

gccaccctgg aggagatgat gaccgcctgc cagggcgtgg gcggccccgg ccacaaggcc   1080

cgcgtgctgt aa                                                        1092
```

<210> SEQ ID NO 41
<211> LENGTH: 363
<212> TYPE: PRT
<213> ORGANISM: Human immunodeficiency virus type 1

<400> SEQUENCE: 41

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Val Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240
```

```
Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu
        355                 360


<210> SEQ ID NO 42
<211> LENGTH: 309
<212> TYPE: DNA
<213> ORGANISM: Human immunodeficiency virus type 1

<400> SEQUENCE: 42

atggagccag tagatcctag actagagccc tggaagcatc cagggagtaa gcctaaaact      60

gcttgtacca attgctattg taaaaagtgt tgctttcatt gccaagtttg tttcacaaca     120

aaagccttag gcatctccta tggcaggaag aagcggagac agcgacgaag agctcatcag     180

aacagtcaga ctcatcaagc ttctctatca aagcagccct cctcccagcc tcgaggggac     240

ccgacaggcc cgaaggaaca gaagaagaag gtggagagag agacagagac agatccggtc     300

catcagtga                                                             309


<210> SEQ ID NO 43
<211> LENGTH: 102
<212> TYPE: PRT
<213> ORGANISM: Human immunodeficiency virus type 1

<400> SEQUENCE: 43

Met Glu Pro Val Asp Pro Arg Leu Glu Pro Trp Lys His Pro Gly Ser
1               5                   10                  15

Lys Pro Lys Thr Ala Cys Thr Asn Cys Tyr Cys Lys Lys Cys Cys Phe
            20                  25                  30

His Cys Gln Val Cys Phe Thr Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Ser Ser Gln Pro Arg Gly Asp
65                  70                  75                  80

Pro Thr Gly Pro Lys Glu Gln Lys Lys Lys Val Glu Arg Glu Thr Glu
                85                  90                  95

Thr Asp Pro Val His Gln
            100
```

RECOMBINANT MEASLES VIRUSES EXPRESSING EPITOPES OF ANTIGENS OF RNA VIRUSES—USE FOR THE PREPARATION OF VACCINE COMPOSITIONS

SEQUENCE LISTING

The instant application contains a Sequence Listing which has been submitted in ASCII format via EFS-Web and is hereby incorporated by reference in its entirety. Said ASCII copy, created on Oct. 8, 2012, is named D1200221.txt and is 122,056 bytes in size.

The invention relates to recombinant measles viruses expressing epitopes of antigens of RNA viruses including especially retroviruses and flaviviruses and to their use for the preparation of vaccine compositions.

Measles virus is a member of the order mononegavirales, i.e., viruses with a non-segmented negative-strand RNA genome. The non segmented genome of measles virus (MV) has an antimessage polarity which results in a genomic RNA which is not translated either in vivo or in vitro nor infectious when purified.

Transcription and replication of non-segmented (−) strand RNA viruses and their assembly as virus particles have been studied and reported especially in Fields virology ($3^{rd}$ edition, vol. 1, 1996, Lippincott—Raven publishers—Fields B N et al). Transcription and replication of measles virus do not involve the nucleus of the infected cells but rather take place in the cytoplasm of said infected cells. The genome of the measles virus comprises genes encoding six major structural proteins from the six genes (designated N, P, M, F, H and L) and an additional two-non structural proteins from the P gene. The gene order is the following: 3'-1, N, P (including C and V), M, F, H, and L large polymerase protein at the 5' end. The genome further comprises non coding regions in the intergenic region M/F; this non-coding region contains approximately 1000 nucleotides of untranslated RNA. The cited genes respectively encode the leader peptide (I gene), the proteins of the nucleocapsid of the virus, i.e., the nucleoprotein (N), the phosphoprotein (P), and the large protein (L) which assemble around the genome RNA to provide the nucleocapsid. The other genes encode the proteins of the viral envelope including the hemagglutinin (H), the fusion (F) and the matrix (M) proteins.

The measles virus has been isolated and live attenuated vaccines have been derived from the Edmonston MV isolated in 1954 (Enders, J. F., and T. C. Peebles. 1954. *Propagation in tissue cultures od cytopathogenic agents from patients with measles. Proc. Soc. Exp. Biol. Med.* 86:277-286.), by serial passages on primary human kidney or amnion cells. The used strains were then adapted to chick embryo fibroblasts (CEF) to produce Edmonston A and B seeds (Griffin, D., and W. Bellini. 1996. *Measles virus*, p. 1267-1312. In B. Fields, D. Knipe, et al. (ed.), *Virology, vol.* 2. Lippincott—Raven Publishers, Philadelphia). Edmonston B was licensed in 1963 as the first MV vaccine. Further passages of Edmonston A and B on CEF produced the more attenuated Schwarz and Moraten viruses (Griffin, D., and W. Bellini. 1996. *Measles virus*, p. 1267-1312. In B. Fields, D. Knipe, et al. (ed.), *Virology*, vol. 2. Lippincott—Raven Publishers, Philadelphia) whose sequences have recently been shown to be identical (Parks, C. L., R. A. Lerch, P. Walpita, H. P. Wang, M. S. Sidhu, and S. A. Udem. 2001. *Analysis of the noncoding regions of measles virus strains in the Edmonston vaccine lineage. J Virol.* 75:921-933; Parks, C. L., R. A. Lerch, P. Walpita, H. P. Wang, M. S. Sidhu, and S. A. Udem. 2001. *Comparison of predicted amino acid sequences of measles virus strains in the Edmonston vaccine lineage. J Virol.* 75:910-920). Because Edmonston B vaccine was reactogenic, it was abandoned in 1975 and replaced by the Schwarz/Moraten vaccine which is currently the most widely used measles vaccine in the world (Hilleman, M. 2002. *Current overview of the pathogenesis and prophylaxis of measles with focus on practical implications. Vaccine.* 20:651-665). Several other vaccine strains are also used: AIK-C, Schwarz F88, CAM70, TD97 in Japan, Leningrad-16 in Russia, and Edmonston Zagreb. The CAM70 and TD97 Chinese strains were not derived from Edmonston. Schwarz/Moraten and AIK-C vaccines are produced on CEF. Zagreg vaccine is produced on human diploid cells (WI-38).

The live attenuated vaccine derived from the Schwarz strain is commercialized by Aventis Pasteur (Lyon France) under the trademark ROUVAX®.

In a noteworthy and pioneer work, Martin Billeter and colleagues cloned an infectious cDNA corresponding to the antigenome of Edmonston MV and established an original and efficient reverse genetics procedure to rescue the corresponding virus (Radecke, F., P. Spielhofer, H. Schneider, K. Kaelin, M. Huber, K. Dötsch, G. Christiansen, and M. Billeter., 1995. *Rescue of measles viruses from cloned DNA. EMBO Journal.* 14:5773-5784) and WO 97/06270. They developed an Edmonston vector for the expression of foreign genes (Radecke, F., and M. Billeter. 1997. *Reverse genetics meets the nonsegmented negative-strand RNA viruses. Reviews in Medical Virology.* 7:49-63.) and demonstrated its large capacity of insertion (as much as 5 kb) and its high stability at expressing transgenes (Singh, M., and M. Billeter. 1999. *A recombinant measles virus expressing biologically active human interleukin*-12. *J. Gen. Virol.* 80:101-106; Singh, M., R. Cattaneo, and M. Billeter. 1999. *A recombinant measles virus expressing hepatitis B virus surface antigen induces humoral immune responses in genetically modified mice. J. Virol.* 73:4823-4828; Spielhofer, P., T. Bachi, T. Fehr, G. Christiansen, R. Cattaneo, K. Kaelin, M. Billeter, and H. Naim. 1998. *Chimeric measles viruses with a foreign envelope. J. Virol.* 72:2150-2159); Wang, Z., T. Hangartner, L. Cornu, A. Martin, M. Zuniga, M. Billeter, and H. Naim. 2001. *Recombinant measles viruses expressing heterologus antigens of mumps and simian immunodeficiency viruses. Vaccine.* 19:2329-2336. This vector was cloned from the Edmonston B strain of MV propagated in HeLa cells (Ballart, I., D. Eschle, R. Cattaneo, A. Schmid, M. Metzler, J. Chan, S. Pifko-Hirst, S. A. Udem, and M. A. Billeter. 1990. *Infectious measles virus from cloned cDNA. Embo J.* 9:379-384).

In addition, recombinant measles virus expressing Hepatitis B virus surface antigen has been produced and shown to induce humoral immune responses in genetically modified mice (Singh M. R. et al, 1999, *J. virol.* 73: 4823-4828).

MV vaccine induces a very efficient, life-long immunity after a single low-dose injection ($10^4$ $TCID_{50}$) (33, 34). Protection is mediated both by antibodies and by CD4+ and CD8+ T cells. The MV genome is very stable and reversion to pathogenicitiy has never been observed with this vaccine. MV replicates exclusively in the cytoplasm, ruling out the possibility of integration in host DNA. Furthermore, an infectious cDNA clone corresponding to the anti-genome of the Edmonston strain of MV and a procedure to rescue the corresponding virus have been established (35). This cDNA has been made into a vector to express foreign genes (36). It can accommodate up to 5 kb of foreign DNA and is genetically very stable (37, 38, 39).

From the observation that the properties of the measles virus and especially its ability to elicit high titers of neutralizing antibodies in vivo and its property to be a potent inducer of long lasting cellular immune response, the inventors have proposed that it may be a good candidate for the preparation of compositions comprising recombinant infectious viruses expressing antigenic peptides or polypeptides of determined RNA viruses, including especially retroviruses or flaviviruses, to induce neutralizing antibodies against said RNA virus and especially said retroviruses or flaviviruses which preferably could be suitable to achieve at least some degree of protection against said RNA viruses, especially retroviruses or flaviviruses, in animals and more preferably in human hosts. Especially, MV strains and in particular vaccine strains have been elected in the present invention as candidate vectors to induce immunity against both measles virus and RNA virus whose constituent is expressed in the designed recombinant MV, in exposed infant populations because they are having no MV immunity. Adult populations, even already MV immunized individuals, may however also benefit from MV recombinant immunization because re-administering MV virus under the recombinant form of the present invention may result in a boost of anti-MV antibodies.

Among retroviruses of interest, the inventors have chosen AIDS retroviruses, including HIV-1 and among flaviviruses, some which are important human pathogens such as Yellow Fever Virus (YFV) and West Nile Virus (WNV).

The YFV and WNV belong to the family Flaviviridae described in Fields virology ($3^{rd}$ edition, vol. 1, 1996, Lippincott—Raven publishers—Fields B N et al).

The invention relates to a recombinant mononegavirales virus expressing a heterologous amino acid sequence, said recombinant virus being capable of eliciting a humoral and/or a cellular immune response against said heterologous amino acid sequence including in individuals having preexisting measles virus immunity.

In a first embodiment, the invention especially provides recombinant measles viruses capable of expressing antigens and especially epitopes derived from antigens of RNA viruses including retroviruses or flaviviruses.

The invention also relates to nucleic acid constructs especially to recombinant nucleic acid constructs expressing the recombinant measles viruses and expressing therewith antigens or epitopes of antigens of retroviruses or flaviviruses.

The invention concerns also processes for the preparation of such recombinant measles viruses and especially relates to the production of such recombinant MV in rescue systems.

The invention is also directed to compositions comprising said recombinant measles viruses as active principles for protection of hosts, especially human hosts, against diseases related to infections by said retroviruses, especially by AIDS retroviruses, or said flaviviruses, especially Yellow Fever Virus or West Nile Virus.

Nucleic acid sequences of Measles Viruses have been disclosed in International Patent Application WO 98/13501, especially a DNA sequence of 15,894 nucleotides corresponding to a DNA copy of the positive strand (antigenomic) message sense RNA of various wild-type of vaccine measles strains, including Edmonston Wild-type strain, Moraten strain and Schwarz strain which is identical to the Moraten strain except for nucleotide positions 4917 and 4924 where Schwarz strain has a «C» instead of a «T».

In order to produce recombinant measles viruses, a rescue system has been developed for the Edmonston MV strain and described in International Patent Application WO 97/06270. The description of said rescue system contained in WO 97/06270 is incorporated herewith by reference, and reference is made especially to the examples of this International application, including the Examples related to cells and viruses, to generation of cell line 293-3-46, plasmid constructions, transfection of plasmids and harvest of reporter gene products, experimental set-up to rescue MV, helper cells stably expressing MV N and P proteins as well as T7 RNA polymerase, MV rescue using helper cells 293-3-46 and characterization of rescued MV.

The rescue system disclosed in WO 97/06270 has been further developed to include a heat-shock step described in Parks C. L. et al, 1999, *J. virol.* 73: 3560-3566. The disclosure of this enhanced measles virus cDNA rescue system is incorporated herewith by reference.

The invention thus relates to recombinant measles viruses expressing a heterologous amino acid sequence derived from an antigen of a determined RNA virus, especially from a retrovirus or flavivirus, wherein said recombinant measles virus is capable of eliciting a humoral and/or a cellular immune response against measles virus or against said RNA virus, especially retrovirus or flavivirus or against both measles virus and against said RNA virus, especially retrovirus or flavivirus.

The expression «heterologous amino acid sequence» is directed to an amino acid sequence which is not derived from the antigens of measles viruses, said heterologous amino acid sequence being accordingly derived from a RNA virus, especially from a retrovirus or flavivirus of interest in order to establish an immune response in a host, especially in a human and preferably to establish protection against an infection by said RNA virus, especially retrovirus or flavivirus.

The heterologous amino acid sequence expressed in recombinant measles viruses according to the invention is such that it is capable of eliciting a humoral and/or cellular immune response in a determined host, against the RNA virus, especially retrovirus or flavivirus from which it originates. Accordingly, this amino acid sequence is one which comprises at least one epitope of an antigen, especially a conserved epitope, which epitope is exposed naturally on the antigen or is obtained or exposed as a result of a mutation or modification or combination of antigens.

Antigens used for the preparation of the recombinant measles viruses are especially envelope antigens of RNA viruses such as retroviruses or flaviviruses, especially from envelopes of AIDS viruses including HIV-1 or from envelopes of the Yellow Fever Virus or envelopes from the West Nile Virus. Other retroviral or flaviviral antigens may however be advantageously used in order to derive recombinant measles viruses capable of eliciting antibodies against said retroviruses or flaviviruses, and the invention relates in a particular embodiment to antigens from which amino acid sequences can be derived which elicit the production of neutralizing antibodies against the retrovirus or flavivirus. According to another embodiment of the invention, amino acid sequence of these antigens alternatively or additionally also elicits a cellular immune response against the retrovirus or flaviviruses.

Advantageously, the recombinant measles virus of the invention also elicits a humoral and/or cellular immune response against measles virus. This response is however not mandatory provided the immune response against the RNA virus, especially retrovirus or flavivirus is indeed obtained.

According to a preferred embodiment of the invention, the recombinant measles virus of the invention is obtained within a rescue system for the preparation of infectious measles viruses. Accordingly, the recombinant measles virus is a rescued infectious measles virus recovered from a rescue system.

A particular recombinant measles virus of the invention is derived from the Edmonston strain of measles virus.

Another particular and preferred recombinant measles virus according to the invention is derived from the Schwarz strain and especially from an approved vaccine Schwarz strain such as that produced under the trademark ROUVAX®, available from Aventis Pasteur (France).

The invention thus provides for a recombinant measles virus which is recovered from helper cells transfected with a cDNA encoding the antigenomic RNA ((+)strand) of the measles virus, said cDNA being recombined with a nucleotide sequence encoding the RNA viral, especially retroviral or flaviviral, heterologous amino acid sequence.

The expression «encoding» in the above definition encompasses the capacity of the cDNA to allow transcription of a full length antigenomic (+)RNA, said cDNA serving especially as template for transcription. Accordingly, when the cDNA is a double stranded molecule, one of the strands has the same nucleotide sequence as the antigenomic (+) strand RNA of the measles virus, except that «U» nucleotides are substituted by «T» in the cDNA. Such a cDNA is for example the insert corresponding to the measles virus, contained in the pTM-MVSchw plasmid deposited under No 1-2889 at the COLLECTION NATIONALE DE CULTURES DE MICROORGANISMES (CNCM), 25 rue du Docteur Roux, F-75724 Paris Cedex 15, France on Jun. 12, 2002. This plasmid is represented on FIG. 2A.

The expression "cDNA" used for the description of the nucleotide sequence of the molecule of the invention merely relates to the fact that originally said molecule is obtained by reverse transcription of the full length genomic (−)RNA genome of viral particles of the measles virus.

This should not be regarded as a limitation for the methods used for its preparation. The invention thus encompasses, within the expression "cDNA", every DNA provided it has the above defined nucleotide sequence. Purified nucleic acids, including DNA are thus encompassed within the meaning cDNA according to the invention, provided said nucleic acid, especially DNA fulfils the above-given definitions.

The helper cells according to the rescue system are transfected with a transcription vector comprising the cDNA encoding the full length antigenomic (+)RNA of the measles virus, when said cDNA has been recombined with a nucleotide sequence encoding the heterologous amino acid sequence of interest (heterologous nucleotide sequence) and said helper cells are further transfected with an expression vector or several expression vectors providing the helper functions including those enabling expression of trans-acting proteins of measles virus, i.e., N, P and L proteins and providing expression of an RNA polymerase to enable transcription of the recombinant cDNA and replication of the corresponding viral RNA.

The invention relates in particular to the preparation of recombinant measles viruses bearing epitopes of antigens of HIV retroviruses. It encompasses especially a recombinant measles virus expressing a heterologous amino acid sequence which is derived from an envelope antigen of HIV and which is especially derived from an envelope protein or glycoprotein of HIV-1.

The antigens of interest in this respect are especially gp160, gp120 and gp41 of HIV-1 or gp140, GAG or TAT of HIV-1.

In a particular embodiment of the invention, the heterologous amino acid sequence is derived from a recombinant gp160, gp120 of HIV-1 or gp140, GAG or TAT of HIV-1.

The invention is directed in particular to a recombinant measles virus wherein the V1, V2 and/or V3 loops of the gp120 (or gp160) antigen are deleted or deleted in part, individually or in combination in such a way that conserved epitopes are exposed on the obtained recombinant gp120 antigen.

The V1, V2 and V3 loops of the gp120 (or gp160) antigen of HIV-1 have been especially disclosed in Fields virology (Fields B. N. et al—Lippincott Raven publishers 1996, p. 1953-1977).

According to another embodiment of the invention, the recombinant measles virus is such that it expresses a heterologous amino acid sequence derived from the gp120 (or gp160) antigen of HIV-1, wherein the V1, V2 and/or V3 loops of the gp120 (or gp160) antigen are substituted or substituted in part, individually or in combination, in such a way that conserved epitopes are exposed on the obtained recombinant gp120 (or gp160) antigen.

According to another particular embodiment, the recombinant measles virus expressing a heterologous DNA sequence derived from an envelope antigen of HIV-1 is derived from the gp120 antigen in such a way that the V1 and V2 loops are deleted and the V3 loop is substituted for the sequence AAELDKWASAA (SEQ ID NO: 8).

According to another particular embodiment of the invention, the recombinant measles virus is one expressing an heterologous amino acid sequence selected among gp160ΔV3, gp160ΔV1V2, gp160ΔV1V2V3, gp140ΔV3, gp140ΔV1V2, gp140ΔV1V2V3, which heterologous amino acid sequences are schematically represented on FIG. 1.

The invention also relates to recombinant measles viruses as defined according to the above statements, wherein the amino acid sequence is derived from an antigen of the Yellow Fever virus selected among the envelope (Env) or the NS1 proteins or immunogenic mutants thereof.

The invention also relates to recombinant measles viruses as defined according to the above statements, wherein the amino acid sequence is derived from an antigen of the West Nile virus selected among the envelope (E), premembrane (preM) or immunogenic mutants thereof.

The invention also relates to recombinant measles viruses or to virus like particles (VLP) which express double or multiple recombinant antigens, especially multiple HIV antigens (including fragments thereof) or flavivirus antigens, against which an immune response is sought. Such recombinant measles viruses or VLP may advantageously express antigens from different viruses and thus provide immunogens against various viruses.

The invention further relates to recombinant measles viruses according to anyone of the above definitions, wherein the cDNA required for the expression of the viral particles, which is comprised within the EdB-tag virus vector or preferably within the pTM-MVSchw vector is recombined with the ATU sequence of FIG. 8, said ATU being inserted in a position of the EdB-tag vector or of the pTM-MVSchw vector taking advantage of the gradient of the viral genome to allow various levels of expression of the transgenic sequence encoding the heterologous amino acid sequence inserted in said ATU. The invention advantageously enables the insertion of such heterologous DNA sequences in a sequence which is designated an Additional Transcription Unit (ATU) especially an ATU as disclosed by Billeter et al in WO 97/06270.

The advantageous immunological properties of the recombinant measles viruses according to the invention can be shown in an animal model which is chosen among animals susceptible to measles viruses and wherein the humoral and/or cellular immune response against the heterologous antigen and/or against the measles virus is determined.

Among such animals suitable to be used as model for the characterization of the immune response, the skilled person can especially use mice and especially recombinant mice susceptible to measles viruses, or in monkeys.

In a preferred embodiment of the invention, the recombinant measles virus of the invention is suitable to elicit neutralizing antibodies against the heterologous amino acid sequence in a mammalian animal model susceptible to measles virus. Especially, this immune response comprising elicitation of neutralizing antibodies can be sought in recombinant mice or monkeys.

According to another particular embodiment of the invention, especially when the heterologous amino acid sequence is derived from one of the envelope proteins of HIV-1 and where it elicits antibodies capable of neutralizing a primary HIV isolate, the response is advantageously tested on indicator cells such as P4-CCR5 cells available from the NIH (NIH AIDS Research and Reference Reagent Program). (Charneau P. et al—1994—*J. Mol. Biol.* 241: 651-662).

According to another preferred embodiment, the recombinant measles virus according to the invention elicits neutralizing antibodies against the heterologous amino acid sequence in a mammal, with a titre of at least 1/40000 when measured in ELISA, and a neutralizing titre of at least 1/20.

The invention also relates to a recombinant measles virus nucleotide sequence comprising a replicon comprising (i) a cDNA sequence encoding the full length antigenomic (+)RNA of measles virus operatively linked to (ii) an expression control sequence and (iii) a heterologous DNA sequence coding for a determined heterologous amino acid sequence, said heterologous DNA sequence being cloned in said replicon in conditions allowing its expression and in conditions not interfering with transcription and replication of said cDNA sequence, said replicon having a total number of nucleotides which is a multiple of six.

A particular cDNA sequence is the sequence of the cDNA of the Schwarz strain depicted on FIG. 11. Such a cDNA can be obtained from pTM-MVSchw.

pTM-MVSchw is a plasmid derived from Bluescript containing the complete sequence of the measles virus, vaccine strain Schwarz, under the control of the promoter of the T7 RNA polymerase. Its size is 18967 nt.

The invention concerns also a recombinant measles virus vector comprising the above defined recombinant measles virus nucleotide sequence.

The «rule of six» is expressed in the fact that the total number of nucleotides present in the recombinant cDNA resulting from recombination of the cDNA sequence derived from reverse transcription of the antigenomic RNA of measles virus, and the heterologous DNA sequence finally amount to a total number of nucleotides which is a multiple of six, a rule which allows efficient replication of genome RNA of the measles virus.

A preferred recombinant measles virus vector according to the above definition is such that the heterologous DNA virus vector wherein the heterologous DNA sequence is cloned within an Additional Transcription Unit (ATU) inserted in the cDNA corresponding to the antigenomic RNA of measles virus.

The additional transcription unit (ATU) is disclosed on FIG. 2A; it can be modified provided it ultimately enables the obtained replicon in the vector to comply with the rule of six.

The location of the ATU within the cDNA derived from the antigenomic RNA of the measles virus can vary along said cDNA. It is however located in such a site that it will benefit from the expression gradient of the measles virus.

This gradient corresponds to the mRNA abundance according to the position of the gene relative to the 3' end of the template. Accordingly, when the polymerase operates on the template (either genomic and anti-genomic RNA or corresponding cDNAs), it synthetizes more RNA made from upstream genes than from downstream genes. This gradient of mRNA abondance is however relatively smooth for measles virus. Therefore, the ATU or any insertion site suitable for cloning of the heterologous DNA sequence can be spread along the cDNA, with a preferred embodiment for an insertion site and especially in an ATU, present in the N-terminal portion of the sequence and especially within the region upstream from the L-gene of the measles virus and advantageously upstream from the M gene of said virus and more preferably upstream from the N gene of said virus.

Depending on the expression site and the expression control of the heterologous DNA, the vector of the invention allows the expression of the heterologous amino acid sequence as a fusion protein with one of the measles virus proteins.

Alternatively, the insertion site of the DNA sequence in the cDNA of the measles virus can be chosen in such a way that the heterologous DNA expresses the heterologous amino acid sequence in a form which is not a fusion protein with one of the proteins of the measles virus.

The recombinant measles virus vector according to any of the preferred definitions contains advantageously a heterologous DNA sequence which encodes a retroviral, a flaviviral amino acid sequence.

As an example, this amino acid sequence is derived from an antigen of a retrovirus selected among HIV retroviruses, or a flavivirus, especially the Yellow Fever virus or the West Nile virus.

In a particular embodiment of the invention, the heterologous amino acid sequence encoded by the recombinant measles virus vector is derived from an envelope antigen of an HIV retrovirus, especially from HIV-1.

In a preferred embodiment, this amino acid sequence encoded by the heterologous DNA sequence is selected among the gp160, the gp120 or gp41 of HIV-1, or the gp140 of HIV-1, or a mutated version of said antigens.

As one result which is expected by expressing the recombinant measles virus vector of the invention is the elicitation of an immune response, especially a humoral and/or cellular immune response, against the heterologous amino acid sequence encoded by the vector, it is preferred that the heterologous DNA sequence used is one which codes for an antigen or a mutated antigen which enables exposition of neutralizing epitopes on the produced expression product of said vector.

In a particular embodiment, the heterologous amino acid sequence expressed, can expose epitopes which are not accessible or not formed in the native antigen from which the heterologous amino acid sequence derives.

In a preferred embodiment of the invention, the heterologous DNA sequence encodes gp160ΔV3, gp160ΔV1V2, gp160ΔV1V2V3, gp140ΔV3, gp140ΔV1V2, gp140ΔV1V2V3.

Heterologous amino acid sequences are especially disclosed on FIG. 1 and can be prepared according to well-known methods starting from sequences of antigens or corresponding DNA sequences of said antigens obtained from various HIV-1 isolates.

According to a preferred embodiment of the invention, the recombinant measles virus vector is designed in such a way that the particles produced in helper cells transfected or transformed with said vector containing the DNA encoding the full length antigenomic (+)RNA of measles virus, originated from a measles virus strain adapted for vaccination, enable the production of viral particles for use in immunogenic compositions, preferably protective or even vaccine compositions.

Among measles virus strains adapted for vaccination, one can cite the Edmonston B. strain and the Schwarz strain, the latter being preferred and distributed by the company Aventis Pasteur (Lyon France) as an approved vaccination strain of measles virus.

The nucleotide sequences of the Edmonston B. strain and of the Schwarz strain, have been disclosed in WO 98/13505.

In order to prepare the recombinant measles virus vector of the invention, the inventors have designed plasmid pTM-MVSchw which contains the cDNA resulting from reverse transcription of the antigenomic RNA of measles virus and an adapted expression control sequence including a promoter and terminator for the T7 polymerase.

The recombinant measles virus vector according to the invention is preferably a plasmid.

Preferred vectors are those obtained with the nucleotide sequence of the Edmonston B. strain deposited on Jun. 12, 2002 especially:

| | |
|---|---|
| pMV2(EdB)gp160[delta]V3HIV89.6P | CNCM I-2883 |
| pMV2(EdB)gp160HIV89.6P | CNCM I-2884 |
| pMV2(EdB)gp140HIV89.6P | CNCM I-2885 |
| pMV3(EdB)gp140[delta]V3HIV89.6P | CNCM I-2886 |
| pMV2(EdB)-NS1YFV17D | CNCM I-2887 |
| pMV2(EdB)-EnvYFV17D | CNCM I-2888. |

Other preferred vectors are those obtained with the nucleotide sequence of the Schwarz strain, deposited at the CNCM on May 26, 2003:

| | |
|---|---|
| pTM-MVSchw2-Es(WNV) | CNCM I-3033 |
| pTM-MVSchw2-GFPbis- | CNCM I-3034 |
| pTM-MVSchw2-p17p24[delta]myr(HIVB) | CNCM I-3035 |
| pTM-MVSchw3-Tat(HIV89-6p) | CNCM I-3036 |
| pTM-MVschw3-GFP | CNCM I-3037 |
| pTM-MVSchw2-Es (YFV) | CNCM I-3038 and the vectors deposited at the CNCM on Jun. 19, 2003: |
| pTM-MVSchw2-gp140 [delta] V1 V2 V3 (HIV89-6) | CNCM I-3054 |
| pTM-MVSchw2-gp140 [delta] V3 (HIV89-6) | CNCM I-3055 |
| pTM-MVSchw2-gp160 [delta] V1 V2 V3 (HIV89-6) | CNCM I-3056 |
| pTM-MVSchw2-gp160 [delta] V1 V2 (HIV89-6) | CNCM I-3057 |
| pTM-MVSchw2-Gag SIV239 p17-p24 [delta] myr-3-gp140 (HIV89-6) | CNCM I-3058. |

I-2883 (pMV2(EdB)gp160[delta]V3HIV89.6P) is a plasmid derived from Bluescript containing the complete sequence of the measles virus (Edmonston strain B), under the control of the T7 RNA polymerase promoter and containing the gene of the gp160ΔV3+ELDKWAS (residues 3-9 of SEQ ID NO: 8) of the virus SVIH strain 89.6P inserted in an ATU at position 2 (between the N and P genes of measles virus). The size of the plasmid is 21264 nt.

I-2884 (pMV2(EdB)gp160HIV89.6P) is a plasmid derived from Bluescript containing the complete sequence of the measles virus (Edmonston strain B), under the control of the T7 RNA polymerase promoter and containing the gene of the gp160 of the SVIH virus strain 89.6P inserted in an ATU at position 2 (between the N and P genes of measles virus). The size of the plasmid is 21658 nt.

I-2885 (pMV2(EdB)gp140HIV89.6P) is a plasmid derived from Bluescript containing the complete sequence of the measles virus (Edmonston strain B), under the control of the T7 RNA polymerase promoter and containing the gene of the gp140 of the SVIH virus strain 89.6P inserted in an ATU at position 2 (between the N and P genes of measles virus). The size of the plasmid is 21094 nt.

I-2886 (pMV3(EdB)gp140[delta]V3HIV89.6P) is a plasmid derived from Bluescript containing the complete sequence of the measles virus (Edmonston strain B), under the control of the T7 RNA polymerase promoter and containing the gene of the gp140ΔV3 (ELDKWAS; residues 3-9 of SEQ ID NO: 8) of the SVIH virus strain 89.6P inserted in an ATU at position 2 (between the N and P genes of measles virus). The size of the plasmid is 21058 nt.

I-2887 (pMV2(EdB)-NS1YFV17D) is a plasmid derived from Bluescript containing the complete sequence of the measles virus (Edmonston strain B), under the control of the T7 RNA polymerase promoter and containing the NS1 gene of the Yellow Fever virus (YFV 17D) inserted in an ATU at position 2 (between the N and P genes of measles virus). The size of the plasmid is 20163 nt.

I-2888 (pMV2(EdB)-EnvYFV17D) is a plasmid derived from Bluescript containing the complete sequence of the measles virus (Edmonston strain B), under the control of the T7 RNA polymerase promoter and containing the Env gene of the Yellow Fever virus (YFV 17D) inserted in an ATU at position 2 (between the N and P genes of measles virus). The size of the plasmid is 20505 nt.

I-3033 (pTM-MVSchw2-Es(WNV) is a plasmid derived from Bluescript containing a cDNA sequence of the complete infectious genome of the measles virus (Schwarz strain), under the control of the T7 RNA polymerase promoter and expressing the gene of the secreted envelope, (E) of the West Nile virus (WNV), inserted in an ATU.

I-3034 (pTM-MVSchw2-GFPbis) is a plasmid derived from Bluescript containing a cDNA sequence of the complete infectious genome of the measles virus (Schwarz strain), under the control of the T7 RNA polymerase promoter and expressing the gene of the GFP inserted in an ATU.

I-3035 (pTM-MVSchw2-p17p24[delta]myr(HIVB) is a plasmid derived from Bluescript containing a cDNA sequence of the complete infectious genome of the measles virus (Schwarz strain), under the control of the T7 RNA polymerase promoter and expressing the gene of the gag gene encoding p17p24Δmyrproteins of the HIVB virus inserted in an ATU.

I-3036 (pTMVSchw3-Tat(HIV89-6p) is a plasmid derived from Bluescript containing a cDNA sequence of the complete infectious genome of the measles virus (Schwarz strain), under the control of the T7 RNA polymerase promoter and expressing the gene of the Tat gene of the virus strain 89.6P inserted in an ATU.

I-3037 (pTM-MVSchw3-GFP) is a plasmid derived from Bluescript containing a cDNA sequence of the complete infectious genome of the measles virus (Schwarz strain) under the control of the T7 RNA polymerase promoter and expressing the gene of the GFP gene inserted in an ATU having a deletion of one nucleotide.

I-3038 (pTM-MVSchw2-Es) (YFV) is a plasmid derived from Bluescript containing a cDNA sequence of the complete infectious genome of the measles virus (Schwarz strain) under the control of the T7 RNA polymerase promoter and expressing the gene of the secreted protein of the Fever virus (YFV) inserted in an ATU.

I-3054 (pTM-MVSchw2-gp140 [delta] V1 V2 V3 (HIV89-6)) is a plasmid derived from Bluescript containing a cDNA sequence of the complete infectious genome of the measles virus (Schwarz strain), under the control of the T7 RNA polymerase promoter and expressing the gene encoding gp140 [delta] V1 V2 (HIV 89-6) inserted in an ATU.

I-3055 (pTM-MVSchw2-gp140 [delta] V3 (HIV89-6)) is a plasmid derived from Bluescript containing a cDNA sequence of the complete infectious genome of the measles virus (Schwarz strain), under the control of the T7 RNA polymerase promoter and expressing the gene encoding gp14 [delta] V3 (HIV 89-6) inserted in an ATU.

I-3056 (pTM-MVSchw2-gp160 [delta] V1 V2 V3 (HIV89-6)) is a plasmid derived from Bluescript containing a cDNA sequence of the complete infectious genome of the measles virus (Schwarz strain), under the control of the T7 RNA polymerase promoter and expressing the gene encoding gp160 [delta] V1 V2 V3 (HIV 89-6) inserted in an ATU.

I-3057 (pTM-MVSchw2-gp160 [delta] V1 V2 (HIV89-6)) is a plasmid derived from Bluescript containing a cDNA sequence of the complete infectious genome of the measles virus (Schwarz strain), under the control of the T7 RNA polymerase promoter and expressing the gene encoding gp160 [delta] V1 V2 (HIV 89-6) inserted in an ATU.

I-3058 (pTM-MVSchw2-Gag SIV239 p17-p24 [delta] myr-3-gp140 (HIV89-6)) is a plasmid derived from Bluescript containing a cDNA sequence of the complete infectious genome of the measles virus (Schwarz strain), under the control of the T7 RNA polymerase promoter and expressing the gene encoding Gag SIV239 p17-p24 [delta] myr-3-gp140 (HIV89-6) inserted in an ATU.

In a particular embodiment of the invention, the replicon contained in the recombinant measles virus vector is designed according to the map of FIG. 2 wherein «insert» represents the heterologous DNA sequence.

When the heterologous DNA sequence present in the recombinant measles virus vector of the invention is derived from the Yellow Fever Virus (YFV), it is advantageously selected among YFV 17D 204 commercialized by Aventis Pasteur under the trademark STAMARIL®.

When the heterologous DNA sequence present in the recombinant measles virus vector of the invention is derived from the West Nile Virus (WNV), it is advantageously selected among the neurovirulente strain IS 98-ST1.

The invention also relates to a rescue system for the assembly of recombinant measles virus expressing a heterologous amino acid sequence, which comprises a determined helper cell recombined with at least one vector suitable for expression of T7 RNA polymerase and expression of the N, PandL proteins of the measles virus transfected with a recombinant measles virus vector according to anyone of the definitions provided above.

The recombinant viruses of the invention or the VLP can also be produced in vivo by a live attenuated vaccine like MV.

The recombinant viruses of the invention or the VLP can be used in immunogenic compositions or in vaccine compositions, for the protection against RNA viruses, which antigens are expressed in the recombinant virus or in the VLP, as disclosed above and illustrated in the following examples.

The invention especially provides for immunogenic compositions or for vaccine compositions useful against HIV virus, West Nile virus or Yellow Fever virus.

The invention also concerns the use of the recombinant viruses disclosed or of the VLP, or of the recombinant vectors, for the preparation of immunogenic compositions or for the preparation of vaccine compositions.

The invention also relates to antibodies prepared against said recombinant viruses or against said VLP, especially to protective antibodies and to neutralizing antibodies. Antibodies may be polyclonal antibodies, or monoclonal antibodies.

The recombinant viruses of the invention or the VLP can be associated with any appropriate adjuvant, or vehicle which may be useful for the preparation of immunogenic compositions.

Various aspects of the invention will appear in the examples which follow and in the drawings.

ATU sequence: small letters represent additional sequences (copy of the N-P intergenic region of measles virus) plus cloning sites. Capital letters correspond to the inserted enhanced GFP sequence. This sequence is inserted at the SpeI site (position 3373) of the cDNA sequence of the Schwarz strain of the measles virus for ATU2 and at the SpeI site (position 9174) for the ATU3. The mutation which distinguishes normal ATU from bis (in pTM-MVSchw2-gfp and pTM-MVSchw2-GFPbis) is a substituted C (Capital letter) at the end of ATU.

Figure 3A:
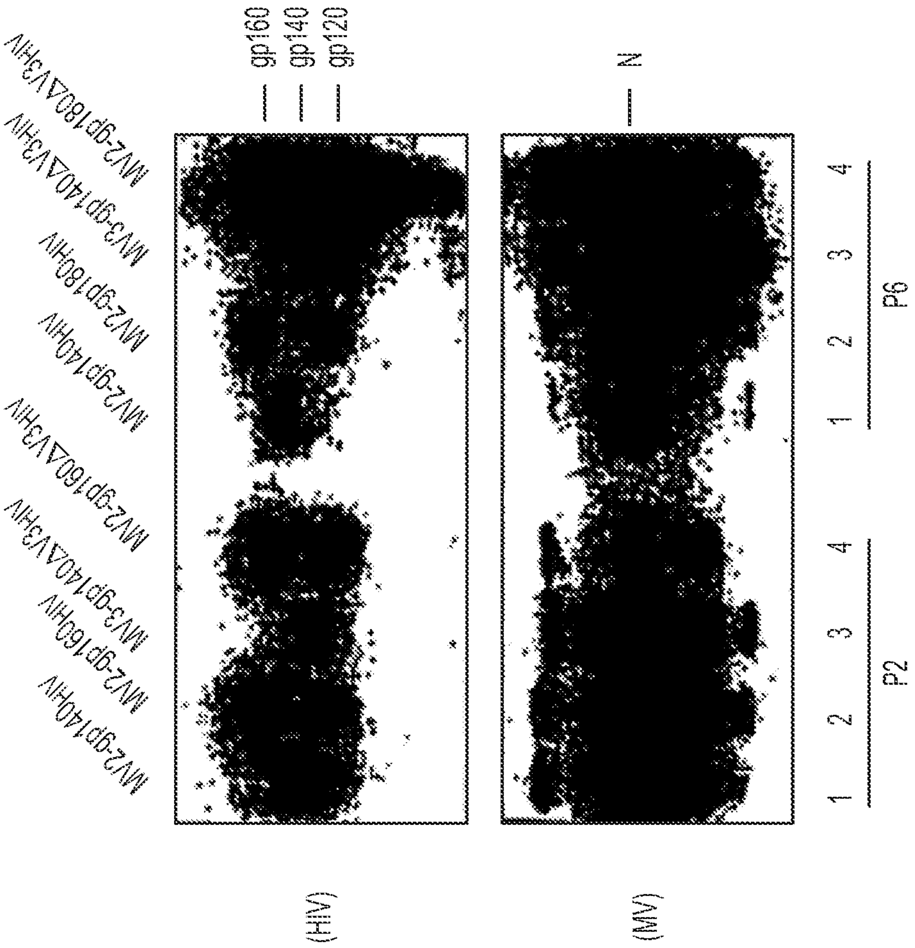

FIG. 3A: shows that $ENV_{HIV89.6}$ expression was similar for passages 2 and 5, confirming the stability of expression of transgenes in this system.

Figure 3B:
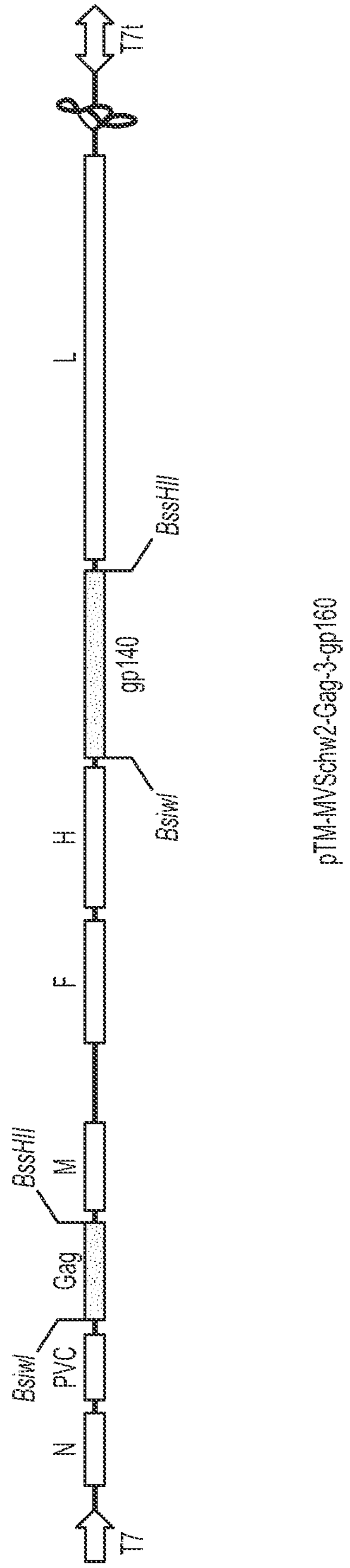

FIG. 3B: Construct of double recombinant pTM-MVSchw2-Gag-3gp140

Some recombinant vectors expressing two different heterologous antigens have been constructed. They were obtained by ligation of two different recombinant pTM-MVSchw plasmids containing different inserts in position 2 and position 3. Plasmid pTM-MVSchw2-Gag-3-gp140 is shown. From this plasmid a recombinant virus was rescued that expressed both Gag and gp140 proteins (FIG. 3B(2) Western blot). Using appropriate constructions of the different inserted heterologous genes, such recombinant MV expressing two heterologous viral proteins may produce «virus like particles» (VLP) assembled in infected cells and secreted: Gag-Env from retroviruses or prM/E from flaviviruses. Such VLP are good immunogens. Produced in vivo by a live attenuated vaccine like MV, they should be even more immunogenic.

Figure 3C:
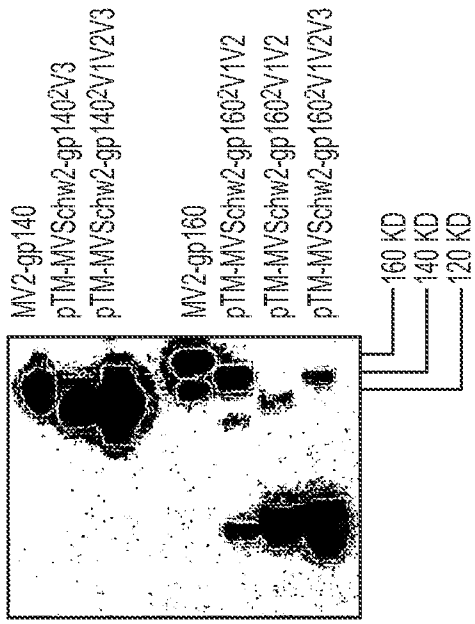

FIG. 3C: Expression of HIV-1 envelope glycoproteins in recombinant pTM-MVSchw. Vero cells were infected with the different recombinant viruses for 48H and expression of HIV Env was determined by western blot. 30 μg of each cell lysate were resolved on 4-12% SDS-PAGE, blotted onto nitrocellulose membranes and probed with a mouse monoclonal anti-HIV gp120 (Chessie, NIH) antibody. Anti-mouse IgG RPO conjugate was used as second antibody and proteins were detected using an ECL detection kit.

Figure 3D:
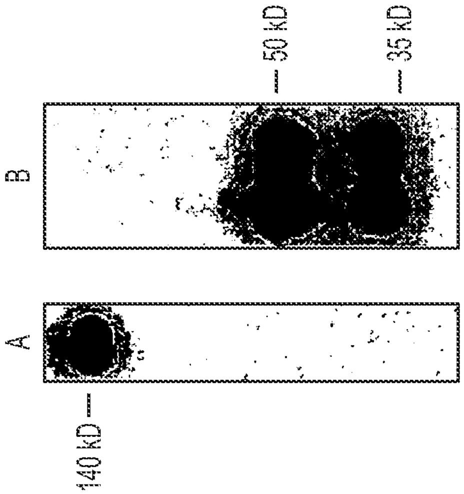

FIG. 3D: Expression of HIV-1 gp140 and SIV239 Gag in recombinant pTM-MVSchw2-Gag$_{SIV}$ (p17-p24 [delta] myr)-3-gp140$_{HIV}$. HIV gp140 and SIV Gag were detected in lysates of infected Vero cells. (A) a mouse monoclonal anti-HIV gp120 and (B) serum from macaque infected with SIVmac251.

Figure 3E:
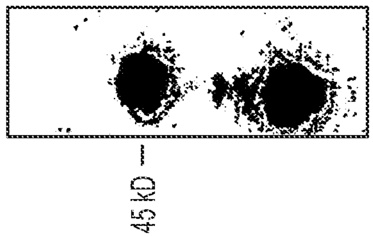

FIG. 3E: Expression of HIV-1 Gag (p17-p24 Δmyr) in recombinant pTM-MVSchw2-Gag$_{HIV}$ (p17-p24 [delta] myr). HIV Gag were detected in lysates of infected Vero cells with a mouse monoclonal anti-HIV Gag antibody.

Figure 3F:
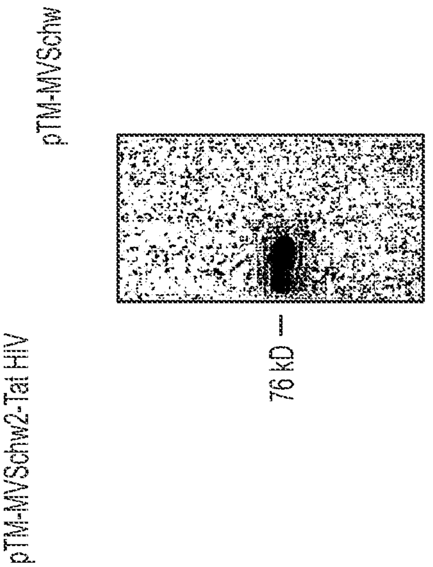

FIG. 3F: Expression of HIV-1 Tat protein in recombinant pTM-MVSchw. Vero cells were infected with MVSchw-Tat HIV recombinant or control MVSchw viruses for 48H and expression of HIV Tat was determined by western blot. 30 μg of each cell lysate were resolved on 4-12% SDS-PAGE, blotted onto nitrocellulose membranes and probed with a mouse monoclonal anti-HIV Tat (BH10, NIH) antibody. Anti-mouse IgG RPO conjugate was used as second antibody and proteins were detected using an ECL detection kit.

Figure 4B:
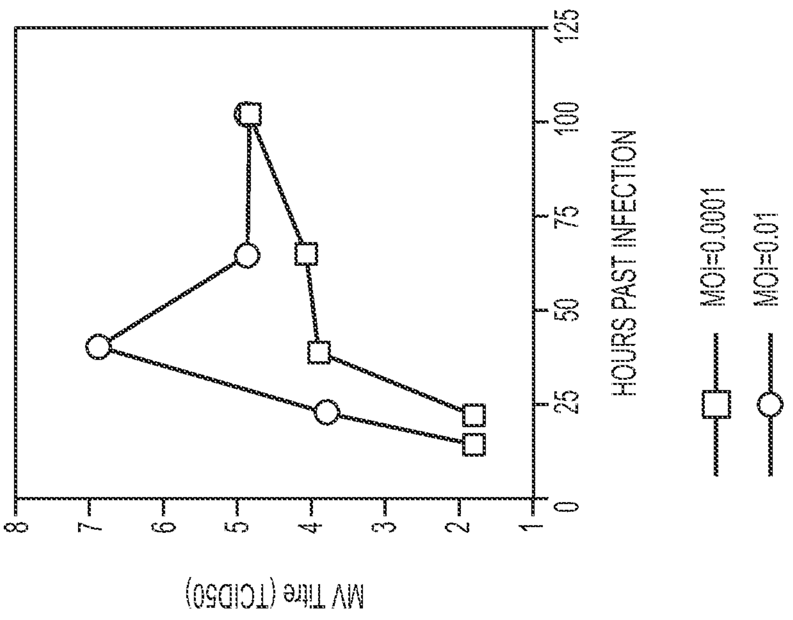
Figure 4A:
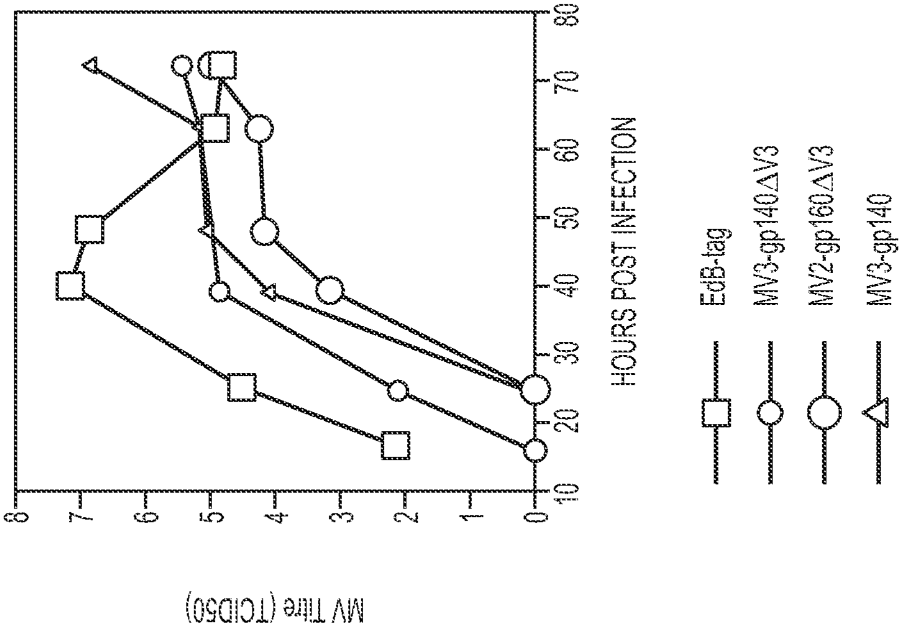

FIGS. 4A and 4B. Growth kinetics of recombinant MV$_{EdB}$-Env$_{HIV}$ viruses on Vero cells. Cells on 35 mm dishes were infected with recombinant viruses at different MOI (as indicated). At each time point, cells were collected and cell-associated virus titers were determined using the TCID$_{50}$ method on Vero cells. (A) Infections with MV EdB-tag and different MV-HIV recombinant viruses at MOI=0.0001. (B) Infections with MV2-gp160$_{HIV}$ at two different MOI (0.0001 and 0.01).

FIGS. 5A through 5F. Anti-HIV and anti-MV humoral immune responses in mice inoculated with recombinant MV$_{EdB}$-Env$_{HIV}$ viruses. A-B Four groups of 3 mice were immunized with $10^7$ TCID$_{50}$ of each MV-HIV recombinant virus. Antibody titers against MV (A) and HIV Env (B) were determined by ELISA in sera collected 28 days post inoculation. C-F: Anti-HIV and anti-MV antibody titers in IFNAR$^{-/-}$/CD46$^{+/-}$ mice immunized with MV-Env$_{HIV}$ viruses. (C) Anti-MV and anti-HIV titers detected 28 days after injection of increasing doses of MV$_{EdB}$-gp160 (3 mice per group). (D) Anti-MV (black bars), anti-HIV (gray bars) and anti-ELDKWAS (Residues 3-9 of SEQ ID NO: 8; white bars) titers detected 28 days after injection of 5 106 TCID$_{50}$ of MV-Env$_{HIV}$ viruses (6 mice per group). Results are expressed as the mean values±SD.

Figure 6:
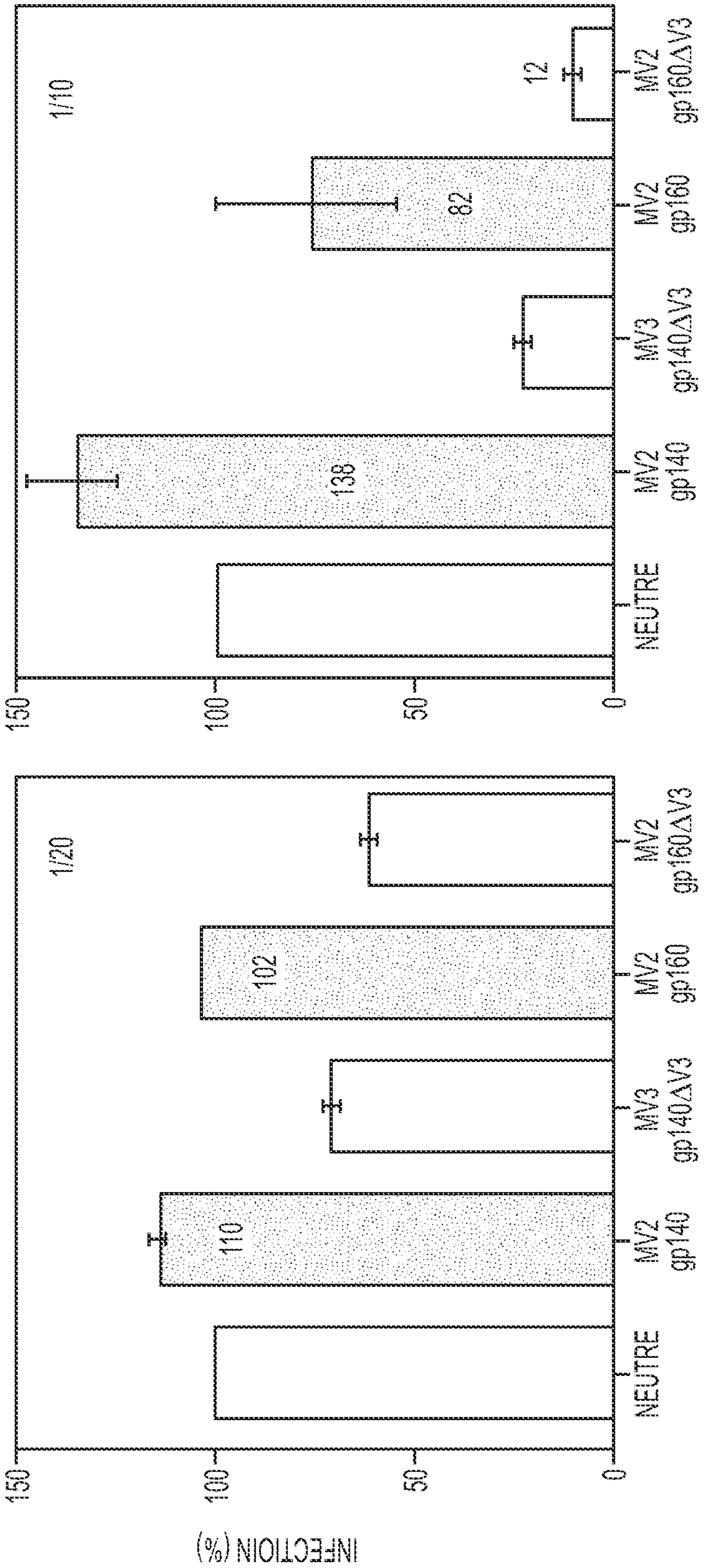

FIG. 6. Neutralizing activities against Bx08 of sera from mice immunized with MV2-gp140$_{HIV89.6}$ and MV2-gp160$_{HIV89.6}$ viruses. Primary isolate Bx08 was provided by C.Moog (Strasbourg, France) and propagated once on PHA-stimulated PBMC to obtain viral stocks. 2 ng of virus was incubated for 30 min at 37° C. with 25 μl of each mouse serum (collected one month post-infection) before infection of P4R5 cells in a 96-well plate. Cells were then cultured in DMEM containing 10% of fetal calf serum until 2 days post-infection, at which time β Galactosidase activity was measured with a chemiluminescence test (Roche, Germany). Lane 1: serum of a MV$_{EdB}$-Tag immunized mouse; Lane 2: serum of a MV2-gp140$_{HIV}$-1 immunized mouse; Lane 3: serum of a MV2-gp160$_{HIV}$-1 immunized mouse; Lane 4: non-infected cells. All assays were performed in triplicate.

FIGS. 7A through 7D. Edm-HIV Env vaccine candidate stimulates env-specific lymphocytes in vivo. Two groups of 3 mice were inoculated with $10^7$ TCID$_{50}$ of MV2-gp160$_{HIV}$ virus, and euthanized 7 day and one 1 month post inoculation. (A) ELISpot assays performed with splenocytes from immunized mice. Stimulation with HIV-gp120 purified protein (black) or irrelevant BSA (white). (B) Splenocytes collected 7 days after immunization were stimulated either with medium alone (left panel), HIV gp120 (middle panel) or EdB-tag virus (right panel). Three-color cytofluorometry detected both CD8+ (upper panel) and CD4+(lower panel) lymphocytes producing γ-IFN after HIV gp120 and measles virus stimulations. Percentages are given according to the total CD8+(upper panel) and CD4+(lower panel) lymphocyte gates respectively. (C and D). Anti-MV and anti-HIV antibody titers in mice and macaques immunized with MV2-gp140HIV89.6 virus months after MV priming. (C) Mice (3 per group) were vaccinated with $10^5$ TCID$_{50}$ of EdB-tag MV then inoculated twice with 5 $10^6$ TCID$_{50}$ of MV2-gp140$_{HIV89.6}$ virus as indicated (arrows). (D) Cynomolgus macaques (#432 and 404) were vaccinated with ROUVAX® then inoculated twice with 5 $10^6$ TCID$_{50}$ of MV2 (gp140$_{HIV89.6}$ virus as indicated (arrows).

Figure 8A:
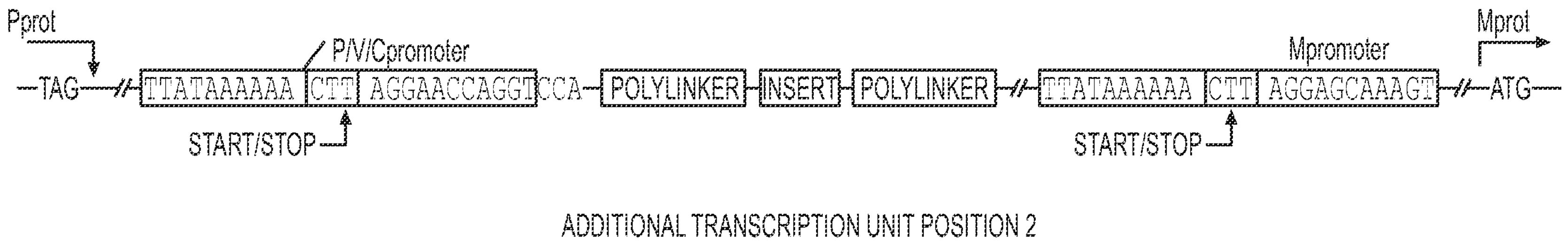
Figure 8B:
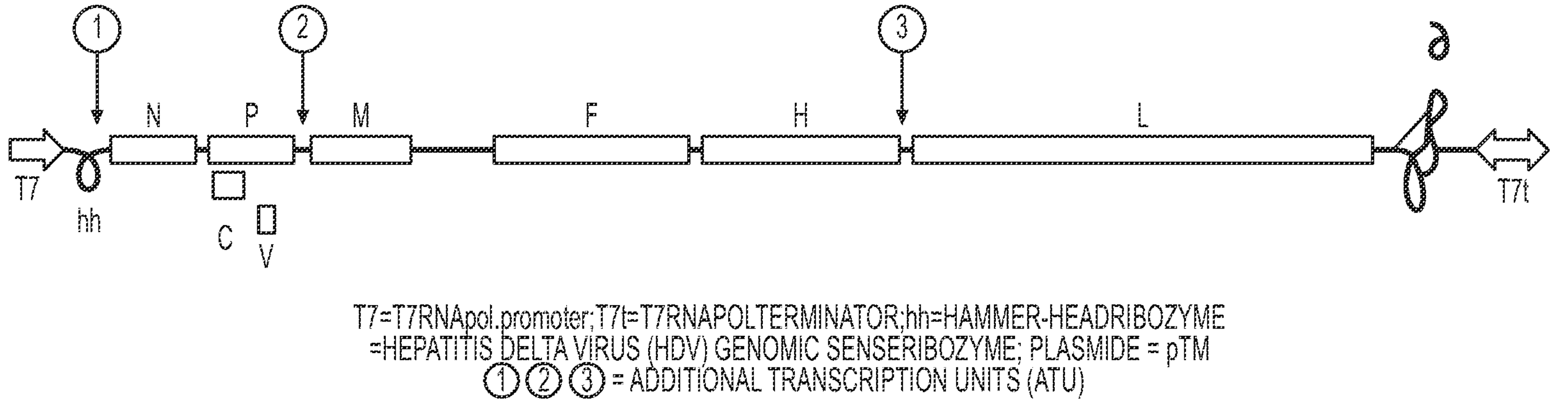

FIGS. 8A and 8B. Schematic representation the additional transcription unit (ATU) (Residues 1817-1843 of SEQ ID NO: 16 and 3475-3498 of SEQ ID NO: 16, respectively, in order of appearance) and Schwarz MV vector plasmid. (A) Cis-acting elements of the ATU inserted in position 2 between phosphoprotein (P) and matrix (M) MV open reading frames. (B). Representation of the three positions of ATU insertion in the Schwarz MV vector plasmid.

Figure 9:

FIG. 9. Expression of YFV proteins by recombinant MV. Vero cells were infected by recombinant EdB-Env$_{YFV}$ and EdB-NS1$_{YFV}$ MV at an MOI of 0.01. Immunofluorescence was performed using a mouse polyclonal anti-YFV serum and a Cy3 secondary anti-mouse IgG antibody. All the syncytia observed in infected Vero cells were positive.

Figure 10:
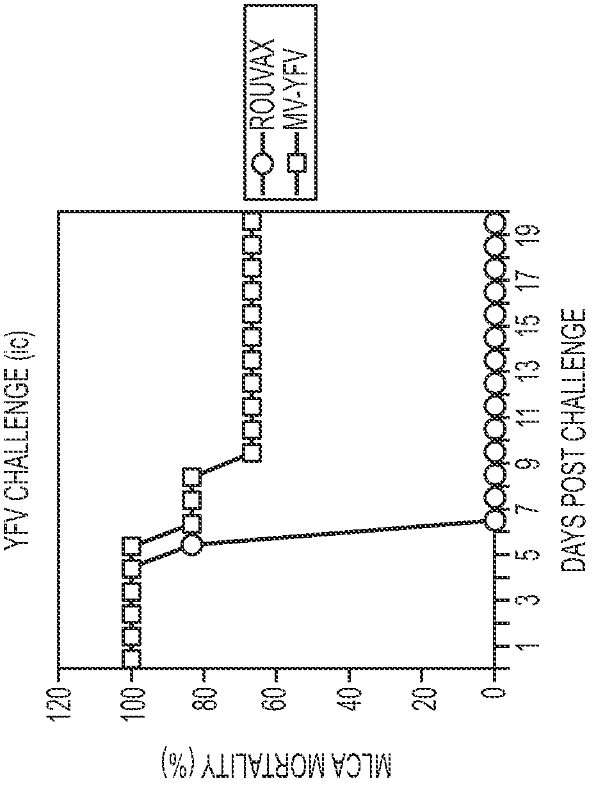

FIG. 10. YFV challenge. Six 4-weeks old mice were inoculated with a mixture of EdB-Env$_{YFV}$ and EdB-NS1$_{YFV}$ viruses ($10^7$ TCID$_{50}$) and 6 control mice were inoculated with the same dose of standard EdB-tag virus. After 1 month, anti-MV serologies were determined and a similar level of antibodies was observed in the two groups. Mice were challenged and mortality was observed.

FIGS. 11A through 11E. Complete nucleotide sequence of the pTM-MVSchw plasmid (CNCM 1-2889; SEQ ID NO: 16). The sequence can be described as follows with reference to the position of the nucleotides

| | |
|---|---|
| 1-8 | NotI restriction site |
| 9-28 | T7 promoter |
| 29-82 | Hammer head ribozyme |
| 83-15976 | MV Schwarz antigenome |
| 15977-16202 | HDV ribozyme and T7 terminator |
| 16203-16210 | NotI restriction site |

-continued

| | |
|---|---|
| 16211-16216 | ApaI restriction site |
| 16220-16226 | KpnI restriction site |
| 16226-18967 | pBluescript KS(+) plasmid (Stratagene) |

FIGS. 12A and 12B. (SEQ ID NO: 17):

The flaviral sequences which have been expressed in MV are the following:

YFV Env seq: This is the Env YFV 17D204 sequence cloned by the inventors.

| | |
|---|---|
| pos 1 à 3 | START codon |
| pos 4 à 51 | Env signal peptide |
| pos 52 à 1455 | Env sequence |
| pos 1456 à 1458 | STOP codon |

The stop and start codons have been added.

YFV NS1 seq: This is the NS1 YFV 17D204 sequence cloned by the inventors.

| | |
|---|---|
| pos 1 à 3 | START codon |
| pos 4 à 78 | NS1 signal peptide |
| pos 79 à 1110 | NS1 sequence |
| pos 1111 à 1113 | STOP codon |

The stop and start codons have been added.

FIG. 12C: WNV Env seq (SEQ ID NO: 18): this is the Env WNV sequence cloned by the inventors.

| | |
|---|---|
| pos 1 à 3 | START codon |
| pos 4 à 51 | env signal peptide |
| pos 52 à 1485 | Env sequence |
| pos 1486 à 1488 | STOP codon |

The stop and start codons have been added.

FIG. 12D: WNV NS1 seq (SEQ ID NO: 19): This is the NS1 WNV sequence cloned by the inventors.

| | |
|---|---|
| pos 1 à 3 | START codon |
| pos 4 à 78 | NS1 signal peptide |
| pos 79 à 1104 | NS1 sequence |
| pos 1105 à 1107 | STOP codon |
| pos 1108 à 1110 | STOP codon (a second is added in order to respect the rule six.) |

The stop and start codons have been added.

Figure 13:
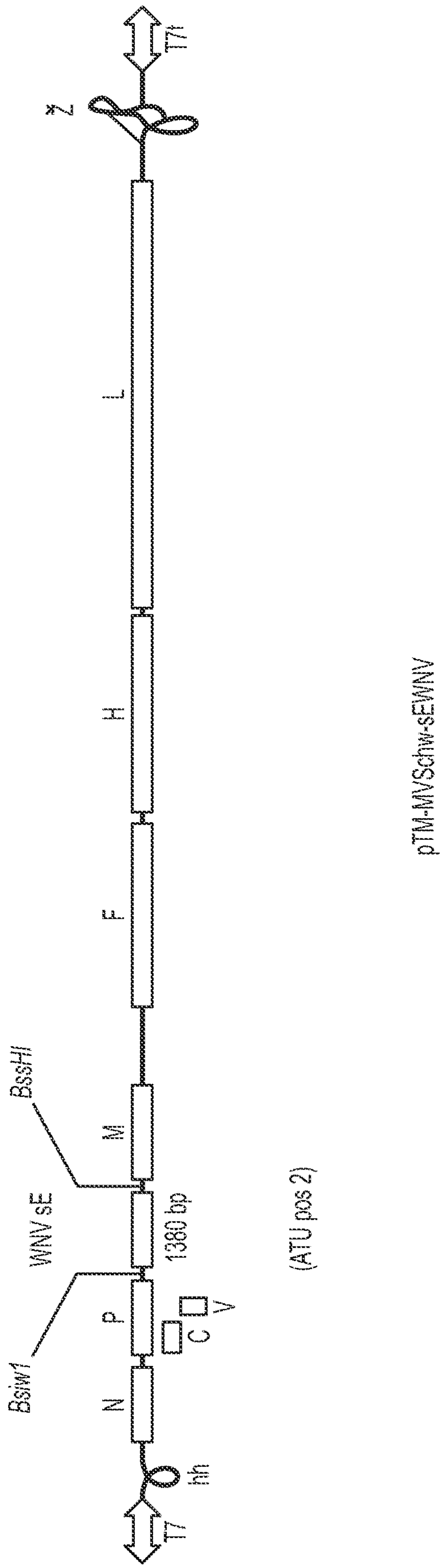
Figure 14A:
Figure 14B:
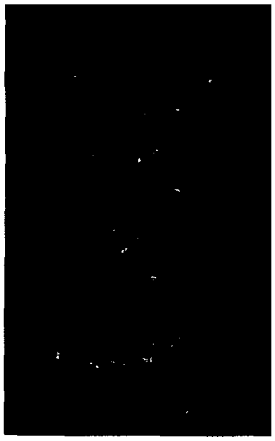
Figure 14C:
Figure 14D:
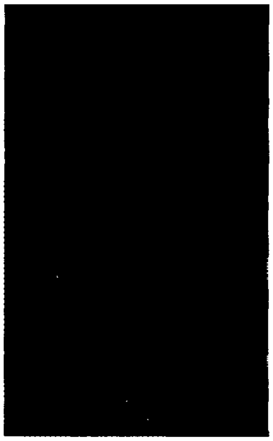

FIG. 13: Schematic representation of recombinant pTM-MVSchw-sE$_{WNV}$. The MV genes are indicated: N (nucleoprotein), PVC (phosphoprotein and V, C proteins), M (matrix), F (fusion), H (hemmaglutinin), L (polymerase). T7: T7 RNA polymerase promoter; T7t: T7 RNA polymerase terminator; b hepatitis delta virus (HDV) ribozyme; ATU: additional transcription unit.

After rescue, the recombinant virus was grown on Vero cell monolayers. The procedure used to prepare the recombinant virus was similar to the standard procedures used to prepare the live attenuated measles vaccines, except for the lyophilization that was not used.

The WNV sE expression in Vero cells infected by the MV-WN sE virus was verified by using indirect immunofluorescence assay as shown in FIG. 14.

FIGS. 14A through 14D: Expression of sE protein from WNV in MV induced syncytia. Immunofluorescence detection of secreted WNV Env (sE) protein in syncytia induced by recombinant MV-WN sE in Vero cells. (A, B) sE protein detected at the external surface all around recombinant MV-induced syncytia. (C, D) intracellular sE protein in recombinant MV-induced syncytia.

Figure 15:
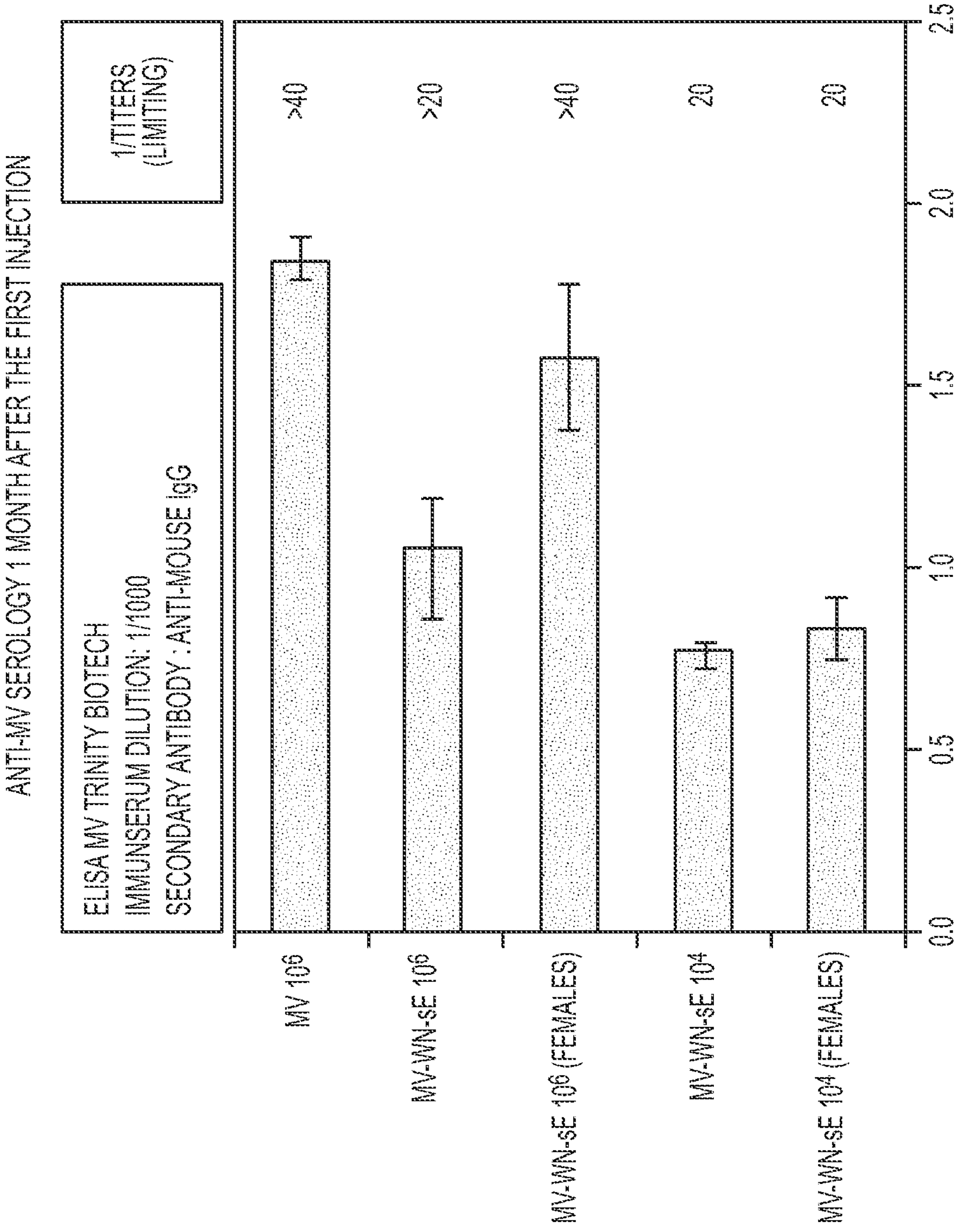

FIG. 15: Anti-MV serology 1 month after the first injection.

FIGS. 16A through 16T: HIV-1 immunogenic sequences prepared for insertion in plasmid pTM-MVSchw2 illustrated in Example II (SEQ ID NOS: 24-43, respectively, in order of appearance).

EXAMPLE I: RECOMBINANT MEASLES VIRUSES EXPRESSING THE NATIVE ENVELOPE GLYCOPROTEIN OF HIV1 CLADE B, OR ENVELOPES WITH DELETED VARIABLE LOOPS, INDUCE HUMORAL AND CELLULAR IMMUNE RESPONSES

Preparing a vaccine against HIV with its formidable ability at evading the host immune responses is certainly a daunting task. However, what we have learned about the immunopathogenesis of the infection and results already obtained with animal models indicate that it may be possible (Mascola, J. R., and G. J. Nabel. 2001. *Vaccines for prevention of HIV-*1 *disease. Immunology.* 13:489-495). Ideally, a preventive immunization should induce 1) antibodies that neutralize primary isolates, thereby preventing entry into host cells, and 2) CTL that eliminate the cells that were nevertheless infected. Antibodies and CTL should be directed at conserved epitopes that are critical for viral entry and replication into host cells.

Several studies, in particular with various candidate vaccines, show that a good cellular immune response might be able to control viral load, although not to eliminate the agent (Mascola, J. R., and G. J. Nabel. 2001. *Vaccines for prevention of HIV-*1*disease. Immunology.* 13:489-495). On the other hand humoral immune responses induced so far by subunit vaccines have been disappointing, mainly because the antibodies induced did not neutralize primary isolates of HIV. For example, recombinant vaccines expressing the SIV Env were able to protect macaques against an homologous, but not an heterologous, challenge (Hu, S., et al 1996. *Recombinant subunit vaccines as an approach to study correlates of protection against primate lentivirus infection. Immunology Letters.* 51:115-119). DNA immunization combined with boosting with soluble recombinant gp could protect macaques against an heterologous challenge but only against a strain of SIV genetically related to the vaccine (Boyer, J. et al 1997. *Protection of chimpanzees from high-dose heterologous HIV-*1 *challenge by DNA vaccination. Nature Medicine.* 3:526-532). More recently, various «prime-boost» regimen, using combinations of naked DNA and viral vectors such as MVA (Amara, R. et al. 2001. *Control of a mucosal challenge and prevention of AIDS by a multiprotein DNA/MVA vaccine. Science.* 292:69-74) or Adenovirus (Shiver, J. W., et al 2002. *Replication-incompetent adenoviral vaccine vector elicits effective anti-immunodeficiency-virus immunity. Nature.* 415:331-335), gave reasonable protection against a challenge with pathogenic SHIV89.6P. «Prime-boost» might not be an absolute requirement since using recombinant live attenuated polio virus vaccine protected macaques against an SIV251 challenge (Crotty, S., et al 2001. *Protection against simian immunodeficiency virus vaginal challenge by using Sabin poliovirus vectors. J Virol.* 75:7435-7452). It is interesting to note that in all these experiments, even when the animals were not protected against the infection, immunization caused a delay in, or even abrogated, clinical disease.

As shown by crystallography, the V1 and V2 loops of gp120 mask the CD4 binding site and the V3 loop masks the binding sites for the CXCR4 and CCR5 co-receptors (Kwong, P. D., et al 2000. *Structures of HIV-1 gp120 envelope glycoproteins from laboratory-adapted and primary isolates. Structure Fold Des.* 8:1329-1339; Kwong, P. D. et al 1998. *Structure of an HIV gp120 envelope glycoprotein in complex with the CD4 receptor and a neutralizing human antibody. Nature.* 393:648-659; Kwong, P. D., et al 2000. *Oligomeric modeling and electrostatic analysis of the gp120 envelope glycoprotein of human immunodeficiency virus. J Virol.* 74:1961-1972). In spite of this, antibodies against the gp120 CD4 binding site are present in the sera of HIV seropositive individuals and are able to neutralize several HIV-1 isolates in in vitro tests (Burton, D. 1997. *A vaccine for HIV type 1: the antibody perspective. Proceedings of the National Academy of Sciences of the United States of America.* 94:10018-10023; Hoffman, T. L et al., 1999. *Stable exposure of the coreceptor-binding site in a CD4-independent HIV-1 envelope protein. Proc Nat Acad Sci USA.* 96:6359-6364). Also, some epitopes which are buried in the 3-D structure of the glycoprotein but become exposed after binding to the co-receptor, can induce highly neutralizing antibodies (Muster, T., et al 1993. *A conserved neutralizing epitope on gp41 of human immunodeficiency virus type 1. J Virol.* 67:6642-6647). Furthermore, neutralizing monoclonal antibodies have been obtained from patient's B cells (Parren, P. W., et al 1997. *Relevance of the antibody response against human immunodeficiency virus type 1 envelope to vaccine design. Immunol Lett.* 57:105-112). They are directed at gp41 linear epitopes (2F5) (Muster, T., F. et al 1993. *A conserved neutralizing epitope on gp41 of human immunodeficiency virus type 1. J Virol.* 67:6642-6647), or at gp120 conformational epitopes (2G12, 17b, 48db12) (Thali, M., et al 1993. *Characterization of conserved human immunodeficiency virus type 1 gp120 neutralization epitopes exposed upon gp120-CD4 binding. J Virol.* 67:3978-3988; Trkola, A., et al. 1996. *Human monoclonal antibody 2G12 defines a distinctive neutralization epitope on the gp120 glycoprotein of human immunodeficiency virus type 1. J Virol.* 70:1100-1108). Used in synergy they can neutralize in vitro several primary isolates (Mascola, J. R. et al 1997. *Potent and synergistic neutralization of human immunodeficiency virus (HIV) type 1 primary isolates by hyperimmune anti-HIV immunoglobulin combined with monoclonal antibodies 2F5 and 2G12. J Virol.* 71:7198-7206) and protect macaques against a mucosal challenge with SHIV (Baba, T. W et al, 2000. *Human neutralizing monoclonal antibodies of the IgG1 subtype protect against mucosal simian-human immunodeficiency virus infection. Nat Med.* 6:200-206; Mascola, J. R., et al 1999. *Protection of Macaques against pathogenic simian/human immunodeficiency virus 89.6PD by passive transfer of neutralizing antibodies. J Virol.* 73:4009-4018; Mascola, J. R., et al 2000. *Protection of macaques against vaginal transmission of a pathogenic HIV-1/SIV chimeric virus by passive infusion of neutralizing antibodies. Nat Med.* 6:207-210). However in infected people, all these antibodies are present in very low amounts, diluted in large quantities of non-neutralizing antibodies directed mainly at the antigenically variable V1, V2 and V3 gp120 loops. Therefore, there is hope that if one could induce high levels of such cross-neutralizing antibodies one may achieve at least some degree of protection. A major goal is to design a vector that will favor the production of such neutralizing antibodies.

For this reason, we engineered mutant gp160 (anchored) and gp140 (soluble) by deleting the hypervariable V1, V2 and V3 loops individually or in combination to expose conserved epitopes and induce antibodies able to neutralize primary isolates. In some of the constructions, we also replaced the V3 loop by the AAELDKWASAA (SEQ ID NO: 8) sequence, especially ELDKWAS (SEQ ID NO: 8) sequence flanked on both sides by two Alanine to maintain the conformation of this gp41 conserved epitope normally buried in the native protein but able to induce large spectrum neutralizing antibodies (Muster, T., F. et al 1993. *A conserved neutralizing epitope on gp41 of human immunodeficiency virus type 1. J Virol.* 67:6642-6647; Binley, J. M., et al 2000. *A recombinant human immunodeficiency virus type 1 envelope glycoprotein complex stabilized by an intermolecular disulfide bond between the gp120 and gp41 subunits is an antigenic mimic of the trimeric virion-associated structure. J Virol.* 74:627-643; Sanders, R. W., et al 2000. *Variable-loop-deleted variants of the human immunodeficiency virus type 1 envelope glycoprotein can be stabilized by an intermolecular disulfide bond between the gp120 and gp41 subunits. J Virol.* 74:5091-5100). The normal alpha helical structure of this peptide should be conserved when exposed in our constructions at the tip of a deleted V3 loop. These constructions, in which the "immunological decoys" have been eliminated and the neutralizing epitopes have been exposed, should be good candidates for the induction of robust neutralizing antibody responses.

The HIV gp constructions were introduced into a measles vaccine vector because it induces very high titers (1/80,000) of neutralizing anti-measles antibodies. (This is probably because it replicates in a large number of cells of different types.) One may hope, therefore, that the antibody response against the engineered HIV gps will also be strong. Furthermore, measles vaccine is also a potent inducer of long lasting cellular responses. The recombinant vaccines induced cross-neutralizing antibodies as well as cellular immune responses after a single injection in $CD46^{+/-}$ $IFN\text{-}\alpha/\beta\_R^{-/-}$ mice. Furthermore, they induced immune responses against HIV in mice and macaques with a pre-existing anti-MV immunity.

Construction of Mutant HIV-1 Envelope Glycoproteins.

The envelope glycoproteins used in this study (FIG. 1) were derived from SHIV89.6P, a chimeric simian/human immunodeficiency virus which contains tat, rev, vpu and env genes of HIV1 in an SIVmac239 background (Reimann, K. A., et al 1996. *A chimeric simian/human immunodeficiency virus expressing a primary patient human immunodeficiency virus type 1 isolate env causes an AIDS-like disease after in vivo passage in rhesus monkeys. J Virol.* 70:6922-6928). The env gene is derived from a cytopathic primary HIV1 isolate, 89.6, which is tropic for both macrophages and T cells (Collman, R., et al 1992. *An infectious molecular clone of an unusual macrophage-tropic* and *highly cytopathic* strain *of human immunodeficiency virus type 1. J Virol.* 66:7517-7521). The env sequence was amplified from the plasmid pSHIV-KB9 (NIH) that was previously cloned after in vivo passages of the original virus (Karlsson, G. B., et al 1997. Characterization of molecularly cloned simian-human immunodeficiency viruses causing rapid CD4+ lymphocyte depletion in rhesus monkeys. *J Virol.* 71:4218-4225). The full-length env (gp160) was amplified by PCR (Pfu polymerase) using primers that contain unique BsiWI and BssHII sites for subsequent cloning in measles vector:

```
160E5
(5'-TATCGTACGATGAGAGTGAAGGAGAAATAT-3'; SEQ ID
NO: 1)
and

160E3
(5'ATAGCGCGCATCACAAGAGAGTGAGCTCAA-3'; SEQ ID
NO: 2).
```

The env sequence corresponding to the secreted form (gp140) was amplified using primers 160E5 and

```
140E3
(5'-TATGCGCGCTTATCTTATATACCACAGCCAGT-3'; SEQ ID
NO: 3).
```

A start and a stop codon were added at both ends of the genes as well as several nucleotides after the stop codon in order to respect the "rule of six", stipulating that the number of nucleotides of MV genome must be a multiple of 6 (Calain, P., and L. Roux. 1993. *The rule of six, a basic feature for efficient replication of Sendai virus defective interfering RNA. J Virol.* 67:4822-4830; Schneider, H., et al 1997. *Recombinant measles viruses defective for RNA editing and V protein synthesis are viable in cultured cells. Virology.* 227:314-322). Both gp160 and gp140 env fragments were cloned in PCR®2.1-TOPO® plasmid (Invitrogen) and sequenced to check that no mutations were introduced.

Mutants with loop-deletions were generated by PCR amplification of two overlapping fragments flanking the sequence to be deleted and annealing of these fragments by PCR. To replace the V3 sequence by the AAELDKWASAA (SEQ ID NO: 8) sequence containing the gp41 epitope (Muster, T., F. et al 1993. *A conserved neutralizing epitope on gp*41 *of human immunodeficiency virus type* 1. *J Virol.* 67:6642-6647), four primers were designed on both sides of BbsI and MfeI sites encompassing the V3 sequence:

```
ΔV3A1
                                  (SEQ ID NO: 4)
(5'-ATAAGACATTCAATGGATCAGGAC-3'),

ΔV3A2
                                  (SEQ ID NO: 5)
(5'TGCCCATTTATCCAATTCTGCAGCATTGTTGTTGGGTCTTGTACAA
TT-3'),

ΔV3B1
                                  (SEQ ID NO: 6)
(5'-GATAAATGGGCAAGTGCTGCAAGACAAGCACATTGTAACATTG
T-3'),
and

ΔV3B2
                                  (SEQ ID NO: 7)
(5'-CTACTCCTATTGGTTCAATTCTTA-3')
```

The underlined sequences in ΔV3A2 and ΔV3B1 correspond to the AAELDKWASAA (SEQ ID NO: 8) epitope with a 12 nucleotides overlap. PCR amplifications with primer pairs ΔV3A1/ΔV3A2 and ΔV3B1/ΔV3B2 produced two fragments of 218 and 499 bp respectively. After gel purification, these fragments were annealed together by 15 PCR cycles without primers and amplified with ΔV3A1/ΔV3B2 primers. The resulting 705 bp fragment was cloned in PCR®2.1-TOPO® plasmid and sequenced. After digestion by BbsI and MfeI, the fragment lacking the sequence encoding the V3 loop (ΔV3-AAELDKWASAA; SEQ ID NO: 8)) was purified and introduced in place of the corresponding fragment in the gp160 and gp140 in PCR®2.1-TOPO® plasmids.

The resulting plasmids were designated pMV2-gp160ΔV3 and pMV2-gp140ΔV3.

The ΔV1V2 mutants were produced using the same procedure. Two fragments were amplified on both sides of V1V2 loop using the following primers:

```
160E5
(5'-TATCGTACG ATGAGAGTGAAGGAGAAATAT-3'; SEQ ID
NO: 1),

ΔV1V2A1
(5'-ATTTAAAGTAACACAGAGTG GGGTTAATTT-3'; SEQ ID
NO: 9),

ΔV1V2B1
(5'-GTTACTTTAAATTGTAACACCTCAGTCATTAC ACAGGCCTGT-
3'; SEQ ID NO: 10),

ΔV1V2B2
(5'-TTGCATAAAATGCTCTCCCTGGTCCTATAG-3'; SEQ ID
NO: 11)
```

The italicized sequences in ΔV1V2A1 and ΔV1V2B1 correspond to a 12 nucleotide overlap generated between the two fragments. PCR amplifications with primer pairs 160E5/ΔV1V2A1 and ΔV1V2B1/ΔV1V2B2 produced two fragments of 400 and 366 bp respectively. After gel purification, these fragments were annealed together by 15 PCR cycles without primers and amplified with 160E5/ΔV1V2B2 primers. The resulting 766 bp fragment was cloned in PCR®2.1-TOPO® plasmid and sequenced. After digestion with BsiWI (in 160E5 primer) and BbsI, the fragment lacking the sequence encoding the V1V2 loop was purified and introduced in place of the corresponding fragment in the gp160 and gp140 in PCR®2.1-TOPO® plasmids.

To obtain the ΔV1V2V3 mutants, the BsiWI BbsI fragment lacking the sequence encoding the V1V2 loop was introduced in place of the corresponding fragment in the PCR®2.1-TOPO®-gp140ΔV3 and PCR®2.1-TOPO®-gp160ΔV3 plasmids.

Figure 2A:
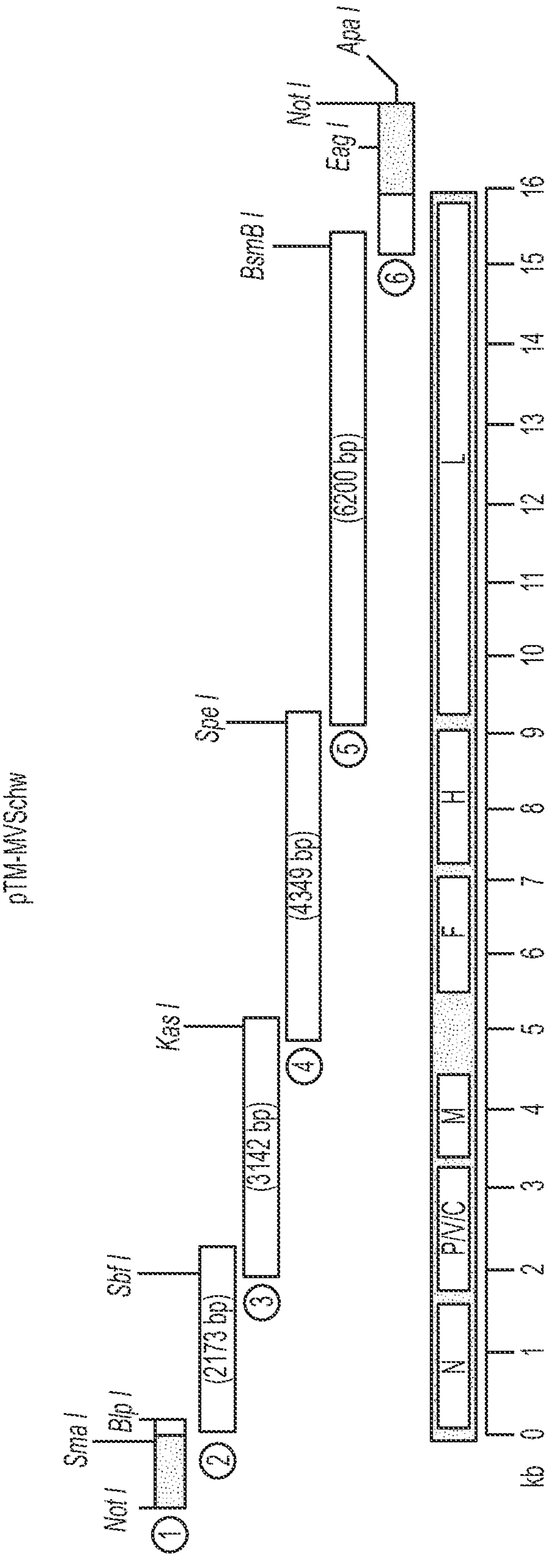
FIG. 2A. Schematic map of the pTM-MV Schw plasmid. To construct the complete sequence, the six fragments represented in the upper part were generated and recombined step by step using the unique restriction sites indicated. T7=T7 promoter; hh=hammerhead ribozyme; hΔv=hepatitis delta ribozyme (=δ); T7t=T7 RNA polymerase terminator.
Figure 2B:
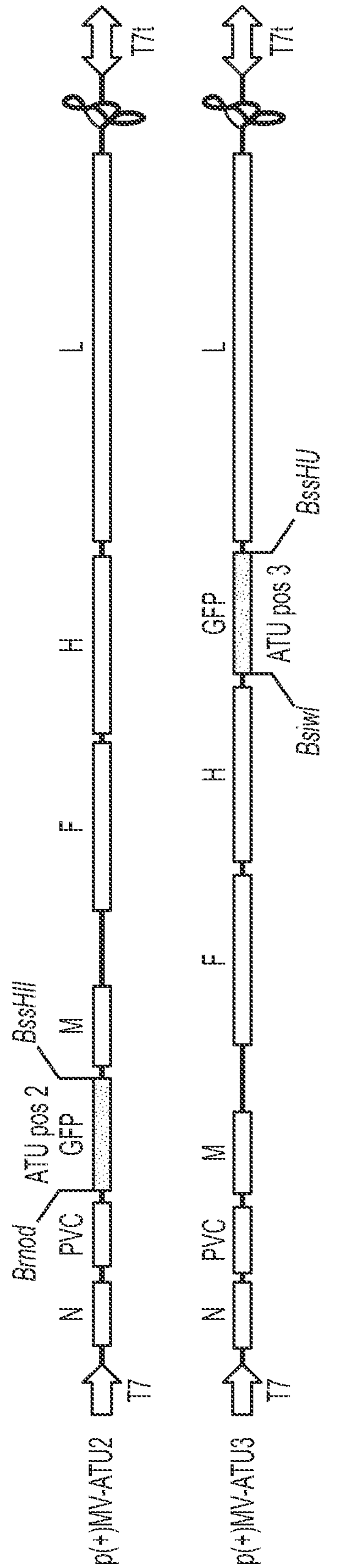
FIG. 2B. The pMV(+) vectors with ATU containing a green fluorescent protein (GFP) gene in position 2 and position 3. The MV genes are indicated: N (nucleoprotein), PVC (phosphoprotein and V C proteins), M (matrix), F (fusion), H (hemaglutinin), L (polymerase). T7: T7 RNA polymerase promoter; T7t: T7 RNA polymerase terminator; b: hepatitis delta virus (HDV) ribozyme; ATU: additional transcription unit.

After BsiWI/BssHII digestion of the different PCR®2.1-TOPO® plasmids, the native and mutant gp160 and gp140 sequences were cloned in the EdB-tag vector in ATU position 2 and ATU position 3 (FIG. 2B). The resulting plasmids were designated pMV2-gp160$_{HIV}$, pMV2-gp140$_{HIV}$.

Cells were maintained in Dubelbecco's modified Eagle's medium (DMEM) supplemented with 5% fetal calf serum (FCS) for Vero cells (African green monkey kidney), or with 10% FCS, 1 mg/ml G418 for helper 293-3-46 cells (35) and for P4-CCR5 cells (Hela-CD4-CXCR4-CCR5-HIVLTR-LacZ) (12).

Recovery of Recombinant MV$_{EdB}$-Env$_{HIV89.6}$ Virus.

To recover the recombinant MV$_{EdB}$-HIV viruses from the plasmids, the different EdB-HIV Env plasmids were used to transfect 293-3-46 helper cells.

To recover the measles virus from the EdB-HIV-Envplasmids cDNA, we used the helper-cell-based rescue system described by Radecke et al. (Radecke, F., et al 1995. *Rescue of measles viruses from cloned DNA. EMBO Journal.* 14:5773-5784) and modified by Parks et al. (Parks, C. L., et al 1999. Enhanced measles virus cDNA rescue and gene expression after heat shock. *J Virol.* 73:3560-3566). Human helper cells stably expressing T7 RNA polymerase and measles N and P proteins (293-3-46 cells, disclosed by Radecke et al) were co-transfected using the calcium phosphate procedure with the EdB-HIV-Env plasmids (5 μg) and a plasmid expressing the MV polymerase L gene (pEMC-La, 20 ng, disclosed by Radecke et al). The virus was rescued after cocultivation of transfected 293-3-46 helper cells at 37° C. with primate Vero cells (african green monkey kidney). In this case, syncytia appeared systematically in all transfections after 2 days of coculture.

In a further experiment (FIGS. 3C-D), after overnight incubation at 37° C., the cells were heat shocked at 43° C. for 3 hours in fresh medium (40). Heat-shocked cells were incubated at 37° C. for 2 days, then transferred onto a 70% confluent Vero cells layer (10 cm Petri dishes). Syncytia appeared in Vero cells after 2-5 days of coculture. Single syncytia were harvested and transferred to Vero cells grown in 35 mm wells. The infected cells were expanded in 75 and 150 cm3 flasks. When syncytia reached 80-90% confluence, the cells were scraped in a small volume of OptiMEM (Gibco BRL) and frozen and thawed once. After centrifugation, the supernatant, which contained virus, was stored at −80° C.

Expression of HIV1 Glycoproteins by Recombinant MV.

The rescued recombinant viruses MV2-gp140, MV2-gp160, MV3-gp140ΔV3 and MV2-gp160ΔV3 were propagated on Vero cells and the expression of HIV Env glycoproteins was analyzed by western blotting and immunofluorescence. Infection of Vero cells by recombinant MV2 viruses (with transgene insertion in position 2) showed a high expression of the HIV Env gp160 and gp140. The cleaved recombinant Env protein (gp120) was also detected. The MV3 virus (with transgene insertion in position 3) expressed lower levels of transgene, as expected due to the transcription gradient observed in MV expression. Taken together, these results indicate that HIV1 Env glycoprotein and ΔV3 mutant are efficiently expressed by the recombinant MVs.

Virus titration. The titers of recombinant MV were determined by an endpoint limit dilution assay on Vero cells. 50% tissue culture infectious dose ($TCID_{50}$) were calculated using the Karber method.

Growth Capacity of the $MV_{EdB}$-$Env_{HIV89.6}$ Recombinant Viruses.

To analyze the growth capacity of $MV_{EdB}$-$Env_{HIV89.6}$ viruses, Vero cells were infected at different MOI (0.01 and 0.0001), incubated at 37° C., and collected at different time points. Titers of cell-associated viruses were determined for each sample using the $TCID_{50}$ method on Vero cells. FIG. 4 shows that using MOI of 0.0001, the growth kinetics of $MV_{EdB}$-$Env_{HIV89.6}$ viruses was delayed, as compared to standard $MV_{EdB\text{-}tag}$. However, using an MOI of 0.01 the production of recombinant viruses was comparable to that of standard virus, and peak titers of $10^7$ $TCID_{50}$/ml or even more were easily obtained.

In particular, monolayers of Vero cells (T-25 flasks) were infected at an MOI of 0.05 with the recombinant viruses. When syncytia reached 80-90% confluence, cells were lysed in 150 mM NaCl, 50 mM Tris pH=8, 1% NP40, 0.5 mM PMSF and 0.2 mg/ml Pefabloc (Interbiotech, France). Chromatin was removed by centrifugation and the concentration of protein in the supernatant was determined with a Bradford assay. Proteins (50 μg) were fractionated by sodium dodecyl sulfate polyacrylamide gel electrophoresis (SDS-PAGE) and transferred to cellulose membranes (Amersham Pharmacia Biotech). The blots were probed with a mouse monoclonal anti-HIV gp120 antibody (Chessie 13-39.1, NIH-AIDS Research & Reference Reagent Program) or with a monoclonal anti-MV N antibody (Chemicon, Temecula, USA). A goat anti-mouse IgG antibody-horseradish peroxidase (HRP) conjugate (Amersham) was used as second antibody. Peroxidase activity was visualized with an enhanced chemiluminescence detection Kit (Pierce).

Mice Immunizations

Mice susceptible for MV infection were obtained as described previously (21). Transgenic FVB mice heterozygous for CD46 (32), the receptor for MV vaccine strains (24) were crossed with 129sv IFN-α/$\beta R^{-/-}$ mice lacking the type I interferon receptor (22). The F1 progeny was screened by PCR and the $CD46^{+/-}$ animals were crossed again with 129sv IFN-α/$\beta R^{-/-}$ mice. IFN-α/$\beta R^{-/-}$ $CD46^{+/-}$ animals were selected and used for immunization experiments. The same type of mice have already been shown to be susceptible to MV infection (20, 21).

Six-weeks-old female $CD46^{+/-}$ IFN-α/$\beta R^{-/-}$ mice were inoculated intraperitoneally with $10^7$ $TCID_{50}$ of MV2-gp140, MV2-gp160, MV3-gp140ΔV3 or MV2-gp160ΔV3 recombinant viruses prepared and titrated as described above. Mice were euthanized 7 days and 1 month post-infection. Spleens and whole blood were collected. Splenocytes were extracted from spleens and kept frozen in liquid nitrogen until use. Serums were decanted and serology was analyzed by ELISA for MV (Trinity Biotech, USA) and HIV (Sanofi Diagnostics, France).

Monkey Immunization

Two colony-bred rhesus macaques (*Macaca mulatto*) (seronegative for simian type D retrovirus, simian T-cell lymphotropic virus, simian immunodeficiency virus and MV) were vaccinated subcutaneously with 104 TCID50 of MV vaccine (Rouvax, Aventis Pasteur, France). They were boosted one year later by two injections of 5 106 TCID50 of MV2-gp140 recombinant virus done at 1 month interval. Blood samples were collected at different time points and anti-MV and anti-HIV antibodies were looked for.

Humoral Immune Response to Rescued Recombinant Viruses.

1st Experiment

Humoral immune responses against MV and HIV Env were analyzed by ELISA in serums collected 1 month after immunization of mice. Titers were determined by limiting dilutions. The results presented in FIG. 5 show that all the vaccinated mice responded to measles with high titers of antibodies (1/50000 to 1/80000) and to HIV Env with titers between 1/1000 and 1/5000 depending on the inserted sequence. The antibody titers between MV and HIV cannot be compared because the ELISA used have not the same sensitivity. The MV ELISA (Trinity Biotech, USA) detected the whole response against all MV proteins, while the HIV ELISA (Sanofi Diagnostics) detected only the anti-HIV Env antibodies. The capacity of these sera to neutralize a primary HIV clade B isolate was tested using indicator cells, P4R5, that express beta-galactosidase when infected with HIV (HeLa-CD4-CXCR4-CCR5-HIV LTR-LacZ cells). In preliminary experiments, we tested sera of mice immunized with recombinant MV-HIV viruses expressing native envelope glycoproteins (MV-$gp160_{HIV}$-1 or $MV_{EdB}$-$gp140_{HIV89.6}$). The results showed that these sera had a 70-50% neutralizing activity against a primary isolate, Bx08, when used at a 1/20 dilution (FIG. 6). The neutralizing activity of sera raised against the genetically engineered Env molecules is currently under study.

2nd Experiment

In another experiment (FIG. 5C-F), sera were collected one month after immunization and heat inactivated. Anti-MV (Trinity Biotech, USA) and anti-HIV Env (Sanofi Diagnostic Pasteur, Biorad, France) antibodies were detected using commercial ELISA kits. An anti-mouse antibody-HRP conjugate (Amersham) was used as the secondary antibody. Titers were determined by limiting dilutions and calculated as the highest dilution of serum giving twice the absorbence of a 1/100 dilution of a mixture of control sera. The same ELISA kits were used for sera from macaque monkeys. An anti-monkey IgG secondary antibody was used to detect anti-HIV antibodies. Anti-MV antibodies were detected with an anti-human IgG in order to be able to calibrate the assay with standards supplied in the MV ELISA kit. They were expressed in mIU/ml. A mixture of 5 samples from negative monkeys was used as the negative control. The titer of anti-ELDKWAS (Residues 3-9 of SEQ ID NO: 8) antibodies was determined by ELISA using 96-well NeutrAvidin plates (Pierce) coated with the ELDKWAS (Residues 3-9 of SEQ ID NO: 8) biotynilated peptide (Neosystem, 5 μg/ml in $NaHCO_3$ 2M, $Na_2CO_3 \cdot H_2O$ 2M, pH 9.6). Sera from mice immunized with standard MV were used as negative controls. Peptide-bound antibodies were detected with anti-mouse antibody-HRP conjugate.

HIV-1 neutralization assays. Sero-neutralization was tested against SHIV89.6p (A. M. Aubertin, Université Louis Pasteur, Strasbourg, H. Fleury, Bordeaux, France), 92US660, 92US714, 92HT593 (NIH-AIDS Research & Reference Reagent Program), and a clade A primary isolate: 3253 (G. Pancino, Institut Pasteur, Paris). These viruses were propagated on PHA-stimulated human PBMC as already described (42). HIV-1 neutralization assays were performed using the P4-CCR5 indicator cell line (43). P4-CCR5 cells were seeded in 96-well plates (20 000 cells per well) and incubated at 37° C. in DMEM, 10% FCS for 24 h. The medium was replaced by 100 μl DMEM, 10% FCS, DEAE dextran (100 μg/ml) and the cells were incubated at 37° C. for 30 minutes. Virus (0.5 ir 1 ng p24) was incubated with serum dilutions in 50 μl PBS at 37° C. for 20 minutes and the virus-serum mixtures were added to the cells in triplicate. After 48 hours of incubation, the β-galactosidase activity was measured using a Chemiluminescence Reporter Gene Assay (Roche, USA).

Cellular Immune Responses to Rescued Recombinant Viruses.

The capacity of splenocytes from vaccinated mice to secrete α-IFN upon in vitro stimulation was tested by flow-cytometry and ELISpot assays. Frozen cells from immunized mice were thawed 18 h before functional assays and incubated in RPMI medium supplemented with 10% 56° C.-heated FCS (Gibco) and 10 U rh-IL2 (Boehringer Mannheim). Cell viability was evaluated by trypan-blue exclusion.

To perform γ-IFN ELISpot assay, multiscreen-HA 96-wells plates were coated with capture anti-mouse γ-IFN (R4-6A2, Pharmingen) in PBS solution (6 μg/ml). After overnight incubation at 4° C., wells were washed 4 times with PBS. The remaining protein binding sites were blocked by incubating wells with 100 μl RPMI/FCS 10% for 1 h at 37° C. Medium was withdrawn just before addition of cell suspensions (100 μl) and stimulating agents (100 μl). Splenocytes from immunized mice were plated at $5.10^5$ cell per well in duplicate in RPMI. Concanavalin A (5 μg/ml, Sigma) was used as a positive control, and RPMI/IL2 (10 U/ml) as a negative control. Cells were stimulated either with 1 μg/ml HIV1 gp120, 1 μg/ml Bovine Serum Albumin (Sigma), or Edm-Tag virus (MOI=1). After incubation for 2 h at 37° C. for viral adsorption, heated-FCS (10 μl) was added in each well (10% final concentration) and plates were incubated for 24-36 h at 37° C. To remove cells, the plates were washed twice with PBS, 4 times with PBS containing 0.05% TWEEN™ 20 (Sigma), and 2 times again with PBS. For detection, a biotinylated anti-mouse γ-IFN antibody (XMG1.2, Pharmingen) was added to each well (100 μl, 4 μg/ml in PBS-0.1% FCS). After incubation for 2 h at room temperature, plates were washed 4 times with PBS-0.1% TWEEN™ 20 and twice with PBS. Streptravidin-Alkaline Phosphatase (AP) conjugate (Roche) (100 μl, 1/2000 dilution in PBS) was added and incubated for 1-2 hours at room temperature. The enzyme was removed by 4 washes with PBS-0.1% TWEEN™ 20 and 2 washes with PBS. Spots were then developed with BCIP/NBT color substrate (Promega) prepared in AP buffer pH 9.5 (1 M Tris, 1.5 M NaCl, 0.05 M MgCl2). Wells were monitored for spot formation by eye: after a 15-30 minutes incubation the reaction was stopped by washing under running tap water. After drying at least overnight at room temperature, colored spots were counted using an automated image analysis system ELISpot Reader (Bio-Sys).

For Flow-cytometry assays, 5 $10^5$ splenocytes (diluted in 100 μl RPMI) were stimulated in V-bottomed 96-wells plates with either 1 μg/ml HIV1 gp120 protein (AbCys) in RPMI/IL2 (10 U/ml), or EdB-tag virus (MOI=1) diluted in 100 μl RPMI/IL2. Non stimulated control cells were incubated with RPMI/IL2 (10 U/ml). After incubation for 2 h at 37° C. for viral adsorption, 10 μl FCS were added in each well (10% final concentration) and plates were incubated overnight at 37° C. The medium was then replaced by 150 μl RPMI-10% FCS containing 10 U rh-IL2 and 10 μg/ml Brefeldin A (Sigma). Cells were incubated for 4 hours at 37° C., harvested, stained with anti-mouse CD8-APC (Pharmingen) and anti-mouse CD4-CyCr (Pharmingen) for 20 minutes at room temperature, washed with PBS-BSA (0.5%), then fixed for 5 minutes at 37° C. in CytoFix (Pharmingen). After washing cells were resuspended in 100 μl PBS-BSA (0.5%) containing 0.1% Saponin (Sigma) and incubated for 30 minutes at room temperature with anti-mouse γ-IFN-PE (Pharmingen). Cells were washed again and samples were analyzed using a FACSCalibur cytometer (Becton Dickinson). The data were analyzed using Cell Quest software.

Recombinant MV Express HIV89.6 Env Glycoproteins and Replicate Efficiently.

The anchored (gp160) and soluble (gp140) forms of the HIV Env glycoprotein (strain SHIV89.6p), with or without deletion of the V3 loop and insertion of an additional ELDKWAS (Residues 3-9 of SEQ ID NO: 8) epitope, were inserted into one of the ATU of the p(+)MV vector (FIG. 2). Recombinant viruses MV2-gp140, MV2-gp160, MV3-gp140ΔV3 and MV2-gp160ΔV3 were obtained after transfection of the plasmids into the 293-3-46 helper cell line and propagation in Vero cells. MV2- and MV3- refers to the site of the insertion, position 2 or 3 respectively, of the EnvHIV89.6 construction. Expression of the EnvHIV89.6 protein was analyzed by western blotting of infected-cells lysates (FIG. 3) and immunofluorescence (not shown). The MV2-gp140 and MV2-gp160 viruses showed a high level of expression of the EnvHIV89.6 protein (FIG. 3C, lanes 1, 2, 4). As expected, the MV2-gp160Δ viruses expressed the env gp160 precursor as well as the cleaved gp120 protein (FIG. 3C, lanes 2, 4). In contrast, the MV2-gp140 and MV3-gp140ΔV3 viruses expressed only the secreted, uncleaved gp140 form. The MV3-gp140ΔV3 virus expressed slightly lower levels of transgene than viruses of the MV2- series, as expected, due to the transcription gradient observed in MV expression (FIG. 3C, lane 3). Taken together, these results indicate that $Env_{HIV89.6}$ and the ΔV3 mutants were efficiently expressed and correctly matured. The recombinant MV were passaged 5 times on Vero cells and the expression of the transgene was compared to that of the MV nucleoprotein. FIG. 3 shows that $Env_{HIV89.6}$ expression was similar for passages 2 and 5, confirming the stability of expression of transgenes in this system.

The growth of MV-$Env_{HIV89.6}$ recombinant viruses was analyzed on Vero cells using an MOI of 0.0001 or 0.01. The growth of recombinant viruses was only slightly delayed compared to that of standard EdB-tag MV rescued from p+(MV). Viruses expressing the secreted gp140 were less affected than viruses expressing the anchored gp160. The gp140ΔV3 recombinant grew at the same rate as control MV. The delay observed with viruses expressing the anchored gp160 may be due either to lower replication rate, because of the larger size of the transgene, or to reduced MV budding because of the insertion of gp160 at the surface of the infected cells. Nevertheless, the final yield of recombinant viruses was comparable to that of control MV and peak titers of about $10^6$ to $10^7$TCID50/ml were obtained routinely.

Induction of Humoral Immune Response to Recombinant MV in Susceptible Mice.

Figure 5B:
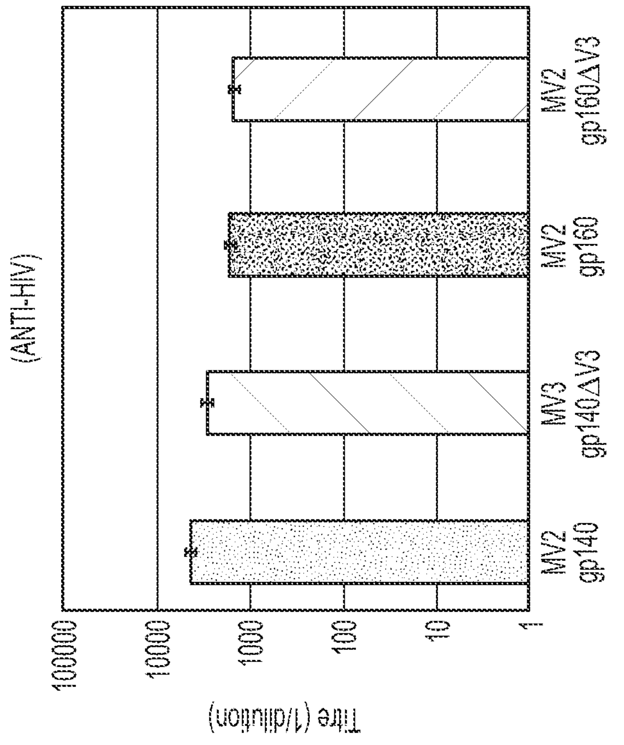
Figure 5A:
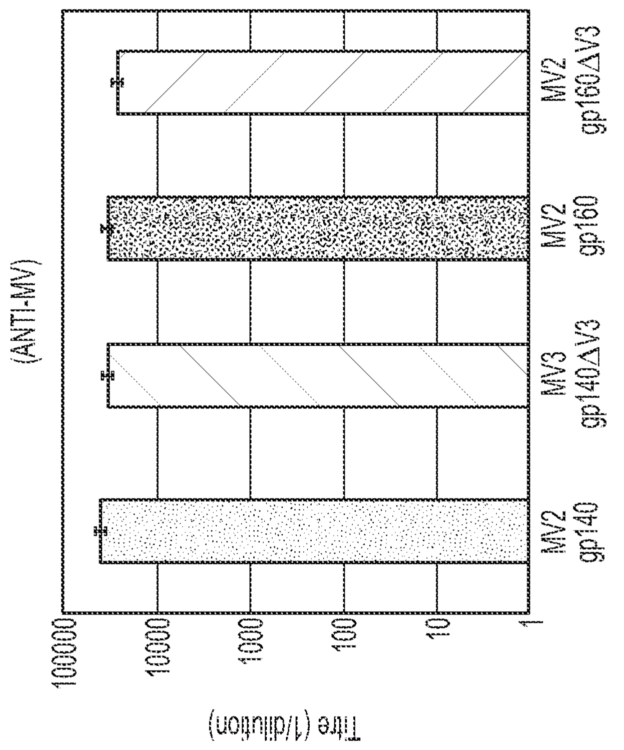
Figure 5C:
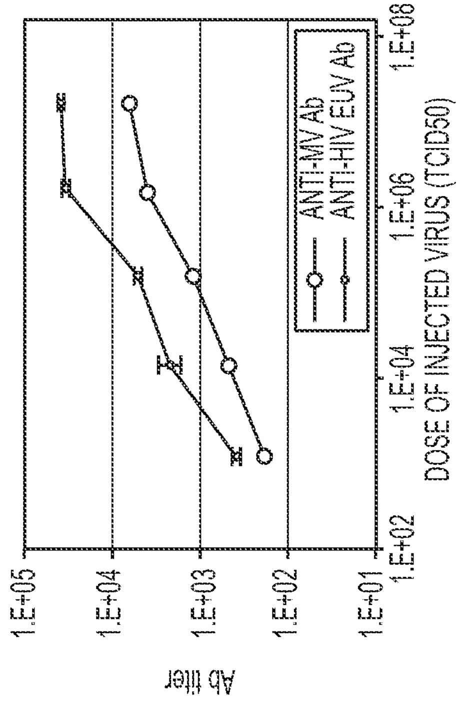
Figure 5D:
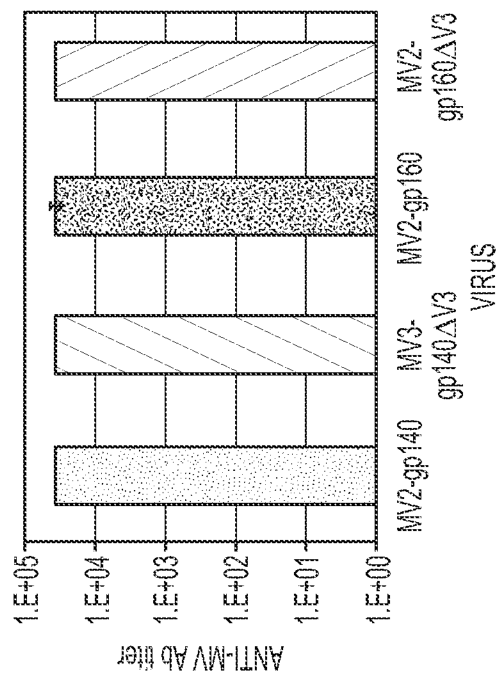
Figure 5E:
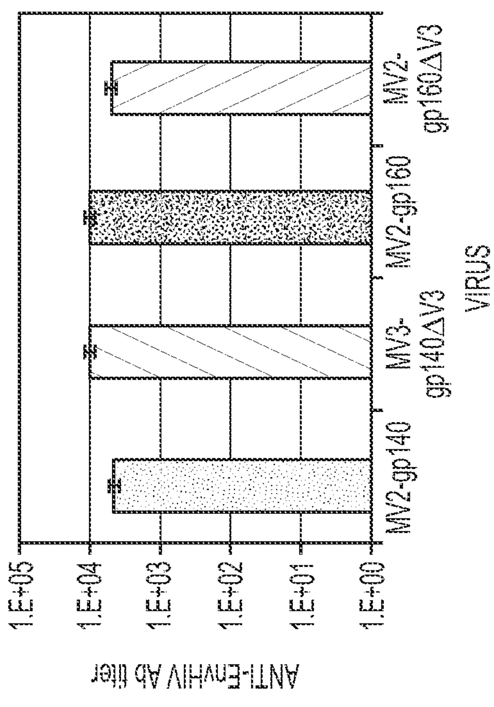
Figure 5F:
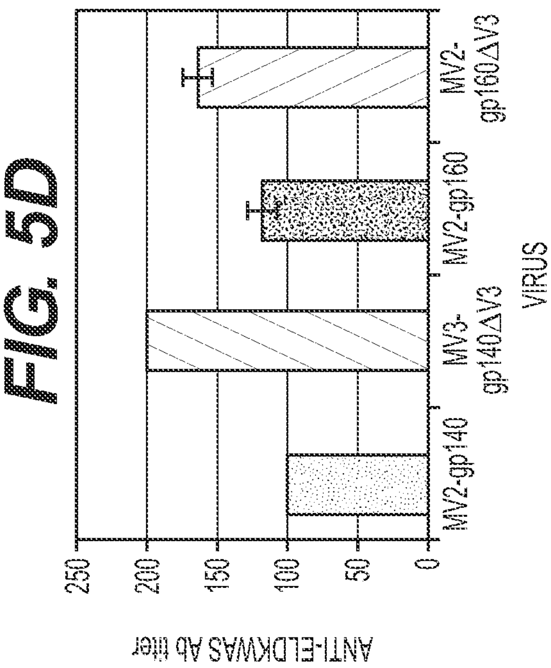

The immunogenicity of MV-$Env_{HIV89.6}$ viruses was tested in genetically modified mice expressing the human CD46 MV receptor and lacking the Type I IFN receptor. Increasing doses of MV2-gp160 virus (103-107 TCID50) were tested in 5 groups of 3 mice. Antibodies to MV and HIV Env were looked for by ELIA in sera collected 1 month after immunization (FIG. 5C). Both anti-MV and anti-HIV antibody titers increased when the dose of recombinant MV increased. Since high anti-MV titers were obtained when animals were inoculated with $10^6$ to $10^7$ $TCID_{50}$, mice were immunized with $5.10^6$ $TCID_{50}$ in all further experiments. At this dose, anti-MV antibody titers were six fold higher than anti-HIV titers. One should keep in mind that immunization was against HIV Env only, whereas all MV proteins were expressed during infection. To compare the immunogenicity of the different $Env_{HIV}$ constructs, four groups of 6 mice were inoculated intraperitoneally with various MV-$Env_{HIV89.6}$ viruses (FIGS. 5B, 5E). All mice responded to MV (mean anti-MV titer: 5 $10^4$) and to HIV Env (mean anti-HIV titer: 8 $10^3$). No difference in anti-MV or anti-HIV or antiHIV titers was observed between the four constructs tested. Interestingly, expression from the ATU 2 or the ATU 3 position of the MV vector did not affect the antibody response. Because the ΔV3 constructions expressed an additional ELDKWAS (Residues 3-9 of SEQ ID NO: 8) epitope, the antibody response against this gp41 epitope was examined separately using a specific ELISA assay (FIG. 5F). The results showed that the ΔV3-ELDKWAS (Residues 3-9 of SEQ ID NO: 8) constructions induced higher titers of anti-ELDKWAS (Residues 3-9 of SEQ ID NO: 8) antibodies. The titer of 1/50 000 corresponds to the dilution of an immune serum capable of recognizing the antigen administered for the immunization, in ELISA assay.

MV-$Env_{HIV}$89.6 Viruses Induce Neutralizing Anti-HIV Antibodies.

The capacity of these sera to neutralize either homologous SHIV89.6p virus or various heterologous primary HIV-1 isolates was tested using a single cycle virus infectivity assay on P4-CCR5 indicator cells (43). P4-CCR5 cells express the CD4, CXCR4 and CCR5 HIV-1 receptors and have been stably transfected with an HIV LTR LacZ. Therefore, they are susceptible to HIV-1 isolates and express 3-galactosidase upon infection. The sero-neutralization assay was validated using a combination of anti-HIV immunoglobulin (HIVIG) and monoclonal antibodies (2F5 and 2G12) previously shown to synergistically neutralize primary HIV isolates (17). We also used sera from infected patients that neutralize primary HIV isolates (17). We also used sera from infected patients that neutralize primary HIV primary isolates using a standard neutralization assay on human PBMCs (42). The neutralizing activity of a serum (Table 1) is expressed as the ratio of the reduction of infection obtained with this serum over the reduction obtained with negative control sera used at the same dilution (sera from HIV negative individuals and from infected patients neutralized clade B and A viruses equally well in this assay.

As shown in Table 1, antibodies induced in mice by the four MV-$Env_{HIV89.6}$ viruses neutralized the homologous SHIV89.6p at both dilutions tested (1/30 and 1/60). No significant difference was observed between the sera obtained with the different Env constructs, indicating that the secreted and anchored from of HIV glycoprotein induced neutralizing antibodies against homologous virus equally well when expressed by MV. Deleting the V3 loop, known to contain type-specific neutralizing epitopes, had no significant effect on the induction of antibodies that neutralized the homologous virus. This suggests that the deletion might have been compensated either by the addition of a second ELDKWAS (Residues 3-9 of SEQ ID NO: 8) gp41 neutralizing epitope, or by the uncovering of other neutralizing epitopes.

The antibodies induced by the recombinant viruses neutralized heterologous primary clade B isolates, except the 92HT593 isolate, as well as a clade A virus. In each case, antibodies induced by the anchored gp160 were slightly more neutralizing than antibodies induced by the secreted gp140, especially against the clade A 3253 virus. The antibodies induced by the ΔV3-ELDKWAS (Residues 3-9 of SEQ ID NO: 8) $Env_{HIV89.6}$ neutralized heterologous viruses more efficiently than those induced by the native envelope. This was particularly striking for the Bx08 virus which could be neutralized up to 90% by sera from mice immunized with MV2-gp160ΔV3 (1/30 dilution) but not by sera from mice immunized with MV expressing the native $Env_{HIV89.6}$. This neutralization was just as efficient as neutralization by positive control sera. These results show that replacing the V3 loop of $Env_{HIV89.6}$ by an additional ELDKWAS (Residues 3-9 of SEQ ID NO: 8) gp41 epitope and expressing the construct with a MV vector allowed the induction of antibodies with cross-neutralizing activity against clade A and B HIV-1 primary isolates, at least in the context of recombinant MV infection of mice.

TABLE 1

Neutralization of HIV-1 primary heterologous isolates by sera from MV-Env$_{HIV89.6}$ immunized mice[a].

| | | | | | | | | | Positive controls | | |
|---|---|---|---|---|---|---|---|---|---|---|---|
| | Mice Sera (1/60) | | | | Mice Sera (1/30) | | | | | Human HIV | |
| | | MV2 | | MV2 | | MV2 | | MV2 | Mab | sera[c] | |
| Virus isolate (subtype) | MV2 Gp140 | Gp140 ΔV3 | MV2 Gp160 | Gp160 ΔV3 | MV2 Gp140 | Gp140 ΔV3 | MV2 Gp160 | Gp160 ΔV3 | (2F5/2G12/ HIV-IG | 4 61/40) | 33 −1/30) |
| SHIV 89.6 | 40 | 50 | 52 | 45 | 76 | 57 | 72 | 68 | ND | ND | ND |
| Bx08 (B) | 0 | 31 | 0 | 40 | 0 | 76 | 18 | 90 | 94 | 94 | 90 |
| 92 US 660 (B) | 2.5 | 15 | 13 | 17 | ND | ND | ND | ND | ND | ND | ND |
| 92 US 714 (B) | 45 | 49 | 45 | 68 | ND | ND | ND | ND | ND | ND | ND |
| 92 HT 593 (B) | 0 | 0 | 0 | 0 | 0 | 0 | 0 | 0 | ND | ND | ND |
| 3253 (A) | 0 | 0 | 18 | 30 | 0 | 10 | 43 | 49 | 73 | 54 | 45 |

[a]Serum was evaluated for neutralizing antibodies at two dilutions. Values are % reduction in infection of primary HIV isolates on P4-CCR5 cells in presence of mice sera (three mice per point). Determinations were made in triplicate and the standard deviations were <10%.

[b] Mix of HIVIG (2.5 mg/ml) and Mabs 2F5 and 2G12 (25 μg/ml).

[c]Numbers correspond to the nomemclature used in Burrer et al.

Induction of Cellular Immune Response Against Recombinant MV

Figure 7A:
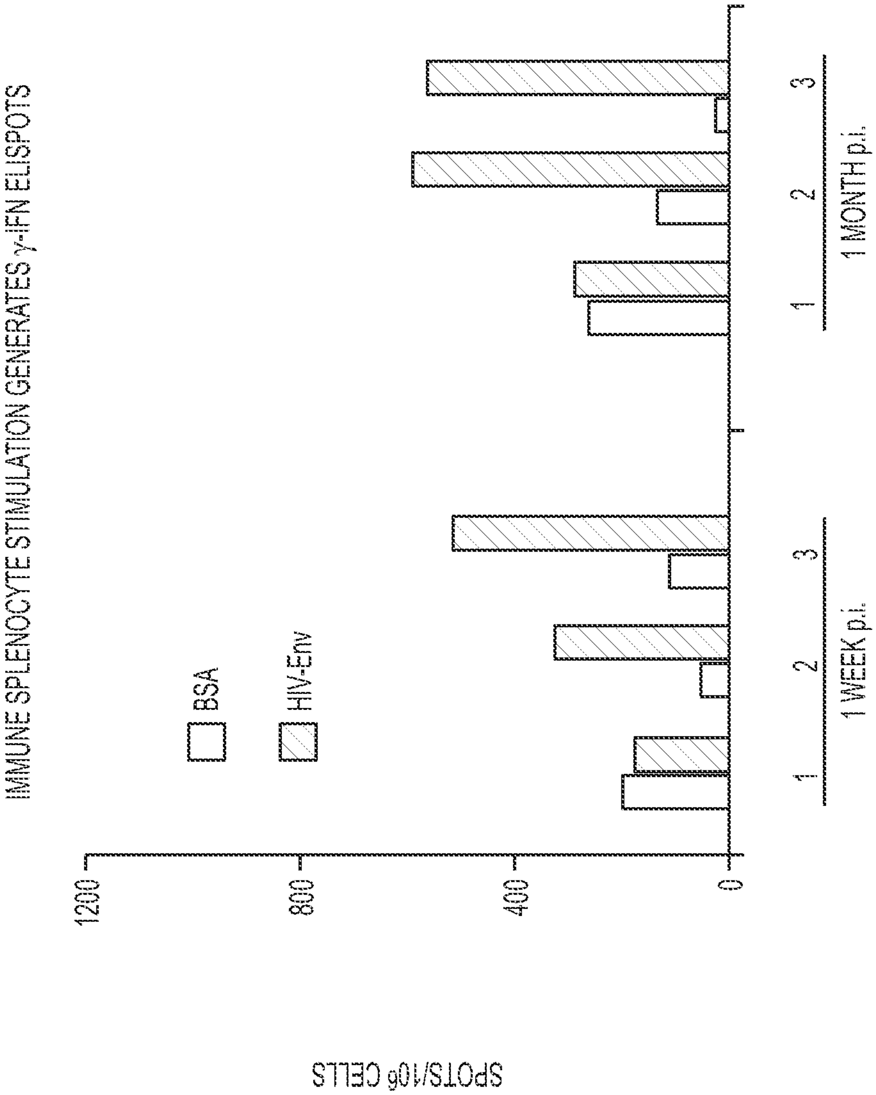
Figure 7B:
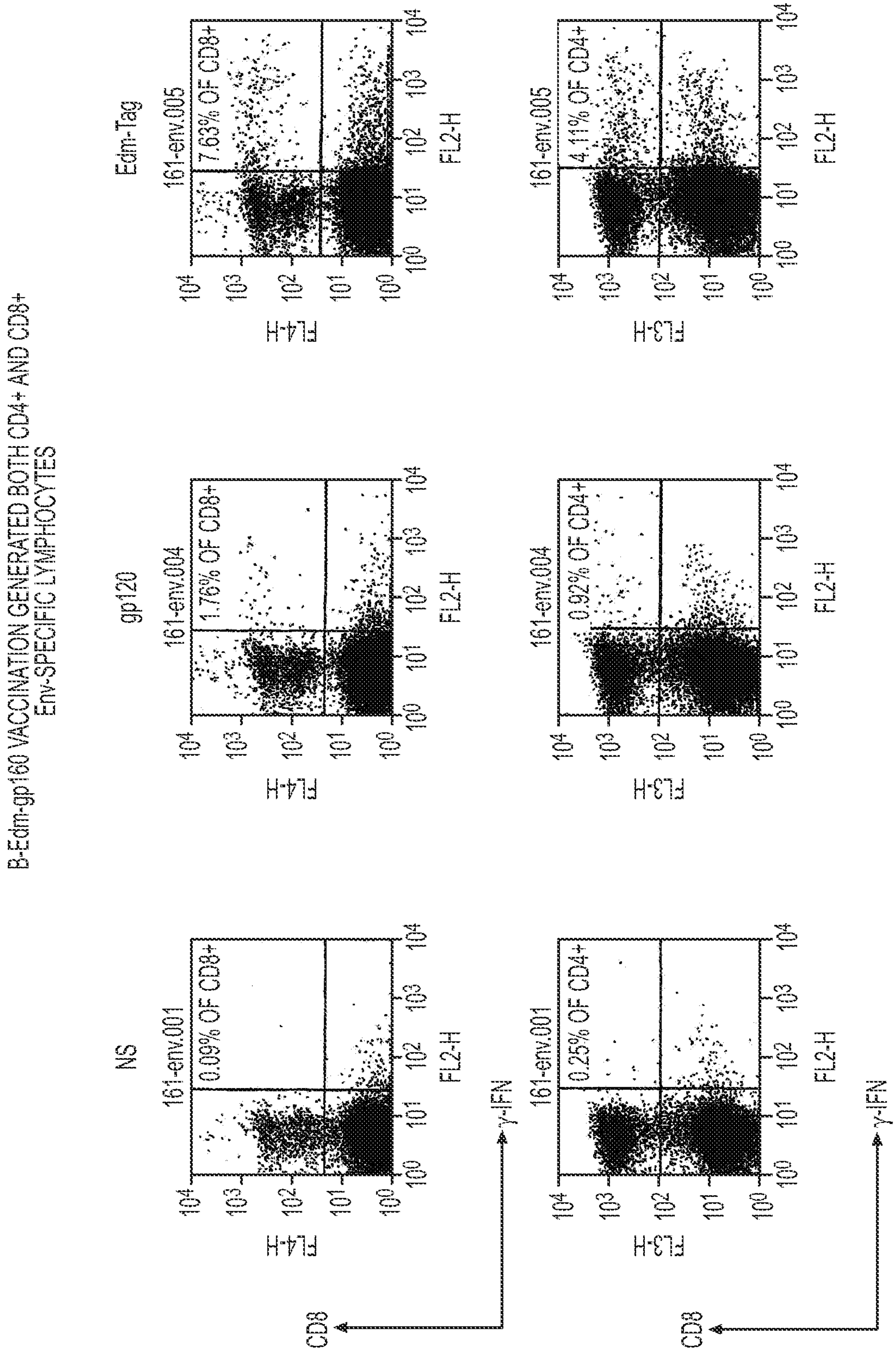

The results of these experiments performed with splenocytes from mice immunized with MV2-gp160$_{HIV}$ virus (FIG. 7) demonstrated that a single immunization with MV2-gp160$_{HIV}$ virus was able to prime HIV Env-specific lymphocytes in vivo. The γ-IFN-ELISpot assay is a sensitive method for antigen-specific cell numeration in fresh cells after in vivo immunization. This assay was used to determine whether HIV-Env-specific γ-IFN-secreting cells could be detected after a single immunization with the MV2-gp160$_{HIV}$ virus. FIG. 7A shows that a significant number of Env-specific cells were present in 2/3 mice tested, 7 days as well as 1 month after immunization. (For one mouse in each group the number of spots was the same after BSA or gp120 stimulation). The number of HIV-specific spots detected (up to 600/$10^6$ cells) represents 15-20% of MV-specific spots detected in the same mice (not shown), indicating that recombinant MV is able to efficiently immunize against the foreign gene expressed.

To assess the phenotype of these Env-specific cells, 3-color cytofluorometry experiments were performed on mice euthanized 7 days after immunization, at the theoretical peak of effector cells proliferation. A representative result is shown on FIG. 7B. The background γ-IFN production level for both CD4+ and CD8+ lymphocytes is shown on the left panel. For this animal, 0.09% of CD8+ lymphocytes (mean calculated for 3 mice: 0.31%) and 0.25% of CD4+ lymphocytes (mean: 0.41%) were spontaneously producing γ-IFN. The frequencies of HIV-gp120 T-cells (middle panel) in the CD8+ and CD4+ subsets were 1.76% (mean: 1.69%) and 0.92% (mean: 0.76%) respectively. It's interesting to take into account that in the same immunized mouse the frequencies of Measles specific cells in CD8+ and CD4+ subsets were 7.63% (mean: 7.03%) and 4.11% (mean: 3.50%) respectively. Indeed the recombinant MV2-gp160$_{HIV}$ virus expresses 6 measles proteins plus one gp160 foreign protein. Thus, the frequencies of antigen-specific lymphocytes followed the recombinant gene proportions. As a conclusion, 3-color cytofluorometry performed 7 days after MV2-gp160$_{HIV}$ virus vaccination showed that both CD8+(FIG. 7B, upper panel) and CD4+(FIG. 7B, lower panel) lymphocytes specific for HIV gp120 and measles virus were primed in vivo Inducing an Anti-HIV Response in Animals with Pre-Existing Anti-MV Immunity.

We first tested the possibility of boosting the anti-HIV response by a second injection of recombinant MV. Mice immunized with 5.$10^6$ $TCID_{50}$ of MV2-gp140 recombinant virus (3 mice per group) were boosted with a second injection of the same recombinant MV one month after the first injection. The mean anti-MV and anti-HIV antibody titers at the time of boosting were 5 $10^4$ and 8 $10^3$ respectively. These titers increased to, respectively 5 $10^5$ and 5 $10^4$ one month after boosting. Thus, anti-MV and HIV responses can be boosted 10 times by injecting the same dose of recombinant MV one month after the first immunization.

We then tested the ability of recombinant MV to induce anti-HIV antibodies in mice and monkeys in the presence of pre-existing anti-MV immunity. Mice (3 mice per point) were first immunized with $10^5$ $TCID_{50}$ of EdB-tag MV (without an HIV insert). High levels of anti-MV antibodies were induced (FIG. 7C). The titer decreased slightly after 2 months and remained stable for the following 9 months. Mice were then inoculated with 5 $10^6$ $TCID_{50}$ of MV2-gp140$_{HIV89.6}$, and boosted with the same dose one month later. The titer of anti-MV antibodies was increased 100 times and high titers of anti-HIV antibodies (5 $10^4$) were induced. These titers were similar to those obtained after immunization of naïve animals with two injections.

Figure 7D:
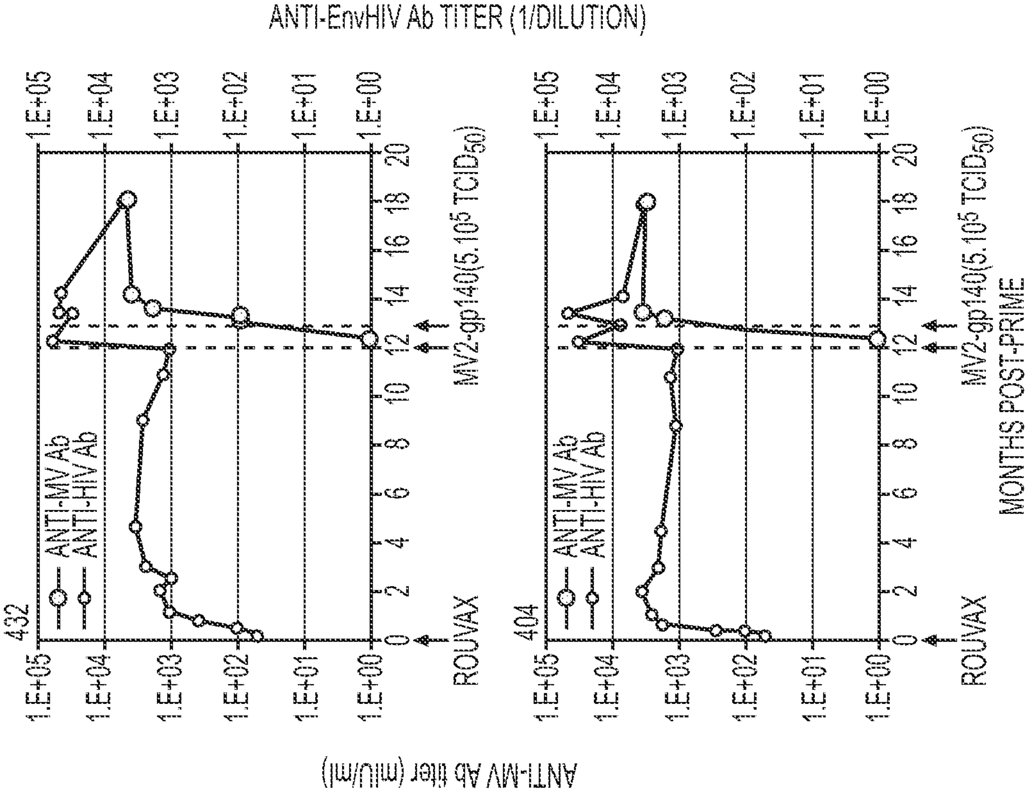
Figure 7C:
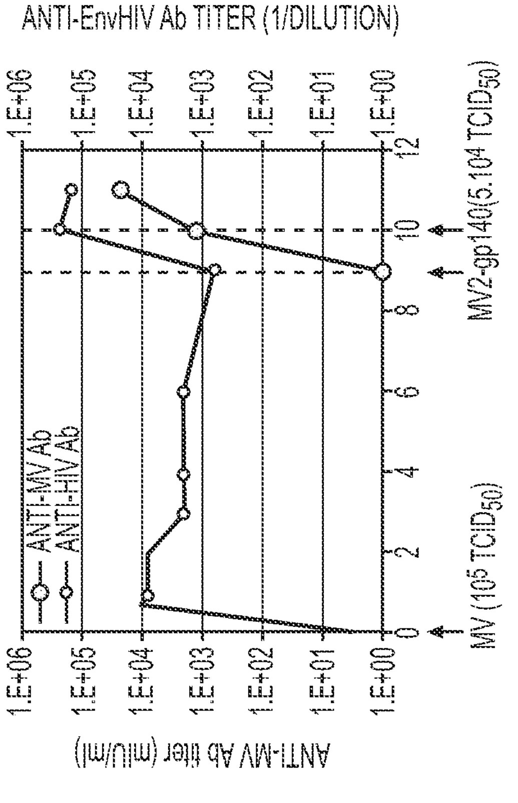

The same experiment was performed with rhesus macaques (FIG. 7D). Two macaques were immunized with a standard dose ($10^4$ $TCID_{50}$) of MV vaccine (Rouvax, Aventis Pasteur). As for mice, high anti-MV antibody levels were induced and remained stable during one year. Macaques were then inoculated with 5 $10^6$ $TCID_{50}$ of MV2-gp140$_{HIV89.6}$ twice at one month interval. Anti-MV titers increased 150 times after the first injection of MV-HIV, while the second injection had no or little effect. Anti-HIV antibodies were induced by the first MV2-gp140$_{HIV89.6}$ injection despite the presence of pre-existing anti-MV immunity. One month after the second MV2-gp140$_{HIV89.6}$ injection, the anti-HIV antibody level had increased about 10 times and had reached titers similar to those obtained in mice. This level remained stable for the following 5 months.

The main goal of the present work was to test the immunogenicity of attenuated MV-Env$_{HIV}$ recombinant viruses. We showed that such recombinants were genetically stable, expressed the HIV Env protein at high levels, and induced high titers of antibodies against both MV and the HIV Env constructs in transgenic mice. The anti-HIV antibodies titers were approximately 15-20% of those of the anti-MV antibodies. This corresponds roughly to the ratio of HIV/MV proteins expressed by the recombinant viruses. HIV Env constructions with a deleted V3 loop and an additional ELDKWAS gp41 epitope induced twice as much anti-ELDKWAS (Residues 3-9 of SEQ ID NO: 8) antibodies as native constructions, suggesting that the native conformation of the additional peptide was conserved in spite of its ectopic position. A high level of HIV-specific CD8+ and CD4+ cells was also induced. As much as 1.5-2% of the total CD8+ T-cells and 0.9% of the total CD4+ T-cells were HIV-specific.

However, the most important aspect of our results is that these anti-HIV antibodies were neutralizing for the homologous SHIV89.6p virus as well as for several heterologous clade A and clade B HIV-1 primary isolates. Interestingly, the anchored gp160 ΔV3-ELDKWAS (Residues 3-9 of SEQ ID NO: 8) construction induced antibodies that neutralized heterologous viruses more efficiently than those induced by the native envelope. Their neutralizing titers were similar to those of reference human HIV-neutralizing sera. The broader neutralizing capacity of these antibodies could be due either to the addition of a second ELDKWAS (Residues 3-9 of SEQ ID NO: 8) gp41 neutralizing epitope, or to the exposure of previously masked conserved neutralizing epitopes. Several groups have inserted the ELDKWAS (Residues 3-9 of SEQ ID NO: 8) epitope into various immunogenic molecules (44, 45, 46, 47). These studies showed that the conformational context in which the epitope is displayed is essential for the induction of neutralizing antibodies. A 3-turn-like constraint was shown to be the most likely conformation structure of the ELDKWAS (Residues 3-9 of SEQ ID NO: 8) epitope recognized by the 2F5 neutralizing antibody (46). In our constructions, the insertion of the short AAELDKWASAA (SEQ ID NO: 8) epitope in place of the V3 loop, which is flanked by β-strands (28, 29), may have such a 3-turn-like conformation.

It has been shown, already, that deleting the hypervariable loops of HIV Env can enhance its immunogenicity (3, 48, 39). However, in previous studies neutralizing antibodies were obtained only after multiple injections of high amounts of soluble protein (23), or with a "prime boost" regimen using very large amounts of DNA and pure protein (3, 39). In contrast, we observed the same levels of neutralizing antibodies in mice injected with a single dose of MV-gp160ΔV3-ELDKWAS (Residues 3-9 of SEQ ID NO: 8). Good immunogenicity in our system results probably from the fact that the HIV Env is expressed and processed by the immune system n the same way as proteins from the live MV vaccine, a highly potent immunogen. One may hope that such levels of neutralizing antibodies could at least induce partial protection in vaccinated individuals. According to the data of others (3, 39), it might be possible to increase the immunogenicity of M-HIV Env recombinants even further by deleting the V1 and V2 loops of HIV gp120, notably to induce antibodies directed against the CD4-binding site. However, it has been recently reported that this receptor-binding site can escape from the immune response by conformational and entropic masking (49).

The presence of anti-MV immunity in nearly the entire adult human population would seem to restrict the use of MV recombinants to infants, an already worthy goal in any event. However, several studies showed that revaccinating already immunized individuals results in a boost of anti-MV antibodies, suggesting that the attenuated live vaccine replicated and expressed its proteins in spite of preexisting immunity (50). Under such circumstances, one might hope to be able to vaccinate adults against a foreign antigen with a MV recombinant. Indeed, our results demonstrate, both with mice and macaques, that high levels of anti-HIV neutralizing antibodies can be obtained in the presence of pre-existing anti-MV immunity.

Various "prime-boost" regimen, using combinations of naked DNA and viral vectors such a sMVA (1) or Adenovirus (29), gave reasonable protection against a challenge with pathogenic SHIV89.6p. In the present study, we show that a single injection of MV is able to combine humoral and cellular responses at levels similar to those induced by these complex combinations.

The same recombinants have been prepared using the cloned Schwarz strain as a vector. This should raise their immunogenicity even further.

EXAMPLE II: CONSTRUCTION OF SCHWARZ MEASLES VIRUSES (MVSCHW) EXPRESSING HIV-1 ANTIGENS

In order to test their capacity as vaccine candidates against HIV infection, we constructed several recombinant Schwarz measles viruses (MV) expressing HIV-1 antigens. Different HIV-1 genes from different open reading frames were constructed and introduced in additional transcription units in the Schwarz MV cDNA that we previously cloned (pTM-MVSchw). After rescue of the different recombinant Schwarz measles viruses, the expression of the different HIV-1 proteins was analyzed by western blotting of infected-cells lysates (FIGS. 3A-D).

Different immunogens were constructed from HIV-1 Env glycoprotein (hereafter 1-8), Gag protein (hereafter 9), and Tat protein (hereafter 10):

1. Secreted glycoprotein gp140 from HIV-1 89.6p
2. Anchored glycoprotein gp160 from HIV-1 89.6p
3. Secreted glycoprotein gp140 from HIV-1 89.6p deleted from hypervariable region V3 and additional AAELDKWASAA (SEQ ID NO: 8) epitope ($gp140_{HIV89.6}$ ΔV3-ELDKWAS (Residues 3-9 of SEQ ID NO: 8))
4. Anchored glycoprotein gp160 from HIV-1 89.6p deleted from hypervariable region V3 with an additional AAELDKWASAA (SEQ ID NO: 8) epitope ($gp160_{HIV89.6}$ ΔV3-ELDKWAS(Residues 3-9 of SEQ ID NO: 8))
5. Secreted glycoprotein gp140 from HIV-1 89.6p deleted from hypervariable regions V1-V2 ($gp140_{HIV89.6}$ ΔV1V2)
6. Anchored glycoprotein gp160 from HIV-1 89.6p deleted from hypervariable regions V1-V2 ($gp160_{HIV89.6}$ ΔV1V2)
7. Secreted glycoprotein gp140 from HIV-1 89.6p deleted from hypervariable regions V1-V2-V3 ($gp140_{HIV89.6}$ΔV1V2V3)
8. Anchored glycoprotein gp160 from HIV-1 89.6p deleted from hypervariable regions V1-V2-V3 ($gp160_{HIV89.6}$ΔV1V2V3)
9. Gag polyprotein (p17p24, delta myr) from HIV-1 (clade B consensus) truncated from the nucleoprotein ORF in C-terminal (p17p24∂myrHIV-1B)
10. Tat protein from HIV-1 89.6p ($TatHIV_{89.6}$)

Figure 1A:
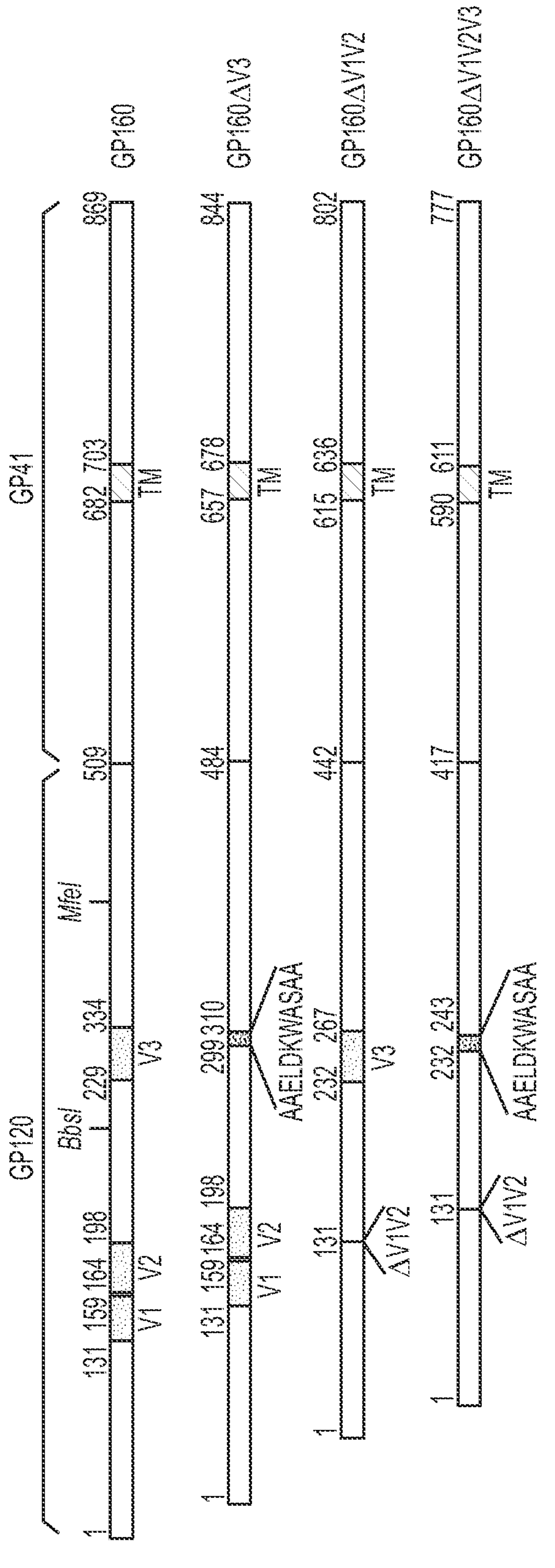
FIGS. 1A and 1B. HIV1 Env glycoprotein constructions. (A) gp160 constructions full-length and ΔV3-AAELDK-WASAA (SEQ ID NO: 8), ΔV1V2 and ΔV1V2V3 (SEQ ID NO: 8) mutants (from top to bottom). The BbsI and MfeI restriction sites used to introduce the ΔV3 deletion in the other constructions are indicated. (B) gp140 constructions are the same as gp160 except that the intracytoplasmic and transmembrane regions of the gp41 have been deleted (AAELDKWASAA disclosed as SEQ ID NO: 8).
Figure 1B:
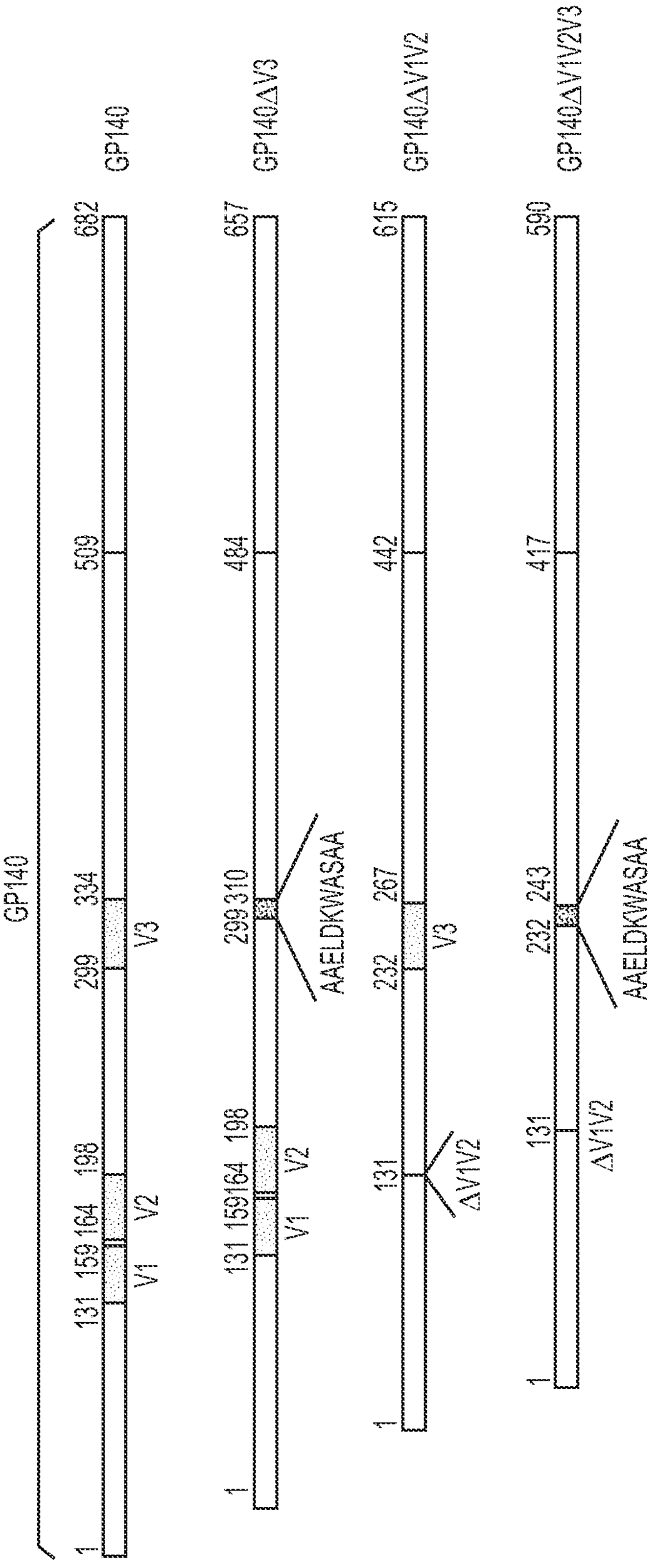

The HIV env genes encoding the different forms of the Env protein were generated by PCR amplification from plasmid pSHIV-KB9 (NIH-AIDS Research & Reference Reagent Program). The specific sequences were amplified using PfuTurbo DNA polymerase (Stratagene) and specific primers. To generate the different deletions, overlapping fragments flanking the sequences to be deleted were generated and annealed together by PCR. They were then introduced by enzyme restriction cloning in place of the corresponding fragment in the gp160 and gp140 sequences already cloned in PCR®2.1-TOPO® plasmids (FIG. 1A). The different sequences generated include a start and a stop codon at both ends and respect the "rule of six", stipulating that the nucleotides number of MV genome must be divisible by 6 (7, 8). After BsiWI/BssHII digestion, the different HIV sequences were introduced in the pTM-MVSchw vector in ATU position 2 or 3 (FIG. 1B). The resulting plasmids were designated:

1. pTM-MVSchw2-gp140$_{H}$v
2. pTM-MVSchw2-gp160$_{HIV}$
3. pTM-MVSchw2-gp140ΔV3$_{HIV}$
4. pTM-MVSchw2-gp160ΔV3$_{HIV}$
5. pTM-MVSchw2-gp140$_{HIV}$ ΔV1V2
6. pTM-MVSchw2-gp160$_{HIV}$ ΔV1V2
7. pTM-MVSchw2-gp140$_{HIV}$ ΔV1V2V3
8. pTM-MVSchw2-gp160$_{HIV}$ ΔV1V2V3
9. pTM-MVSchw2-Gag$_{HIV}$ (p17-p24 Δmyr)
10. pTM-MVSchw3-Tat$_{HIV}$ A recombinant virus expressing both Gag and gp140 in both positions 1 and 2 of the measles Schwarz vector was produced.

11. pTM-MVSchw2-Gag$_{SIV239}$ (p17-p24 Δmyr)-3-gp140$_{HIV}$

This virus expressed both proteins (Fig z). Such constructs allow the production of HIV, SHIV or SIV assembled Gag-Env "virus like particles" in cells infected by recombinant measles virus.

The HIV-1 immunogenic sequences represented in FIG. 16 have been generated:

EXAMPLE III: RECOMBINANT MEASLES VIRUSES EXPRESSING DIFFERENT VIRAL TRANSGENES

In order to demonstrate the immunizing and protective capacities of MV as a pediatric vaccination vector, a series of recombinant measles viruses expressing different viral transgenes (listed below) from other viruses were constructed and studied. The results presented here were obtained with the old EdB-tag vector. However, we have shown that the EdB-tag was 100 times less immunogenic than the Schwarz vaccine. Thus MV$_{EdB}$ recombinant viruses were inoculated at higher doses. All the inserted sequences with good immunological records can be obviously inserted in the Schwarz vector.

Viral genes which have been already inserted in the recombinant measles viruses:

| | | |
|---|---|---|
| HIV clade B 89.6P | gp160 | gp140 |
| | gp160ΔV3 | gp140ΔV3 |
| | gp160ΔV1V2 | gp140ΔV1V2 |
| | gp160ΔV1V2V3 | gp140ΔV1V2V3 |
| | tat | |

HIV clade B consensus codon optimized Gag (p17-p24)

| | |
|---|---|
| SIV Mac 239 | Nef |
| | NefΔMyr |
| | Nef29-236 |
| | Tat |
| HTLV-I | Env |
| | Gag (p19-p24) |
| | Tax |

EXAMPLE IV: RECOMBINANT MEASLES VIRUSES EXPRESSING ENV AND NS1 FROM YELLOW FEVER VIRUS HAVE IMMUNE CAPACITY

Because a pediatric bivalent vaccine against measles and yellow fever should be useful, we constructed recombinant MV expressing the Env and NS1 proteins from Yellow Fever Virus (YFV 17D204, Pasteur vaccine strain) and tested their capacity to protect mice from a lethal YFV challenge.

Construction of MV-YFV Recombinant Plasmids.

The env gene was PCR amplified with Pfu polymerase using primers that contain unique BsiWI and BssHII sites for subsequent cloning in MV vector:

```
MV-YFVEnv5
(5'-TATCGTACGATGCGAGTCGTGATTGCCCTACTG-3'; SEQ ID
NO: 12)
and

MV-YFVEnv3
(5'-ATAGCGCGCTTATGTGTTGATGCCAACCCA-3'; SEQ ID
NO: 13).
```

The Env protein thus generated (amino acids 270-753 in YFV polyprotein) contained the signal peptide in N-terminal and a part of the transmembrane region in C-terminal. The NS1 sequence was PCR amplified in the same way with Pfu polymerase using primers:

```
MVYFVNS5
(5'-TATCGTACGATGAGAAACA TGACAATGTCC-3'; SEQ
ID NO: 14)
and

MVYFVNS3
(5'-ATAGCGCGCTTAATGGCTTTCATGCGTTT TCC-3'; SEQ
ID NO: 15)
```

The NS1 protein (amino acids 754-1122 in YFV polyprotein) contained its signal peptide sequence. A start and a stop codon were added at both ends of the genes as well as several nucleotides after the stop codon in order to respect the "rule of six", stipulating that the nucleotides number of MV genome must be a multiple of 6 (7). Both env and NS1 fragments were cloned in PCR2.1-TOPO® plasmid (Invitrogen) and sequenced to check that no mutations had been introduced. After BsiWI BssHII digestion of the PCR®2.1-TOPO® plasmids, the env and NS1 sequences were cloned in the EdB-tag vector in ATU position 2 giving plasmids: EdB-Env$_{YFV}$ and EdB-NS1$_{YFV}$.

Recovery of Recombinant EdB-Env$_{YFV}$ and EdB-NS1$_{YFV}$ Viruses.

EdB-Env$_{YFV}$ and EdB-NS1$_{YFV}$ plasmids were used to transfect 293-3-46 helper cells as described above, and recombinant viruses were rescued from transfected cells cocultivated with Vero cells. Recombinant viruses were passaged two times on Vero cells and tested for transgene expression.

Expression of YFV Proteins by Recombinant MV.

The rescued recombinant viruses MV2-Env$_{YFV}$ and MV2-NS1$_{YFV}$ were propagated on Vero cells and the expression of YFV proteins was analyzed by immunofluorescence. FIG. 9 shows that syncytia of Vero cells infected by recombinant MV2-YFV viruses showed a high expression of the YFV Env and NS1 proteins as detected with a mouse anti-YFV polyclonal serum. In order to determine whether the expression of YFV genes was stable, the rescued recombinant viruses were serially passaged on Vero cells. After 10 passages all the syncytia observed in infected cells were positive for YFV (not shown). Taken together, these results indicate that Env and NS1 proteins from YFV are efficiently and stably expressed over several passages by the recombinant MVs.

Mice Immunization with MV-YFV Recombinant Viruses.

A mixture of both MV2-$Env_{YFV}$ and MV2-$NS1_{YFV}$ viruses ($10^7$ $TCID_{50}$) was inoculated intraperitoneally to six $CD46^{+/-}$ IFN-a/$bR^{-/-}$ mice as described above (see MV-HIV gp experiments). As a control, six other mice received the same dose of standard measles vaccine. After one month, mice were intracranially challenged with YFV 17D204 (10 $LD_{50}$ determined on FVB mice). FIG. 10 shows that 65% of MV-YFV immunized animals were fully protected against the challenge, while all animals vaccinated with standard MV died between 6 and 7 days post-challenge. Moreover, a 4-days delay in mortality was observed in mice immunized with MV-YFV, and these mice did not die with the same encephalitic clinical symptoms than mice vaccinated with standard MV vaccine. The disease was attenuated and consisted of limb paralysis. It has to be noticed that IFN-a/$bR^{-/-}$ mice are much more sensitive to viral infections than immunocompetent mice ($10^2$-$10^4$ times). For this reason, the lethal dose determined on immunocompetent mice was probably too high for IFN-a/$bR^{-/-}$ mice. The same experiment is underway using several decreasing doses of YFV challenge viruses.

In conclusion, this preliminary experiment shows that the immune responses induced by recombinant MV against YFV proteins are able to protect mice against a lethal challenge.

The above constructs were made by using the sequences disclosed on FIGS. 12A and 12B.

The same principles for the preparation of constructs would apply with sequences disclosed on FIGS. 12C and 12D.

EXAMPLE V: VACCINATION AGAINST WNV WITH A LIVE ATTENUATED MEASLES VIRUS (SCHWARZ STRAIN) EXPRESSING THE SECRETED FORM OF THE E GLYCOPROTEIN OF THE WNV (WEST NILE VIRUS)

We constructed a recombinant Schwarz measles attenuated virus expressing the WNV E soluble form and tested its capacity as vaccine candidate against WN encephalitis. The WN cDNA corresponding to the sE protein of IS-98-ST1 strain of WNV was introduced in an additional transcription unit in the Schwarz MV cDNA (pTM-MVSchw CNCM 1-2889). After rescue of the recombinant Schwarz measles virus, its capacity to protect mice from a lethal WNV encephalitis following intraperitoneal challenge was tested.

A) Materials and Methods

A.1 Cells and WN Virus

The IS-98-ST1 strain of WN virus was produced on *Aedes* AP61 mosquito cells according to the protocol described in Desprès et al (51), Mashimo et al (52) and Lucas et al (53). The Vero-NK cell clone used in this study was selected for its capacity to fuse after infection with measles virus and to amplify the WN virus.

A.2 Titration of WN Virus on AP61 Mosquito Cells by Immunodetection of Focuses Viral Replication (Focus Immuno Assay, FIA).

The titration was performed according to the protocol described in Despres et al (51), Mashimo et al (52) and Lucas et al (53).

The infectious titer of WN virus on AP61 cells was determined as focus forming units on AP61 cells (AP61 UFF/ml).

A.3 Purification of WN Virus Produced on AP 61 Cells.

The purification was carried out according to the protocol described in Despres et al (51), Mashimo et al (52) and Lucas et al (53).

Briefly, the viral particles present in supernatants of AP61 cells infected during 3 days with WN virus strain IS-98-ST1 (MOI 0.4) were concentrated in 7% PEG 6000 and then purified in 30-60% discontinuous saccharose gradient and in 10-50% linear saccharose gradient. WN virious in 30% saccharose were stored at −80° C. The obtained infectious titers were about $10^{10}$ AP61 FFU/ml.

A.4 Anti-WN Antibody Detection in ELISA

The anti-WN antibody titers of diluted sera (1:100) were determined by ELISA on a given quantity of $10^6$ AP61 FFU of WN IS-98-ST1 virions purified in saccharose gradient. The protocol is described in Despres et al (1993) and Mashimo et al (2002).

A.5 Anti-WN Immune Sera

Anti-WN immune sera were collected in adult mice genetically resistant to viral encephalitis (Mashimo et al—2002) which were tested during at least one month with intraperitoneal inoculation of $10^3$ $AP_{61}$ FFU of WN virus strain IS-98-ST1.

The anti-WN antibody titer of 1:100 diluted immunsera were measured in ELISA and were about 1.4 DO units. The neutralizing titers (TNRF90) of anti-WN sera were about 1600.

Ascites of mice (HMAF) against WN strain IS-98-ST1 were obtained from animals which had been hyperimmunized with brain homogenates of baby mice inoculated with WN. The ELISA titers of anti-WN HMAF, diluted to 1:1000 were about 1 DO unit.

The anti-WN immune sera were used for indirect immunofluorescence and for passive seroprotection assays against the disease. Anti-WN HMAF were used for membrane immunodetection of viral proteins.

A6. Construction of Recombinant Schwarz Measles Virus Expressing WN sE

The WNV env gene encoding the secreted form of the protein was generated by RT-PCR amplification of viral RNA purified from viral particles (WNV IS-98-ST1 strain). The specific sequence was amplified using PfuTurbo DNA polymerase (Stratagene) and specific primers that contain unique sites for subsequent cloning in pTM-MVSchw vector:

```
MV-WNEnv5
5'-TATCGTACGATGAGAGTTGTGTTTGTCGTGCTA-3' (SEQ
ID NO: 20; BsiWI site italicized)
and

MV-WNEnv3
5'-ATAGCGCGCTTAGACAGCCTTCCCAACTGA-3' (SEQ ID
NO: 21; BssH11 site italicized).
```

A start and a stop codon were added at both ends of the gene. The whole sequence generated is 1380 nucleotides long, including the start and the stop codons and respects the "rule of six", stipulating that the nucleotides number of MV genome must be divisible by 6 [Calain, 1993 (7); Schneider, 1997 (28)]. The Env protein thus generated contains its signal peptide in N-term (18 aa) and no transmembrane region. Thus, It represents amino acids 275-732 in WNV polyprotein and has the following sequence:

(SEQ ID NO: 22)

```
atgagagttgtgtttgtcgtgctattgcttttggtggccccagcttacag
cttcaactgccttggaatgagcaacagagacttcttggaaggagtgtctg
gagcaacatgggtggatttggttctcgaaggcgacagctgcgtgactatc
atgtctaaggacaagcctaccatcgatgtgaagatgatgaatatggaggc
ggtcaacctggcagaggtccgcagttattgctatttggctaccgtcagcg
atctctccaccaaagctgcgtgcccgaccatgggagaagctcacaatgac
aaacgtgctgacccagcttttgtgtgcagacaaggagtggtggacagggg
ctggggcaacggctgcggattatttggcaaaggaagcattgacacatgcg
ccaaatttgcctgctctaccaaggcaataggaagaaccatcttgaaagag
aatatcaagtacgaagtggccatttttgtccatggaccaactactgtgga
gtcgcacggaaactactccacacaggttggagccactcaggcagggagat
tcagcatcactcctgcggcgccttcatacacactaaagcttggagaatat
ggagaggtgacagtggactgtgaaccacggtcagggattgacaccaatgc
atactacgtgatgactgttggaacaaagacgttcttggtccatcgtgagt
ggttcatggacctcaacctcccttggagcagtgctggaagtactgtgtgg
aggaacagagagacgttaatggagtttgaggaaccacacgccacgaagca
gtctgtgatagcattgggctcacaagagggagctctgcatcaagctttgg
ctggagccattcctgtggaattttcaagcaacactgtcaagttgacgtcg
ggtcatttgaagtgtagagtgaagatggaaaaattgcagttgaagggaac
aacctatggcgtctgttcaaaggctttcaagtttcttgggactcccgcag
acacaggtcacggcactgtggtgttggaattgcagtacactggcacggat
ggaccttgcaaagttcctatctcgtcagtggcttcattgaacgacctaac
gccagtgggcagattggtcactgtcaacccttttgtttcagtggccacgg
ccaacgctaaggtcctgattgaattggaaccaccctttggagactcatac
atagtggtgggcagaggagaacaacagatcaatcaccattggcacaagtc
tggaagcagcattggcaaagcctttacaaccaccctcaaaggagcgcaga
gactagccgctctaggagacacagcttgggactttggatcagttggaggg
gtgttcacctcagttgggaaggctgtctaa
```

(SEQ ID NO: 23)

```
MRVVFVVLLLLVAPAYSFNCLGMSNRDFLEGVSGATVVVDLVLEGDSCVT
IMSKDKPTIDVKMMNMEAVNLAEVRSYCYLATVSDLSTKAACPTMGEAHN
DKRADPAFVCRQGVVDRGWGNGCGLFGKGSIDTCAKFACSTKAIGRTILK
ENIKYEVAIFVHGPTTVESHGNYSTQVGATQAGRFSITPAAPSYTLKLGE
YGEVTVDCEPRSGIDTNAYYVMTVGTKTFLVHREWFMDLNLPWSSAGSTV
WRNRETLMEFEEPHATKQSVIALGSQEGALHQALAGAIPVEFSSNTVKLT
SGHLKCRVKMEKLQLKGTTYGVCSKAFKFLGTPADTGHGTVVLELQYTGT
DGPCKVPISSVASLNDLTPVGRLVTVNPFVSVATANAKVLIELEPPFGDS
YIVVGRGEQQINHHWHKSGSSIGKAFTTTLKGAQRLAALGDTAWDFGSVG
GVFTSVGKAV*
```

After agarose gel purification, the PCR fragment was cloned in PCR®2.1-TOPO® plasmid (Invitrogen) and sequenced to check that no mutations were introduced. After BsiWI/BssHII digestion of the PCR®2.1-TOPO® plasmid, the DNA fragment was cloned in the pTM-MVSchw vector in ATU position 2 giving plasmid pTM-MVSchw-sE$_{WNV}$ according to FIG. 13.

A7. Production of Recombinant Measles Virus Expressing WN sE

To recover recombinant MV from plasmid, we used the helper-cell-based rescue system described by Radecke et al. [Radecke, 1995 (35)] and modified by Parks et al. [Parks, 1999 (40)]. Human helper cells stably expressing T7 RNA polymerase and measles N and P proteins (293-3-46 cells, a kind gift from MA Billeter, University of Zurich) were transfected using the calcium phosphate procedure with pTM-MVSchw-sE$_{WNV}$ plasmid (5 μg) and a plasmid expressing the MV polymerase L gene (pEMC-La, 20 ng). After overnight incubation at 37° C., the transfection medium was replaced by fresh medium and a heat shock was applied (43° C. for two hours) [Parks, 1999 (40)]. After two days of incubation at 37° C., transfected cells were transferred on a CEF cells layer and incubated at 32° C. in order to avoid adaptation of the Schwarz vaccine that was originally selected on CEF cells and is currently grown on these cells. Infectious virus was recovered between 3 and 7 days following cocultivation. The recombinant virus was also rescued by the same technique after cocultivation of transfected 293-3-46 helper cells at 37° C. with Vero cells (african green monkey kidney, clone Vero-NK). In order to increase the yield of rescue and because these recombinant viruses were prepared to be used be used in mice experiments, we used Vero cells as producing cells in place of the usual chick embryo fibroblasts (CEF). Single syncytia were harvested and transferred to Vero cells grown in 35 mm wells in Dulbebecco's modified Eagle's medium (DMEM) supplemented with 5% fetal calf serum (FCS). The infected cells were expanded in 75 and 150 cm3 flasks. When syncytia reached 80-90% confluence (usually 36-48 hours post infection), the cells were scraped in a small volume of OptiMEM (Gibco BRL) and frozen and thawed once. After low-speed centrifugation to pellet cellular debris, the supernatant, which contained virus, was stored at −80° C. We have shown that two passages of the Schwarz virus on Vero cells did not change its immunogenic capacities in macaques.

A8. Titration of Recombinant MV-WN Virus

The titers of recombinant MV were determined by an endpoint limit dilution assay on Vero cells. 50% tissue culture infectious dose ($TCID_{50}$) were calculated using the Karber method [Karber, 1931 (41)].

A9. Immunofluorescence Detection of WNV sE Expressed in Vero Cells Infected by MV-WN sE Recombinant Virus.

The expression of the WN sE protein in cells infected by recombinant MV-WN sE was detected by immunofluorescence. Vero cells were grown on polyornithine-coated coverslips and infected by MV-WN sE at an MOI of 0.05. After two days of infection, coverslips were washed twice in PBS and fixed for 15 minutes in paraformaldehyde (4% in PBS). In some cases, cells were permeabilized by Triton X100 (0.1%, 5 min). After two PBS washes, coverslips were incubated for 15 minutes at room temperature in PBS with 2% goat serum, then incubated for 1 hour at room temperature with mouse anti-WNV immune sera or mouse anti-WNV HMAF (see A5) diluted in PBS with 2% goat serum. After washing in PBS, cells were incubated for 45 minutes at room temperature with R-phycoerythrin-conjugated goat anti-mouse IgG (SBA, Birmingham). Following washing in PBS, coverslips were mounted on slides with fluoromount (Southern Biotech Associates inc., Birmingham, Alabama).

A10. Anti-MV Antibody Detection by ELISA

Anti-MV antibodies were detected using a standard ELISA kit (Trinity Biotech, USA). An anti-mouse antibody-HRP conjugate (Amersham) was used as the secondary antibody. Titers were determined by limiting dilutions and calculated as the highest dilution of serum giving twice the absorbence of a 1/100 dilution of a mixture of control sera.

A.11 Neutralization Test by Reduction of Viral Replication Focuses (TNRF90) on VERO Cells.

Successive dilutions of sera were prepared for testing in DMEM Glutamax with 2% decomplemented FCS (Fetal Calf Serum) in tubes of 0.5 ml.

For 0.1 ml of diluted serum in DMEM Glutamax with 2% FCS, 0.1 ml of DMEM Glutamax/2% FCS containing 100 $_{AP}$61 UFF of WN virus strain IS-98-ST1 was added.

Control cell: 0.2 ml of DMEM 0.2% FCS

Control virus: 0.2 ml of DMEM Glutamax/2% FCS containing 100 AP61UFF of WN virus strain IS-98-ST1.

2 hours with mild rotation at 37° C.

Plates with 12 cups with ~150 000 VERO HK cells per cup which are grown in monolayers for 24 hours in DMEM Glutamax 5% FCS 1 washing in DMEM of cell layers.

Add 0.2 ml of DMEM Glutamax/2% SVF

Add 0.2 ml of a mixture serum/WN virus on cell layers.

Incubate 2 hours at 37° C. in $CO_2$.

Withdraw the serum/WN virus mixture of infected cell layers.

1 washing in DMEM of infected cell layers.

Add 1 ml of DMEM 2% SVF per cup.

Add 1 ml of CMC 1.6% diluted in DMEM Glutamax/2% SVF

Incubate 2 days at 37° C. in $CO_2$.

The plaques were revealed through FIA technique. The last dilution of immunsera which neutralize at least 90 of 100 UFF of WN virus tested on VERO cells were determined (TNRF90: Test de Neutralisation par Reduction de Foyers de replication virale à 90%). The titer of neutralizing antibodies of the sera was determined by TNRF90.

A.12 Production of WN Virus Pseudo-Particles by Cell Line MEF/3T3.Tet-Off/Pr ME.WN #h2.

Pseudo-particles of WN virus strain IS-98-ST1 composed of prME complexed glycoproteins were secreted by MEF/3T3.Tet-Off/pr ME.WN #h2 line induced for the expression of viral proteins (CNCM 1-3018). They were purified for supernatants of 3-day cell culture according to the protocol used for WN virus purification.

Passive seroprotection assay against WN virus in adult BALB/c mice.

6-week-old BALB/c mice were provided by the Janvier breeding Center. The dose for viral test is 100 ap61 UFF, i.e., 10 DL 50 (Tomoshi et al 2002) diluted in 100 μl of DPBS supplemented with 0.2% BSA (Bovine Serum Albumine) pH7.5 (Sigma) which are inoculated intraperitoneally. The average time for lethal effect was 10 days. Animals were observed for 2 to 3 weeks.

The sera to be tested for passive seroprotection in mice are diluted in 0.1% DPBS/0.2% BSA and inoculated 24 hours prior to viral test.

B) Results and Conclusions

B1. Production of Recombinant Measles Virus Expressing WN sE cDNA encoding E protein of WNV strain IS-98-ST1 deleted for its transmembrane anchoring region was inserted in the genome of measles virus (Schwarz strain) according to FIG. 13.

B.2. Preliminary Assays of Passive Seroprotection Against WN Virus in Mice

Anti-WN immune sera to be tested were obtained from mice genetically resistant to the disease (52). The anti-WN sera, late taken, were injected at dilutions 1:10 (16 $TNRF_{90}$) et 1:40 (4 $TNRF_{90}$) in a final volume of 0.1 ml DPBS/0.2% SAB intraperitoneally in adult BALB/c mice genetically sensitive. The antibodies were administered only 24 hours prior to the viral test or 24 hours before and 24 hours after the test with 10 $DL_{50}$ of strain IS-98-ST1 of WN virus. The negative control was the injection of normal serum of mice at 1:10. The neurovirulence of WN virus was evaluated in mice tested with DPBS/0.2% SAB. The results of passive protection after two weeks of viral tests were as follows:

TABLE 1

Passive seroprotection against WNV encephalitis in adult BALB/c mice.

| Passive transfer | Mortality | MDOD* |
|---|---|---|
| PBS/BSA (0.2%) | 6\6 | 10.5 (±1.5) |
| normal serum (1:10) | 6\6 | 12.5 (±1.5) |
| anti-WNV serum (1:10), 2 doses** | 0\6 | NA |
| anti-WNV serum (1:40), 2 doses | 0\6 | NA |
| anti-WNV serum (1:10), 1 dose*** | 1\6 | 12 |
| anti-WNV serum (1:40), 1 dose | 0\6 | NA |

(*Mean Day Of Death ± SD)
(**Day −1 and Day +1 of virus challenge)
(***Day −1 of virus challenge)

To conclude, a unique injection of anti-WN antibodies (2.5 à 10 μl of serum) obtained from mice genetically resistant to WN virus, said injection being carried out intraperitoneally in adult mice sensitive to viral encephalitis provides passive protection against a test dose.

It is noted that the sera of BALB/c mice having received anti-WN protective antibodies and resisting to viral infection have anti-WN antibody titers by ELISA which are of about 1 DO unit (for a dilution of serum of 1:100) after one month of test. This indicates that the WN virus inoculated for the test has achieved replication in protected mice, inducing a humoral response. If passive seroprotection protects against lethal encephalitis due to WN virus, it does not seem to be appropriate in order to prevent viral propagration in infected individual.

B.3. Vaccination of $CD46^{+/-}$ IFN-$\alpha/\beta R^{-/-}$ Mice with MVWN sE Virus Mice susceptible for MV infection were obtained as described previously [Mrkic, 1998 (21)]. FVB mice heterozygous for the CD46 MV receptor transgene [Yannoutsos, 1996 (32)] were crossed with 129Sv IFN-$\alpha/\beta R^{-/-}$ mice [Muller, 1994 (22)]. The F1 progeny was screened by PCR and the $CD46^{+/-}$ animals were crossed again with 129Sv IFN-$\alpha/\beta R^{-/-}$ mice. IFN-$\alpha/\beta R^{-/-}$ $CD46^{+/-}$ animals were selected and used for immunization experiments. Six-week-old $CD46^{+/-}$ IFN-$\alpha/\beta R^{-/-}$ mice were inoculated intraperitoneally with a single dose of standard MV vaccine ($10^6$ $TCID_{50}$, 3 mice) or MV-WN sE recombinant virus ($10^4$ or $10^6$ $TCID_{50}$, 6 mice per dose) in 300 μl phosphate buffer saline (PBS).

A serum has been taken from eye after one month of vaccination with a unique dose in order to determine the production of anti-MV, anti-WN E and neutralizing antibodies against the test virus.

b) Sera Diluted to 1:100 and Tested for Antibodies by ELISA on Purified NV Virion, for:

| | DO unit |
|---|---|
| Ascite of anti-WN mice: | 1 (control+) |
| Serum of anti-WN mice: | 0.8 (control+) |
| Serum of MV vaccinated mice: | 0.110 ± 0.005 |
| Serum of MV/WN sE vaccinated mice, $10^4$ $DCIP_{50}$: | 0.635 ± 0.040 (males) |
| Serum of MV/WN sE vaccinated mice, $10^4$ $DCIP_{50}$: | 0.815 ± 0.005 (females) |
| Serum of MV/WN sE vaccinated mice, $10^6$ $DCIP_{50}$: | 0.800 ± 0.200 (males) |
| Serum of MV/WN sE vaccinated mice, $10^6$ $DCIP_{50}$: | 0.900 ± 0.195 (females) |

c) In Vitro seroneutralization test for WNV on VERO cells. $TNRF_{90}$ of pools of sera on 100 AP61UFF of strain IS-98-ST1 of WN virus in VERO cells:

| | $TNRF_{90}$ |
|---|---|
| Serum of MV vaccinated mice: | <10 |
| Serum of MV vaccinated mice MV-WN sE, $10^4$ $DCIP_{50}$: | 400 |
| Serum of MV vaccinated mice MV-WN sE, $10^6$ $DCIP_{50}$: | 800 |

To conclude, antibodies directed against soluble E glycoprotein WN virus have the capacity to neutralize strain IS-98-ST1 used for the test by WN virus in mice in vitro.

A vaccine boost in immunized $CD46^{+/-}$ IFN-$\alpha/\beta R^{-/-}$ mice has been carried out 1 month after the beginning of vaccination with a unique dose, identical to the dose of the first injection.

After 2 weeks of boosting, sera were tested by ELISA and in $TNRF_{90}$ as above:

a) Sera Diluted to 1:100 and Tested for Antibodies by ELISA on Purified WN Virion:

| | DO Unit |
|---|---|
| Ascite of anti-WN mice: | 1.4 (control+) |
| Serum of anti-WN mice: | 1 (control+) |
| Serum of MV vaccinated mice: | 0.110 ± 0.005 |
| Serum of MV-WN sE vaccinated mice, $10^4$ $DCIP_{50}$: | 0.810 ± 0.100 (males) |
| Serum of MV-WN sE vaccinated mice, $10^4$ $DCIP_{50}$: | 1.150 ± 0.015 (females) |
| Serum of MV-WN sE vaccinated mice, $10^6$ $DCIP_{50}$: | 0.965 ± 0.230 (males) |
| Serum of MV-WN sE vaccinated mice, $10^6$ $DCIP_{50}$: | 1.075 ± 0.240 (females) |

b) Seroneutralization test in vitro on VERO cells $TNRF_{90}$ of pools of sera on 100 $_{AP61}$UFF of strain IS-98-ST1 of WN virus in VERO cells:

| | $TNRF_{90}$ |
|---|---|
| Serum of boosted MV mice: | <10 |
| Serum of boosted MV-WN sE, $10^4$ $DCIP_{50}$ mice: | >1600 |
| Serum of boosted MV-WN sE, $10^6$ $DCIP_{50}$ mice: | >1600 |

After 4 weeks of boosting, the sera were tested by ELISA and in $TNRF_{90}$ as above:

a) Sera Diluted at 1:100 and Tested for Antibodies by ELISA on Purified WN Virion:

| | DO unit |
|---|---|
| Ascite of anti-WN mice: | 1.7 (control+) |
| Serum of anti-WN mice: | 1.2 (control+) |
| Serum of MV vaccinated mice: | 0.2 |
| Serum of MV-WN sE vaccinated mice, $10^4$ $DCIP_{50}$: | 1.52 (±0.15) |
| Serum of MV-WN sE vaccinated mice, $10^6$ $DCIP_{50}$: | 1.76 (±0.10) |

b) Seroneutralization In Vitro on VERO Cells $TNRF_{90}$ of pools of sera on 100 AP61UFF of strain IS-98-ST1 of WN virus on VERO cells:

| | $TNRF_{90}$ |
|---|---|
| Serum of MV-WN sE vaccinated mice, $10^4$ $DCIP_{50}$: | 4000 (males) |
| Serum of MV-WN sE vaccinated mice, $10^4$ $DCIP_{50}$: | 8000 (females) |
| Serum of MV-WN sE vaccinated mice, $10^6$ $DCIP_{50}$: | 10 000-12 000 |

To conclude, after a boost with a unique dose, the anti-WNV antibody titers and the anti-WNV neutralizing antibody titers were significantly increased by a 10-fold factor or more.

Splenocytes of $CD46^{+/-}$ IFN-$\alpha/\beta R^{-/-}$ mice immunized with two injections separated by 4 weeks with the MV-WN sE virus with doses of $10^4$ or $10^6$ $DCIP_{50}$ are tested in ELISpot and flux/cytometry for the T CD4 and CD8 response after in vitro stimulation with purified viral pseudo-particles in saccharose gradients starting from supernatants of induced MEF/3T3.Tet-Off/prME.WN #h-2 (CNCM 1-3018) cell line.

B.4. Passive Anti-WN Seroprotection Test in BALB/c with Anti-E Antibodies

Immune sera of $CD46^{+/-}$ IFN-$\alpha/\beta R^{-/-}$ mice vaccinated with a unique dose of recombinant measles virus has been collected after one month. Various dilutions of these sera have been injected in a final volume of 0.1 ml in κ-week-old BALB/c mice and only 24 hours before inoculation of 100 $_{AP61}$UFF of strain IS-98-ST1 of WN virus (10 $DL_{50}$) intraperitoneally (see protocol in § B2).

The results of passive protection after two weeks of viral test are as follows:

TABLE 2

Recombinant MV-WN sE induce antibodies that provide full protection against WNV encephalitis in BALB/c mice

| Passive transfer | Mortality | Day |
|---|---|---|
| PBS/BSA (0.2%) | 6\6 | 10 to 11 |
| anti-WNV serum (1:10), 1 dose* | 0\6 | NA |

TABLE 2-continued

Recombinant MV-WN sE induce antibodies that provide full protection against WNV encephalitis in BALB/c mice

| Passive transfer | Mortality | Day |
|---|---|---|
| anti-WNV serum (1:40), 1 dose | 1\6 | 20 |
| anti-MV (1:10), 1 dose | 4\6 | 10 to 11 |
| anti-MV-WN sE 10e4 (1:10), 1 dose | 3\6 | 8 to 10 |
| anti-MV-WN sE 10e6 (1:10), 1 dose | 0\6 | NA |
| anti-MV-WN sE 10e6 (1:40), 1 dose | 0\6 | NA |
| anti-MV-WN sE 10e6 (1:100), 1 dose | 3\6 | 10 to 11 |

(*Day −1 of virus challenge)

To conclude, antibodies directed against WN-virus soluble glycoprotein E have the capacity to protect in vivo against WN-virus encephalitis. The vaccination of $CD46^{+/-}$ IFN-α/$\beta R^{-/-}$ mice with a dose of $10^6$ $DCIP_{50}$ of MV-WN sE virus as a unique injection is required to induce an anti-WN E humoral response on a four-week period of time which is capable of protecting against the disease by passive sero-protection. A minimal volume of 2.5 μl of immune serum of mice vaccinated with MV-WN sE virus, is sufficient to provide a complete protection in adult BALB/c mice tested with a lethal dose of WN-virus (i.e., a ratio of about 0.1 ml of immune serum/kg). It is noted that anti-lethal sera diluted to 1:10 induce a partial protection (about 30%) against West Nile virus encephalitis.

Sera obtained in vaccinated $CD46^{+/-}$ IFN-α/$\beta R^{-/-}$ mice which have then been boosted with a weak dose ($10^4$ TCID50) will be tested for their capacity to provide passive protection in BALB/c mice.

B.5. Viral Test on $CD46^{+/-}$ IFN-α/$\beta R^{-/-}$ Mice Vaccinated with MV-WN sE $CD46^{+/-}$ IFN-α/$\beta R^{-/-}$ mice vaccinated 2 months after the 2 injections of $10^6$ $DCIP_{50}$ of MV-WN sE virus, these injections being done at 4 weeks internal have been tested with 100 AP61UFF of strain IS-98-ST1 of WN virus administered intraperitoneally.

The 2 mice vaccinated with standard measles virus died the 3rd day of the test. No morbidity or lethality was observed for mice vaccinated with MV-WN sE on the $7^{th}$ day of the test. To conclude, $CD46^{+/-}$ IFN-α/$\beta R^{-/-}$ mice immunized against soluble gpE of WN virus are protected against a lethal test dose of WN virus in the absence of anti-viral activity of alpha-interferon.

B6. New Test of Anti-WN Vaccination with an Antigen Boost

Adult $CD46^{+/-}$ IFN-α/$\beta R^{-/-}$ mice are vaccinated on a 4 week period of time with MV-WN sE virus at a dose of $10^4$ $DCIP_{50}$ which is proposed for human and a boost with an antigen is carried out with purified pseudo-particles of WN-virus which are secreted by the cell line MEF/3T3.Tet-Off/WN prME #h2.

BIBLIOGRAPHY

1. Amara, R. R., F. Villinger, J. D. Altman, S. L. Lydy, S. P. O'Neil, S. I. Staprans, D. C. Montefiori, Y. Xu, J. G. Herndon, L. S. Wyatt, M. A. Candido, N. L. Kozyr, P. L. Earl, J. M. Smith, H. L. Ma, B. D. Grimm, M. L. Hulsey, J. Miller, H. M. McClure, J. M. McNicholl, B. Moss, and H. L. Robinson. 2001. Control of a mucosal challenge and prevention of AIDS by a multiprotein DNA/MVA vaccine. Science. 292:69-74.
2. Baba, T. W., V. Liska, R. Hofmann-Lehmann, J. Vlasak, W. Xu, S. Ayehunie, L. A. Cavacini, M. R. Posner, H. Katinger, G. Stiegler, B. J. Bernacky, T. A. Rizvi, R. Schmidt, L. R. Hill, M. E. Keeling, Y. Lu, J. E. Wright, T. C. Chou, and R. M. Ruprecht. 2000. Human neutralizing monoclonal antibodies of the IgG1 subtype protect against mucosal simian-human immunodeficiency virus infection. Nat Med. 6:200-206.
3. Barnett, S. W., S. Lu, I. Srivastava, S. Cherpelis, A. Gettie, J. Blanchard, S. Wang, I. Mboudjeka, L. Leung, Y. Lian, A. Fong, C. Buckner, A. Ly, S. Hilt, J. Ulmer, C. T. Wild, J. R. Mascola, and L. Stamatatos. 2001. The ability of an oligomeric human immunodeficiency virus type 1 (HIV-1) envelope antigen to elicit neutralizing antibodies against primary HIV-1 isolates is improved following partial deletion of the second hypervariable region. J Virol. 75:5526-5540.
4. Binley, J. M., R. W. Sanders, B. Clas, N. Schuelke, A. Master, Y. Guo, F. Kajumo, D. J. Anselma, P. J. Maddon, W. C. Olson, and J. P. Moore. 2000. A recombinant human immunodeficiency virus type 1 envelope glycoprotein complex stabilized by an intermolecular disulfide bond between the gp120 and gp41 subunits is an antigenic mimic of the trimeric virion-associated structure. J Virol. 74:627-643.
5. Boyer, J., K. Ugen, B. Wang, M. Agadjanyan, L. Gilbert, M. Bagarazzi, M. Chattergoon, P. Frost, A. Javadian, W. Williams, Y. Refaeli, R. Ciccarelli, D. McCallus, L. Coney, and D. Weiner. 1997. Protection of chimpanzees from high-dose heterologous HIV-1 challenge by DNA vaccination. Nature Medicine. 3:526-532.
6. Burton, D. 1997. A vaccine for HIV type 1: the antibody perspective. Proceedings of the National Academy of Sciences of the United States of America. 94:10018-10023.
7. Calain, P., and L. Roux. 1993. The rule of six, a basic feature for efficient replication of Sendai virus defective interfering RNA. J Virol. 67:4822-4830.
8. Collman, R., J. W. Balliet, S. A. Gregory, H. Friedman, D. L. Kolson, N. Nathanson, and A. Srinivasan. 1992. An infectious molecular clone of an unusual macrophage-tropic and highly cytopathic strain of human immunodeficiency virus type 1. J Virol. 66:7517-7521.
9. Crotty, S., C. J. Miller, B. L. Lohman, M. R. Neagu, L. Compton, D. Lu, F. X. Lu, L. Fritts, J. D. Lifson, and R. Andino. 2001. Protection against simian immunodeficiency virus vaginal challenge by using Sabin poliovirus vectors. J Virol. 75:7435-7452.
10. Hoffman, T. L., C. C. LaBranche, W. Zhang, G. Canziani, J. Robinson, I. Chaiken, J. A. Hoxie, and R. W. Doms. 1999. Stable exposure of the coreceptor-binding site in a CD4-independent HIV-1 envelope protein. Proc Natl Acad Sci USA. 96:6359-6364.
11. Hu, S., P. Polacino, V. Stallard, J. Klaniecki, S. Pennathur, B. Travis, L. Misher, H. Kornas, A. Langlois, W. Morton, and R. Benveniste. 1996. Recombinant subunit vaccines as an approach to study correlates of protection against primate lentivirus infection. Immunology Letters. 51:115-119.
12. Karlsson, G. B., M. Halloran, J. Li, I. W. Park, R. Gomila, K. A. Reimann, M. K. Axthelm, S. A. Iliff, N. L. Letvin, and J. Sodroski. 1997. Characterization of molecularly cloned simian-human immunodeficiency viruses causing rapid CD4+ lymphocyte depletion in rhesus monkeys. J Virol. 71:4218-4225.
13. Kwong, P. D., R. Wyatt, S. Majeed, J. Robinson, R. W. Sweet, J. Sodroski, and W. A. Hendrickson. 2000. Structures of HIV-1 gp120 envelope glycoproteins from laboratory-adapted and primary isolates. Structure Fold Des. 8:1329-1339.

14. Kwong, P. D., R. Wyatt, J. Robinson, R. W. Sweet, J. Sodroski, and W. A. Hendrickson. 1998. Structure of an HIV gp120 envelope glycoprotein in complex with the CD4 receptor and a neutralizing human antibody. Nature. 393:648-659.
15. Kwong, P. D., R. Wyatt, Q. J. Sattentau, J. Sodroski, and W. A. Hendrickson. 2000. Oligomeric modeling and electrostatic analysis of the gp120 envelope glycoprotein of human immunodeficiency virus. J Virol. 74:1961-1972.
16. Mascola, J. R., M. G. Lewis, G. Stiegler, D. Harris, T. C. VanCott, D. Hayes, M. K. Louder, C. R. Brown, C. V. Sapan, S. S. Frankel, Y. Lu, M. L. Robb, H. Katinger, and D. L. Birx. 1999. Protection of Macaques against pathogenic simian/human immunodeficiency virus 89.6PD by passive transfer of neutralizing antibodies. J Virol. 73:4009-4018.
17. Mascola, J. R., M. K. Louder, T. C. VanCott, C. V. Sapan, J. S. Lambert, L. R. Muenz, B. Bunow, D. L. Birx, and M. L. Robb. 1997. Potent and synergistic neutralization of human immunodeficiency virus (HIV) type 1 primary isolates by hyperimmune anti-HIV immunoglobulin combined with monoclonal antibodies 2F5 and 2G12. J Virol. 71:7198-7206.
18. Mascola, J. R., and G. J. Nabel. 2001. Vaccines for prevention of HIV-1 disease. Immunology. 13:489-495.
19. Mascola, J. R., G. Stiegler, T. C. VanCott, H. Katinger, C. B. Carpenter, C. E. Hanson, H. Beary, D. Hayes, S. S. Frankel, D. L. Birx, and M. G. Lewis. 2000. Protection of macaques against vaginal transmission of a pathogenic HIV-1/SIV chimeric virus by passive infusion of neutralizing antibodies. Nat Med. 6:207-210.
20. Mrkic, B., B. Odermatt, M. Klein, M. Billeter, J. Pavlovic, and R. Cattaneo. 1999. Lymphatic dissemination and comparative pathology of recombinant measles viruses in genetically modified mice. Journal of Virology. 74:1364-1372.
21. Mrkic, B., J. Pavlovic, T. Rulicke, P. Volpe, C. J. Buchholz, D. Hourcade, J. P. Atkinson, A. Aguzzi, and R. Cattaneo. 1998. Measles virus spread and pathogenesis in genetically modified mice. J Virol. 72:7420-7427.
22. MOller, U., U. Steinhoff, L. F. L. Reis, S. Hemmi, J. Pavlovic, R. M. Zinkernagel, and M. Aguet. 1994. Functional role of type I and type II interferons in antiviral defense. Science. 264:1918-1921.
23. Muster, T., F. Steindl, M. Purtscher, A. Trkola, A. Klima, G. Himmler, F. Ruker, and H. Katinger. 1993. A conserved neutralizing epitope on gp41 of human immunodeficiency virus type 1. J Virol. 67:6642-6647.
24. Naniche, D., G. Varior-Krishnan, F. Cervoni, T. F. Wild, B. Rossi, C. Rabourdin-Combe, and D. Gerlier. 1993. Human membrane cofactor protein (CD46) acts as a cellular receptor for measles virus. J Virol. 67:6025-6032.
25. Parren, P. W., M. C. Gauduin, R. A. Koup, P. Poignard, P. Fisicaro, D. R. Burton, and Q. J. Sattentau. 1997. Relevance of the antibody response against human immunodeficiency virus type 1 envelope to vaccine design. Immunol Lett. 57:105-112.
26. Reimann, K. A., J. T. Li, R. Veazey, M. Halloran, I. W. Park, G. B. Karlsson, J. Sodroski, and N. L. Letvin. 1996. A chimeric simian/human immunodeficiency virus expressing a primary patient human immunodeficiency virus type 1 isolate env causes an AIDS-like disease after in vivo passage in rhesus monkeys. J Virol. 70:6922-6928.
27. Sanders, R. W., L. Schiffner, A. Master, F. Kajumo, Y. Guo, T. Dragic, J. P. Moore, and J. M. Binley. 2000. Variable-loop-deleted variants of the human immunodeficiency virus type 1 envelope glycoprotein can be stabilized by an intermolecular disulfide bond between the gp120 and gp41 subunits. J Virol. 74:5091-5100.
28. Schneider, H., K. Kaelin, and M. A. Billeter. 1997. Recombinant measles viruses defective for RNA editing and V protein synthesis are viable in cultured cells. Virology. 227:314-322.
29. Shiver, J. W., T. M. Fu, L. Chen, D. R. Casimiro, M. E. Davies, R. K. Evans, Z. Q. Zhang, A. J. Simon, W. L. Trigona, S. A. Dubey, L. Huang, V. A. Harris, R. S. Long, X. Liang, L. Handt, W. A. Schleif, L. Zhu, D. C. Freed, N. V. Persaud, L. Guan, K. S. Punt, A. Tang, M. Chen, K. A. Wilson, K. B. Collins, G. J. Heidecker, V. R. Fernandez, H. C. Perry, J. G. Joyce, K. M. Grimm, J. C. Cook, P. M. Keller, D. S. Kresock, H. Mach, R. D. Troutman, L. A. Isopi, D. M. Williams, Z. Xu, K. E. Bohannon, D. B. Volkin, D. C. Montefiori, A. Miura, G. R. Krivulka, M. A. Lifton, M. J. Kuroda, J. E. Schmitz, N. L. Letvin, M. J. Caulfield, A. J. Bett, R. Youil, D. C. Kaslow, and E. A. Emini. 2002. Replication-incompetent adenoviral vaccine vector elicits effective anti-immunodeficiency-virus immunity. Nature. 415:331-335.
30. Thali, M., J. P. Moore, C. Furman, M. Charles, D. D. Ho, J. Robinson, and J. Sodroski. 1993. Characterization of conserved human immunodeficiency virus type 1 gp120 neutralization epitopes exposed upon gp120-CD4 binding. J Virol. 67:3978-3988.
31. Trkola, A., M. Purtscher, T. Muster, C. Ballaun, A. Buchacher, N. Sullivan, K. Srinivasan, J. Sodroski, J. P. Moore, and H. Katinger. 1996. Human monoclonal antibody 2G12 defines a distinctive neutralization epitope on the gp120 glycoprotein of human immunodeficiency virus type 1. J Virol. 70:1100-1108.
32. Yannoutsos, N., J. N. Ijzermans, C. Harkes, F. Bonthuis, C. Y. Zhou, D. White, R. L. Marquet, and F. Grosveld. 1996. A membrane cofactor protein transgenic mouse model for the study of discordant xenograft rejection [published erratum appears in Genes Cells 1996 August; 1(8):785]. Genes Cells. 1:409-419.
33. Griffin, D. 2001. Measles virus, P. 1401-1441. In D. Knipe and P. Howley (ed.), Field's Virology, 4$^{th}$ Editiion, vol. 2. Lippincott—Raven Publishers, Philadelphia.
34. Hilleman, M. 2002. Current overview of the pathogenesis and prophylaxis of measles with focus on practical implications. Vaccine. 20:651-665.
35. Radecke, F., P. Spielhofer, H. Schneider, K. Kaelin, M. Huber, C. Dotsch, G. Christiansen, and M. A. Billeter. 1995. Rescue of measles viruses from cloned DANN. Embdo J. 14: 5773-5784.
36. Radecke, F., and Billeter. 1997. Reverse genetics meets the nonsegmented negative-strand RNA viruses. Reviews in Medical Virology. 7:49-63.
Singh, M., R. Cattaneo, and M. A. Billeter. 1999. A recombinant measles virus expressing hepatitis B virus surface antigen induces humoral immune responses in genetically modified mice. J. Virol. 73: 4823-4828.
Spielhofer, P., T. Bachi, T. Fehr, G. Christiansen, R. Cattaneo, K. Kaelin, M. Billeter, and H. Naim. 1998. Chimeric measles viruses with a foreign envelope. J. Virol. 72: 2150-2159.
39. Srivastava, I., K. Vandorsten, L. Vojtech, S. Barnett, and L. Stamatos. 2003. Changes in the immunogenic properties of soluble gp140 human immunodeficiency virus envelope constructs upon partial deletion of the second hypervariable region. J. Virol. 77:2310-2320.

40. Parks, C. L., R. A. Lerch, P. Walpita, M. S. Sidhu, and S. A. Udem. 1999. Enhanced measles virus cDNA rescue and gene expression after heat shock. J. Virol. 73: 3560-3566.
41. Karber, G. 1931. Breitag zur kollektiven Behandlung pharmakologischer Reihenversuche. Arch Exp Path Pharmak. 162: 480-483.
42. Burrer, R., D. Salmon-Ceron, S. Richert, G. Pancino, G. Spiridon, S. Haessig, V. Roques, F. Barre-Sinoussi, A. M. Aubertin, and C. Moog. 2001. Immunoglobulin G (IgG) and IgA, but also nonantibody factors, account for in vitro neutralization of human immunodeficiency virus (HIV) type 1 primary isolates by serum and plasma of HIV-infected patients. J Virol. 75: 5421-5424.
43. Charneau, P., G. Mirambeau, P. Roux, S. Paulous, H. Buc, and F. Clavel 1994. HIV-1 reverse transcription. A termination step at the center of the genome. J Mol Biol. 241:651-662.
44. Coeffier, E., J. Clement, V. Cussac, N. Khodaei-Boorane, M. Jehanno, M. Rojas, A. Dridi, M. Latour, R. El Habib, F. Barre-Sinoussi, M. Hofnung, and C. Leclerc. 2001. Antigenicity and immunogenicity of the HIV-1 gp41 epitope ELDKWA inserted into permissive sites of the MalE protein. Vaccine. 19:684-693.
45. Mascola, J. R., M. K. Louder, T. C. VanCott, C. V. Sapan, J. S. Lambert, L. R. Muenz, B. Bunow, D. L. Birx, and M. L. Robb. 1997. Potent and synergistic neutralization of human immunodeficiency virus (HIV)) type 1 primary isolates by hyperimmune anti-HIV immunoglobulin combined with monoclonal antibodies 2F5 and 2G12. J Virol. 71: 7198-7206.
45. Eckhart, L., W. Raffelberger, B. Ferko, A. Klima, M. Purtscher, H. Katinger, and F. Raker. 1996. Immunogenic presentation of a conserved gp41 epitope of human immunodeficiency virus type I on recombinant surface antigen of hepatitis B. virus. J. Gene. Virol. 77: 2001-2008.
46. Ho, J., K. MacDonald, and B. Barber. 2002. Construction of recombinant targeting immunogens incorporating an HIV-1 neutralizing epitope into sites of differing conformational constrain. Vaccine. 20: 1169-1180.
47. Liang, X., S. Munshi, J. Shendure, Mark, M. Davies, D. Freed, D. Montefiori, and J. Shiver. 1999. Epitope insertion into variable loops of HIV-1 gp120 as a potential means to improve immunogenicity of viral envelope protein. Vaccine. 17: 2862-2872.
48. Jeffs, S., C. Shotton, P. Balfe, and J. McKeating. 2002. Truncated gp120 envelope glycoprotein of human immunodeficiency virus 1 elicits broadly reactive neutralizing immune response. J. Gen. Virol. 83: 2723-2732.
49. Kwong, P., and et al. 2002. HIV evades antibody-mediated neutralization through conformational masking of receptor-binding sites. Nature. 420-678-682.
50. Dilraj. A., F. T. Cutts, J. F. de Castro, J. G. Wheeler, D. Brown, C. Roth, H. M. Coovadia, and J. V. Benett. 2000, Lancet. 355:798-803.
51. Despres et al, 1993. Virology 196: 209-219
52. Mashimo et al. 2002. PNAS. USA 99: 11311-11316
53. Lucas et al. 2003. Immunol. Cell. Biol. 81(3): 230-6.

The invention claimed is:

1. A method of making an immunogenic composition, comprising:

providing (i) a recombinant measles virus expressing a heterologous amino acid sequence, or a recombinant measles virus expression vector for expressing a heterologous amino acid sequence, wherein said virus or vector comprises a sequence comprising:

A) a nucleotide sequence encoding the full length antigenomic (+)RNA strand of a measles virus;

B) a T7 promoter sequence comprising a GGG motif at its 3' end, operably linked to the nucleotide sequence of A;

C) a hammerhead ribozyme sequence located adjacent to the GGG motif at one end and adjacent to the first nucleotide of the nucleotide sequence encoding the full length anti-genomic (+)RNA strand of the measles virus strain at the other end;

D) a T7 terminator sequence operably linked to the nucleotide sequence of A;

E) the sequence of a hepatitis delta virus ribozyme located adjacent to the last nucleotide of the nucleotide sequence encoding the full length anti-genomic (+)RNA strand of the measles virus; and F) a heterologous coding sequence encoding a heterologous amino acid sequence comprising an antigen of a heterologous RNA virus, wherein the heterologous RNA virus is not a flavivirus or a retrovirus; and combining the recombinant measles virus expressing a heterologous amino acid sequence, or a recombinant measles virus expression vector for expressing a heterologous amino acid sequence, with (ii) an acceptable vehicle, to thereby provide the immunogenic composition.

2. The method of claim 1, wherein the measles virus is a measles virus vaccine strain.

3. The method of claim 1, wherein the heterologous coding sequence is cloned between the P and M genes of the measles virus.

4. The method according to claim 1, wherein the heterologous coding sequence is cloned between the H and L genes of the measles virus.

5. The method of claim 2, wherein the RNA virus is not a flavivirus or a retrovirus.

6. The method of claim 2, wherein the heterologous coding sequence is cloned between the P and M genes of the measles virus.

7. The method according to claim 2, wherein the heterologous coding sequence is cloned between the H and L genes of the measles virus.

8. The method of claim 5, wherein the heterologous coding sequence is cloned between the P and M genes of the measles virus.

9. The method according to claim 5, wherein the heterologous coding sequence is cloned between the H and L genes of the measles virus.

* * * * *